US012240839B2

(12) United States Patent
Milgram et al.

(10) Patent No.: US 12,240,839 B2
(45) Date of Patent: Mar. 4, 2025

(54) CYCLOBUTYL DIHYDROQUINOLINE SULFONAMIDE COMPOUNDS

(71) Applicant: AMGEN INC., Thousand Oaks, CA (US)

(72) Inventors: Benjamin C Milgram, Cambridge, MA (US); Isaac E Marx, Arlington, MA (US); Haoxuan Wang, Somerville, MA (US); Alan H Cherney, Somerville, MA (US)

(73) Assignee: AMGEN INC., Thousand Oaks, CA (US)

( * ) Notice: Subject to any disclaimer, the term of this patent is extended or adjusted under 35 U.S.C. 154(b) by 381 days.

(21) Appl. No.: 17/633,151

(22) PCT Filed: Jun. 10, 2021

(86) PCT No.: PCT/US2021/036896
§ 371 (c)(1),
(2) Date: Feb. 4, 2022

(87) PCT Pub. No.: WO2021/252820
PCT Pub. Date: Dec. 16, 2021

(65) Prior Publication Data
US 2022/0306604 A1   Sep. 29, 2022

Related U.S. Application Data

(60) Provisional application No. 63/037,001, filed on Jun. 10, 2020.

(51) Int. Cl.
| | |
|---|---|
| C07D 413/12 | (2006.01) |
| A61P 25/04 | (2006.01) |
| C07D 215/36 | (2006.01) |
| C07D 401/12 | (2006.01) |

(52) U.S. Cl.
CPC ............ *C07D 413/12* (2013.01); *A61P 25/04* (2018.01); *C07D 215/36* (2013.01); *C07D 401/12* (2013.01)

(58) Field of Classification Search
None
See application file for complete search history.

(56) References Cited

U.S. PATENT DOCUMENTS

| | | | |
|---|---|---|---|
| 4,412,994 A | 11/1983 | Sloan et al. | |
| 7,009,052 B2 | 3/2006 | Du et al. | |
| 8,101,647 B2 | 1/2012 | Chafeev et al. | |
| 8,314,097 B2 | 11/2012 | Ksander et al. | |
| 9,212,182 B2 * | 12/2015 | Weiss ...................... | A61P 25/04 |
| 9,458,152 B2 | 10/2016 | Weiss et al. | |
| 10,383,866 B2 | 8/2019 | Weiss et al. | |
| 10,472,356 B2 | 11/2019 | Weiss et al. | |
| 10,729,684 B2 | 8/2020 | Weiss et al. | |
| 11,807,634 B2 | 11/2023 | Milgram et al. | |
| 2014/0371201 A1 | 12/2014 | Weiss et al. | |
| 2016/0046626 A1 | 2/2016 | Weiss et al. | |
| 2021/0387977 A1 | 12/2021 | Milgram et al. | |
| 2021/0387978 A1 | 12/2021 | Milgram et al. | |
| 2023/0234948 A1 | 7/2023 | Milgram et al. | |

FOREIGN PATENT DOCUMENTS

| | | | |
|---|---|---|---|
| CN | 102458394 A | | 5/2012 |
| CN | 109563045 A | | 4/2019 |
| EP | 0039051 A2 | | 11/1981 |
| EP | 0039051 B1 | | 7/1985 |
| JP | 2018537505 A | | 12/2018 |
| WO | WO-199640641 A1 | | 12/1996 |
| WO | WO-199832732 A1 | | 7/1998 |

(Continued)

OTHER PUBLICATIONS

Berge, et al., "Pharmaceutical salts," J Pharm Sci. Jan. 1977; 66(1):1-19.
Bugera, M., et al., "Deoxofluorination of Aliphatic Carboxylic Acids: A Route to Trifluoromethyl-Substituted Derivative," J Org. Chem. 2019; 84(24):16105-16115.
Bundgaard, Design of Prodrugs, Elsevier, 1985; pp. 1-94.
Bundgaard, et al., "A novel solution-stable, water-soluble prodrug type for drugs containing a hydroxyl or an NH-acidic group," J Med Chem., Dec. 1989; 32(12):2503-7.
CAS STNext® No. 2306248-65-5 [database online]. 2 pages. [retrieved on Oct. 1, 2024], Retrieved from the Internet: <http://www.cas.org/training/stn/database-specific>.

(Continued)

*Primary Examiner* — Samantha L Shterengarts
(74) *Attorney, Agent, or Firm* — Cooley LLP

(57) ABSTRACT

The present invention provides a cyclobutyl dihydroquinoline sulfonamide compound of Formula (I), an enantiomer, diastereoisomer, atropisomer thereof, a mixture thereof, or a pharmaceutically acceptable salt thereof, that inhibits voltage-gated sodium channels, in particular Nav1.7. The compounds are useful for the treatment of diseases associated with the activity of sodium channels such as pain disorders, cough, and itch. Also provided are pharmaceutical compositions containing the compounds of the present invention. Also further provided is an atropi-selective preparation of said compounds of Formula (I), and intermediate thereof.

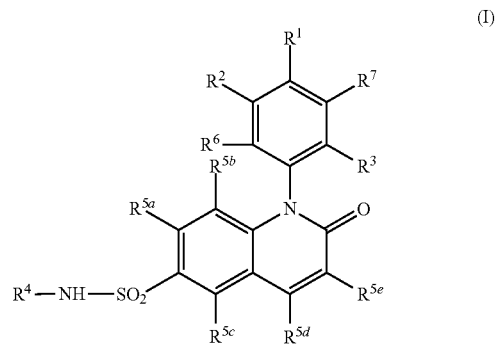

14 Claims, No Drawings

(56) References Cited

FOREIGN PATENT DOCUMENTS

| | | |
|---|---|---|
| WO | WO-2003090672 A2 | 11/2003 |
| WO | WO-2004065379 A1 | 8/2004 |
| WO | WO-2004083204 A1 | 9/2004 |
| WO | WO-2006117762 A2 | 11/2006 |
| WO | WO-2006122014 A2 | 11/2006 |
| WO | WO-2006124744 A1 | 11/2006 |
| WO | WO-2007089034 A1 | 8/2007 |
| WO | WO-2010125350 A1 | 11/2010 |
| WO | WO-2011006621 A1 | 1/2011 |
| WO | WO-2013025883 A1 | 2/2013 |
| WO | WO-2013086229 A1 | 6/2013 |
| WO | WO-2013122897 A1 | 8/2013 |
| WO | WO-2013134518 A1 | 9/2013 |
| WO | WO-2014201173 A1 | 12/2014 |
| WO | WO-2014201206 A1 | 12/2014 |
| WO | WO-2017106871 A1 | 6/2017 |
| WO | WO-2017106872 A1 | 6/2017 |
| WO | WO-2017165304 A2 | 9/2017 |
| WO | WO-2021252818 A1 | 12/2021 |
| WO | WO-2021252820 A1 | 12/2021 |
| WO | WO-2023016562 A1 | 2/2023 |
| WO | WO-2023023202 A1 | 2/2023 |

OTHER PUBLICATIONS

Chaplan, S.R., et al., "Qualitative Assessment of Tactile Allodynia in the Rat Paw," Journal of Neuroscience Methods 1994; 53:55-63.
Chung, et al., "Segmental spinal nerve ligation model of neuropathic pain," Methods Mol Med. 2004; 99:35-45.
Cox, J.J., et al., "An SCN9A channelopathy causes congenital inability to experience pain, " Nature 2006; 444:894-898.
Deuis, et al., "An animal model of oxaliplatin-induced cold allodynia reveals a crucial role for Nav1.6 in peripheral pain pathways," Pain 2013; 154(9):1749-1757.
Dib-Hajj, et al., "NaN, a novel voltage-gated Na channel, is expressed preferentially in peripheral sensory neurons and down-regulated after axotomy," Proc. Natl. Acad. Sci. USA 1998; 95(15):8963-8968.
Dib-Hajj, et al., "The Nav1.7 sodium channel: from molecule to man," Nature Reviews Neuroscience 2013; 14, 49-62.
Do, M.T., et al., "Subthreshold Sodium Currents and Pacemaking of Subthalamic Neurons: Modulation by Slow Inactivation," Neuron. 2003; 39:109-120.
Drenth J.P.H., et al., "SCN9A mutations define primary erythermalgia as a neuropathic disorder of voltage gated sodium channels," J Invest Dermatol 2005; 124:1333-1338.
Ettinger, A., et al., "Use of Antiepileptic Drugs for Nonepileptic Conditions: Psychiatric Disorders and Chronic Pain," Neurotherapeutics 2007; 4:75-83.
Federal Register/vol. 71(176) Notices, Department of Health and Human Services, Food and Drug Admin., Draft Guidance for Industry on Drug Interaction Studies-Study Design, Data Analysis, and Implications for Dosing and Labelling; Availability, pp. 53696-53769, Sep. 12, 2006.
Fertleman, et al., "SCN9A mutations in paroxysmal extreme pain disorder: allelic variants underlie distinct channel defects and phenotypes," Neuron 2006; 52:767-774.
Gillet, L., et al., "Voltage-gated Sodium Channel Activity Promotes Cysteine Cathepsin-dependent Invasiveness and Colony Growth of Human Cancer Cells," J. Biological Chemistry 2009; 284:8680-8691.
Goldberg Y.P., et al., "Loss-of-function mutations in the Nav1.7 gene underlie congenital indifference to pain in multiple human populations," Clin Genet 2007; vol. 71, Issue 4, pp. 311-319.
Goldin, A.L., "Resurgence of sodium channel research," Ann Rev Physiol. 2001; 63:871-894.
Gonzalez, J.E., et al., "Small Molecule Blockers of Voltage-gated Sodium Channels," Methods Principles in Med. Chem. 2006; 29:168-192.

Hains, B., et al., "Upregulation of Sodium Channel NaV1.3 and Functional Involvement in Neuronal Hyperexcitability Associated with Central Neuropathic Pain after Spinal Cord Injury," J. Neuroscience. 2003; 23(26):8881-8892.
Halford, Bethany, C & E News, "Changing the Channel," 2014, pp. 10-14.
Halladay, et al., "An 'all-inclusive' 96-well cytochrome P450 induction method: measuring enzyme activity, mRNA levels, protein levels, and cytotoxicity from one well using cryopreserved human hepatocytes," J Pharmacol Toxicol Methods. Nov.-Dec. 2012; 66(3):270-5. Epub Jul. 15, 2012.
Hamann, M., et al., "Motor disturbances in mice with deficiency of the sodium channel gene Scn8a show features of human dystonia," Exp. Neurol. 2003; 184(2):830-838.
Haufe, V., et al., "The promiscuous nature of the cardiac sodium current," J Mol. Cell Cardiol. 2007; 42(3):469-477.
International Preliminary Report on Patentability for International Application No. PCT/US2014/042055 mailed Dec. 23, 2015, 6 pages.
International Preliminary Report on Patentability for International Application No. PCT/US2021/036894 mailed Dec. 22, 2022, 7 pages.
International Preliminary Report on Patentability for International Application No. PCT/US2021/036896 mailed Dec. 22, 2022, 7 pages.
International Preliminary Report on Patentability for International Application No. PCT/US2022/040666 mailed Feb. 29, 2024, 12 pages.
International Search Report and Written Opinion for PCT Application No. PCT/US2014/042055 mailed Aug. 12, 2014, 7 pages.
International Search Report and Written Opinion for PCT Application No. PCT/US2021/036894 mailed Sep. 22, 2021, 9 pages.
International Search Report and Written Opinion for PCT Application No. PCT/US2021/036896 mailed Aug. 18, 2021, 9 pages.
International Search Report and Written Opinion for PCT Application No. PCT/US2022/040666 mailed Jan. 13, 2023, 16 pages.
Kim, D.Y., et al., "BACE1 regulates voltage-gated sodium channels and neuronal activity," Nat. Cell Biol. 2007; 9(7):755-764.
Kornecook, T.J., et al., "Pharmacologic Characterization of AMG8379, a Potent and Selective Small Molecule Sulfonamide Antagonist of the Voltage-Gated Sodium Channel NaV1.7," J. Pharmacol. Ex Ther. 2017; 362:146-160.
Landmark, C.J., "Antiepileptic drugs in non-epilepsy disorders: relations between mechanisms of action and clinical efficacy," CNS Drugs 2008; 22(1)27-47.
Liu, H., et al., "Mutations in Cardiac Sodium Channels," Am. J. Pharmacogenomics 2003; 3(3): 173-179.
McKinney, B.C. et al., "Exaggerated emotional behavior in mice heterozygous null for the sodium channel Scn8a (NaV1.6)," Genes Brain Behav. 2008; 7(6):629-638.
Morinville, A., et al., "Distribution of the Voltage-Gated Sodium Channel NaV1.7 in the Rat: Expression in the Autonomic and Endocrine Systems," J. Comp. Neurol. 2007; 504:680-689.
Non Final Office Action dated Aug. 30, 2022 for U.S. Appl. No. 17/344,947, 10 pages.
Non Final Office Action dated Dec. 18, 2015 for U.S. Appl. No. 14/920,833, 6 pages.
Notice of Allowance dated Apr. 17, 2015 for U.S. Appl. No. 14/302,337, 9 pages.
Notice of Allowance dated Aug. 12, 2015 for U.S. Appl. No. 14/302,337, 5 pages.
Notice of Allowance dated Jul. 7, 2016 for U.S. Appl. No. 14/920,833, 5 pages.
Notice of Allowance dated May 30, 2023 for U.S. Appl. No. 17/344,939, 12 pages.
Puopolo, M., et al., "Roles of Subthreshold Calcium Current and Sodium Current in Spontaneous Firing of Mouse Midbrain Dopamine Neurons," J. of Neuro. 2007; 27(3):645-656.
Raymond, C.K., et al., "Expression of Alternatively Spliced Sodium Channel Subunit Genes," J. Bio. Chem. 2004; 279(44):46234-46241.
Restriction Requirement dated Dec. 8, 2022 for U.S. Appl. No. 17/344,939, 7 pages.

(56) References Cited

OTHER PUBLICATIONS

Restriction Requirement dated Feb. 6, 2015 for U.S. Appl. No. 14/302,337, 7 pages.
Svensson, L., et al., "The Design and Bioactivation of Presystemically Stable Prodrugs," Drug Metabolism Rev. 1988; 19(2):165-194.
Tamaoka, A., et al., "Paramyotonia Congenita and Skeletal Sodium Channelopathy," Internal Med. 2003; 42(9):769-770.
U.S. Appl. No. 18/291,294, filed Jan. 23, 2024, by Ortiz, et al.
Waxman, S.G., "Axonal conduction and injury in multiple sclerosis: the role of sodium channels," Nature Neurosci. 2006; 7:932-941.
Wiberg, et al., "Conformational Equilibration among 1,3-Dihalocyclobutanes 1," J. Am. Chem. Soc. 1966; 88:19, 4429-4433.
Wood, J.N., et al., "Voltage-Gated Sodium Channel Blockers; Target Validation and Therapeutic Potential," Curr. Top Med. Chem. 2005; 5:529-537.
Woodruff-Pak, D.S., et al., "Inactivation of sodium channel SCN8A (Nav1.6) in purkinje neurons impairs learning in Morris Water Maze and delay but not trace eyeblink classical conditioning," Behav. Neurosci. 2006; 120(2):229-240.
Yang, et al., "Mutations in SCN9A, encoding a sodium channel alpha subunit, in patients with primary erythermalgia," J. Med. Genet. 2004; 41:171-174.
Yu et al., "Reduced sodium current in GABAergic interneurons in a mouse model of severe myoclonic epilepsy in infancy," Nature Neuroscience, 2006; 9(9):1142-1149.

\* cited by examiner

CYCLOBUTYL DIHYDROQUINOLINE SULFONAMIDE COMPOUNDS

CROSS REFERENCES TO RELATED APPLICATIONS

This application is a National Stage Application under 35 U.S.C. § 371 of International Application No. PCT/US21/36896, having an international filing date of Jun. 10, 2021, which is claiming priority from U.S. Provisional Application No. 63/037,001, having a filing date of Jun. 10, 2020.

FIELD OF THE INVENTION

The present invention provides cyclobutyl dihydroquinoline compounds that are inhibitors of voltage-gated sodium channels (Nav), in particular Nav 1.7, and are useful for the treatment of diseases treatable by inhibition of sodium channels such as pain disorders. Also provided are pharmaceutical compositions containing compounds of the present invention.

BACKGROUND OF THE INVENTION

A 2011 report of the institute of medicine estimates that 100 million adults in the US, roughly 30% of the population, suffer from chronic pain (C & E News, Bethany Halford, "Changing the Channel", published 3-24). Chronic pain by definition involves abnormal electrical spiking of neurons in the pain pathways: peripheral sensory neurons, spinal cord neurons, neurons in the pain matrix of the brain (e.g., somatosensory cortex, insular cortex, anterior cingular cortex), and/or neurons in brainstem. Although firing of these neurons is modulated and governed by many different receptors, enzymes, and growth factors, in most neurons the fast upstroke of the electrical spike is produced by entry of sodium ions through voltage-gated sodium channels (Hille B, Ion Channels of Excitable Membranes. Sinauer Associates, Inc.: Sunderland MA, $3^{rd}$ Ed. 2001). There are nine different isoforms of voltage-gated sodium channel (Nav 1.1-Nav 1.9), and they have distinct expression patterns in tissues including neurons and cardiac and skeletal muscle (Goldin, A. L, "Resurgence of sodium channel research," Ann Rev Physiol 63:871-894, 2001; Wood, J. N. and, Boorman, J. "Voltage-gated sodium channel blockers; target validation and therapeutic potential" Curr. Top Med. Chem. 5:529-537, 2005).

Nav1.1 and Nav1.2 are highly expressed in the brain (Raymond, C. K., et al., J. Biol. Chem. (2004) 279 (44): 46234-41) and are vital to normal brain function. Some loss of function due to Nav 1.1 mutations in humans, have resulted in epilepsy, presumably as these channels are expressed in inhibitory neurons (Yu, F. H., et al., Nat. Neuroscience (2006), 9 (9) 1142-1149). Nav1.1 is also expressed in the peripheral nervous system and inhibition of Nav1.1 in the periphery may provide relief of pain. Hence, while inhibiting Nav1.1 may provide use for treating pain, it may also be undesirable possibly leading to anxiety and over excitability. Nav1.3 is expressed primarily in the fetal central nervous system, and expression was found to be upregulated after nerve injury in rats (Hains, B. D., et al., J. Neuroscience (2030) 23(26):8881-8892). Nav1.4 is expressed primarily in skeletal muscle. Mutations of the gene and its' product have significant impact on muscle function, including paralysis (Tamaoka A., Internal Medicine (2003), (9):769-770). Nav1.5 is expressed mainly in cardiac myocytes, including atria, ventricles, the sino-atrial node, atrioventricular node and cardiac Purkinje fibers. The rapid upstroke of the cardiac action potential and the rapid impulse conduction through cardiac tissue is due to the opening of the Nav1.5 channel. Mutations of the Nav1.5 channel have resulted in arrhythmic syndromes, including QTc prolongation, Brugada syndrome (BS), sudden unexpected nocturnal death syndrome (SUNDS) and sudden infant death syndrome (SIDS) (Liu, H., et al., Am. J. Pharmacogenomics (2003), 3(3):173-179). Nav1.6 is widely distributed voltage-gated sodium channel expressed throughout the central and peripheral nervous system. Nav1.8 is expressed primarily in sensory ganglia of the peripheral nervous system, such as the dorsal root ganglia. There are no identified Nav1.8 mutations that produce varied pain responses in humans. Nav1.8 differs from most neuronal Nav isotypes in that it is insensitive to inhibition by tetrodotoxin. Nav1.9, similar to Nav1.8, is also a tetrodotoxin insensitive sodium channels expressed primarily in dorsal root ganglia neurons (Dib-Hajj, S. D., et al., Proc. Natl. Acad. Sci. USA (1998), 95(15):8963-8968).

Recent evidence from several independent genetic studies has shown that the tetrodotoxin-sensitive voltage-gated sodium ion channel Nav 1.7 (SCN9A) is required to sense pain. Rare genetic forms of severe chronic of pain, Primary Erythromelalgia and Paroxysmal Extreme Pain Disorder, result from mutations that increase the activity of Nav 1.7 (Fertleman C. R., Baker M. D., Parker K. A., Moffatt S., et al., "SCN9A mutations in paroxysmal extreme pain disorder: allelic variants underlie distinct channel defects and phenotypes," Neuron 52:767-774, 2006; Yang Y., Wang Y., Li S, et al., "Mutations in SCN9A, encoding a sodium channel alpha subunit, in patients with primary erythermalgia," J. Med. Genet. 41:171-174, 2004; Drenth J. P. H., te Morsche R. H. M., Guillet G., Taieb A., et al., "SCN9A mutations define primary erythermalgia as a neuropathic disorder of voltage gated sodium channels," J Invest Dermatol 124:1333-1338). Conversely, two separate clinical studies have determined that the root cause of the genetic disorder Congenital Indifference to Pain (CIP) is a loss of function of Nav 1.7 via mutations that truncate the protein and destroy function (Cox J. J., Reimann F, Nicholas A. K., et al. "An SCN9A channelopathy causes congenital inability to experience pain," Nature 444:894-898, 2006; Goldberg Y. P., MacFarlane J., MacDonald M. L., Thompson J., et al. "Loss-of-function mutations in the Nav1.7 gene underlie congenital indifference to pain in multiple human populations," Clin Genet 71:311-319, 2007). The disorder is inherited in Mendelian recessive manner with 100% penetrance. The phenotype associated with CIP is extreme: affected individuals are reported to have experienced painless burns, childbirth, appendicitis, and bone fractures, as well as to have insensitivity to clinical measures of pain such as pinprick or tendon pressure. Yet sensory, motor, autonomic, and other measured functions are normal, with the only reported abnormality being anosmia (inability to smell). These studies indicate that among the many possible targets in the pain pathway, Nav 1.7 governs one or more control points critical for pain perception.

Nonselective sodium channel inhibitors such as lidocaine, mexiletine, and carbamazepine show clinical efficacy in chronic pain, including neuropathic pain, but they are limited in dose and in use, likely due to effects on sodium channels outside the pain pathway. Lidocaine is a local anesthetic doctors use for minor surgery. Dentists use novocaine. However, these compounds do not distinguish between the various sodium channel subtypes, making them unsuitable for use as systemic pain killers. "If you give a drug that blocks Nav1.7 but also blocks Nav1.5, the patient will die of heart failure," says Glenn F. King, a professor at Australia's University of Queensland who studies venoms that block ion channels. "It will be a completely painless death, but the patient will die nonetheless." Thus, selectivity for Nav1.7 is desired, particularly over Nav1.5. Researchers have tailored their efforts to find a molecule that inhibitors or block the activity of only Nav1.7. To compound this problem, the identity, every location, every function and/or the tertiary structures of each subtype of voltage gated sodium channel proteins are not known or completely understood.

Consequently, a number of researchers are attempting to identify small molecule inhibitors of Nav1.7. For example, Chafeev et al disclose spiro-oxindole compound for the treatment and/or prevention of sodium channel-mediated diseases, such as pain, in U.S. Pat. No. 8,101,647. International Publications WO 2013/134518 and WO 2014/201206 disclose sulfonamide derivatives which are different from the sulfonamide derivatives of the present invention. Thus, there is a need to identify Nav1.7 inhibitors selective over at least Nav1.5 to treat pain. The present invention provides compounds that are selective inhibitors of Nav 1.7. over at least Nav1.5.

SUMMARY OF THE INVENTION

In embodiment 1, the present invention provides a compound of Formula (I), an enantiomer, diastereoisomer, atropisomer thereof, or a mixture thereof, or a pharmaceutically acceptable salt thereof,

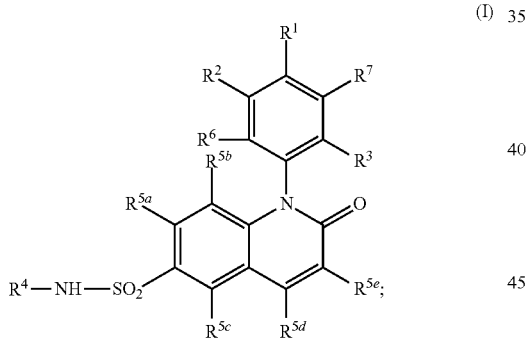

(I)

wherein:
R$^1$ is a saturated or partially-saturated 4-membered monocyclic ring; or a 4-, 5-, 6-, 7-, 8-, 9-, 10-, 11-, or 12-membered bicyclic ring; wherein said monocyclic ring or bicyclic ring contains 0, 1, 2 or 3 N atoms and 0, 1, or 2 atoms selected from O and S; and wherein said monocyclic ring or bicyclic ring is substituted by 0, 1, 2 or 3 R$^{1a}$ groups selected from hydroxy, halo, C$_{1-8}$alk, C$_{1-8}$haloalk, —O—C$_{1-4}$alk, —O—C$_{1-8}$haloalk, —C(=O)C$_{1-4}$alk, —O—C(=O)C$_{1-4}$alk, —NH$_2$, —NHC$_{1-4}$alk, or —N(C$_{1-4}$alk)C$_{1-4}$alk;

R$^2$ is H, halo, C$_{1-6}$alk, or C$_{1-6}$haloalk;
R$^3$ is C$_{1-6}$alk, C$_{1-6}$haloalk, —O—C$_{1-6}$alk, or —CN;
R$^4$ is a 5- to 6-membered heteroaryl;
Each of R$^6$ and R$^7$ is hydrogen; and
Each of R$^{5a}$; R$^{5b}$; R$^{5c}$; R$^{5d}$; and R$^{5e}$ is independently hydrogen or halo.

In sub-embodiment 1a of embodiment 1, the compound of Formula (I) has a sub-Formula of (Ia):

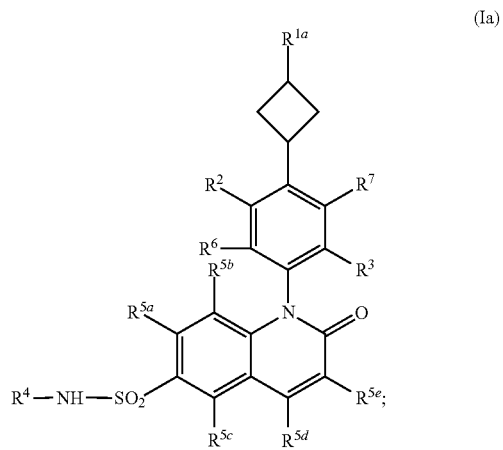

(Ia)

wherein R$^{1a}$ is fluoro, chloro, methyl, —O—CF$_3$, or CF$_3$.

In a more preferred sub embodiment 1a of embodiment 1, R$^{1a}$ is CF$_3$ or —O—CF$_3$; R$^2$ is H, F, or methyl; and R$^4$ is isoxazolyl or pyridazinyl.

In a most preferred sub embodiment 1a of embodiment 1, R$^{1a}$ is CF$_3$; R$^2$ is F; and R$^4$ is isoxazolyl.

In sub-embodiment 1b of embodiment 1, the compound of Formula (I) has a sub-Formula of (Ib):

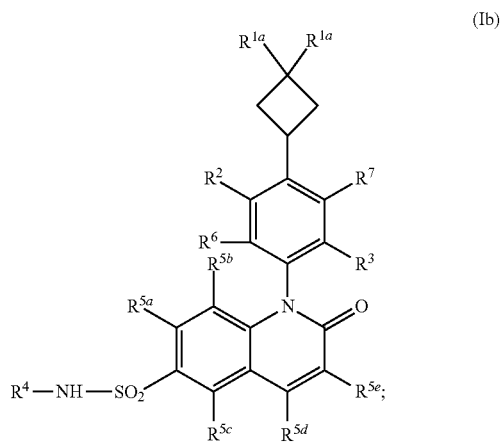

(Ib)

wherein each R$^{1a}$ is fluoro or CF$_3$.

In a more preferred sub embodiment 1b of embodiment 1, each R$^{1a}$ is F; R$^2$ is F or Cl; and R$^4$ is isoxazolyl.

In a most preferred sub embodiment 1b of embodiment 1, each R$^{1a}$ is F; R$^2$ is F; and R$^4$ is isoxazolyl.

In sub-embodiment 1c of embodiment 1, the compound of Formula (I) has a sub-Formula of (Ic):

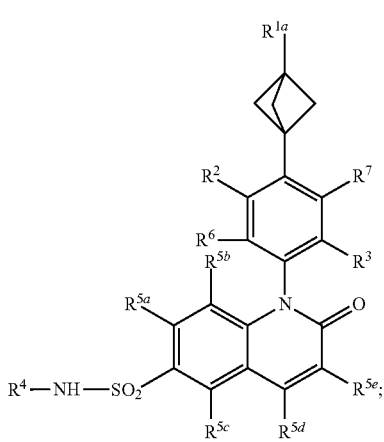

(Ic)

wherein $R^{1a}$ is $CF_3$.

In a more preferred sub embodiment 1c of embodiment 1, $R^{1a}$ is $CF_3$; $R^2$ is F; and $R^4$ is isoxazolyl or pyrimidyl.

In a most preferred sub embodiment 1c of embodiment 1, $R^{1a}$ is $CF_3$; $R^2$ is F; and $R^4$ is isoxazolyl.

In embodiment 2, the present invention provides compounds of Formula (I), an enantiomer, diastereoisomer, atropisomer thereof, or a mixture thereof, or a pharmaceutically acceptable salt thereof, wherein the $R^{1a}$ group is selected from halo, $C_{1-8}$alk, —O—$C_{1-4}$alk, or $C_{1-8}$haloalk, wherein said $C_{1-8}$haloalk is $C_{1-8}$fluoroalkyl.

In embodiment 3, the present invention provides compounds of Formula (I), an enantiomer, diastereoisomer, atropisomer thereof, or a mixture thereof, or a pharmaceutically acceptable salt thereof, wherein $R^1$ is a cyclobutyl ring; or a 5-, or 6-membered bicyclic ring; wherein said cyclobutyl ring or bicyclic ring contains 0 N, O, and S atoms; and wherein said cyclobutyl ring or bicyclic ring is substituted by 1, 2 or 3 $R^{1a}$ groups selected from F, —$CF_3$, —O—$CF_3$, or —$C(CH_3)_3$.

In embodiment 4, the present invention provides compounds of Formula (I), an enantiomer, diastereoisomer, atropisomer thereof, or a mixture thereof, or a pharmaceutically acceptable salt thereof, wherein $R^1$ is a cyclobutyl ring or bicyclo[1.1.1]pentan-1-yl ring; wherein each ring is substituted by 1 or 2 F or —$CF_3$.

In embodiment 5, the present invention provides compounds of Formula (I), an enantiomer, diastereoisomer, atropisomer thereof, or a mixture thereof, or a pharmaceutically acceptable salt thereof, wherein $R^1$ is a cyclobutyl ring substituted by 1 or 2 F or —$CF_3$.

In sub-embodiment 5a of embodiment 5, the compound of Formula (I) has the above sub-Formula of (Ia) and $R^{1a}$ is F.

In sub-embodiment 5b of embodiment 5, the compound of Formula (I) has the above sub-Formula of (Ib) and $R^{1a}$ is —$CF_3$.

In sub-embodiment 5c of embodiment 5, $R^1$ is a cyclobutyl ring substituted by 1 —$CF_3$.

In sub-embodiment 5d of embodiment 5, $R^1$ is a cyclobutyl ring substituted by 1 or 2 F.

In sub-embodiment 5c of embodiment 5, the compound of Formula (I) has the above sub-Formula of (Ic) and $R^{1a}$ is —$CF_3$.

In embodiment 6, the present invention provides compounds of Formula (I), an enantiomer, diastereoisomer, atropisomer thereof, or a mixture thereof, or a pharmaceutically acceptable salt thereof, wherein $R^1$ is a bicyclo[1.1.1]pentan-1-yl ring substituted by 1 or 2 F or —$CF_3$.

In embodiment 7, the present invention provides compounds of Formula (I), an enantiomer, diastereoisomer, atropisomer thereof, or a mixture thereof, or a pharmaceutically acceptable salt thereof, wherein $R^2$ is H, fluoro, chloro, methyl, $CF_3$, $CHF_2$, or $CH_2F$. In sub embodiment 7a of embodiment 7, $R^2$ is fluoro.

In embodiment 8, the present invention provides compounds of Formula (I), an enantiomer, diastereoisomer, atropisomer thereof, or a mixture thereof, or a pharmaceutically acceptable salt thereof, wherein $R^2$ is H, fluoro, chloro, or methyl.

In embodiment 9, the present invention provides compounds of Formula (I), an enantiomer, diastereoisomer, atropisomer thereof, or a mixture thereof, or a pharmaceutically acceptable salt thereof, wherein $R^2$ is H or fluoro.

In embodiment 10, the present invention provides compounds of Formula (I), an enantiomer, diastereoisomer, atropisomer thereof, or a mixture thereof, or a pharmaceutically acceptable salt thereof, wherein $R^3$ is methoxy.

In embodiment 11, the present invention provides compounds of Formula (I), an enantiomer, diastereoisomer, atropisomer thereof, or a mixture thereof, or a pharmaceutically acceptable salt thereof, wherein $R^4$ is a 5-membered heteroaryl.

In embodiment 12, the present invention provides compounds of Formula (I), an enantiomer, diastereoisomer, atropisomer thereof, or a mixture thereof, or a pharmaceutically acceptable salt thereof, wherein $R^4$ is a 6-membered heteroaryl.

In embodiment 13, the present invention provides compounds of Formula (I), an enantiomer, diastereoisomer, atropisomer thereof, or a mixture thereof, or a pharmaceutically acceptable salt thereof, wherein $R^4$ is isoxazolyl, pyridazinyl, thiazolyl, thiadiazolyl, oxazolyl, or pyrimidinyl.

In a sub embodiment of embodiment 13a of embodiment 13, $R^4$ is isoxazolyl, pyridazinyl, or pyrimidyl.

In another sub embodiment 13b of embodiment 13, $R^4$ is isoxazolyl.

In embodiment 14a, the present invention provides compounds of Formula (I), an enantiomer, diastereoisomer, atropisomer thereof, or a mixture thereof, or a pharmaceutically acceptable salt thereof, wherein each of $R^{5a}$; $R^{5b}$; $R^{5c}$; $R^{5d}$; and $R^{5e}$ is hydrogen.

In embodiment 14b, the present invention provides compounds of Formula (I), an enantiomer, diastereoisomer, atropisomer thereof, or a mixture thereof, or a pharmaceutically acceptable salt thereof, wherein $R^{5a}$ is F; and each of $R^{5b}$; $R^{5c}$; $R^{5d}$; and $R^{5e}$ is hydrogen.

In embodiment 14c, the present invention provides compounds of Formula (I), an enantiomer, diastereoisomer, atropisomer thereof, or a mixture thereof, or a pharmaceutically acceptable salt thereof, wherein $R^{5c}$ is F; and each of $R^{5a}$; $R^{5b}$; $R^{5c}$; and $R^{5e}$ is hydrogen.

In embodiment 15, the present invention provides compounds of Formula (I), an enantiomer, diastereoisomer, atropisomer thereof, or a mixture thereof, or a pharmaceutically acceptable salt thereof, wherein said compound of Formula (I) is selected from compounds of Formula (Ia), (Ib), or (Ic):

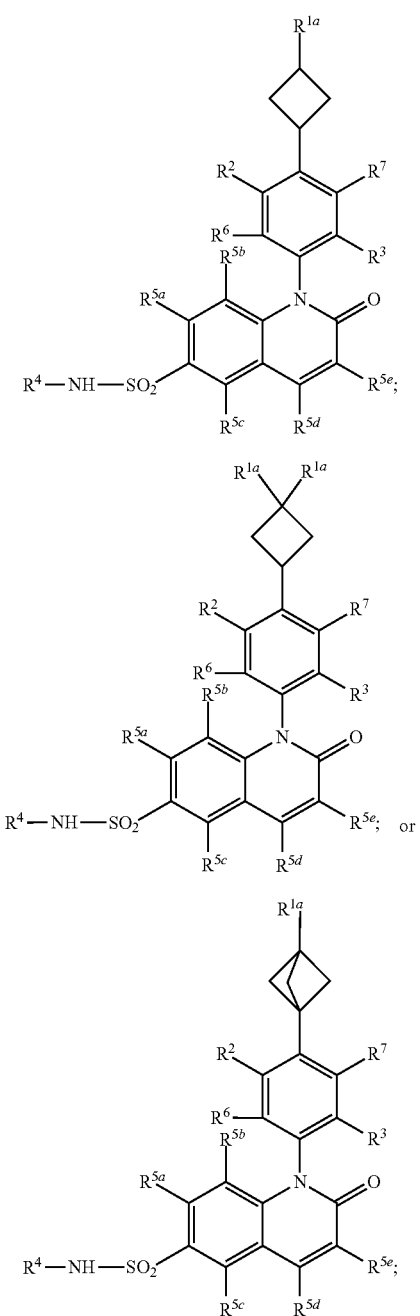

wherein each $R^{1a}$ in said compounds of Formula (Ia), (Ib), or (Ic) is independently fluoro, chloro, methyl, —O—CF$_3$, or CF$_3$.

In embodiment 16, the present invention provides compounds of Formula (I), an enantiomer, diastereoisomer, atropisomer thereof, or a mixture thereof, or a pharmaceutically acceptable salt thereof, wherein said compound of Formula (I) is a compound of Formula (Ia); wherein $R^{1a}$ is CF$_3$; the cyclobutyl ring is a trans isomer; and $R^4$ is isoxazolyl, pyridazinyl, thiazolyl, thiadiazolyl, or oxazolyl.

In embodiment 16a, said compound of Formula (I) is a compound of Formula (Ia); wherein $R^{1a}$ is cis CF$_3$; the cyclobutyl ring is a cis isomer; $R^2$ is F; and $R^4$ is isoxazolyl, pyridazinyl, thiazolyl, thiadiazolyl, or oxazolyl.

In embodiment 16b, said compound of Formula (I) is a compound of Formula (Ib); wherein each $R^{1a}$ is fluoro; $R^2$ is F; and $R^4$ is isoxazolyl, pyridazinyl, thiazolyl, thiadiazolyl, oxazolyl, or pyrimidinyl.

In embodiment 16c, said compound of Formula (I) is a compound of Formula (Ib); wherein each $R^{1a}$ is fluoro; $R^{5a}$ is F; and $R^4$ is isoxazolyl, pyridazinyl, thiazolyl, thiadiazolyl, oxazolyl, or pyrimidinyl.

In embodiment 16d, said compound of Formula (I) is a compound of Formula (Ic); wherein each $R^{1a}$ is CF$_3$.

In embodiment 17, the present invention provides compounds of Formula (I), an enantiomer, diastereoisomer, atropisomer thereof, or a mixture thereof, or a pharmaceutically acceptable salt thereof, wherein the compound is selected from:
1) (M)-1-(4-(3-(tert-Butyl)cyclobutyl)-5-fluoro-2-methoxyphenyl)-N-(isoxazol-3-yl)-2-oxo-1,2-dihydroquinoline-6-sulfonamide;
2) 1-(4-(3-(tert-butyl)cyclobutyl)-5-fluoro-2-methoxyphenyl)-N-(isoxazol-3-yl)-2-oxo-1,2-dihydroquinoline-6-sulfonamide;
3) (P)-1-(4-(3-(tert-butyl)cyclobutyl)-5-fluoro-2-methoxyphenyl)-N-(isoxazol-3-yl)-2-oxo-1,2-dihydroquinoline-6-sulfonamide;
4) (P)-1-(4-(3,3-difluorocyclobutyl)-5-fluoro-2-methoxyphenyl)-N-(isoxazol-3-yl)-2-oxo-1,2-dihydroquinoline-6-sulfonamide;
5) (P)-1-(5-fluoro-4-(3-fluoro-3-(trifluoromethyl)cyclobutyl)-2-methoxyphenyl)-N-(isoxazol-3-yl)-2-oxo-1,2-dihydroquinoline-6-sulfonamide;
6) cis-(P)-1-(5-fluoro-2-methoxy-4-(3-(trifluoromethyl)cyclobutyl)phenyl)-N-(isoxazol-3-yl)-2-oxo-1,2-dihydroquinoline-6-sulfonamide;
7) trans-(P)-1-(5-fluoro-2-methoxy-4-(3-(trifluoromethyl)cyclobutyl)phenyl)-N-(isoxazol-3-yl)-2-oxo-1,2-dihydroquinoline-6-sulfonamide;
8) trans-(P)-1-(5-fluoro-4-(3-fluoro-3-(trifluoromethyl)cyclobutyl)-2-methoxyphenyl)-N-(isoxazol-3-yl)-2-oxo-1,2-dihydroquinoline-6-sulfonamide;
9) cis-(P)-1-(5-fluoro-4-(3-fluoro-3-(trifluoromethyl)cyclobutyl)-2-methoxyphenyl)-N-(isoxazol-3-yl)-2-oxo-1,2-dihydroquinoline-6-sulfonamide;
10) cis-(P)-1-(5-chloro-4-(3-fluoro-3-(trifluoromethyl)cyclobutyl)-2-methoxyphenyl)-N-(isoxazol-3-yl)-2-oxo-1,2-dihydroquinoline-6-sulfonamide;
11) trans-(P)-1-(5-chloro-4-(3-fluoro-3-(trifluoromethyl)cyclobutyl)-2-methoxyphenyl)-N-(isoxazol-3-yl)-2-oxo-1,2-dihydroquinoline-6-sulfonamide;
12) cis-(P)-1-(5-chloro-2-methoxy-4-((1S,3S)-3-(trifluoromethyl)cyclobutyl)phenyl)-N-(isoxazol-3-yl)-2-oxo-1,2-dihydroquinoline-6-sulfonamide;
13) trans-(P)-1-(5-chloro-2-methoxy-4-((1S,3S)-3-(trifluoromethyl)cyclobutyl)phenyl)-N-(isoxazol-3-yl)-2-oxo-1,2-dihydroquinoline-6-sulfonamide;
14) (P)-1-(4-cyclobutyl-5-fluoro-2-methoxyphenyl)-N-(isoxazol-3-yl)-2-oxo-1,2-dihydroquinoline-6-sulfonamide;
15) trans-(P)-1-(5-fluoro-2-methoxy-4-(3-(trifluoromethyl)cyclobutyl)phenyl)-2-oxo-N-(pyrimidin-2-yl)-1,2-dihydroquinoline-6-sulfonamide;
16) cis-(P)-1-(5-chloro-2-methoxy-4-(3-(trifluoromethyl)cyclobutyl)phenyl)-2-oxo-N-(pyrimidin-2-yl)-1,2-dihydroquinoline-6-sulfonamide;
17) trans-(P)-1-(5-chloro-2-methoxy-4-(3-(trifluoromethyl)cyclobutyl)phenyl)-2-oxo-N-(pyrimidin-2-yl)-1,2-dihydroquinoline-6-sulfonamide;

18) (P)-1-(5-chloro-4-cyclobutyl-2-methoxyphenyl)-2-oxo-N-(pyrimidin-2-yl)-1,2-dihydroquinoline-6-sulfonamide;
19) trans-(P)-1-(5-chloro-2-methoxy-4-(3-(trifluoromethyl)cyclobutyl)phenyl)-2-oxo-N-(pyridazin-3-yl)-1,2-dihydroquinoline-6-sulfonamide;
20) trans-(P)—N-(isoxazol-3-yl)-1-(2-methoxy-5-methyl-4-(3-(trifluoromethyl)cyclobutyl)phenyl)-2-oxo-1,2-dihydroquinoline-6-sulfonamide;
21) (P)-1-(5-chloro-4-cyclobutyl-2-methoxyphenyl)-N-(isoxazol-3-yl)-2-oxo-1,2-dihydroquinoline-6-sulfonamide;
22) (P)-1-(4-cyclobutyl-2-methoxy-5-methylphenyl)-N-(isoxazol-3-yl)-2-oxo-1,2-dihydroquinoline-6-sulfonamide;
23) (P)-1-(4-cyclobutyl-5-fluoro-2-methoxyphenyl)-2-oxo-N-(pyridazin-3-yl)-1,2-dihydroquinoline-6-sulfonamide;
24) (P)-1-(4-cyclobutyl-5-fluoro-2-methoxyphenyl)-N-(oxazol-2-yl)-2-oxo-1,2-dihydroquinoline-6-sulfonamide;
25) (P)-1-(4-cyclobutyl-2-methoxyphenyl)-N-(isoxazol-3-yl)-2-oxo-1,2-dihydroquinoline-6-sulfonamide;
26) (P)-1-(4-cyclobutyl-2-methoxyphenyl)-2-oxo-N-(pyrimidin-2-yl)-1,2-dihydroquinoline-6-sulfonamide;
27) (P)-1-(4-cyclobutyl-2-methoxy-5-methylphenyl)-N-(4-methoxybenzyl)-2-oxo-N-(pyrimidin-2-yl)-1,2-dihydroquinoline-6-sulfonamide;
28) (P)-1-(4-cyclobutyl-5-fluoro-2-methoxyphenyl)-2-oxo-N-(pyrimidin-2-yl)-1,2-dihydroquinoline-6-sulfonamide;
29) (P)-1-(4-cyclobutyl-2-methoxyphenyl)-N-(oxazol-2-yl)-2-oxo-1,2-dihydroquinoline-6-sulfonamide;
30) (P)-1-(4-cyclobutyl-2-methoxy-5-methylphenyl)-2-oxo-N-(pyridazin-3-yl)-1,2-dihydroquinoline-6-sulfonamide;
31) (P)-1-(4-cyclobutyl-2-methoxyphenyl)-2-oxo-N-(pyridazin-3-yl)-1,2-dihydroquinoline-6-sulfonamide;
32) (P)-1-(5-chloro-4-cyclobutyl-2-methoxyphenyl)-N-(oxazol-2-yl)-2-oxo-1,2-dihydroquinoline-6-sulfonamide;
33) (P)-1-(5-chloro-4-cyclobutyl-2-methoxyphenyl)-2-oxo-N-(pyridazin-3-yl)-1,2-dihydroquinoline-6-sulfonamide;
34) (P)-1-(4-cyclobutyl-2-methoxy-5-methylphenyl)-N-(oxazol-2-yl)-2-oxo-1,2-dihydroquinoline-6-sulfonamide;
35) trans-(P)—N-(isoxazol-3-yl)-1-(2-methoxy-4-(3-(trifluoromethyl)cyclobutyl)phenyl)-2-oxo-1,2-dihydroquinoline-6-sulfonamide;
36) trans-(P)-1-(2-methoxy-4-((1R,3R)-3-(trifluoromethyl)cyclobutyl)phenyl)-2-oxo-N-(pyrimidin-2-yl)-1,2-dihydroquinoline-6-sulfonamide;
37) trans-(P)-1-(2-methoxy-5-methyl-4-(3-(trifluoromethyl)cyclobutyl)phenyl)-2-oxo-N-(pyrimidin-2-yl)-1,2-dihydroquinoline-6-sulfonamide;
38) trans-(P)-1-(2-methoxy-4-(3-(trifluoromethyl)cyclobutyl)phenyl)-2-oxo-N-(pyridazin-3-yl)-1,2-dihydroquinoline-6-sulfonamide;
39) trans-(P)-1-(5-fluoro-2-methoxy-4-(3-(trifluoromethyl)cyclobutyl)phenyl)-2-oxo-N-(pyridazin-3-yl)-1,2-dihydroquinoline-6-sulfonamide;
40) (P)-7-fluoro-1-(5-fluoro-2-methoxy-4-((1R,3R)-3-(trifluoromethyl)cyclobutyl)phenyl)-N-(isoxazol-3-yl)-2-oxo-1,2-dihydroquinoline-6-sulfonamide;
41) (P)-1-(4-(3,3-difluorocyclobutyl)-5-fluoro-2-methoxyphenyl)-7-fluoro-N-(isoxazol-3-yl)-2-oxo-1,2-dihydroquinoline-6-sulfonamide;
42) (P)-1-(5-fluoro-2-methoxy-4-(3-(trifluoromethyl)bicyclo[1.1.1]pentan-1-yl)phenyl)-N-(isoxazol-3-yl)-2-oxo-1,2-dihydroquinoline-6-sulfonamide;
43) (P)-1-(5-fluoro-2-methoxy-4-(3-(trifluoromethyl)cyclobutyl)phenyl)-N-(oxazol-2-yl)-2-oxo-1,2-dihydroquinoline-6-sulfonamide;
44) cis-(P)-1-(5-fluoro-2-methoxy-4-(3-(trifluoromethoxy)cyclobutyl)phenyl)-N-(isoxazol-3-yl)-2-oxo-1,2-dihydroquinoline-6-sulfonamide;
45) trans-(P)-1-(5-fluoro-2-methoxy-4-(3-(trifluoromethoxy)cyclobutyl)phenyl)-N-(isoxazol-3-yl)-N-(4-methoxybenzyl)-2-oxo-1,2-dihydroquinoline-6-sulfonamide;
46) trans-(P)-5-fluoro-1-(5-fluoro-2-methoxy-4-(3-(trifluoromethyl)cyclobutyl)phenyl)-N-(isoxazol-3-yl)-2-oxo-1,2-dihydroquinoline-6-sulfonamide;
47) (P)-1-(5-fluoro-2-methoxy-4-(3-(trifluoromethyl)bicyclo[1.1.1]pentan-1-yl)phenyl)-2-oxo-N-(pyrimidin-2-yl)-1,2-dihydroquinoline-6-sulfonamide;
48) (P)-1-(5-chloro-4-(3,3-difluorocyclobutyl)-2-methoxyphenyl)-N-(isoxazol-3-yl)-2-oxo-1,2-dihydroquinoline-6-sulfonamide; or
49) trans (P)-1-(5-chloro-2-methoxy-4-((1R,3R)-3-(trifluoromethyl)cyclobutyl)phenyl)-N-(oxazol-2-yl)-2-oxo-1,2-dihydroquinoline-6-sulfonamide.

In embodiment 18, the present invention provides a compound of Formula (I), having sub-Formula of (Ia):

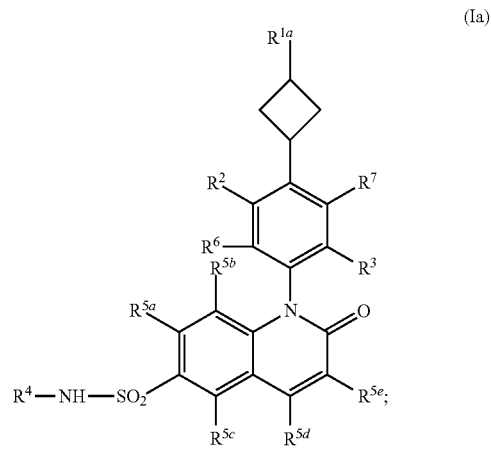

an enantiomer, diastereoisomer, atropisomer thereof, or a mixture thereof, or a pharmaceutically acceptable salt thereof, wherein the compound is selected from:
1) cis-(P)-1-(5-fluoro-2-methoxy-4-(3-(trifluoromethyl)cyclobutyl)phenyl)-N-(isoxazol-3-yl)-2-oxo-1,2-dihydroquinoline-6-sulfonamide;
2) trans-(P)-1-(5-fluoro-2-methoxy-4-(3-(trifluoromethyl)cyclobutyl)phenyl)-N-(isoxazol-3-yl)-2-oxo-1,2-dihydroquinoline-6-sulfonamide;
3) cis-(P)-1-(5-chloro-2-methoxy-4-((1S,3S)-3-(trifluoromethyl)cyclobutyl)phenyl)-N-(isoxazol-3-yl)-2-oxo-1,2-dihydroquinoline-6-sulfonamide;
4) trans-(P)-1-(5-chloro-2-methoxy-4-((1S,3S)-3-(trifluoromethyl)cyclobutyl)phenyl)-N-(isoxazol-3-yl)-2-oxo-1,2-dihydroquinoline-6-sulfonamide;

5) trans-(P)-1-(5-chloro-2-methoxy-4-(3-(trifluoromethyl)cyclobutyl)phenyl)-2-oxo-N-(pyrimidin-2-yl)-1,2-dihydroquinoline-6-sulfonamide;
6) trans-(P)-1-(5-chloro-2-methoxy-4-(3-(trifluoromethyl)cyclobutyl)phenyl)-2-oxo-N-(pyridazin-3-yl)-1,2-dihydroquinoline-6-sulfonamide;
7) trans-(P)—N-(isoxazol-3-yl)-1-(2-methoxy-5-methyl-4-(3-(trifluoromethyl)cyclobutyl)phenyl)-2-oxo-1,2-dihydroquinoline-6-sulfonamide;
8) trans-(P)-1-(2-methoxy-4-((1R,3R)-3-(trifluoromethyl)cyclobutyl)phenyl)-2-oxo-N-(pyrimidin-2-yl)-1,2-dihydroquinoline-6-sulfonamide;
9) trans-(P)-1-(5-fluoro-2-methoxy-4-(3-(trifluoromethyl)cyclobutyl)phenyl)-2-oxo-N-(pyridazin-3-yl)-1,2-dihydroquinoline-6-sulfonamide;
10) (P)-7-fluoro-1-(5-fluoro-2-methoxy-4-((1R,3R)-3-(trifluoromethyl)cyclobutyl)phenyl)-N-(isoxazol-3-yl)-2-oxo-1,2-dihydroquinoline-6-sulfonamide;
11) (P)-1-(5-fluoro-2-methoxy-4-(3-(trifluoromethyl)cyclobutyl)phenyl)-N-(oxazol-2-yl)-2-oxo-1,2-dihydroquinoline-6-sulfonamide;
12) cis-(P)-1-(5-fluoro-2-methoxy-4-(3-(trifluoromethoxy)cyclobutyl)phenyl)-N-(isoxazol-3-yl)-2-oxo-1,2-dihydroquinoline-6-sulfonamide;
13) trans-(P)-1-(5-fluoro-2-methoxy-4-(3-(trifluoromethoxy)cyclobutyl)phenyl)-N-(isoxazol-3-yl)-N-(4-methoxybenzyl)-2-oxo-1,2-dihydroquinoline-6-sulfonamide;
14) trans-(P)-5-fluoro-1-(5-fluoro-2-methoxy-4-(3-(trifluoromethyl)cyclobutyl)phenyl)-N-(isoxazol-3-yl)-2-oxo-1,2-dihydroquinoline-6-sulfonamide; or
15) trans (P)-1-(5-chloro-2-methoxy-4-((1R,3R)-3-(trifluoromethyl)cyclobutyl)
16) phenyl)-N-(oxazol-2-yl)-2-oxo-1,2-dihydroquinoline-6-sulfonamide.

In sub-embodiment 18a of embodiment 18, the present invention provides a compound of Formula (I), having the above sub-Formula of (Ia), an enantiomer, diastereoisomer, atropisomer thereof, or a mixture thereof, or a pharmaceutically acceptable salt thereof, wherein the compound is selected from:
1) trans-(P)-1-(5-fluoro-2-methoxy-4-(3-(trifluoromethyl)cyclobutyl)phenyl)-N-(isoxazol-3-yl)-2-oxo-1,2-dihydroquinoline-6-sulfonamide;
2) trans-(P)—N-(isoxazol-3-yl)-1-(2-methoxy-5-methyl-4-(3-(trifluoromethyl)cyclobutyl)phenyl)-2-oxo-1,2-dihydroquinoline-6-sulfonamide;
3) trans-(P)-1-(2-methoxy-4-((1R,3R)-3-(trifluoromethyl)cyclobutyl)phenyl)-2-oxo-N-(pyrimidin-2-yl)-1,2-dihydroquinoline-6-sulfonamide;
4) trans-(P)-1-(5-fluoro-2-methoxy-4-(3-(trifluoromethyl)cyclobutyl)phenyl)-2-oxo-N-(pyridazin-3-yl)-1,2-dihydroquinoline-6-sulfonamide;
5) trans-(P)-1-(5-fluoro-2-methoxy-4-(3-(trifluoromethoxy)cyclobutyl)phenyl)-N-(isoxazol-3-yl)-N-(4-methoxybenzyl)-2-oxo-1,2-dihydroquinoline-6-sulfonamide; or
6) trans-(P)-5-fluoro-1-(5-fluoro-2-methoxy-4-(3-(trifluoromethyl)cyclobutyl)phenyl)-N-(isoxazol-3-yl)-2-oxo-1,2-dihydroquinoline-6-sulfonamide.

In sub-embodiment 18b of embodiment 18, the present invention provides a compound of Formula (I), having the above sub-Formula of (Ia), an enantiomer, diastereoisomer, atropisomer thereof, or a mixture thereof, or a pharmaceutically acceptable salt thereof, wherein the compound is trans-(P)-1-(5-fluoro-2-methoxy-4-(3-(trifluoromethyl)cyclobutyl)phenyl)-N-(isoxazol-3-yl)-2-oxo-1,2-dihydroquinoline-6-sulfonamide.

In sub-embodiment 18c of embodiment 18, the present invention provides a compound of Formula (I), having the above sub-Formula of (Ia), an enantiomer, diastereoisomer, atropisomer thereof, or a mixture thereof, or a pharmaceutically acceptable salt thereof, which is trans-(P)—N-(isoxazol-3-yl)-1-(2-methoxy-5-methyl-4-(3-(trifluoromethyl)cyclobutyl)phenyl)-2-oxo-1,2-dihydroquinoline-6-sulfonamide.

In sub-embodiment 18d of embodiment 18, the present invention provides a compound of Formula (I), having the above sub-Formula of (Ia), an enantiomer, diastereoisomer, atropisomer thereof, or a mixture thereof, or a pharmaceutically acceptable salt thereof, which is trans-(P)-1-(2-methoxy-4-((1R,3R)-3-(trifluoromethyl)cyclobutyl)phenyl)-2-oxo-N-(pyrimidin-2-yl)-1,2-dihydroquinoline-6-sulfonamide.

In sub-embodiment 18e of embodiment 18, the present invention provides a compound of Formula (I), having the above sub-Formula of (Ia), an enantiomer, diastereoisomer, atropisomer thereof, or a mixture thereof, or a pharmaceutically acceptable salt thereof, which is trans-(P)-1-(5-fluoro-2-methoxy-4-(3-(trifluoromethyl)cyclobutyl)phenyl)-2-oxo-N-(pyridazin-3-yl)-1,2-dihydroquinoline-6-sulfonamide.

In sub-embodiment 18f of embodiment 18, the present invention provides a compound of Formula (I), having the above sub-Formula of (Ia), an enantiomer, diastereoisomer, atropisomer thereof, or a mixture thereof, or a pharmaceutically acceptable salt thereof, which is trans-(P)-1-(5-fluoro-2-methoxy-4-(3-(trifluoromethoxy)cyclobutyl)phenyl)-N-(isoxazol-3-yl)-N-(4-methoxybenzyl)-2-oxo-1,2-dihydroquinoline-6-sulfonamide.

In sub-embodiment 18g of embodiment 18, the present invention provides a compound of Formula (I), having the above sub-Formula of (Ia), an enantiomer, diastereoisomer, atropisomer thereof, or a mixture thereof, or a pharmaceutically acceptable salt thereof, which is trans-(P)-5-fluoro-1-(5-fluoro-2-methoxy-4-(3-(trifluoromethyl)cyclobutyl)phenyl)-N-(isoxazol-3-yl)-2-oxo-1,2-dihydroquinoline-6-sulfonamide.

In embodiment 19, the present invention provides a compound of Formula (I), having sub-Formula of (Ib):

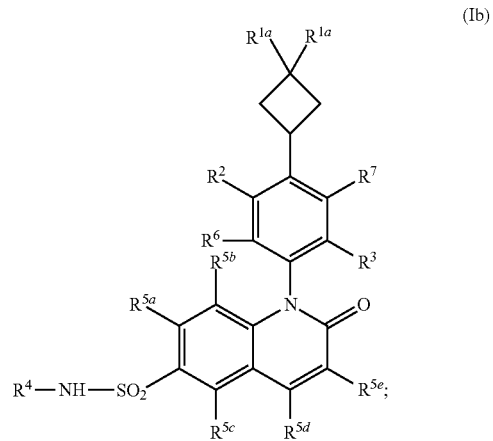

an enantiomer, diastereoisomer, atropisomer thereof, or a mixture thereof, or a pharmaceutically acceptable salt thereof, which is selected from:
1) (P)-1-(4-(3,3-difluorocyclobutyl)-5-fluoro-2-methoxyphenyl)-N-(isoxazol-3-yl)-2-oxo-1,2-dihydroquinoline-6-sulfonamide;
2) (P)-1-(5-fluoro-4-(3-fluoro-3-(trifluoromethyl)cyclobutyl)-2-methoxyphenyl)-N-(isoxazol-3-yl)-2-oxo-1,2-dihydroquinoline-6-sulfonamide;
3) trans-(P)-1-(5-fluoro-4-(3-fluoro-3-(trifluoromethyl)cyclobutyl)-2-methoxyphenyl)-N-(isoxazol-3-yl)-2-oxo-1,2-dihydroquinoline-6-sulfonamide;
4) cis-(P)-1-(5-fluoro-4-(3-fluoro-3-(trifluoromethyl)cyclobutyl)-2-methoxyphenyl)-N-(isoxazol-3-yl)-2-oxo-1,2-dihydroquinoline-6-sulfonamide;
5) cis-(P)-1-(5-chloro-4-(3-fluoro-3-(trifluoromethyl)cyclobutyl)-2-methoxyphenyl)-N-(isoxazol-3-yl)-2-oxo-1,2-dihydroquinoline-6-sulfonamide;
6) trans-(P)-1-(5-chloro-4-(3-fluoro-3-(trifluoromethyl)cyclobutyl)-2-methoxyphenyl)-N-(isoxazol-3-yl)-2-oxo-1,2-dihydroquinoline-6-sulfonamide;
7) (P)-1-(4-(3,3-difluorocyclobutyl)-5-fluoro-2-methoxyphenyl)-7-fluoro-N-(isoxazol-3-yl)-2-oxo-1,2-dihydroquinoline-6-sulfonamide; or
8) (P)-1-(5-chloro-4-(3,3-difluorocyclobutyl)-2-methoxyphenyl)-N-(isoxazol-3-yl)-2-oxo-1,2-dihydroquinoline-6-sulfonamide.

In sub-embodiment 19a of embodiment 19 the present invention provides a compound of Formula (I), having the above sub-Formula of (Ib), an enantiomer, diastereoisomer, atropisomer thereof, or a mixture thereof, or a pharmaceutically acceptable salt thereof, which is selected from:
1) (P)-1-(4-(3,3-difluorocyclobutyl)-5-fluoro-2-methoxyphenyl)-N-(isoxazol-3-yl)-2-oxo-1,2-dihydroquinoline-6-sulfonamide;
2) trans-(P)-1-(5-fluoro-4-(3-fluoro-3-(trifluoromethyl)cyclobutyl)-2-methoxyphenyl)-N-(isoxazol-3-yl)-2-oxo-1,2-dihydroquinoline-6-sulfonamide;
3) cis-(P)-1-(5-chloro-4-(3-fluoro-3-(trifluoromethyl)cyclobutyl)-2-methoxyphenyl)-N-(isoxazol-3-yl)-2-oxo-1,2-dihydroquinoline-6-sulfonamide; or
4) trans-(P)-1-(5-chloro-4-(3-fluoro-3-(trifluoromethyl)cyclobutyl)-2-methoxyphenyl)-N-(isoxazol-3-yl)-2-oxo-1,2-dihydroquinoline-6-sulfonamide.

In sub-embodiment 19b of embodiment 19, the present invention provides a compound of Formula (I), having the above sub-Formula of (Ib), an enantiomer, diastereoisomer, atropisomer thereof, or a mixture thereof, or a pharmaceutically acceptable salt thereof, which is (P)-1-(4-(3,3-difluorocyclobutyl)-5-fluoro-2-methoxyphenyl)-N-(isoxazol-3-yl)-2-oxo-1,2-dihydroquinoline-6-sulfonamide.

In sub-embodiment 19c of embodiment 19, the present invention provides a compound of Formula (I), having the above sub-Formula of (Ib), an enantiomer, diastereoisomer, atropisomer thereof, or a mixture thereof, or a pharmaceutically acceptable salt thereof, which is trans-(P)-1-(5-fluoro-4-(3-fluoro-3-(trifluoromethyl)cyclobutyl)-2-methoxyphenyl)-N-(isoxazol-3-yl)-2-oxo-1,2-dihydroquinoline-6-sulfonamide.

In sub-embodiment 19d of embodiment 19, the present invention provides a compound of Formula (I), having the above sub-Formula of (Ib), an enantiomer, diastereoisomer, atropisomer thereof, or a mixture thereof, or a pharmaceutically acceptable salt thereof, which is cis-(P)-1-(5-chloro-4-(3-fluoro-3-(trifluoromethyl)cyclobutyl)-2-methoxyphenyl)-N-(isoxazol-3-yl)-2-oxo-1,2-dihydroquinoline-6-sulfonamide.

In sub-embodiment 19e of embodiment 19, the present invention provides a compound of Formula (I), having the above sub-Formula of (Ib), an enantiomer, diastereoisomer, atropisomer thereof, or a mixture thereof, or a pharmaceutically acceptable salt thereof, which is trans-(P)-1-(5-chloro-4-(3-fluoro-3-(trifluoromethyl)cyclobutyl)-2-methoxyphenyl)-N-(isoxazol-3-yl)-2-oxo-1,2-dihydroquinoline-6-sulfonamide.

In embodiment 20, the present invention provides a compound of Formula (I) having a sub-Formula of (Ic):

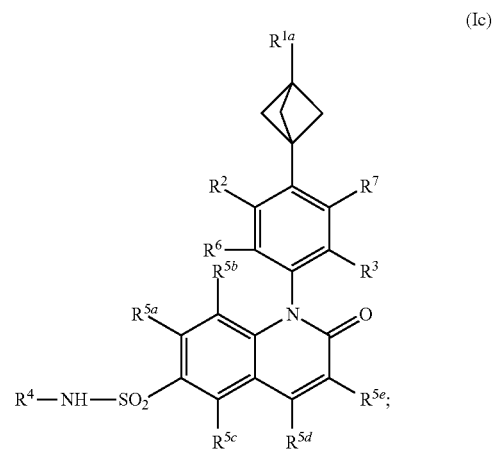

an enantiomer, diastereoisomer, atropisomer thereof, or a mixture thereof, or a pharmaceutically acceptable salt thereof, which is selected from:
(P)-1-(5-fluoro-2-methoxy-4-(3-(trifluoromethyl)bicyclo[1.1.1]pentan-1-yl)phenyl)-N-(isoxazol-3-yl)-2-oxo-1,2-dihydroquinoline-6-sulfonamide; or
(P)-1-(5-fluoro-2-methoxy-4-(3-(trifluoromethyl)bicyclo[1.1.1]pentan-1-yl)phenyl)-2-oxo-N-(pyrimidin-2-yl)-1,2-dihydroquinoline-6-sulfonamide.

In sub-embodiment 20a of embodiment 20, the present invention provides a compound of Formula (I), having the above sub-Formula of (Ic), an enantiomer, diastereoisomer, atropisomer thereof, or a mixture thereof, or a pharmaceutically acceptable salt thereof, which is (P)-1-(5-fluoro-2-methoxy-4-(3-(trifluoromethyl)bicyclo[1.1.1]pentan-1-yl)phenyl)-N-(isoxazol-3-yl)-2-oxo-1,2-dihydroquinoline-6-sulfonamide.

In sub-embodiment 20b of embodiment 20, the present invention provides a compound of Formula (I), having the above sub-Formula of (Ic), an enantiomer, diastereoisomer, atropisomer thereof, or a mixture thereof, or a pharmaceutically acceptable salt thereof, which is (P)-1-(5-fluoro-2-methoxy-4-(3-(trifluoromethyl)bicyclo[1.1.1]pentan-1-yl)phenyl)-2-oxo-N-(pyrimidin-2-yl)-1,2-dihydroquinoline-6-sulfonamide.

In embodiment 21, the present invention provides a P atropisomer of each individual compound, independently, or a mixture thereof, or pharmaceutically acceptable salts thereof, recited in embodiments 18, 19, and 20, or any sub-embodiment thereof.

In embodiment 22, the present invention provides an M atropisomer of each individual compound, independently, or a mixture thereof, or pharmaceutically acceptable salts thereof, recited in embodiments 18, 19, and 20, or any sub-embodiment thereof.

In embodiment 23, the present invention provides pharmaceutical compositions comprising a compound, an enantiomer, diastereoisomer, atropisomer thereof, or a mixture thereof, or pharmaceutically acceptable salts thereof, in accordance with any one of embodiments 1, 2, 3, 4, 5, 6, 7, 8, 9, 10, 11, 12, 13, 14, 15, 16, 17, 18, 19, 20, 21, 22, or any sub embodiment thereof, and a pharmaceutically acceptable excipient.

In embodiment 24, the present invention provides methods of treating pain, cough, or itch, the methods comprising administering to a patient in need thereof a therapeutically effective amount of a compound, an enantiomer, diastereoisomer, atropisomer thereof, or a mixture thereof, or pharmaceutically acceptable salts thereof, in accordance with any one of embodiments 1, 2, 3, 4, 5, 6, 7, 8, 9, 10, 11, 12, 13, 14, 15, 16, 17, 18, 19, 20, 21, 22, or any sub embodiment thereof.

In embodiment 25, the present invention provides methods of embodiment 24 wherein the pain is selected from chronic pain, acute pain, neuropathic pain, pain associated with rheumatoid arthritis, pain associated with osteoarthritis, pain associated with cancer, peripheral diabetic neuropathy, and neuropathic low back pain.

In embodiment 26, the present invention provides methods of embodiment 24 wherein the cough is selected from post viral cough, viral cough, or acute viral cough. See Dib-Hajj. et. al., "The Na$_V$1.7 sodium channel: from molecule to man", *Nature Reviews Neuroscience* (2013), 14, 49-62.

In embodiment 27, the present invention provides a method of preparation of an intermediate compound used in the preparation of a compound of Formula (I), having the Formula (A):

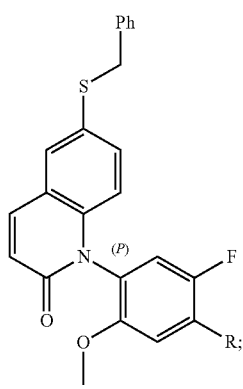

wherein R is halo;
comprising:
1) reacting a trans olefin compound of Formula (B):

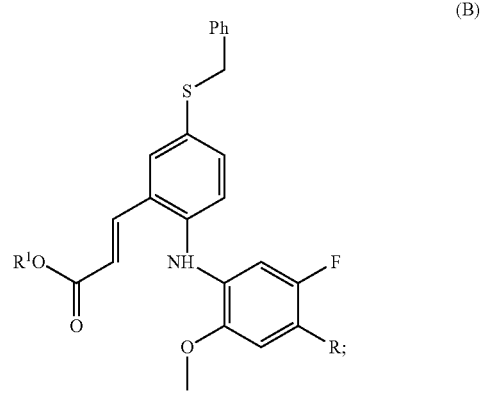

wherein R is halo; and $R^1$ is $C_1$-$C_6$alkyl;
with a UV light or near UV light; to form a cis olefin compound (C); and
2) reacting said compound (C) with a chiral acid in an organic solvent to form said compound of Formula (A).

In embodiment 28, the present invention provides a method of embodiment 27, wherein said chiral acid is a phosphorus chiral acid.

In embodiment 29, the present invention provides a method of embodiment 27, wherein said chiral acid is (S)-TRIP having the Formula:

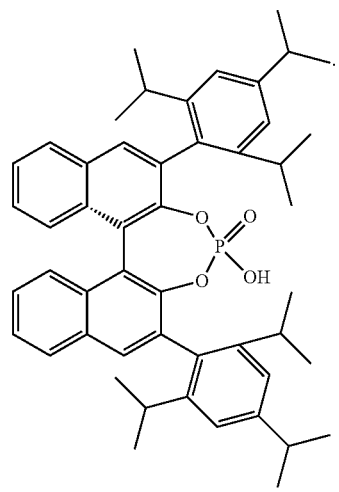

In embodiment 30, the present invention provides a method of embodiment 27, wherein said organic solvent is dichloromethane.

In embodiment 31, the present invention provides a method of embodiment 27, wherein said R is bromo.

In embodiment 32, the present invention provides a method of embodiment 27, wherein said $R^1$ is ethyl; wherein the compound of Formula (B) has the formula:

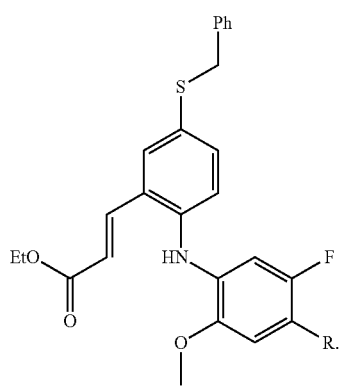

In embodiment 33, the present invention provides a method of embodiment 27, wherein in reaction (2), a P atropisomer of said compound of Formula (A) is selectively formed.

In embodiment 34, the present invention provides a method of embodiment 27, wherein said compound of Formula (A) is used as an intermediate compound in preparation of a compound of Formula (I):

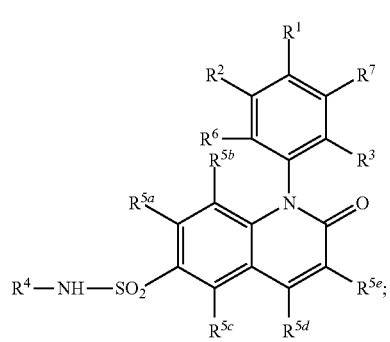

(I)

or a pharmaceutically acceptable salt thereof,
wherein:
$R^1$ is a saturated or partially-saturated 4-membered monocyclic ring; or a 4-, 5-, 6-, 7-, 8-, 9-, 10-, 11-, or 12-membered bicyclic ring; wherein said monocyclic ring or bicyclic ring contains 0, 1, 2 or 3 N atoms and 0, 1, or 2 atoms selected from O and S; and wherein said monocyclic ring or bicyclic ring is substituted by 0, 1, 2 or 3 $R^{1a}$ groups selected from hydroxy, halo, $C_{1-8}$alk, $C_{1-8}$haloalk, —O—$C_{1-4}$alk, —O—$C_{1-8}$haloalk, —C(=O)$C_{1-4}$alk, —O—C(=O)$C_{1-4}$alk, —NH$_2$, —NHC$_{1-4}$alk, or —N(C$_{1-4}$alk)C$_{1-4}$alk;
$R^2$ is H, halo, $C_{1-6}$alk, or $C_{1-6}$haloalk;
$R^3$ is $C_{1-6}$alk, $C_{1-6}$haloalk, —O—$C_{1-6}$alk, or —CN;
$R^4$ is a 5- to 6-membered heteroaryl;
Each of $R^6$ and $R^7$ is hydrogen; and
Each of $R^{5a}$; $R^{5b}$; $R^{5c}$; $R^{5d}$; and $R^{5e}$ is independently hydrogen or halo; and
Wherein a P atropisomer of said compound of Formula (I) is selectively formed.

DETAILED DESCRIPTION OF THE INVENTION

The present invention provides compounds of Formula (I), as defined above, an enantiomer, diastereoisomer, atropisomer thereof, or a mixture thereof, or pharmaceutically acceptable salts thereof. The present invention also provides pharmaceutical compositions comprising a compound of Formula (I), an enantiomer, diastereoisomer, atropisomer thereof, or a mixture thereof, or pharmaceutically acceptable salts thereof, and methods of treating diseases and/or conditions, such as pain, using compounds of Formula (I), an enantiomer, diastereoisomer, atropisomer thereof, or a mixture thereof, or pharmaceutically acceptable salts thereof.

The term "$C_{\alpha-\beta}$alk" means an alkyl group comprising a minimum of $\alpha$ and a maximum of $\beta$ carbon atoms in a branched or linear relationship or any combination of the two, wherein $\alpha$ and $\beta$ represent integers. A designation of $C_0$alk indicates a direct bond. Examples of $C_{1-6}$alk include, but are not limited to, the following:

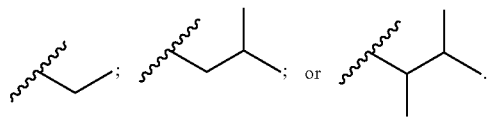

The term "halo" or "halogen" means a halogen atoms selected from F, Cl, Br or I.

The term "$C_{\alpha-\beta}$haloalk" means an alk group, as defined herein, in which at least one of the hydrogen atoms has been replaced with a halo atom, as defined herein. Common $C_{\alpha-\beta}$haloalk groups are $C_{1-3}$fluoroalk. An example of a common $C_{1-3}$fluoroalk group is —CF$_3$.

The term "heteroatom" as used herein means an oxygen, nitrogen or sulfur atom.

The term "monocyclic ring" as used herein means a group that features one single ring. A monocyclic ring can be carbocyclic (all of the ring atoms are carbons), or heterocyclic (the rings atoms include at least 1 heteroatom, for example, 1, 2 or 3 heteroatoms, such as N, O, or S, in addition to carbon atoms). Examples of monocyclic rings include, but are not limited to: cyclobutyl, cyclopentyl, or cyclohexyl.

The term "bicyclic ring" as used herein means a group that features two joined rings. A bicyclic ring can be carbocyclic (all of the ring atoms are carbons), or heterocyclic (the rings atoms include at least one heteroatom, for example. 1, 2 or 3 heteroatoms, such as N, O, or S, in addition to carbon atoms). The two rings can both be aliphatic (e.g. decalin and norbornane), or can be aromatic (e.g. naphthalene), or a combination of aliphatic and aromatic (e.g. tetralin). Bicyclic rings include (a) spirocyclic compounds, wherein the two rings share only one single atom, the spiro atom, which is usually a quaternary carbon. Examples of spirocyclic compound include, but are not limited to:

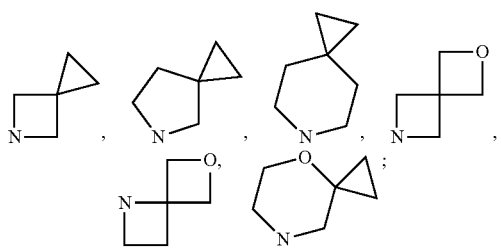

or (b) fused bicyclic compounds, wherein two rings share two adjacent atoms. In other words, the rings share one covalent bond. i.e. the bridgehead atoms are directly connected (e.g. α-thujene and decalin). Examples of fused bicyclic rings include, but are not limited to:

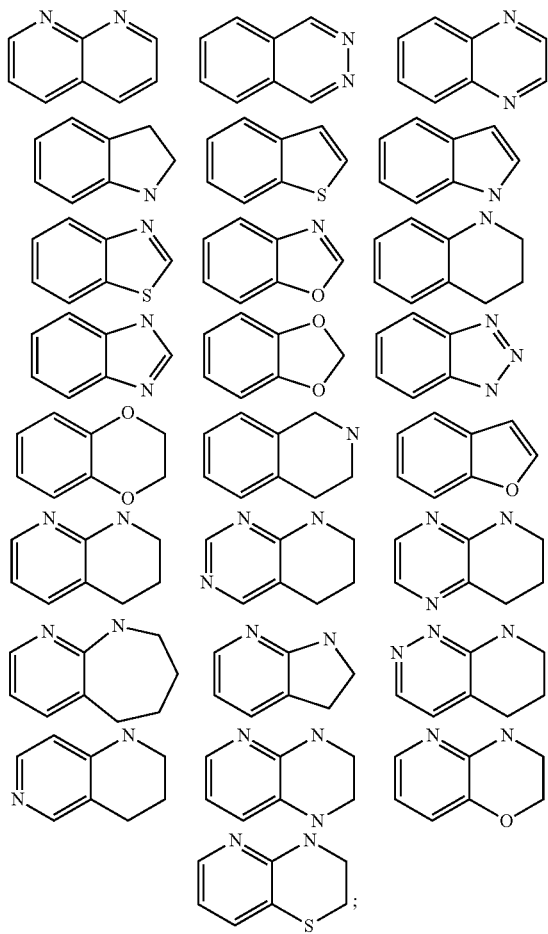

and (c) bridged bicyclic compounds, wherein the two rings share three or more atoms, separating the two bridgehead atoms by a bridge containing at least one atom. For example, norbornane, also known as bicyclo[2.2.1]heptane, can be thought of as a pair of cyclopentane rings each sharing three of their five carbon atoms. Examples of bridged bicyclic rings include, but are not limited to:

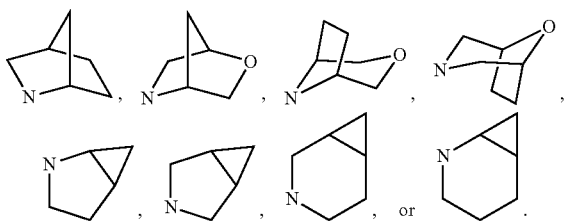

The term "aryl" means a cyclic, aromatic hydrocarbon. Examples of aryl groups include phenyl and naphthyl. Common aryl groups are six to thirteen membered rings.

The term "heteroaryl" means a cyclic, aromatic hydrocarbon in which one or more carbon atoms of an aryl group have been replaced with a heteroatom. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, indolyl, triazolyl, pyridazinyl, indazolyl, purinyl, quinolizinyl, isoquinolyl, quinolyl, naphthyridinyl, quinoxalinyl, isothiazolyl and benzo[b]thienyl. Common heteroaryl groups are five to thirteen membered rings that contain from 1 to 4 heteroatoms. Heteroaryl groups that are five and six membered rings that contain 1 to 3 heteroatoms are particularly common.

The term "saturated, partially-saturated or unsaturated" includes substituents saturated with hydrogens, substituents completely unsaturated with hydrogens and substituents partially saturated with hydrogens.

The term "pharmaceutically acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. For additional examples of "pharmacologically acceptable salts," and Berge et al., J. Pharm. Sci. 66:1 (1977).

The term "substituted" means that a hydrogen atom on a molecule or group is replaced with a group or atom other than hydrogen. Typical substituents include: halogen, $C_{1-8}$alkyl, hydroxyl, $C_{1-8}$alkoxy, —$NR^xR^x$, nitro, cyano, halo or perhalo$C_{1-8}$alkyl, $C_{2-8}$alkenyl, $C_{2-8}$alkynyl, —$SR^x$, —$S(=O)_2R^x$, —$C(=O)OR^x$, —$C(=O)R^x$, wherein each R is independently hydrogen or $C_1$-$C_8$ alkyl. It is noted that when the substituent is —$NR^xR^x$, the R groups may be joined together with the nitrogen atom to form a ring.

A group or atom that replaces a hydrogen atom is also called a substituent.

Any particular molecule or group can have one or more substituent depending on the number of hydrogen atoms that can be replaced.

The term "unsubstituted" means a hydrogen atom on a molecule or group.

The symbol "-" represents a covalent bond and can also be used in a radical group to indicate the point of attachment to another group. In chemical structures, the symbol is commonly used to represent a methyl group in a molecule.

The term "leaving group" generally refers to groups readily displaceable by a nucleophile, such as an amine, a thiol or an alcohol nucleophile, or by metallic agent such as boronic acids or boronates under transition metal catalyzed coupling conditions. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

The term "protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A tert-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bundgaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, 4/11/81) discloses Mannich-base hydroxamic acid prodrugs, their preparation and use.

The term "therapeutically effective amount" means an amount of a compound that ameliorates, attenuates or eliminates one or more symptom of a particular disease or condition, or prevents or delays the onset of one of more symptoms of a particular disease or condition.

The term "patient" means animals, such as dogs, cats, cows, horses, sheep and humans. Particular patients are mammals. The term patient includes males and females.

The term "pharmaceutically acceptable" means that the referenced substance, such as a compound of Formula (I), or a salt of a compound of Formula (I), or a formulation containing a compound of Formula (I), or a particular excipient, are suitable for administration to a patient.

The terms "treating", "treat" or "treatment" and the like include preventative (e.g., prophylactic) and palliative treatment.

The term "excipient" means any pharmaceutically acceptable additive, carrier, diluent, adjuvant, or other ingredient, other than the active pharmaceutical ingredient (API), which is typically included for formulation and/or administration to a patient.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered by a tablet, while another is administered by injection or orally as syrup. All combinations, delivery methods and administration sequences are contemplated.

The compounds of the present invention may be used in the manufacture of a medicament for the treatment of a disease and/or condition mediated by Nav 1.7, such as pain, chronic cough or itch.

Pain is typically divided into primary types: chronic and acute pain based on the duration of the pain. Typically, chronic pain lasts for longer than 3 months. Examples of chronic pain include pain associated with rheumatoid arthritis, osteoarthritis, lumbosacral radiculopathy or cancer.

Chronic pain also includes idiopathic pain, which is pain that has no identified cause. An example of idiopathic pain is fibromyalgia.

Another type of pain is nociceptive pain. Nociceptive pain is caused by stimulation of peripheral nerve fibers that respond to highly noxious events such as thermal, mechanical or chemical stimuli.

Still another type of pain is neuropathic pain. Neuropathic pain is pain that is caused by damage or disease affecting a part of the nervous system. Phantom limb pain is a type of neuropathic pain. In phantom limb pain, the body detects pain from a part of a body that no longer exists. For example, a person who has had a leg amputated may feel leg pain even though the leg no longer exists.

In one embodiment of the methods of treatment provided by the present invention using the compounds of Formula (I), or pharmaceutically acceptable salts thereof, the disease is chronic pain. In another aspect, the chronic pain is associated with, but are not limited to, post-herpetic neuralgia (shingles), rheumatoid arthritis, osteoarthritis, diabetic neuropathy, complex regional pain syndrome (CRPS), cancer or chemotherapy-induced pain, chronic back pain, phantom limb pain, trigeminal neuralgia, HIV-induced neuropathy, cluster headache disorders, and migraine, primary erythromelalgia, and paroxysmal extreme pain disorder. Other indications for Nav 1.7 inhibitors include, but are not limited to, depression (Morinville et al., *J Comp Neurol.*, 504:680-689 (2007)), bipolar and other CNS disorders (Ettinger and Argoff, *Neurotherapeutics*, 4:75-83 (2007)), epilepsy: ibid., and Gonzalez, Termin, Wilson, *Methods and Principles in Medicinal Chemistry*, 29:168-192 (2006)), multiple sclerosis (Waxman, *Nature Neurosci.* 7:932-941 (2006)), Parkinson's (Do and Bean, *Neuron* 39:109-120 (2003); Puopolo et al., *J. Neurosci.* 27:645-656 (2007)), restless legs syndrome, ataxia, tremor, muscle weakness, dystonia, tetanus (Hamann M., et. al., *Exp. Neurol.* 184(2): 830-838, 2003), anxiety, depression: McKinney B. C, et. al., *Genes Brain Behav.* 7(6):629-638, 2008), learning and memory, cognition (Woodruff-Pak D. S., et. al., *Behav. Neurosci.* 120(2):229-240, 2006), cardiac arrhythmia and fibrillation, contractility, congestive heart failure, sick sinus syndrome (Haufe V., et. al., *J. Mol. Cell Cardiol.* 42(3):469-477, 2007), schizophrenia, neuroprotection after stroke, drug and alcohol abuse (Johannessen L. C., *CNS Drugs* 22(1)27-47, 2008), Alzheimer's (Kim D. Y., et. al., *Nat. Cell. Biol.* 9(7):755-764, 2007), and cancer (Gillet L., et. al., *J Biol Chem* 2009, Jan. 28 (epub)).

Another aspect of the invention relates to a method of treating acute and/or chronic inflammatory and neuropathic pain, dental pain, general headache, migraine, cluster headache, mixed-vascular and non-vascular syndromes, tension headache, general inflammation, arthritis, rheumatic diseases, rheumatoid arthritis, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation pain syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound according to the present invention. A preferred type of pain to be treated is chronic neuropathic pain. Another preferred type of pain to be treated is chronic inflammatory pain.

In another aspect of the invention, the compounds of the present invention can be used in combination with other compounds that are used to treat pain. Examples of such other compounds include, but are not limited to aspirin, celecoxib, hydrocodone, oxycodone, codeine, fentanyl, ibuprofen, ketoprofen, naproxen, acetaminophen, gabapentin and pregabalin. Examples of classes of medicines that contain compounds that can be used in combination with the compounds of the present invention include non-steroidal anti-inflammatory compounds (NSAIDS), steroidal compounds, cyclooxygenase inhibitors and opioid analgesics.

The compounds of the present invention may also be used to treat diabetes, obesity and/or to facilitate weight loss.

The compounds of the present invention may be used in combination with other pharmaceutically active compounds. It is noted that the term "pharmaceutically active compounds" can include biologics, such as proteins, antibodies and peptibodies.

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed by said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragées, capsules, pills, and granules can be prepared with coatings and shells, such as enteric coatings and others well known in the art. They may also contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferably suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or fit compounds are admixed under sterile condition with a physiologically acceptable carrier, and any preservatives, buffers, or propellants that may be required. Ophthalmic formulations, eye ointments, powders, and solutions are also contemplated as being within the scope of this invention.

The compounds of the present invention can be administered to a patient at therapeutically effective dosage levels. The specific dosage and dosage range that can be used depends on a number of factors, including the requirements of the patient, the severity of the condition or disease being treated, and the pharmacological activity of the compound being administered.

The compounds of the present invention can be administered as pharmaceutically acceptable salts, co-crystals, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$-$C_{12}$) alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_{2-3}$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

In addition, if a compound of the present invention comprises a sulfonamide moiety, a prodrug can be formed by replacement of the sulfonamide N(H) with a group such as —CH$_2$P(O)(O($C_1$-$C_6$)alkyl)$_2$ or —CH$_2$OC(O)($C_1$-$C_6$)alkyl.

The compounds of the present invention also include tautomeric forms of prodrugs.

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond or disubstituted cycloalkyl group, both the cis and trans isomers, unless the specific isomer is specified, as well as mixtures, are contemplated. In disubstituted cycloalkyl containing compounds, the cis and trans isomers refer to the relative positions of the substitutions. For example:

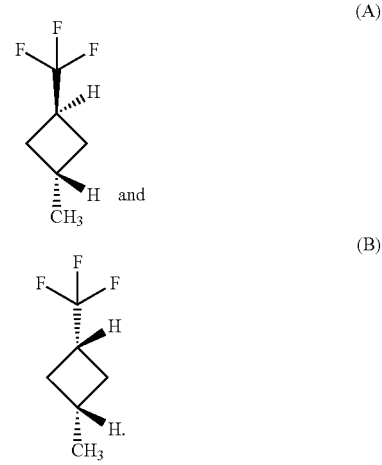

(A) represents trans cyclobutyl isomer because the —CF$_3$ group is pointing up while the —CH$_3$ group is pointing down, while (B) represents cis cyclobutyl isomer because both the —CF$_3$ group and the —CH$_3$ groups are pointing down.

Mixtures of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diasteromeric mixture by reaction with an appropriate optically active compound (e.g., an alcohol), separating the diastereomers and converting (e.g., hydrolyzing) the individual diastereomers to the corresponding pure enantiomers.

The compounds of general Formula (I) may also exist in the form of atropisomers. Atropisomers are compounds with identical structural formulae, but which have a particular spatial configuration resulting from a restricted rotation around a single bond, due to steric hindrance on either side of this single bond. Atropisomerism is independent of the presence of stereogenic elements, such as an asymmetric carbon. The terms "P atropisomer" or "M atropisomer" are used herein in order to be able to clearly name two atropisomers of the same pair. For example, the following intermediate compound having the structure below can be separated into the pair of atropisomers P and M via a chiral column chromatography:

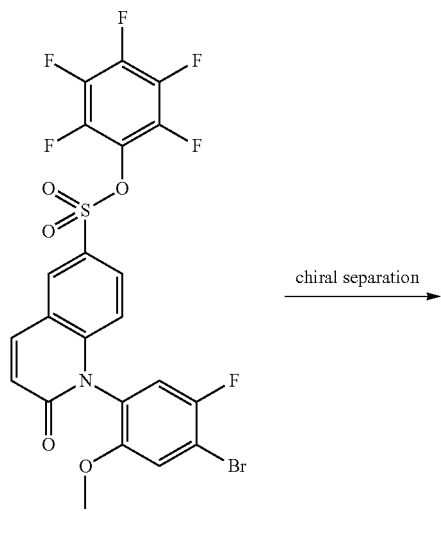

chiral separation

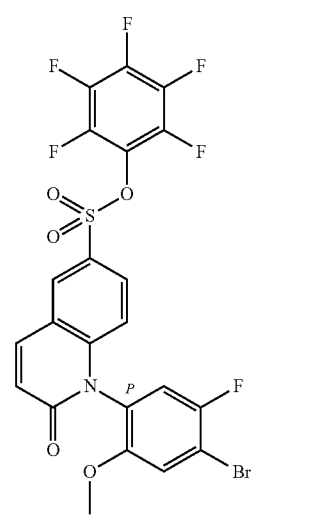

+

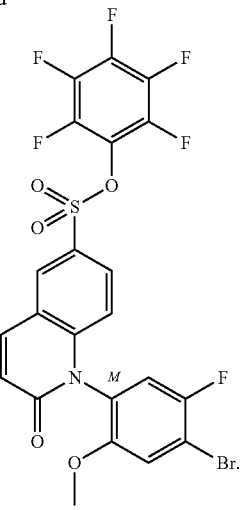

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. For example, all of the tautomeric forms of the tetrazole moiety are included in this invention. Also, for example, all keto-enol or imine-enamine forms of the compounds are included in this invention. Other examples of tautomerism are as follows:

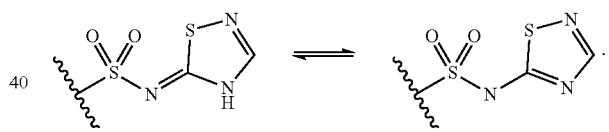

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{16}O$, $^{17}O$, $^{31}P$, $^{32}P$, $^{35}S$, $^{18}F$, and $^{36}Cl$. In another aspect, the compounds of the present invention contain one or more deuterium atoms (2H) in place of one or more hydrogen atoms.

Compounds of the present invention that contain the aforementioned isotopes and/or other isotopes of other atoms are within the scope of this invention. Certain isotopically labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detection. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

All patents and other publications recited herein are hereby incorporated by reference in their entirety.

The examples presented below illustrate specific embodiments of the present invention. These examples are meant to be representative and are not intended to limit the scope of the claims in any manner.

It is noted that when a percent (%) is used with regard to a liquid, it is a percent by volume with respect to the solution. When used with a solid, it is the percent with regard to the solid composition. Materials obtained from commercial suppliers were typically used without further purification. Reactions involving air or moisture sensitive reagents were typically performed under a nitrogen or argon atmosphere. Purity was measured using high performance liquid chromatography (HPLC) system with UV detection at 254 nm and 215 nm (System A: HALO C8, 3.0×50 mm, 2.7 µm, 5 to 95% CH$_3$CN in H$_2$O with 0.1% TFA for 2.0 min at 2.0 mL/min) (Agilent Technologies, Santa Clara, CA). Silica gel chromatography was generally performed with pre-packed silica gel cartridges (BIOTAGE®, Uppsala, Sweden or Teledyne-Isco, Lincoln, NE). $^1$H NMR spectra were recorded on a Bruker AV-400 (400 MHz) spectrometer (Bruker Corporation, Madison, WI) or a Varian (Agilent Technologies, Santa Clara, CA) 400 MHz spectrometer at ambient temperature. All observed protons are reported as parts per million (ppm) downfield from tetramethylsilane (TMS) or other internal reference in the appropriate solvent indicated. Data are reported as follows: chemical shift, multiplicity (s=singlet, d=doublet, t=triplet, q=quartet, br=broad, m=multiplet), coupling constants, and number of protons. Low-resolution mass spectral (MS) data were determined on an Agilent 1100 Series (Agilent Technologies, Santa Clara, CA) LC/MS with UV detection at 254 nm and 215 nm and a low resonance electrospray mode (ESI).

The following abbreviations may be used herein:
2-PrOH Isopropanol
AgOTf silver(I) trifluoromethanesulfonate
AIBN Azobisisobutyronitrile
aq. Aqueous
Bu Butyl
ca. Circa
Cm centimeter(s)
CPhos 2-dicyclohexylphosphino-2',6'-dimethylamino-1,1'-biphenyl
DAST diethylaminosulfur trifluoride
Dba Dibenzylideneacetone
DCM Dichloromethane
Deoxy-Fluor bis(2-methoxyethyl)aminosulfur trifluoride
DIPEA N,N-diisopropylethylamine
DMF N,N-dimethylformamide
DMSO Dimethylsulfoxide
ESI or ES electrospray ionization
Et Ethyl
Et$_2$O diethyl ether
EtOAc ethyl acetate
EtOH Ethanol
G gram(s)
H hour(s)
HPLC high pressure liquid chromatography
IPA 2-propanol
Kg kilogram(s)
L liter(s)
LCMS liquid chromatography mass spectroscopy
LHMDS lithium hexamethyldisilazide
M Molar
m/z mass divided by charge
Me Methyl
MeOH Methanol
Me-THF Methyl tetrahydrofuran
Mg milligram(s)
MHz Megahertz
Min minute(s)
mL or ml milliliter(s)
Mmol millimole(s)
Mol mole(s)
MTBE methyl tert-butyl ether
N Normal
NaOMe sodium methoxide
n-Bu n-butyl
NEt$_3$ Triethylamine
NMR nuclear magnetic resonance
OAc Acetate
OTf Trifluoromethanesulfonate
PFP—OH Perfluorophenol
Ph Phenyl
PhMe Toluene
PMB 4-methoxy benzyl
Ppm parts per million
Pr Propyl
rac racemic
rt room temperature
sat. Saturated
SFC supercritical fluid chromatography
TBAF tetra-n-butylammonium fluoride
TFA trifluoroacetic acid
THF Tetrahydrofuran
Ti(OiPr)$_4$ titanium(IV) isopropoxide
TLC thin-layer chromatography
TMS-CF$_3$ (trifluoromethyl)trimethylsilane
wt % percentage by weight
XantPhos 4,5-bis(diphenylphosphino)-9,9-dimethylxanthene
XtalFluor-M difluoro(morpholino)sulfonium tetrafluoroborate The following compounds presented herein, as examples of the present invention, and intermediates thereof as building blocks to prepare compounds provided by the invention, may be made by the various methods and synthetic strategies taught herein below. These compounds, and others provided by the invention, may also be prepared using methods described in International Publication No. WO2014/201206, filed Jun. 12, 2014, which specification is incorporated herein by reference in their entirety.

In addition, the present inventors have developed a photochemical atrop-selective ring-closure to form N-aryl quinolinones compounds. Specifically, the P atropisomer compound 3 is selectively formed in the photochemical reaction of the invention. A general representation of the photochemistry step of the present invention is described below:

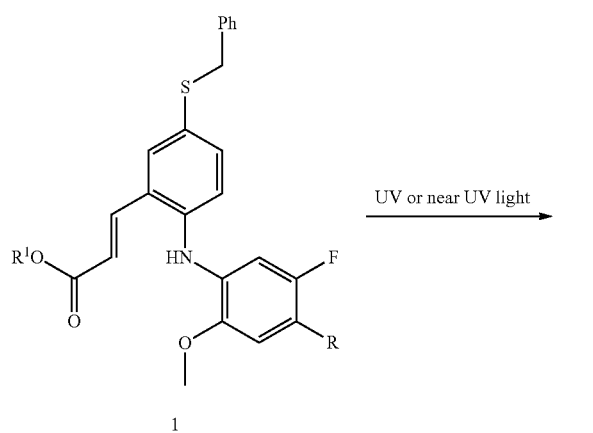

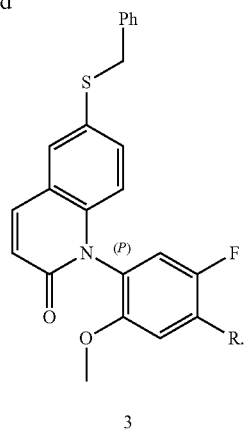

The reaction relies on UV or near-UV light to excite the olefin 1; wherein R is halo; and $R^1$ is $C_1$-$C_6$alkyl; and induce a cis-trans isomerization to transiently form 2; wherein R is halo; and $R^1$ is $C_1$-$C_6$alkyl. Preferably, $R^1$ is ethyl. Cis olefin 2 can then be activated by chiral acid (S)-TRIP to asymmetrically form ring-closed quinolinone 3, wherein R is as defined above. Preferably, R is Br. A screen of chiral phosphoric acids revealed that (S)-TRIP was the preferred chiral acid. The preferred organic solvent is dichloromethane. The photochemical reaction has been scaled to 1 g in a batch reactor and has also been demonstrated in a small photochemical flow reactor.

The present photochemical step can operate well without the present of a bulky barrier substituent to rotation, such as tert-butyl group in the starting material. Rather, the present novel photochemical step has been demonstrated in the presence of a much smaller methoxy group in the starting material. The mild reaction conditions further allow for compounds with low barriers to rotation to be prepared in a stereoselective fashion.

Intermediate A: (P)-1-(4-Bromo-5-Fluoro-2-Methoxyphenyl)-N-(Isoxazol-3-Yl)-2-Oxo-1,2-Dihydroquinoline-6-Sulfonamide

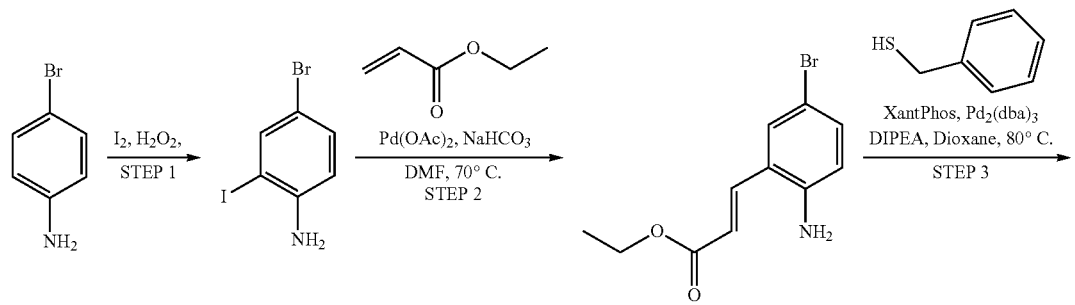

-continued
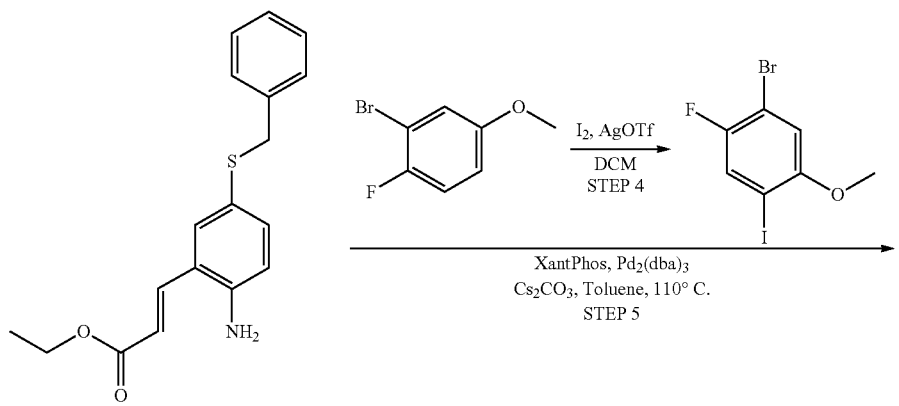
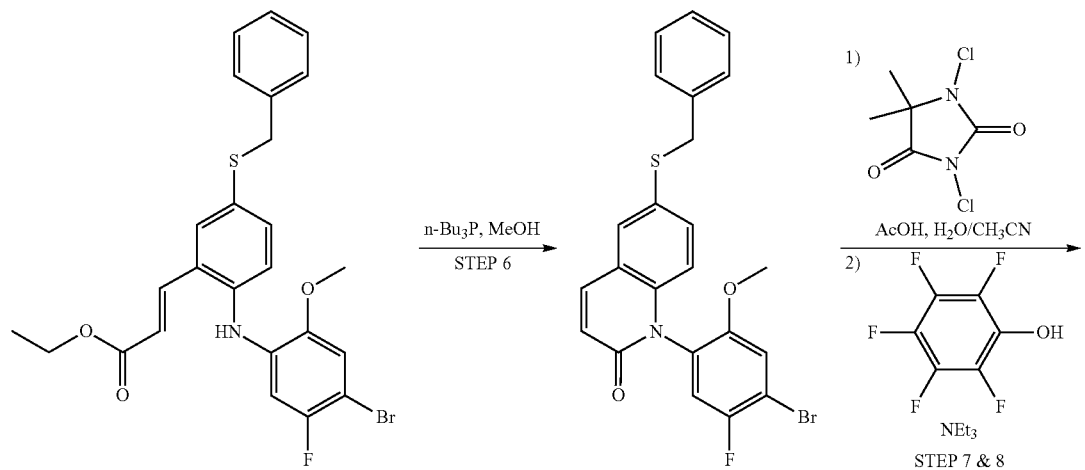
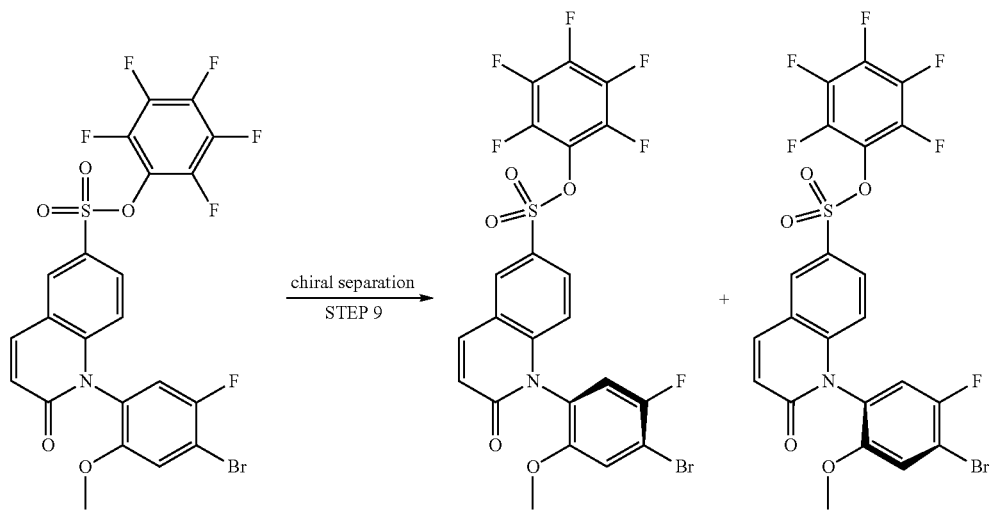

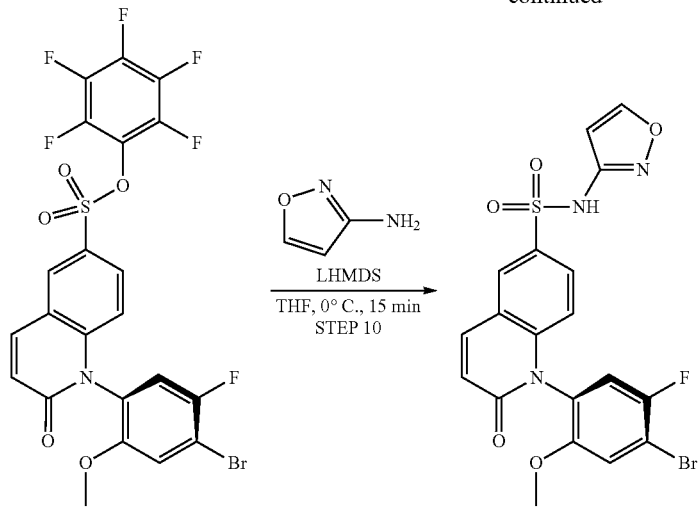

Step 1: 4-Bromo-2-Iodoaniline

To a solution of 4-bromo-aniline (500 g, 2.90 mol) in cyclohexane (2.5 L) was added iodine (368 g, 1.45 mol), and the mixture was heated at 50° C. After 30 min, the reaction mixture became homogenous, and 30% aqueous hydrogen peroxide solution (250 mL) was added to the reaction mixture. The reaction was heated for 4 h at 50° C. The reaction was cooled to room temperature, diluted with ethyl acetate (5.0 L) and washed with aqueous sodium sulphite (2.5 kg in 4.0 L) solution. The organic layer was washed with water (3.0 L) and brine (3.0 L), dried over magnesium sulfate, filtered and concentrated under reduced pressure to obtain the initial product which was purified by column chromatography (silica gel; mesh size 60-120, elution 0-20% ethyl acetate and hexanes) to get 4-bromo-2-iodoaniline (650 g, 75%), as an off white solid. TLC solvent system: 100% hexanes. Product's $R_f$: 0.6. MS (ESI, positive ion) m/z: 297.0 (M+1). $^1$H NMR (400 MHz, CDCl$_3$) δ 7.72 (d, J=2.5 Hz, 1H), 7.23 (dd, J=8.4, 2.1 Hz, 1H), 6.62 (d, J=8.3 Hz, 1H), 4.09 (s, 2H).

Step 2: Ethyl (E)-3-(2-Amino-5-Bromophenyl)Acrylate

To a solution of 4-bromo-2-iodoaniline (750 g, 2.51 mol) in DMF (5.0 L) was added ethyl acrylate (277 g, 2.76 mol) and sodium bicarbonate (680 g, 6.29 mol). The reaction mixture was degassed with nitrogen for 20 min followed by the addition of palladium acetate (28.8 g, 128.27 mmol). The reaction mixture was heated at 70° C. for 3 h. The reaction was filtered through CELITE® and the CELITE bed was washed with ethyl acetate (2×500 mL). The filtrate was concentrated under reduced pressure to obtain a residue which was purified by column chromatography (silica gel; mesh size 60-120, elution 0-20% ethyl acetate in hexanes) to obtain (E)-ethyl 3-(2-amino-5-bromophenyl)acrylate (620 g, 77%), as yellow solid. TLC solvent system: 20% ethyl acetate in hexanes. Product's $R_f$: 0.4. MS (ESI, positive ion) m/z: 270.2 (M+1). $^1$H NMR (400 MHz, DMSO) δ 7.75 (d, J=16.1 Hz, 1H), 7.57 (d, J=2.0 Hz, 1H), 7.16 (dd, J=9.1, 2.4 Hz, 1H), 6.66 (d, J=8.6 Hz, 1H), 6.43 (d, J=8.6 Hz, 1H), 5.81 (s, 2H), 4.20 (q, J=7.2 Hz, 2H), 1.27 (t, J=7.2 Hz, 3H). Other acrylates can be used in place of ethyl acrylate to provide different esters. For example methyl acrylate, propyl acrylate, butyl acrylate, and others may be used instead of ethyl acrylate.

Step 3: Ethyl (E)-3-(2-Amino-5-(Benzylthio)Phenyl) Acrylate

To a solution of (E)-ethyl 3-(2-amino-5-bromophenyl) acrylate (620 g, 2.29 mol) in 1,4-dioxane (4.0 L) was added DIPEA (1.26 L, 8.88 mol, 3.9 equiv, GLR), and the mixture was degassed with nitrogen for 20 mins. XantPhos (92.9 g, 106 mmol), and tris(dibenzylideneacetone)dipalladium(0) (84 g, 91.0 mmol) were added to the reaction mixture. The mixture was purged with nitrogen and heated to 80° C. for 30 min. The reaction was cooled to RT, benzyl mercaptan (455.5 g, 3.67 mol) was added, and the reaction was heated at 80° C. for an additional 4 h. The reaction was cooled to room temperature and diluted with ethyl acetate (4.0 L). The mixture was filtered through CELITE and the CELITE bed was washed with ethyl acetate (2×1.0 L). The filtrate was concentrated under reduced pressure to obtain the initial product which was purified by chromatography (silica gel; mesh size 60-120, elution 0-40% ethyl acetate and petroleum ether) to obtain (E)-ethyl 3-(2-amino-5-(benzylthio) phenyl)acrylate (520 g, 72.0%), as yellow solid. TLC solvent system: 30% ethyl acetate in hexanes. Product's $R_f$: 0.4. MS (ESI, positive ion) m/z: 314.1 (M+1). $^1$H NMR (400 MHz, DMSO) δ 7.79 (d, J=16.1 Hz, 1H), 7.37 (d, J=2.0 Hz, 1H), 7.25-7.17 (m, 5H) 7.10 (dd, J=8.4, 2.1 Hz, 1H), 6.61 (d, J=8.3 Hz, 1H), 6.32 (d, J=15.2 Hz, 1H), 5.75 (s, 2H), 4.20 (q, J=7.2 Hz, 2H), 4.01 (s, 2H), 1.27 (t, J=7.2 Hz, 3H).

Step 4: 1-Bromo-2-Fluoro-4-Iodo-5-Methoxybenzene

To a solution of 2-bromo-1-fluoro-4-methoxybenzene (500.0 g, 2.44 mol) in DCM (5.0 L) was added silver trifluoromethanesulfonate (686.0 g, 2.68 mol) and the reaction mixture was stirred for 20 min. Iodine (678.0 g, 2.68 mol) was added to the reaction and the mixture was stirred at room temperature for 16 h. The mixture was diluted with DCM (3.0 L) and filtered through CELITE. The CELITE bed was washed with DCM (2×1.0 L) and the filtrate was washed with 20% aqueous sodium thiosulfate (3.0 L) and saturated aqueous sodium bicarbonate solution (3.0 L). The organic layer was dried over sodium sulfate, filtered and concentrated under reduced pressure to obtain the initial product which was purified by chromatography (silica gel; mesh size 60-120, elution 0-5% ethyl acetate and petroleum ether) to get 1-bromo-2-fluoro-4-iodo-5-methoxybenzene (720 g, 87%), as off-white solid. TLC solvent system: 100% hexanes. Product's $R_f$: 0.6. MS (ESI, positive ion) m/z: 331.0 (M+1). $^1$H NMR (400 MHz, CDCl$_3$) δ 7.55 (d, J=7.2 Hz, 1H), 6.95 (d, J=5.6 Hz, 1H), 3.89 (s, 3H).

Step 5: Ethyl (E)-3-(5-(Benzylthio)-2-((4-Bromo-5-Fluoro-2-Methoxyphenyl)Amino)Phenyl) Acrylate To a solution of (E)-ethyl 3-(2-amino-5-(benzylthio)phenyl)acrylate (300 g, 958.1 mmol) and 1-bromo-2-fluoro-4-iodo-5-methoxybenzene (348.0 g, 1051.6 mmol) in toluene (2.5 L) was added Cs$_2$CO$_3$ (468 g, 1436.3 mmol). The resulting mixture was degassed with nitrogen for 20 mins. Pd$_2$(dba)$_3$ (35 g, 38.2 mmol) and XantPhos (44.6 g, 76.4 mmol) were added to the reaction mixture and the mixture was heated at 110° C. for 5 h. The reaction mixture was allowed to cool to room temperature, diluted with dichloromethane (2.0 L) and filtered through CELITE. The filtrate was concentrated under reduced pressure to obtain the initial product which was purified by stirring with 5% ethyl acetate in hexanes (3.0 L) for 30 min and filtered to obtain (E)-ethyl 3-(5-(benzylthio)-2-((4-bromo-5-fluoro-2-methoxyphenyl)amino)phenyl)acrylate (350 g, 71%) as yellow solid. TLC solvent system: 30% ethyl acetate in hexanes. Product's $R_f$: 0.5. MS (ESI, positive ion) m/z; 516.2 (M+1). $^1$H NMR (400 MHz, DMSO) δ 7.73-7.61 (m, 3H), 7.34-7.15 (m, 6H), 7.02 (d, J=11.4 Hz, 1H), 6.60 (d, J=21.2 Hz, 1H), 6.33 (d, J=14.1 Hz, 1H), 4.26 (s, 2H), 4.16-4.09 (m, 2H), 3.81 (s, 3H), 1.22 (t, J=7.2 Hz, 3H). Note: NH proton not observed.

Step 6: 6-(Benzylthio)-1-(4-Bromo-5-Fluoro-2-Methoxyphenyl)Quinolin-2(1H)-One

To a solution of (E)-ethyl 3-(5-(benzylthio)-2-((4-bromo-5-fluoro-2-methoxyphenyl)amino)phenyl)acrylate (250.0 g, 484.0 mmol) in methanol (2.5 L) was added tri(n-butyl) phosphine (50% solution in ethyl acetate, 48.9 mL, 96.8 mmol) and the reaction mixture was heated at 70° C. for 5 h. The reaction mixture was allowed to cool to rt, and was then concentrated under reduced pressure to obtain the initial product which was purified by stirring with 5% ethyl acetate in hexanes (1.0 mL) and filtered to obtain 6-(benzylthio)-1-(4-bromo-5-fluoro-2-methoxyphenyl)quinolin-2 (1H)-one (201.0 g, 88%) as an off white solid. TLC solvent system: 30% ethyl acetate in hexanes. Product's $R_f$: 0.3. MS (ESI, positive ion) m/z; 470.0 (M+1). $^1$H NMR (400 MHz, DMSO) δ 7.92 (d, J=9.1 Hz, 1H), 7.79 (d, J=1.7 Hz, 1H), 7.65 (d, J=6.1 Hz, 1H), 7.57 (d, J=8.8 Hz, 1H), 7.40-7.22 (m, 6H), 6.68 (d, J=9.6 Hz, 1H), 6.56 (d, J=8.8 Hz, 1H), 4.24 (s, 2H), 3.69 (s, 3H).

Alternatively, the P atropisomer title compound of step 6 can be selectively prepared by using a photochemistry route from ethyl (E)-3-[5-benzylsulfanyl-2-(4-bromo-5-fluoro-2-methoxy-anilino)phenyl]prop-2-enoate starting material as described in the following procedures:

Photochemistry Preparation Method 1

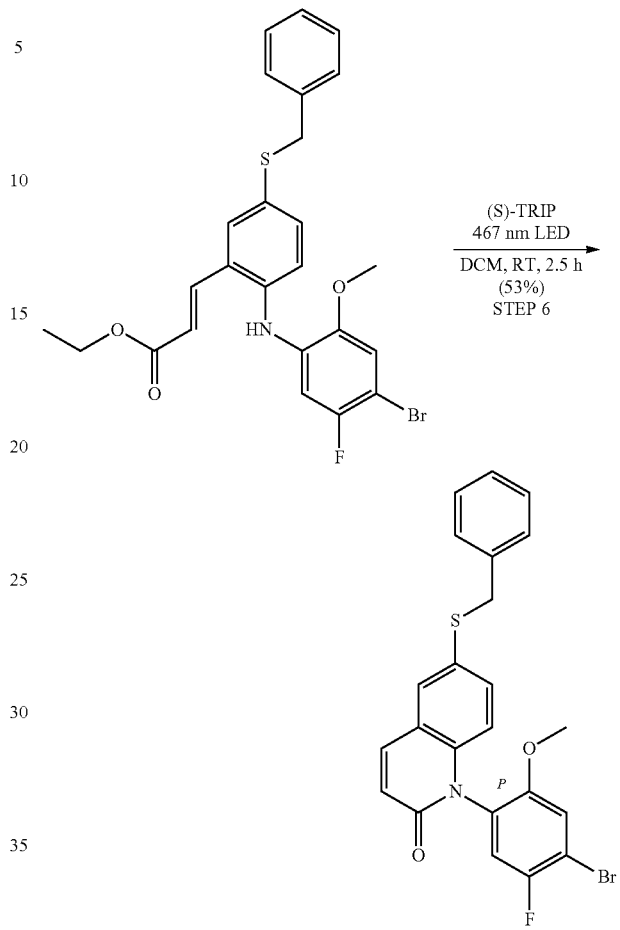

To a flask was added (E)-ethyl 3-(5-(benzylthio)-2-((4-bromo-5-fluoro-2-methoxyphenyl)amino)phenyl)acrylate (4.0 g, 7.6 mmol), (S)-3,3'-bis(2,4,6-triisopropylphenyl)-1, 1'-binaphthyl-2,2'-diyl hydrogen phosphate ((S)-TRIP) (290 mg, 0.38 mmol) and DCM (40 mL). The resulting solution was continuously stirred and recirculated for 2.5 h through narrow-diameter tubing that was exposed to 467 nm LED light. The reaction solution was concentrated to approximately 8 mL and charged with MeOH (80 mL). The solution was concentrated to approximately 50 mL and heated to 60° C. The solution was filtered to remove any precipitate and then allowed to cool to room temperature overnight. The resulting slurry was cooled to 0° C. for 2 h and then filtered. The filter cake was rinsed with cold MeOH to deliver (P)-6-(benzylthio)-1-(4-bromo-5-fluoro-2-methoxyphenyl) quinolin-2(1H)-one as a tan solid (2.12 g, 89 wt %, 4.0 mmol). $^1$H NMR (300 MHz, DMSO-d6) δ 7.95 (d, J=9.6 Hz, 1H), 7.79 (d, J=2.2 Hz, 1H), 7.64 (d, J=6.3 Hz, 1H), 7.55 (d, J=8.7 Hz, 1H), 7.42-7.16 (m, 6H), 6.67 (d, J=9.5 Hz, 1H), 6.55 (d, J=8.8 Hz, 1H), 4.24 (s, 2H), 3.68 (s, 3H). $^{19}$F NMR (282 MHz, DMSO-d6) δ −117.08 (dd, 1F, J=8.7, 6.3 Hz). ee determined by chiral normal phase chromatography (CHIRALPAK IC-3, 4.6×150×3), mobile phase of 60% Heptane/ 40% (0.2% ethanesulfonic acid in Ethanol) v/v, with flow rate of 1.5 mL/min.

Photochemistry Preparation Method 2

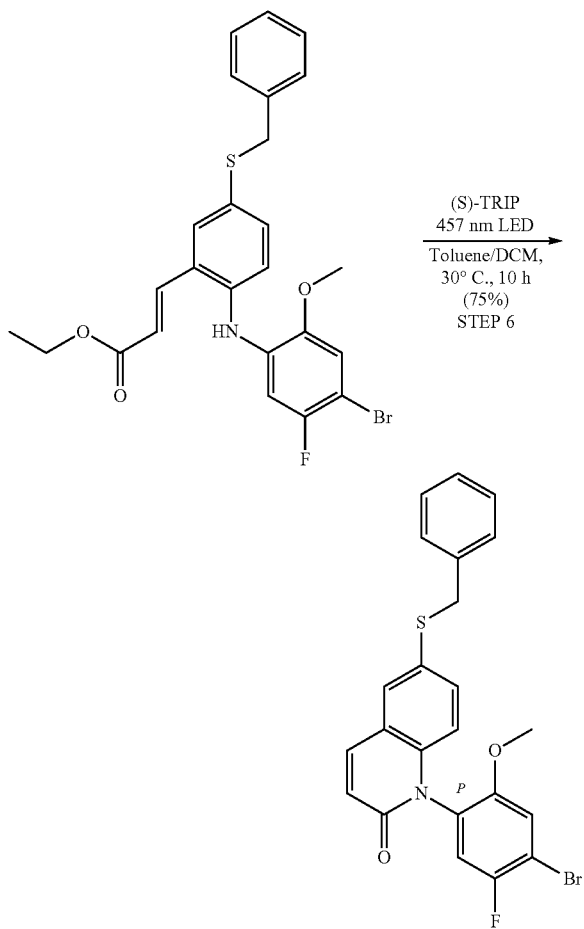

To a flask was added (E)-ethyl 3-(5-(benzylthio)-2-((4-bromo-5-fluoro-2-methoxyphenyl)amino)phenyl)acrylate (50.0 g, 96.8 mmol), (S)-3,3'-bis(2,4,6-triisopropylphenyl)-1,1'-binaphthyl-2,2'-diyl hydrogen phosphate ((S)-TRIP) (1.46 g, 1.94 mmol), toluene (750 mL) and DCM (750 mL). The reaction headspace was purged with $N_2$. The reaction solution was warmed to 30° C. and stirred. The solution was recirculated at a flow rate of 50 g/min via peristaltic pump for 10 h through ⅛" FEP tubing (approximately 10 mL internal volume) that was exposed to 457 nm LED light. The reaction solution was concentrated to a yellow-brown solid and then slurried in $^i$PrOAc (250 mL) for 30 min at 30° C. To the slurry was added heptane (500 mL) over 30 min. The slurry was cooled to 0° C. over 2 h and then placed in a −20° C. freezer for 36 h. The slurry was filtered and the filter cake was rinsed with 10% v/v $^i$PrOAc/heptane (2×150 mL). The solids were dried in a vacuum oven to provide (P)-6-(benzylthio)-1-(4-bromo-5-fluoro-2-methoxyphenyl)quinolin-2(1H)-one as a tan solid (34.7 g, 98 wt %, 72.6 mmol, 89% ee).

Steps 7 & 8: Perfluorophenyl 1-(4-Bromo-5-Fluoro-2-Methoxyphenyl)-2-Oxo-1,2-Dihydro Quinoline-6-Sulfonate To a solution of 6-(benzylthio)-1-(4-bromo-5-fluoro-2-methoxyphenyl)quinolin-2(1H)-one (250.0 g, 531.5 mmol) in acetonitrile (2.5 L) were added acetic acid (200 mL) and water (130 mL). The resulting mixture was cooled to 0° C. and 1,3-dichloro-5,5-dimethylimidazolidine-2,4-dione (188.5 g, 956.7 mmol) was added portion-wise over 20 min keeping the internal temperature below 5° C. The resulting suspension was stirred at 0-5° C. under nitrogen for 45 min. Then a solution of pentafluorophenol (127.2 g, 690.95 mmol) in acetonitrile (200 mL) was added over 5 min followed by $NEt_3$ (307.7 mL, 2.12 mol) over 20 min keeping the internal temperature below 5° C. The mixture was continued to be stirred at 0-5° C. for 30 min. Water (4.0 L) was added and extracted with ethyl acetate (2×2.0 L). The organic layer was washed with brine (1.0 L), dried over sodium sulfate, filtered and concentrated under reduced pressure to obtain the initial product which was purified by stirring with isopropyl alcohol:hexanes (1:1, 1.0 L) and filtered to obtain perfluorophenyl 1-(4-bromo-5-fluoro-2-methoxyphenyl)-2-oxo-1,2-dihydroquinoline-6-sulfonate (190 g, 60%) as white solid. TLC solvent system: 30% ethyl acetate in pet ether, Product's $R_f$: 0.4. MS (ESI, positive ion) m/z; 594.2 (M+1). $^1$H-NMR (400 MHz, DMSO) δ ppm 8.60 (d, J=2.0 Hz, 1H), 8.26 (d, J=9.8 Hz, 1H), 7.95 (dd, J=2.2, 9.1 Hz, 1H), 7.70 (t, J=8.6 Hz, 2H), 6.95-6.88 (m, 2H), 3.72 (s, 3H).

Step 9: (P)-Perfluorophenyl 1-(4-Bromo-5-Fluoro-2-Methoxyphenyl)-2-Oxo-1,2-Dihydroquinoline-6-Sulfonate Racemic perfluorophenyl 1-(4-bromo-5-fluoro-2-methoxyphenyl)-2-oxo-1,2-dihydroquinoline-6-sulfonate (76.90 g) was separated via Chiralcel OJ column (40% MeOH/60% $CO_2$) to give (P)-perfluorophenyl 1-(4-bromo-5-fluoro-2-methoxyphenyl)-2-oxo-1,2-dihydroquinoline-6-sulfonate and (M)-perfluorophenyl 1-(4-bromo-5-fluoro-2-methoxyphenyl)-2-oxo-1,2-dihydroquinoline-6-sulfonate as pale yellow flocculent solids. Data for peak 1: m/z (ESI) 594.0 (M+H)+. Data for peak 2: m/z (ESI) 594.0 (M+H)$^+$.

Step 10: (P)-1-(4-Bromo-5-Fluoro-2-Methoxyphenyl)-N-(Isoxazol-3-Yl)-2-Oxo-1,2-Dihydroquinoline-6-Sulfonamide A THF (200 mL) solution of (P)-perfluorophenyl 1-(4-bromo-5-fluoro-2-methoxyphenyl)-2-oxo-1,2-dihydroquinoline-6-sulfonate (6.00 g, 10.10 mmol) and 3-aminoisoxazole (0.821 mL, 11.11 mmol) in a 250-mL round-bottom flask was cooled to 0° C., and lithium bis(trimethylsilyl)amide, (1.0 M solution in THF, 21.20 mL, 21.20 mmol) was added dropwise. After stirring the yellow solution at 0° C. for 15 min, it was quenched at 0° C. with 1 N HCl and extracted thrice with EtOAc. The organic extracts were combined, dried over $MgSO_4$, filtered, and concentrated to a light tan residue. $Et_2O$ was added, and the slurry was triturated and sonicated. Filtration afforded an off-white solid, which was washed twice with $Et_2O$ and dried in vacuo to afford 3.88 g of product as an off-white solid. The filtrate was concentrated in vacuo and purified via column chromatography (12 g silica gel, 35% to 100% EtOAc/hept gradient) to afford an additional 1.36 g of product as a pale yellow flocculent solid. A total of 5.24 g of (P)-1-(4-bromo-5-fluoro-2-methoxyphenyl)-N-(isoxazol-3-yl)-2-oxo-1,2-dihydroquinoline-6-sulfonamide was afforded. m/z (ESI) 494.1 (M+H)$^+$.

Intermediate a: (3-(Tert-Butyl)Cyclobutyl)Zinc(II) Iodide, 0.2 M in THF

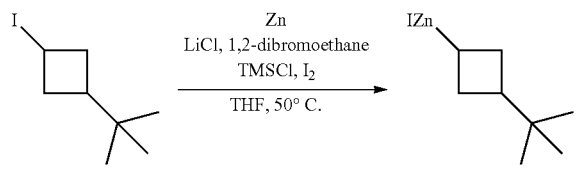

A three-necked oven-dried round-bottom flask equipped with a magnetic stir bar and a rubber septum was charged with lithium chloride (96 mg, 2.3 mmol). The vessel was heated with a heat gun for 10 min under vacuum and backfilled with nitrogen after cooling to room temperature. Zinc (148 mg, 2.27 mmol) was added. The vessel was again heated with a heat gun for 10 min under vacuum and backfilled with nitrogen after cooling to room temperature. THF (3.4 mL) and 1,2-dibromoethane (4.9 µL, 0.057 mmol) were added via syringe and the reaction mixture was heated at 60° C. until bubbling occurred. After cooling to room temperature, chlorotrimethylsilane (4.4 µL, 0.034 mmol) and a solution of iodine (2.9 mg, 0.011 mmol) in THF (0.1 mL) were added via syringe. The reaction mixture was heated at 60° C. for 20 min and then cooled to room temperature. 1-(tert-Butyl)-3-iodocyclobutane (270 mg, 1.13 mmol) was added, and the reaction was stirred at 50° C. for 18 h. The reaction mixture was allowed to stand at room temperature for 1 h. The solution was titrated by adding dropwise to a cooled (0° C.) solution of iodine (3 mg, 0.012 mmol) in lithium chloride (0.5 M in THF, 2.3 mL, 1.1 mmol) until the orange color disappeared. 0.06 mL of solution was used, corresponding to a concentration of 0.2 M.

Intermediate B: 5,8-Dioxaspiro[3.4]Octan-2-Ylzinc(II) Bromide, 0.1 M in THF

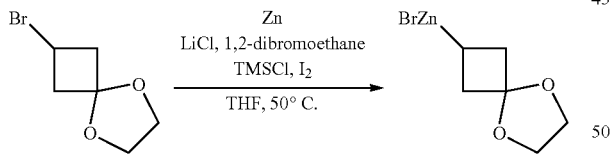

An oven-dried round-bottom flask equipped with a magnetic stir bar and a rubber septum was charged with lithium chloride (0.878 g, 20.72 mmol). The vessel was heated with a heat gun for 10 min under vacuum and backfilled with nitrogen after cooling to room temperature. Zinc (1.355 g, 20.72 mmol) was added. The vessel was again heated with a heat gun for 10 min under vacuum and backfilled with nitrogen after cooling to room temperature. THF (13.8 mL) and 1,2-dibromoethane (0.045 mL, 0.518 mmol) were added via syringe and the reaction mixture was heated at 60° C. until bubbling occurred. After cooling to room temperature, chlorotrimethylsilane (0.040 mL, 0.311 mmol) and a solution of iodine (0.026 g, 0.104 mmol) in THF (0.2 mL) were added via syringe. The reaction mixture was heated at 60° C. for 20 min and then cooled to room temperature. 2-Bromo-5,8-dioxaspiro[3.4]octane (1.3 mL, 10 mmol) was added and the reaction was stirred at 50° C. for 16 h. The resulting solution was used as is.

Intermediate C: (3-(Trifluoromethyl)Cyclobutyl) Zinc(II) Bromide, 0.15 M in THF

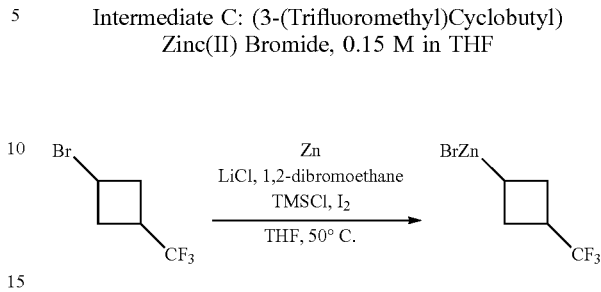

This intermediate was synthesized in the same manner and stoichiometry as Intermediate B using 1-bromo-3-(trifluoromethyl)cyclobutane (2.00 g, 9.85 mmol).

Intermediate D: Perfluorophenyl (P)-1-(4-Bromo-2-Methoxyphenyl)-2-Oxo-1,2-Dihydroquinoline-6-Sulfonate

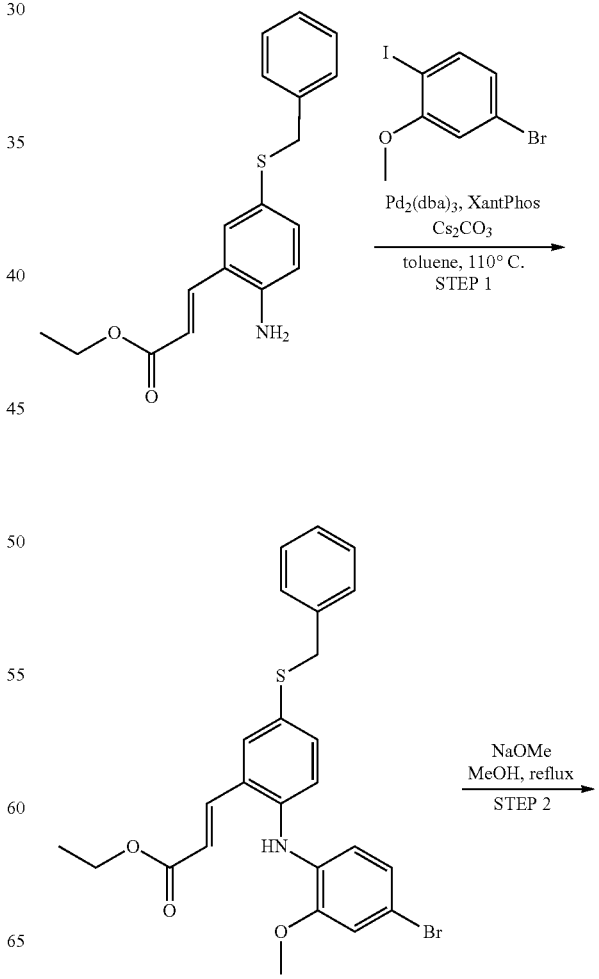

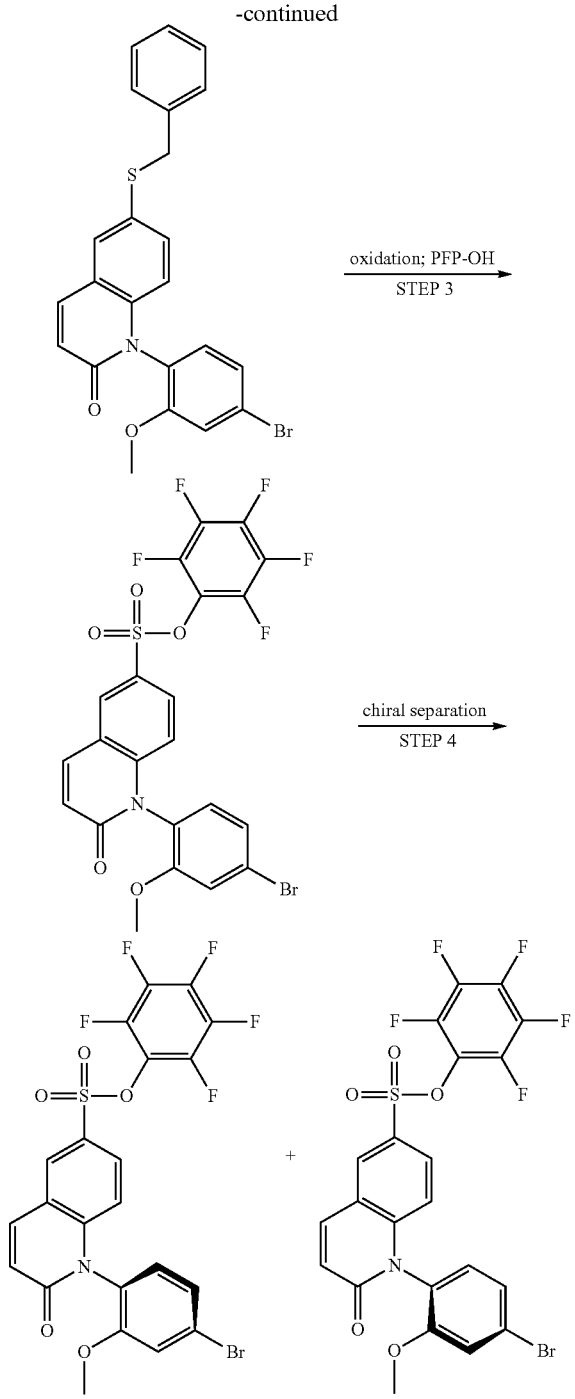

Step 1: (E)-Ethyl 3-(5-(Benzylthio)-2-((4-Bromo-2-Methoxyphenyl)Amino)Phenyl)Acrylate A round-bottom flask was charged with (E)-ethyl 3-(2-amino-5-(benzylthio)phenyl)acrylate (2.39 g, 7.63 mmol), 4-bromo-1-iodo-2-methoxybenzene (2.86 g, 9.15 mmol), XantPhos (0.221 g, 0.381 mmol), tris(dibenzylideneacetone)dipalladium(0) (0.175 g, 0.191 mmol), and cesium carbonate (4.97 g, 15.25 mmol) were added. A reflux condenser was attached, and the flask was lowered into a 110° C. heating bath. After 2 h, an additional portion of cesium carbonate (1.4 g) was added, and the bath temperature was raised to 120° C. The mixture was heated for another 2 h then cooled to room temperature, diluted with EtOAc, and filtered through CELITE with the aid of EtOAc. The filtrate was concentrated. The oily residue was taken up in 2-PrOH. The mixture was concentrated to give a yellow solid with some oily solid present. The mixture was taken up in 2-PrOH to give a suspension, and the suspension was stirred for 16 h. The mixture was filtered, and the filtered solid was washed with 2-PrOH (3×). The collected solid was dried on the filter under a flow of $N_2$ for 15 min to give (E)-ethyl 3-(5-(benzylthio)-2-((4-bromo-2-methoxyphenyl)amino)phenyl)acrylate (3.136 g, 6.29 mmol, 83% yield) as a bright-yellow solid. $^1$H NMR (400 MHz, DMSO-$d_6$) δ ppm 7.72 (d, J=16.0 Hz, 1H), 7.68 (d, J=2.2 Hz, 1H), 7.47 (s, 1H), 7.37-7.19 (m, 6H), 7.13 (d, J=2.2 Hz, 1H), 6.94 (dd, J=2.2, 8.4 Hz, 1H), 6.86 (d, J=8.5 Hz, 1H), 6.55 (s, 1H), 6.52 (d, J=7.7 Hz, 1H), 4.24 (s, 2H), 4.15 (q, J=7.1 Hz, 2H), 3.82 (s, 3H), 1.23 (t, J=7.1 Hz, 3H). m/z (ESI) 498.0 (M+H)$^+$.

STEP 2: 6-(Benzylthio)-1-(4-Bromo-2-Methoxyphenyl)Quinolin-2(1H)-One

A round-bottom flask was charged with (E)-ethyl 3-(5-(benzylthio)-2-((4-bromo-2-methoxyphenyl)amino)phenyl)acrylate (3.13 g, 6.28 mmol) and MeOH (31.4 mL) to give a yellow suspension. Sodium methoxide (25 wt % in MeOH, 0.271 mL, 1.256 mmol) was added. A reflux condenser was attached, and the flask was lowered into a 75° C. heating bath. The bath quickly spiked to ca. 80-85° C., but returned to 70-75° C. after 30 min. The reaction was stirred for 16 h, and the mixture was diluted with DCM and concentrated. The residue was purified by chromatography on silica gel (50-g SNAP Ultra column, 25-g silica gel loading column, 10-60% EtOAc/Heptane) to give 6-(benzylthio)-1-(4-bromo-2-methoxyphenyl)quinolin-2(1H)-one (1.95 g, 4.31 mmol, 69% yield) as a yellow solid. $^1$H NMR (400 MHz, DMSO-$d_6$) δ ppm 7.94 (d, J=9.5 Hz, 1H), 7.78 (d, J=2.2 Hz, 1H), 7.50 (d, J=2.1 Hz, 1H), 7.43-7.16 (m, 8H), 6.66 (d, J=9.6 Hz, 1H), 6.47 (d, J=8.8 Hz, 1H), 4.23 (s, 2H), 3.69 (s, 3H). m/z (ESI) 452.0 (M+H)$^+$.

Step 3: Perfluorophenyl 1-(4-Bromo-2-Methoxyphenyl)-2-Oxo-1,2-Dihydroquinoline-6-Sulfonate A round-bottom flask was charged with 6-(benzylthio)-1-(4-bromo-2-methoxyphenyl)quinolin-2(1H)-one (1.777 g, 3.93 mmol), acetonitrile (18.49 mL), acetic acid (0.693 mL), and water (0.462 mL) to give a solution. The flask was cooled in an ice-water bath for 10 min, then 1,3-dichloro-5,5-dimethylimidazolidine-2,4-dione (0.813 g, 4.12 mmol) was added in one portion. After 20 min, an additional portion of 1,3-dichloro-5,5-dimethylimidazolidine-2,4-dione (0.813 g, 4.12 mmol) was added in one portion. After another 20 min, 2,3,4,5,6-pentafluorophenol (1.085 g, 5.89 mmol) was added, and the mixture was stirred for 5 min. Triethylamine (2.190 mL, 15.71 mmol) was added dropwise over 30 s then the mixture was stirred for 20 min. The reaction mixture was diluted with water and extracted with DCM (3×). The combined organic extracts were dried over sodium sulfate, filtered, and concentrated. The residue was purified by chromatography on silica gel (50-g SNAP Ultra column, 25-g silica gel loading column, 10-60% EtOAc/Heptane). Perfluorophenyl 1-(4-bromo-2-methoxyphenyl)-2-oxo-1,2-dihydroquinoline-6-sulfonate (1.644 g, 2.85 mmol, 72.6% yield) was isolated as a white foam. $^1$H NMR (400 MHz, DMSO-$d_6$) δ ppm 8.59 (d, J=2.2 Hz, 1H), 8.24 (d, J=9.6 Hz, 1H), 7.95 (dd, J=2.3, 9.1 Hz, 1H), 7.56 (d, J=1.9 Hz, 1H), 7.44-7.26 (m, 2H), 6.86 (dd, J=9.4, 13.7 Hz, 2H), 3.72 (s, 3H). m/z (ESI) 575.9 (M+H)⁺.

Step 4: Perfluorophenyl (P)-1-(4-Bromo-2-Methoxyphenyl)-2-Oxo-1,2-Dihydroquinoline-6-Sulfonate and Perfluorophenyl (M)-1-(4-Bromo-2-Methoxyphenyl)-2-Oxo-1,2-Dihydroquinoline-6-Sulfonate Racemic perfluorophenyl 1-(4-bromo-2-methoxyphenyl)-2-oxo-1,2-dihydroquinoline-6-sulfonate (3000 g) was separated in 5 600-g batches using a Regis Whelk-O (S,S), 3×15 cm column. The mobile phase was run under isocratic conditions; supercritical $CO_2$ with 60% [2:3 isopropanol:dichloromethane]; flow rate: 150 mL/min. The first eluting peak was assigned perfluorophenyl (P)-1-(4-bromo-2-methoxyphenyl)-2-oxo-1,2-dihydroquinoline-6-sulfonate (1459.2 g). The second eluting peak was assigned perfluorophenyl (M)-1-(4-bromo-2-methoxyphenyl)-2-oxo-1,2-dihydroquinoline-6-sulfonate (1492.9 g).

Step 5: (P)-1-(4-Bromo-2-Methoxyphenyl)-N-(Isoxazol-3-Yl)-2-Oxo-1,2-Dihydroquinoline-6-Sulfonamide Racemic 1-(4-bromo-2-methoxyphenyl)-N-(isoxazol-3-yl)-2-oxo-1,2-dihydroquinoline-6-sulfonamide (400 mg) was purified using a (S,S) Whelk-O, 2×15 cm column. The mobile phase was run under isocratic conditions; supercritical $CO_2$ with 60% isopropanol; flow rate: 80 mL/min. The first eluting peak was assigned (M)-1-(4-bromo-2-methoxyphenyl)-N-(isoxazol-3-yl)-2-oxo-1,2-dihydroquinoline-6-sulfonamide (150 mg). The second eluting peak was assigned (P)-1-(4-bromo-2-methoxyphenyl)-N-(isoxazol-3-yl)-2-oxo-1,2-dihydroquinoline-6-sulfonamide (154 mg). Data for peak 1: ¹H NMR (400 MHz, ACETONITRILE-$d_3$) δ ppm 8.65-8.94 (m, 1H), 8.37 (d, J=1.9 Hz, 1H), 8.23 (d, J=2.3 Hz, 1H), 7.97 (d, J=9.3 Hz, 1H), 7.78 (dd, J=8.9, 2.3 Hz, 1H), 7.43 (d, J=2.1 Hz, 1H), 7.34 (dd, J=8.3, 2.1 Hz, 1H), 7.16 (d, J=8.3 Hz, 1H), 6.70-6.80 (m, 2H), 6.45 (d, J=1.9 Hz, 1H), 3.69 (s, 3H). m/z (ESI, positive ion) 476.0 (M+H)⁺. Data for peak 2: ¹H NMR (400 MHz, ACETONITRILE-$d_3$) δ ppm 8.72-8.87 (m, 1H), 8.37 (d, J=1.7 Hz, 1H), 8.23 (d, J=2.1 Hz, 1H), 7.97 (d, J=9.5 Hz, 1H), 7.78 (dd, J=9.0, 2.2 Hz, 1H), 7.43 (d, J=2.1 Hz, 1H), 7.34 (dd, J=8.3, 1.9 Hz, 1H), 7.16 (d, J=8.3 Hz, 1H), 6.69-6.80 (m, 2H), 6.45 (d, J=1.9 Hz, 1H), 3.69 (s, 3H). m/z (ESI, positive ion) 476.0 (M+H)⁺.

Intermediate E:
N-(4-Methoxybenzyl)Isoxazol-3-Amine

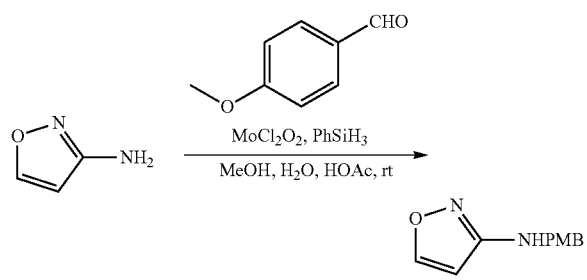

To a 20-L round-bottom flask was added isoxazol-3-amine (150 g, 1784 mmol) and 4-methoxybenzaldehyde (274 g, 2016 mmol) in methanol (9000 mL), water (150 mL), and acetic acid (101 mL) and stirred for 15 min at room temperature. Then molybdenum dichloride dioxide (17.74 g, 89 mmol) and phenylsilane (193 g, 1784 mmol) were added. The reaction mixture was stirred at room temperature for 16 h. After completion of the reaction, the reaction mass was concentrated, diluted with dichloromethane (5000 mL) and washed with sat. aq. $NaHCO_3$ (2000 mL). The organic layer was washed with water (2000 mL) and dried over $Na_2SO_4$. The solution was filtered and concentrated in vacuo to give the initial product as an orange solid. The initial product was absorbed onto a plug of silica gel and purified by column chromatography (Silica gel, 60-120 mesh) eluting with a gradient of 0% to 30% EtOAc in hexane, to provide N-(4-methoxybenzyl)isoxazol-3-amine (272 g, 1332 mmol, 75% yield) as an off-white solid. ¹H NMR (400 MHz, DMSO-$d_6$) δ ppm 8.36 (d, J=1.8 Hz, 1H), 7.16-7.37 (m, 2H), 6.71-6.97 (m, 2H), 6.56 (t, J=6.0 Hz, 1H), 5.97 (d, J=1.8 Hz, 1H), 4.18 (d, J=6.0 Hz, 2H), 3.73 (s, 3H). m/z (ESI, positive ion) 205.1 (M+H)⁺.

Intermediate F: (P)-1-(4-Bromo-5-Fluoro-2-Methoxyphenyl)-N-(Isoxazol-3-Yl)-N-(4-Methoxybenzyl)-2-Oxo-1,2-Dihydroquinoline-6-Sulfonamide

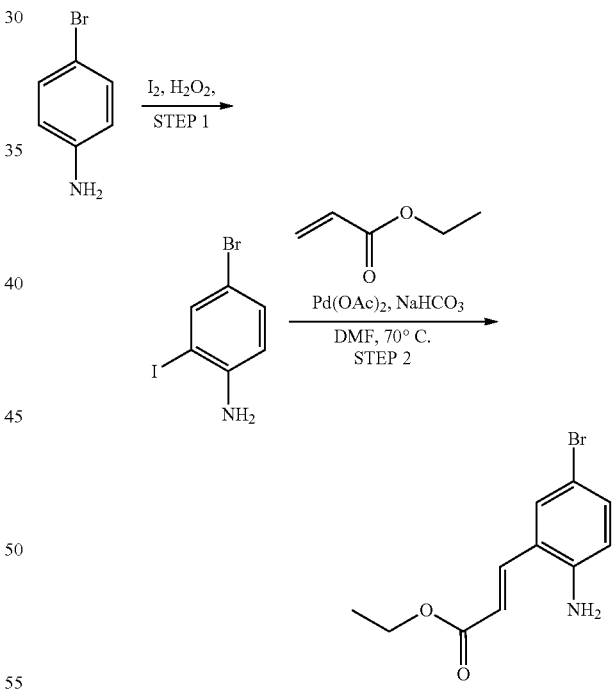

Step 1: 4-Bromo-2-Iodoaniline

To a solution of 4-bromo-aniline (500 g, 2.90 mol, 2.0 equiv, Saibain Chem) in cyclohexane (2.5 L) was added iodine (368 g, 1.45 mol, 1.0 equiv, Qualigens) and the mixture was heated at 50° C. After 30 min, the reaction mixture became homogenous. 30% aqueous hydrogen peroxide solution (250 mL, Spectrochem) was added to the reaction mixture. The reaction was heated for 4 h at 50° C. The reaction was cooled to room temperature, diluted with ethyl acetate (5.0 L) and washed with aqueous sodium-sulphite (2.5 Kg in 4.0 L) solution. The organic layer was washed with water (3.0 L) and brine (3.0 L) dried over magnesium sulfate, filtered and concentrated under reduced pressure to obtain the initial product which was purified by column chromatography (silica gel; mesh size 60-120, elution 0-20% ethyl acetate and hexanes) to get 4-bromo-2-iodoaniline (650 g, 75.0%), as off white solid. TLC solvent system: 100% hexanes. Product's $R_f$: 0.6. MS (ESI, positive ion) m/z: 297.0 (M+1). $^1$H NMR (400 MHz, CDCl$_3$) δ 7.72 (d, J=2.5 Hz, 1H), 7.23 (dd, J=8.4, 2.1 Hz, 1H), 6.62 (d, J=8.3 Hz, 1H), 4.09 (s, 2H).

Step 2: Ethyl (E)-3-(2-Amino-5-Bromophenyl)Acrylate

To a solution of 4-bromo-2-iodoaniline (750 g, 2.51 mol, 1.0 equiv) in DMF (5.0 L) was added ethyl acrylate (277 g, 2.76 mol, 1.1 equiv, Avra) and sodium bicarbonate (680 g, 6.29 mol, 2.5 equiv). The reaction mixture was degassed with nitrogen for 20 min followed by the addition of palladium acetate (28.8 g, 128.27 mmol, 0.05 equiv, Hindustan Platinum). The reaction mixture was heated at 70° C. for 3 h. The reaction was filtered through CELITE® and the CELITE® bed was washed with ethyl acetate (2×500 mL). The filtrate was concentrated under reduced pressure to obtain the initial product which was purified by column chromatography (silica gel; mesh size 60-120, elution 0-20% ethyl acetate in hexanes) to obtain (E)-ethyl 3-(2-amino-5-bromophenyl)acrylate (620 g, 77.0%), as yellow solid. TLC solvent system: 20% ethyl acetate in hexanes. Product's $R_f$: 0.4. MS (ESI, positive ion) m/z; 270.2 (M+1). $^1$H NMR (400 MHz, DMSO) δ 7.75 (d, J=16.1 Hz, 1H), 7.57 (d, J=2.0 Hz, 1H), 7.16 (dd, J=9.1, 2.4 Hz, 1H), 6.66 (d, J=8.6 Hz, 1H), 6.43 (d, J=8.6 Hz, 1H), 5.81 (s, 2H), 4.20 (q, J=7.2 Hz, 2H), 1.27 (t, J=7.2 Hz, 3H).

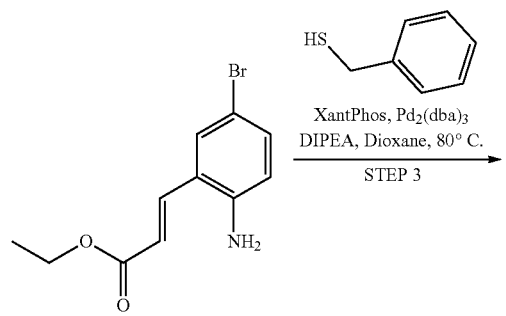

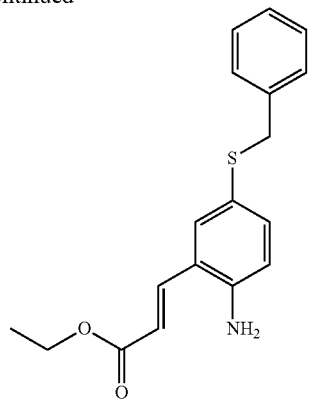

Step 3: Ethyl (E)-3-(2-Amino-5-(Benzylthio)Phenyl)Acrylate

To a solution of (E)-ethyl 3-(2-amino-5-bromophenyl)acrylate (620 g, 2.29 mol, 1.0 equiv) in 1,4-dioxane (4.0 L) was added DIPEA (1.26 L, 8.88 mol, 3.9 equiv, GLR) and degassed with nitrogen for 20 mins. XantPhos (92.9 g, 106 mmol, 0.05 equiv, GLR), and tris(dibenzylideneacetone)dipalladium (84 g, 91.0 mmol, 0.04 equiv, Hindustan Platinum) was added to the reaction mixture. The mixture was purged with nitrogen and heated to 80° C. for 30 mins. The reaction was cooled to RT and benzyl mercaptan (455.5 g, 3.67 mol, 1.6 equiv, Alfa Aesar) was added and the reaction was heated at 80° C. for an additional 4 h. The reaction was cooled to room temperature and diluted with ethyl acetate (4.0 L). The mixture was filtered through CELITE® and the CELITE® bed was washed with ethyl acetate (2×1.0 L). The filtrate was concentrated under reduced pressure to obtain the initial product which was purified by chromatography (silica gel; mesh size 60-120, elution 0-40% ethyl acetate and petroleum ether) to obtain (E)-ethyl 3-(2-amino-5-(benzylthio)phenyl)acrylate (520 g, 72.0%), as yellow solid. TLC solvent system: 30% ethyl acetate in hexanes. Product's $R_f$: 0.4. MS (ESI, positive ion) m/z; 314.1 (M+1). $^1$H NMR (400 MHz, DMSO) δ 7.79 (d, J=16.1 Hz, 1H), 7.37 (d, J=2.0 Hz, 1H), 7.25-7.17 (m, 5H) 7.10 (dd, J=8.4, 2.1 Hz, 1H), 6.61 (d, J=8.3 Hz, 1H), 6.32 (d, J=15.2 Hz, 1H), 5.75 (s, 2H), 4.20 (q, J=7.2 Hz, 2H), 4.01 (s, 2H), 1.27 (t, J=7.2 Hz, 3H).

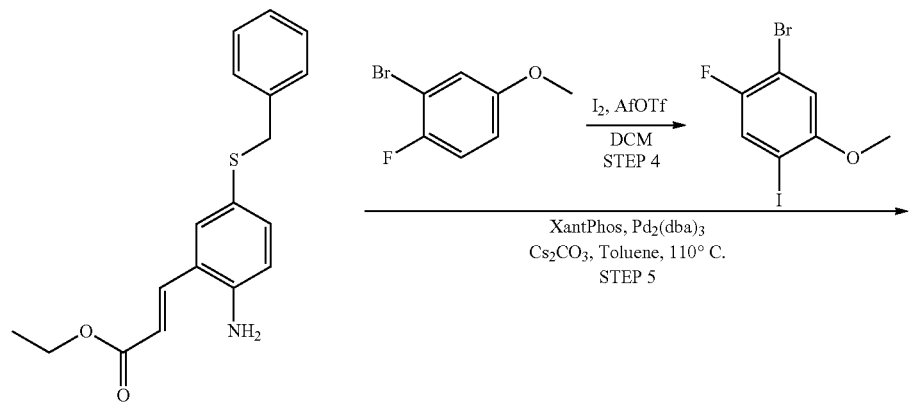

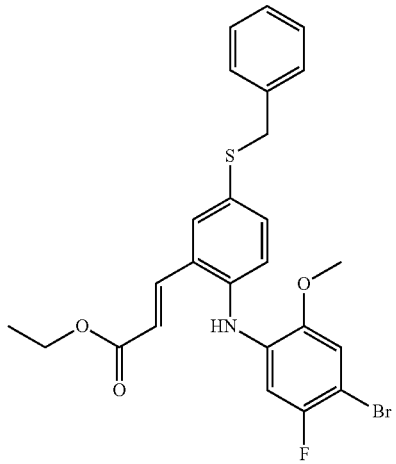

Step 4: 1-Bromo-2-Fluoro-4-Iodo-5-Methoxybenzene

To a solution of 2-bromo-1-fluoro-4-methoxybenzene (500.0 g, 2.44 mol, 1.0 equiv) in DCM (5.0 L) was added silver trifluoromethane sulfonate (686.0 g, 2.68 mol, 1.1 equiv, Angene) and the reaction mixture was stirred for 20 mins. Iodine (678.0 g, 2.68 mol, 1.1 equiv) was added to the reaction and the mixture was stirred at room temperature for 16 h. The mixture was diluted with DCM (3.0 L) and filtered through CELITE®. The CELITE bed was washed with DCM (2×1.0 L) and the filtrate was washed with 20% aqueous sodium thiosulfate (3.0 L) and saturated aqueous sodium bicarbonate solution (3.0 L). The organic layer was dried over sodium sulfate, filtered and concentrated under reduced pressure to obtain the initial product which was purified by chromatography (silica gel; mesh size 60-120, elution 0-5% ethyl acetate and petroleum ether) to get 1-bromo-2-fluoro-4-iodo-5-methoxybenzene (720 g, 87%), as off-white solid. TLC solvent system: 100% hexanes. Product's $R_f$: 0.6. MS (ESI, positive ion) m/z: 331.0 (M+1). $^1$H NMR (400 MHz, CDCl$_3$) δ 7.55 (d, J=7.2 Hz, 1H), 6.95 (d, J=5.6 Hz, 1H), 3.89 (s, 3H).

Step 5: Ethyl (E)-3-(5-(Benzylthio)-2-((4-Bromo-5-Fluoro-2-Methoxyphenyl)Amino)Phenyl) Acrylate To a solution of (E)-ethyl 3-(2-amino-5-(benzylthio)phenyl)acrylate (300 g, 958.1 mmol, 1.0 equiv) and 1-bromo-2-fluoro-4-iodo-5-methoxybenzene (348.0 g, 1051.6 mmol, 1.1 equiv) in toluene (2.5 L) was added Cs$_2$CO$_3$ (468 g, 1436.3 mmol, 1.5 equiv, Spectrochem) and the mixture was degassed with nitrogen for 20 mins. Pd$_2$(dba)$_3$ (35 g, 38.2 mmol, 0.04 equiv, Hindustan Platinum) and XantPhos (44.6 g, 76.4 mmol, 0.08 equiv, GLR) were added to the reaction mixture and the mixture was heated at 110° C. for 5 h. The reaction mixture was allowed to cool to room temperature, diluted with dichloromethane (2.0 L) and filtered through CELITE® The filtrate was concentrated under reduced pressure to obtain the initial product which was purified by stirring with 5% ethyl acetate in hexanes (3.0 L) for 30 min and filtered to obtain (E)-ethyl 3-(5-(benzylthio)-2-((4-bromo-5-fluoro-2-methoxyphenyl)amino)phenyl)acrylate (350 g, 71%) as yellow solid. TLC solvent system: 30% ethyl acetate in hexanes. Product's $R_f$: 0.5. MS (ESI, positive ion) m/z: 516.2 (M+1). $^1$H NMR (400 MHz, DMSO) δ 7.73-7.61 (m, 3H), 7.34-7.15 (m, 6H), 7.02 (d, J=11.4 Hz, 1H), 6.60 (d, J=21.2 Hz, 1H), 6.33 (d, J=14.1 Hz, 1H), 4.26 (s, 2H), 4.16-4.09 (m, 2H), 3.81 (s, 3H), 1.22 (t, J=7.2 Hz, 3H). Note: NH proton not observed.

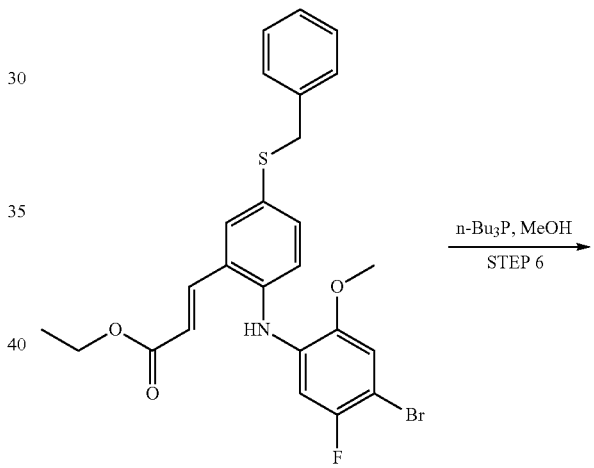

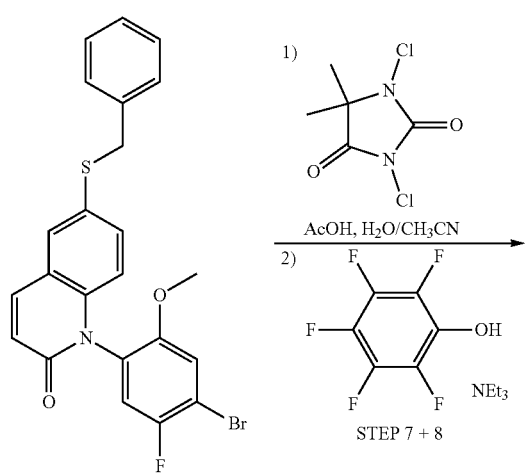

Step 6: 6-(Benzylthio)-1-(4-Bromo-5-Fluoro-2-Methoxyphenyl) Quinolin-2(1H)-One

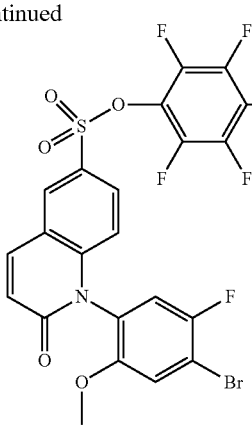

To a solution of (E)-ethyl 3-(5-(benzylthio)-2-((4-bromo-5-fluoro-2-methoxyphenyl)amino)phenyl)acrylate (250.0 g, 484.0 mmol, 1.0 equiv) in methanol (2.5 L) was added tri(n-butyl)phosphine (50% solution in ethyl acetate, 48.9 mL, 96.8 mmol, 0.2 equiv, Spectrochem) and the reaction mixture was heated at 70° C. for 5 h. The reaction mixture was allowed to cool to rt, concentrated under reduced pressure to obtain the initial product which was purified by stirring with 5% ethyl acetate in hexanes (1.0 mL) and filtered to obtain 6-(benzylthio)-1-(4-bromo-5-fluoro-2-methoxyphenyl)quinolin-2(1H)-one (201.0 g, 88%) as off white solid. TLC solvent system: 30% ethyl acetate in hexanes. Product's $R_f$: 0.3. MS (ESI, positive ion) m/z; 470.0 (M+1). $^1$H NMR (400 MHz, DMSO) δ 7.92 (d, J=9.1 Hz, 1H), 7.79 (d, J=1.7 Hz, 1H), 7.65 (d, J=6.1 Hz, 1H), 7.57 (d, J=8.8 Hz, 1H), 7.40-7.22 (m, 6H), 6.68 (d, J=9.6 Hz, 1H), 6.56 (d, J=8.8 Hz, 1H), 4.24 (s, 2H), 3.69 (s, 3H).

Steps 7+8: Perfluorophenyl 1-(4-Bromo-5-Fluoro-2-Methoxyphenyl)-2-Oxo-1,2-Dihydroquinoline-6-Sulfonate To a solution of 6-(benzylthio)-1-(4-bromo-5-fluoro-2-methoxyphenyl)quinolin-2(1H)-one (250.0 g, 531.5 mmol, 1.0 equiv) in acetonitrile (2.5 L) were added acetic acid (200 mL) and water (130 mL). The resulting mixture was cooled to 0° C. and 1,3-dichloro-5,5-dimethylimidazolidine-2,4-dione (188.5 g, 956.7 mmol, 1.8 equiv, Aldrich) was added portion-wise over 20 min keeping the internal temperature below 5° C. The resulting suspension was stirred at 0-5° C. under nitrogen for 45 min. Then a solution of pentafluorophenol (127.2 g, 690.95 mmol, 1.3 equiv, Apollo) in acetonitrile (200 mL) was added over 5 min followed by NEt$_3$ (307.7 mL, 2.12 mol, 4.0 equiv) over 20 min keeping the internal temperature below 5° C. The mixture was continued to be stirred at 0-5° C. for 30 min. Water (4.0 L) was added and extracted with ethyl acetate (2×2.0 L). The organic layer was washed with brine (1.0 L), dried over sodium sulfate, filtered and concentrated under reduced pressure to obtain the initial material which was purified by stirring with isopropyl alcohol:hexanes (1:1, 1.0 L) and filtered to obtain racemic perfluorophenyl 1-(4-bromo-5-fluoro-2-methoxyphenyl)-2-oxo-1,2-dihydroquinoline-6-sulfonate (190 g, 60%) as white solid. TLC solvent system: 30% ethyl acetate in pet ether, Product's $R_f$: 0.4. MS (ESI, positive ion) m/z; 594.2 (M+1). $^1$H-NMR (400 MHz, DMSO) δ 8.60 (d, J=2.0 Hz, 1H), 8.26 (d, J=9.8 Hz, 1H), 7.95 (dd, J=2.2, 9.1 Hz, 1H), 7.70 (t, J=8.6 Hz, 2H), 6.95-6.88 (m, 2H), 3.72 (s, 3H).

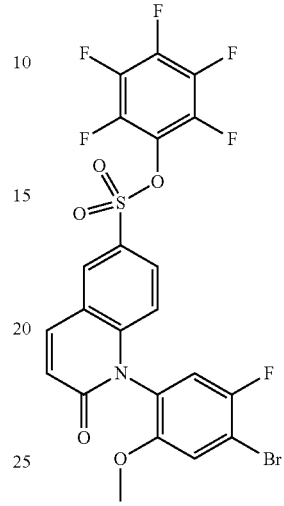

chiral separation
STEP 9
⟶

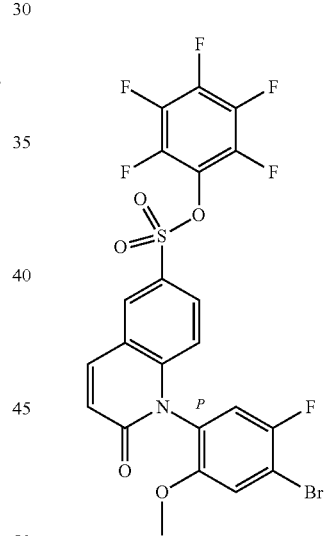 + 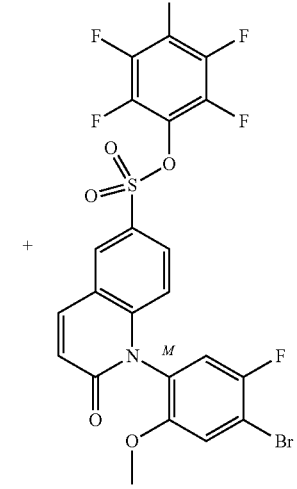

Step 9: (P)-1-(4-Bromo-5-Fluoro-2-Methoxyphenyl)-N-(Isoxazol-3-Yl)-2-Oxo-1,2-Dihydroquinoline-6-Sulfonamide Racemic perfluorophenyl 1-(4-bromo-5-fluoro-2-methoxyphenyl)-2-oxo-1,2-dihydroquinoline-6-sulfonate was separated via Chiralcel OJ column (40% MeOH/60% CO$_2$) to give (P)-perfluorophenyl 1-(4-bromo-5-fluoro-2-methoxyphenyl)-2-oxo-1,2-dihydroquinoline-6-sulfonate and (M)-perfluorophenyl 1-(4-bromo-5-fluoro-2-methoxyphenyl)-2-oxo-1,2-dihydroquinoline-6-sulfonate as pale yellow flocculent solids. Data for peak 1: m/z (ESI) 594.0 (M+H)$^+$. Data for peak 2: m/z (ESI) 594.0 (M+H)$^+$.

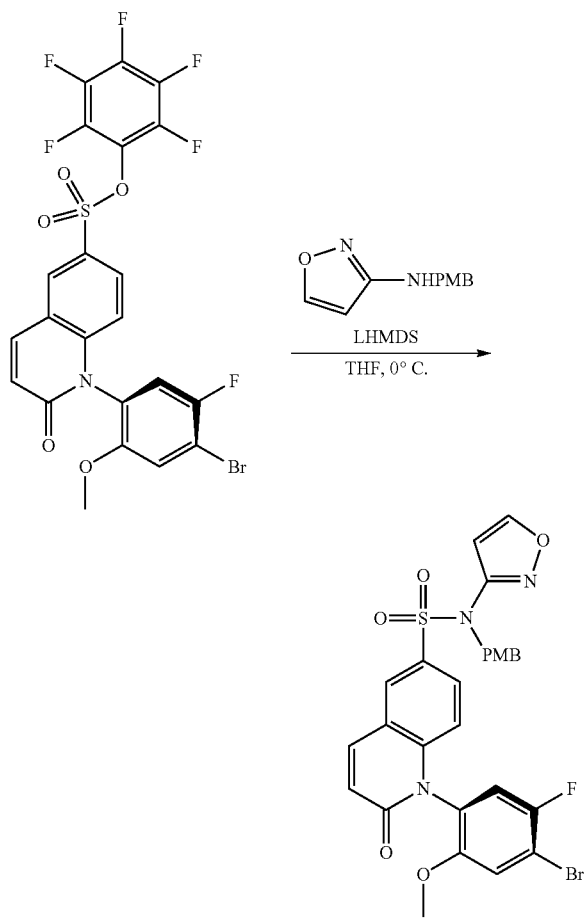

Step 10: (P)-L-(4-Bromo-5-Fluoro-2-Methoxyphenyl)-N-(Isoxazol-3-Yl)-N-(4-Methoxybenzy 1)-2-Oxo-1,2-Dihydroquinoline-6-Sulfonamide A 250-mL round-bottom flask was charged with (P)-perfluorophenyl 1-(4-bromo-5-fluoro-2-methoxyphenyl)-2-oxo-1,2-dihydroquinoline-6-sulfonate (11.34 g, 19.08 mmol) and N-(4-methoxybenzyl)isoxazol-3-amine (4.09 g, 20.04 mmol), then purged with nitrogen. Tetrahydrofuran (191 mL) was introduced, and the resultant brown solution cooled to 0° C. A solution of lithium bis(trimethylsilyl) amide (1.0 M in THF, 21.0 mL, 21.0 mmol) was added dropwise via syringe to the stirred reaction mixture over 10 min. After 15 min, 1.0 N HCl (100 mL) was introduced and the resultant reaction mixture was allowed to warm to rt. The mixture was diluted with and EtOAc (100 mL) and the layers were separated, and the aqueous layer was further extracted with EtOAc (2×100 mL). The combined organic layers were then washed with brine (100 mL), dried over anhydrous sodium sulfate, filtered, and concentrated under reduced pressure. The residue was then purified by flash column chromatography (100-g BIOTAGE® column, eluent: gradient, 0 to 100% EtOAc in heptane with 10% CH$_2$Cl$_2$ as an additive) to afford (P)-1-(4-bromo-5-fluoro-2-methoxyphenyl)-N-(isoxazol-3-yl)-N-(4-methoxybenzy 1)-2-oxo-1,2-dihydroquinoline-6-sulfonamide (9.54 g, 15.53 mmol, 81% yield) as a white amorphous solid. $^1$H NMR (400 MHz, DMSO-d$_6$) δ ppm 8.82 (d, J=2.0 Hz, 1H), 8.38 (d, J=2.3 Hz, 1H), 8.17 (d, J=9.4 Hz, 1H), 7.76 (t, J=5.1 Hz, 1H), 7.68 (d, J=6.1 Hz, 1H), 7.63 (d, J=8.5 Hz, 1H), 7.26 (d, J=7.9 Hz, 2H), 6.91-6.78 (m, 4H), 6.74 (d, J=2.0 Hz, 1H), 4.92 (s, 2H), 3.73-3.69 (m, 6H), 3.32 (s, 1H). m/z (ESI) 615.1 (M+H)$^+$.

Intermediate G:
1-Bromo-2-Chloro-4-Iodo-5-Methoxybenzene

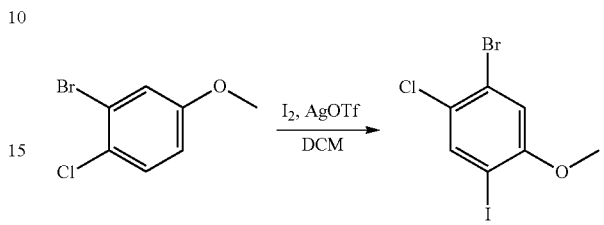

To a solution of 2-bromo-1-chloro-4-methoxybenzene (500 g, 2258 mmol) in dichloromethane (7500 mL) was added silver(I) trifluoromethanesulfonate (638 g, 2483 mmol) at ambient temperature under nitrogen environment. The reaction mixture was stirred for 20 mins at ambient temperature and iodine (630 g, 2483 mmol) was added. The reaction mixture was stirred at ambient temperature for 16 h. The mixture was then diluted with DCM (4500 mL) and filtered through CELITE. The CELITE bed was washed with DCM (2×1.0 L). The filtrate was washed with 20% aqueous sodium thiosulfate (5.0 L) and saturated aqueous sodium bicarbonate solution (5.0 L). The organic layer was dried over sodium sulfate, filtered and concentrated under reduced pressure to obtain the initial product which was purified by column chromatography (silica gel; mesh size 60-120, elution 0-5% ethyl acetate and petroleum ether) to afford 1-bromo-2-chloro-4-iodo-5-methoxybenzene (610 g, 1756 mmol, 78% yield) as off-white solid. $^1$H NMR (400 MHz, CDCl$_3$) δ ppm 7.83 (s, 1H), 7.03 (s, 1H), 3.89 (s, 3H).

Intermediate H:
N-(4-Methoxybenzyl)Pyrimidin-2-Amine

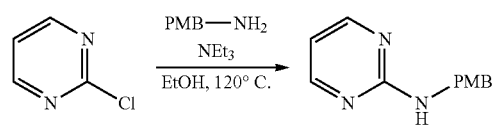

In a 50-mL microwave vial were successively dissolved in EtOH (20 mL), 2-chloropyrimidine (1.5 g, 13.10 mmol), (4-methoxyphenyl)methanamine (2.15 g, 15.72 mmol, 1.2 equiv), and triethylamine (2.65 g, 26.2 mmol, 2.0 equiv). The reaction tube was sealed and irradiated in the cavity of a microwave reactor at a ceiling temperature of 120° C. at 80 W maximum power for 1 h. After the reaction mixture was cooled with an air flow for 15 min, it was diluted with water (100 mL), extracted with CH$_2$Cl$_2$ (2×150 mL) and dried over Na$_2$SO$_4$. The reaction mixture was diluted with water (50 mL) and extracted with ethyl acetate (2×50 mL). The organic extract was washed with sat. aq. NaCl (1×50 mL) and dried over Na$_2$SO$_4$. The solution was filtered and concentrated in vacuo to give the initial product as a yellow oil. The initial product was absorbed onto a plug of silica gel and purified by chromatography through a Redi-Sep prepacked silica gel column (12 g), eluting with a gradient of 20% to 30% EtOAc in hexane, to provide N-(4-methoxybenzyl)pyrimidin-2-amine (1.5 g, 6.97 mmol, 53% yield) as an off white solid. m/z (ESI) 216.2 (M+H)+.

Intermediate I: (P)-1-(4-Bromo-5-Chloro-2-Methoxyphenyl)-N-(4-Methoxybenzyl)-2-Oxo-N-(Pyrimidin-2-Yl)-1,2-Dihydroquinoline-6-Sulfonamide

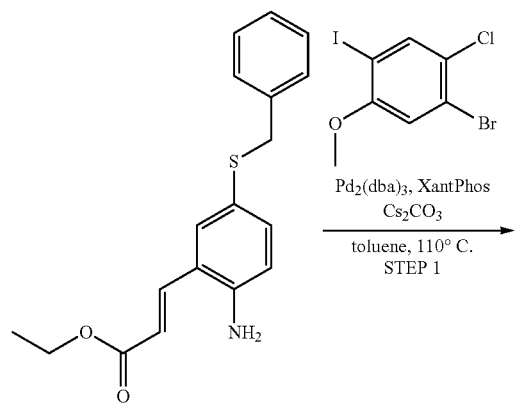

Pd$_2$(dba)$_3$, XantPhos
Cs$_2$CO$_3$
toluene, 110° C.
STEP 1

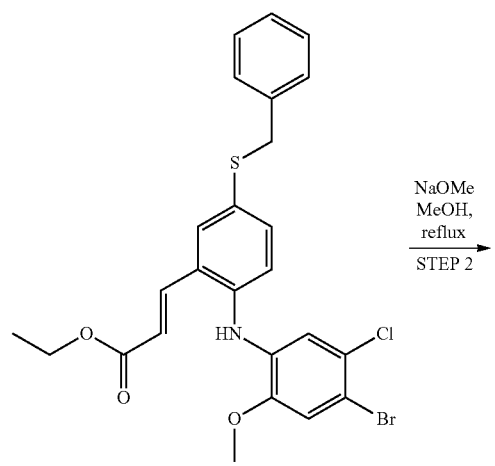

NaOMe
MeOH,
reflux
STEP 2

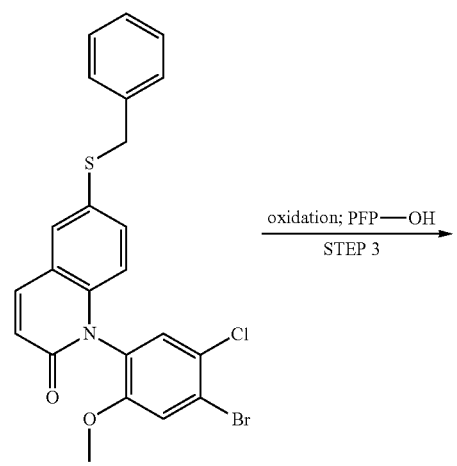

oxidation; PFP—OH
STEP 3

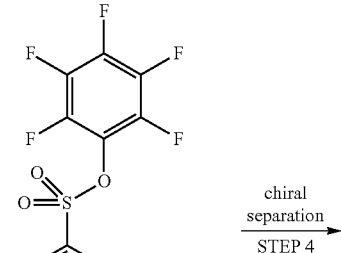

chiral separation
STEP 4

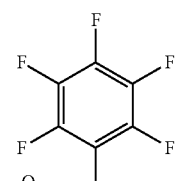 + 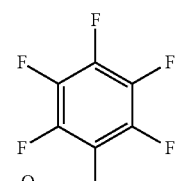

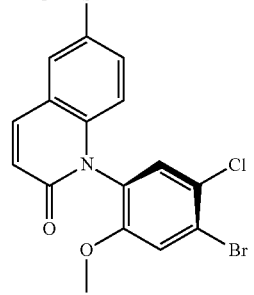 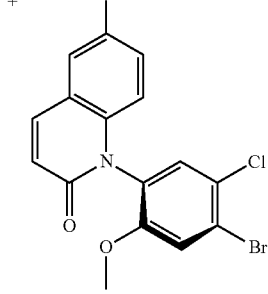

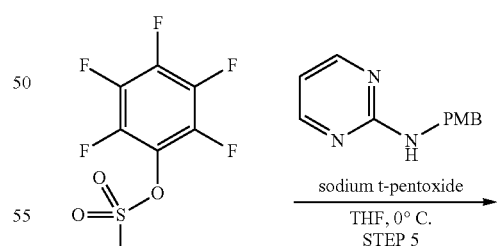

sodium t-pentoxide
THF, 0° C.
STEP 5

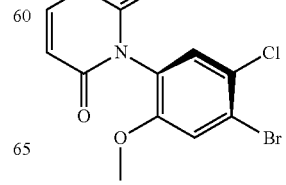

-continued

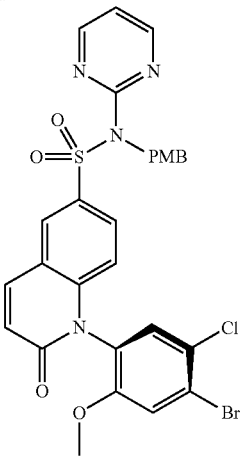

Step 1: (E)-3-(5-(Benzylthio)-2-((4-Bromo-5-Chloro-2-Methoxyphenyl)Amino)Phenyl)Acrylate To a solution of ethyl (E)-3-(2-amino-5-(benzylthio)phenyl)acrylate (175 g, 555.0 mmol) and 1-bromo-2-chloro-4-iodo-5-methoxybenzene (231.3 g, 666.2, mmol) in toluene (1.5 L) was added cesium carbonate (357.5 g, 1100 mmol) and the mixture was degassed with nitrogen for 20 mins. tris(dibenzylideneacetone)dipalladium(0) (12.5 g, 13.0 mmol) and XantPhos (15.8 g, 27.2 mmol, 0.05 equiv) were added to the reaction mixture and the mixture was heated at 110° C. for 5 h. The reaction mixture was allowed to cool to room temperature, diluted with dichloromethane (1.0 L) and filtered through CELITE. The filtrate was concentrated under reduced pressure to obtain the initial product which was purified by stirring with 5% ethyl acetate in hexane (1.5 L) for 30 min and filtered to obtain ethyl (E)-3-(5-(benzylthio)-2-((4-bromo-5-chloro-2-methoxyphenyl)amino)phenyl)acrylate (290 g, 85% yield) as yellow solid. m/z (ESI) 532.2 (M+H)$^+$.

Step 2: 6-(Benzylthio)-1-(4-Bromo-5-Chloro-2-Methoxyphenyl)Quinolin-2(1H)-One To a solution of ethyl (E)-3-(5-(benzylthio)-2-((4-bromo-5-chloro-2-methoxyphenyl)amino)phenyl)acrylate (300.0 g, 5630.0 mmol) in methanol (3.0 L) was added tri(n-butyl)phosphine (50% solution in ethyl acetate, 56.2 mL, 1126 mmol) and the reaction mixture was heated at 70° C. for 5 h. The reaction mixture was allowed to cool to room temperature, concentrated under reduced pressure to obtain the initial product which was purified by stirring with 5% ethyl acetate in hexane (1.0 mL) and filtered to obtain 6-(benzylthio)-1-(4-bromo-5-chloro-2-methoxyphenyl)quinolin-2(1H)-one (210.0 g, 76.6%) as an off white solid, m/z (ESI) 486.0 (M+H)$^+$.

Step 3: Perfluorophenyl 1-(4-Bromo-5-Fluoro-2-Methoxyphenyl)-2-Oxo-1,2-Dihydroquinoline-6-Sulfonate To a solution of 6-(benzylthio)-1-(4-bromo-5-chloro-2-methoxyphenyl)quinolin-2(1H)-one (400.0 g, 824.9 mmol) in acetonitrile (2.5 L) and THF (2.5 L) were added acetic acid (1.0 L) and water (700 mL). The resulting mixture was cooled to 0° C. and 1,3-dichloro-5,5-dimethylimidazolidine-2,4-dione (292 g, 1484.8 mmol) was added portionwise over 30 min keeping the internal temperature below 5° C. The resulting suspension was stirred at 0° C. under nitrogen for 45 min. Then a solution of pentafluorophenol (197.4 g, 1072.3 mmol) in acetonitrile (500 mL) was added over 5 min followed by triethylamine (477 mL, 3299 mmol) over 30 min keeping the internal temperature below 5° C. The mixture was continued to be stirred at 0° C. for 50 min. Water (4.0 L) was added and extracted with ethyl acetate (3×2.0 L). The organic layer was washed with brine (2.0 L), dried over sodium sulfate, filtered and concentrated under reduced pressure to obtain the initial product which was purified by stirring with isopropyl alcohol/hexane (1:1, 2.0 L) and filtered to obtain perfluorophenyl 1-(4-bromo-5-fluoro-2-methoxyphenyl)-2-oxo-1,2-dihydro quinoline-6-sulfonate (360 g, 72%) as a white solid. m/z (ESI) 610.6 (M+H)$^+$.

Step 4: (P)-Perfluorophenyl 1-(4-Bromo-5-Fluoro-2-Methoxyphenyl)-2-Oxo-1,2-Dihydro Quinoline-6-Sulfonate & (M)-Perfluorophenyl 1-(4-Bromo-5-Fluoro-2-Methoxyphenyl)-2-Oxo-1,2-Dihydro Quinoline-6-Sulfonate Perfluorophenyl 1-(4-bromo-5-fluoro-2-methoxyphenyl)-2-oxo-1,2-dihydro quinoline-6-sulfonate (156 g, 255 mmol) was purified via chiral SFC chromatography ((S,S) Whelk-O, 45% isopropanol) to afford (P)-perfluorophenyl 1-(4-bromo-5-chloro-2-methoxyphenyl)-2-oxo-1,2-dihydroquinoline-6-sulfonate (72.66 g, 93% yield) and (M)-perfluorophenyl 1-(4-bromo-5-chloro-2-methoxyphenyl)-2-oxo-1,2-dihydroquinoline-6-sulfonate (76.13 g, 98% yield) as white solids, m/z (ESI) 610.6 (M+H)$^+$.

Step 5: (P)-1-(4-Bromo-5-Chloro-2-Methoxyphenyl)-N-(4-Methoxybenzyl)-2-Oxo-N-(Pyrimidin-2-Yl)-1,2-Dihydroquinoline-6-Sulfonamide N-(4-Methoxybenzyl)pyrimidin-2-amine (9.72 g, 45.1 mmol) and (P)-perfluorophenyl 1-(4-bromo-5-chloro-2-methoxyphenyl)-2-oxo-1,2-dihydroquinoline-6-sulfonate (25.06 g, 41.0 mmol) were added to a 500-mL flask. The flask was flushed with N$_2$ stream then tetrahydrofuran (136 mL) was added and the reaction was cooled to 2° C. under N$_2$. Sodium tert-pentoxide (30% solution in THF, 197 mL, 492 mmol) was added over 30 min via addition funnel maintaining internal temperature around 5° C., and the pale yellow solution turned orange upon the addition. The reaction was stirred for 30 min in the ice bath. The reaction was then quenched with sat. aq. NH$_4$Cl and diluted with EtOAc. The layers were separated and the water layer was extracted twice with EtOAc. The combined organics were dried with Na$_2$SO$_4$, filtered, and evaporated. IPA was added and a white precipitate crashed out. The solvent was evaporated to approximately 100 mL then additional IPA was added and the reaction was stirred for 18 h. The slurry was filtered and the solid was washed with IPA.

The solid was taken up in 150 mL of MTBE and heated at 40° C. for 2 hours. The slurry was cooled to ambient temperature and filtered to obtain a white solid. The impure material was dissolved in 500 mL of 10% MeOH/DCM and stirred with 500 mL of sat. aq. NaHCO$_3$ for 30 minutes. The layers were separated and the water layer was extracted twice with 10% MeOH/DCM. The combined organics layers were dried and evaporated. The filtrates from IPA and MTBE titrations were combined and loaded onto 25 g silica cartridge and purified by column chromatography (RediSep Rf Gold 120 g column, gradient elution 10% to 50% 3:1 EtOAc:EtOH in heptane with 10% dichloromethane additive). The pure product of the column and the product from the NaHCO₃ extraction were combined to afford (P)-1-(4-bromo-5-chloro-2-methoxyphenyl)-N-(4-methoxybenzyl)-2-oxo-N-(pyrimidin-2-yl)-1,2-dihydroquinoline-6-sulfonamide (16.94 g, 26.4 mmol, 64% yield) as a pale yellow foam. $^1$H NMR (500 MHz, DMSO-$d_6$) δ ppm 8.58 (d, J=4.9 Hz, 2H), 8.39 (d, J=2.1 Hz, 1H), 8.13 (d, J=9.6 Hz, 1H), 7.96 (dd, J=9.1, 2.3 Hz, 1H), 7.76 (s, 1H), 7.73 (s, 1H), 7.29 (d, J=8.8 Hz, 2H), 7.13 (t, J=4.9 Hz, 1H), 6.87 (d, J=8.8 Hz, 2H), 6.78 (d, J=9.6 Hz, 1H), 6.74 (d, J=9.1 Hz, 1H), 5.36 (s, 2H), 3.72 (s, 3H), 3.71 (s, 3H). m/z (ESI, positive ion) 642.8 (M+H)⁺.

Intermediate J:
N-(4-Methoxybenzyl)Pyridazin-3-Amine

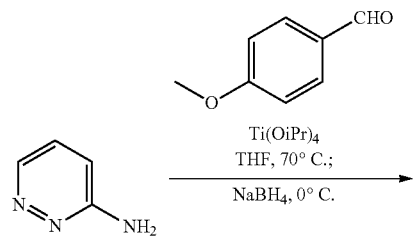

To a 25-mL round-bottomed flask was added 4-methoxybenzaldehyde (1.00 g, 7.34 mmol) and pyridazin-3-amine (0.838 g, 8.81 mmol) in tetrahydrofuran (10 mL). Then, titanium(IV) isopropoxide (6.46 mL, 22.03 mmol) was added, and the reaction mixture was stirred at 70° C. for 16 h. Then the reaction mixture was cooled to 0° C., and sodium borohydride (0.556 g, 14.69 mmol) was added portionwise. The reaction mixture was then stirred for 2 h at 0° C. The reaction mixture was diluted with water (20 mL) and filtered. The filtrate was then extracted with EtOAc (3×50 mL). The organic extract was washed with sat. aq. NaCl (30 mL) and dried over Na₂SO₄. The solution was filtered and concentrated in vacuo to give the initial product as a orange oil. The initial product was absorbed onto a plug of silica gel and purified by chromatography through a Redi-Sep prepacked silica gel column (40 g), eluting with 0% to 15% MeOH in CH₂C₂ to provide N-(4-methoxybenzyl)pyridazin-3-amine (0.680 g, 3.16 mmol, 43.0% yield) as yellow solid. m/z (ESI, positive ion) 216.2 (M+H)⁺.

Intermediate K: (P)-1-(4-Bromo-5-Fluoro-2-Methoxyphenyl)-N-(4-Methoxybenzyl)-2-Oxo-N-(Pyridazin-3-Yl)-1,2-Dihydroquinoline-6-Sulfonamide

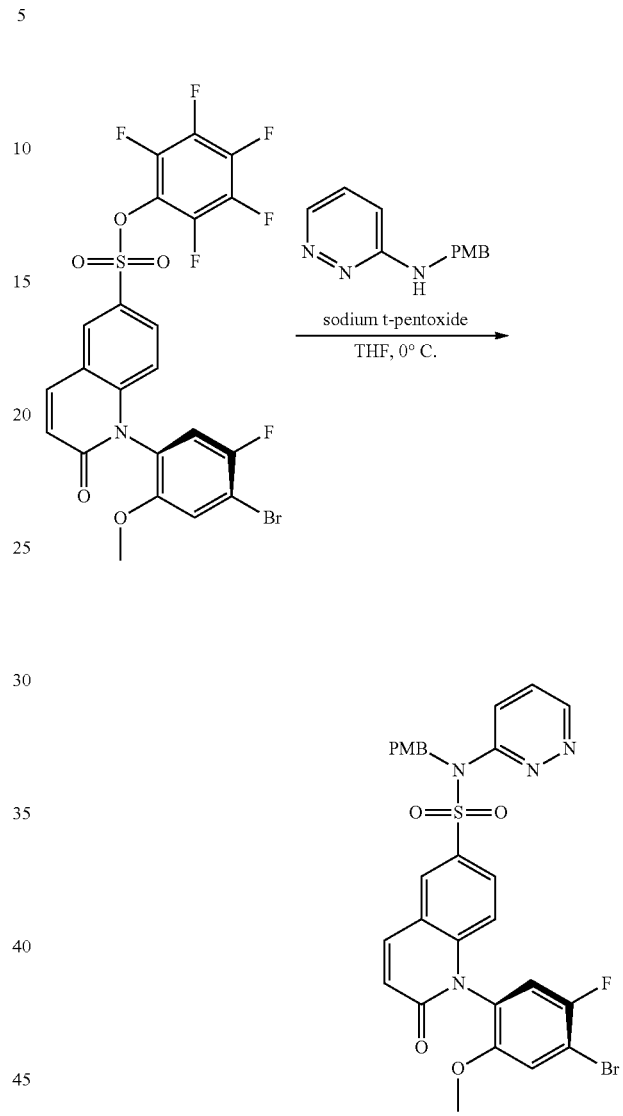

A 100-mL recovery flask containing perfluorophenyl (P)-1-(4-bromo-5-fluoro-2-methoxyphenyl)-2-oxo-1,2-dihydroquinoline-6-sulfonate (5.00 g, 8.41 mmol) and N-(4-methoxybenzyl)pyridazin-3-amine (1.902 g, 8.83 mmol) was flushed with nitrogen and subsequently charged with THF (34 mL). The solution was cooled to 0° C., and sodium tert-pentoxide (8.4 mL, 11.78 mmol, 1.4 M in THF) was added slowly. The pale yellow solution was stirred at 0° C. for 15 min, and then volatiles were removed in vacuo. Water was added to cause formation of a white precipitate. This precipitate was isolated, dissolved in dichloromethane, and treated with heptane to cause formation of (P)-1-(4-bromo-5-fluoro-2-methoxyphenyl)-N-(4-methoxybenzyl)-2-oxo-N-(pyridazin-3-yl)-1,2-dihydroquinoline-6-sulfonamide (4.20 g, 6.71 mmol, 80% yield) as a white precipitate. m/z (ESI, positive ion) 625.0 (M+H)⁺.

Intermediate L: Perfluorophenyl (P)-1-(4-Bromo-2-Methoxy-5-Methylphenyl)-2-Oxo-1,2-Dihydroquinoline-6-Sulfonate

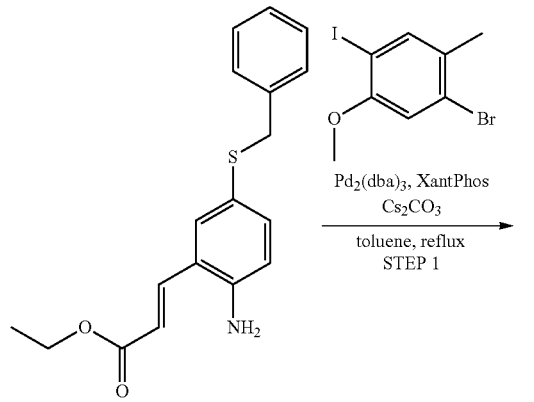

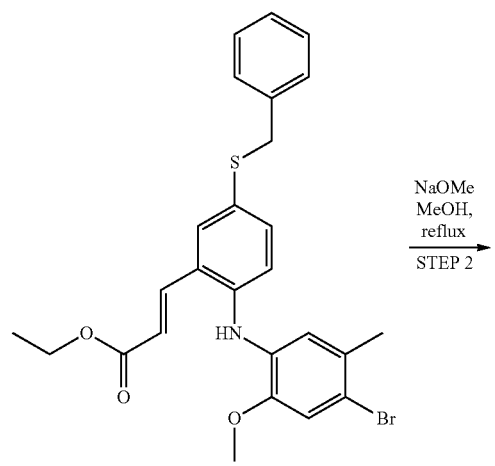

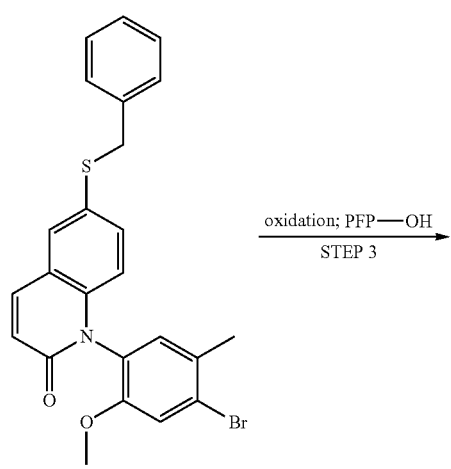

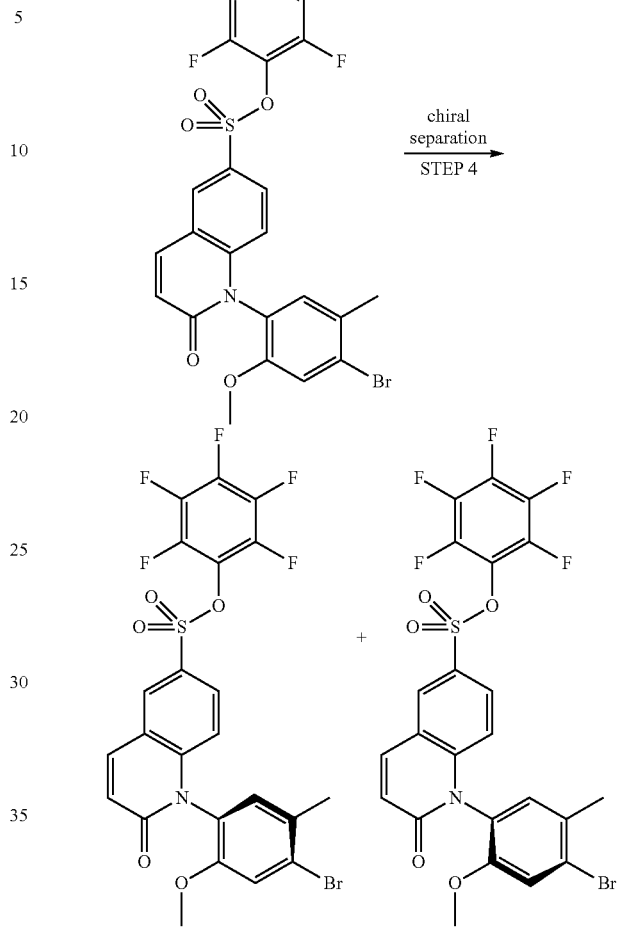

Step 1: (E)-Ethyl 3-(5-(Benzylthio)-2-((4-Bromo-2-Methoxy-5-Methylphenyl)Amino)Phenyl)Acrylate A round-bottom flask was charged with (E)-ethyl 3-(2-amino-5-(benzylthio)phenyl)acrylate (4.729 g, 15.09 mmol), 1-bromo-4-iodo-5-methoxy-2-methylbenzene (5.18 g, 15.84 mmol), XantPhos (0.437 g, 0.754 mmol), tris(dibenzylideneacetone)dipalladium(0) (0.345 g, 0.377 mmol), cesium carbonate (9.83 g, 30.2 mmol), and toluene (30 mL) were added. A reflux condenser was attached, and the mixture was heated to reflux. After 4 h, additional portions of tris(dibenzylideneacetone)dipalladium(0) (172 mg) and XantPhos (213 mg) were added. After 2 h, additional portions of cesium carbonate (ca. 2 g) and 1-bromo-4-iodo-5-methoxy-2-methylbenzene (600 mg) were added. Following an additional 30 min of reflux, the mixture was cooled and filtered through CELITE. The filter pad was washed with EtOAc (3×). The filtrate was concentrated. The residue was concentrated from MeOH, and taken up in MeOH. The resulting suspension was heated to boiling, then sonicated and cooled to RT. The mixture was filtered, and the collected solid was washed with MeOH (3×) and dried under a stream of $N_2$ for 48 h to give (E)-ethyl 3-(5-(benzylthio)-2-((4-bromo-2-methoxy-5-methylphenyl)amino)phenyl)acrylate (5.21 g, 10.17 mmol, 67.4% yield) as a bright-yellow solid. $^1$H NMR (400 MHz, DMSO-d$_6$) δ ppm 7.75 (d, J=15.9 Hz, 1H), 7.66 (d, J=2.1 Hz, 1H), 7.42 (s, 1H), 7.37-7.20 (m, 6H), 7.14 (s, 1H), 6.85 (d, J=8.5 Hz, 1H), 6.62 (s, 1H), 6.51 (d, J=15.9 Hz, 1H), 4.23 (s, 2H), 4.15 (q, J=7.0 Hz, 2H), 3.78 (s, 3H), 2.14 (s, 2H), 1.23 (t, J=7.1 Hz, 3H). m/z (ESI) 512.2 (M+H)$^+$.

Step 2: 6-(Benzylthio)-1-(4-Bromo-2-Methoxy-5-Methylphenyl)Quinolin-2(1H)-One A round-bottom flask was charged with (E)-ethyl 3-(5-(benzylthio)-2-((4-bromo-2-methoxy-5-methylphenyl)amino)phenyl)acrylate (5.12 g, 9.99 mmol) and MeOH (50.0 mL) to give a yellow suspension. Sodium methoxide (25 wt % in MeOH, 0.432 mL, 1.998 mmol) was added. A reflux condenser was attached, and the flask was lowered into a 70° C. heating bath. After 1 h, additional portions of MeOH (25 mL) and sodium methoxide solution (ca. 0.85 mL) were added in sequence. After 7 h, the mixture was cooled and concentrated under vacuum. The residue was purified by chromatography on silica gel (80-g Redi-Sep column, 25-g silica gel loading column, loaded as a solution in MeOH-DCM, then eluted with 25-75% EtOAc/heptane containing 10% DCM). The fractions containing product were combined and concentrated to give 6-(benzylthio)-1-(4-bromo-2-methoxy-5-methylphenyl)quinolin-2(1H)-one (4.233 g, 9.08 mmol, 91% yield) as a tan solid. m/z (ESI) 466.1 (M+H)$^+$.

Step 3: Perfluorophenyl 1-(4-Bromo-2-Methoxy-5-Methylphenyl)-2-Oxo-1,2-Dihydroquinoline-6-Sulfonate A round-bottom flask was charged with 6-(benzylthio)-1-(4-bromo-2-methoxy-5-methylphenyl)quinolin-2(1H)-one (4.23 g, 9.07 mmol), DCM (71.1 mL), acetic acid (2.67 mL), and water (1.778 mL) to give clear, light-brown solution. The flask was cooled in an ice-water bath for 10 min, then 1,3-dichloro-5,5-dimethylimidazolidine-2,4-dione (3.66 g, 18.59 mmol) was added in one portion. After 40 min, an additional portion of oxidant (850 mg) was added. The mixture was stirred for another 20 min, then 2,3,4,5,6-pentafluorophenol (2.504 g, 13.60 mmol) and triethylamine (5.06 mL, 36.3 mmol) were added in sequence. After 20 min, the mixture was diluted with water. The layers were separated, and the aq. layer was extracted with DCM. The combined organic extracts were dried over sodium sulfate, filtered, and concentrated. The residue was purified by chromatography on silica gel (80-g Redi-Sep Gold column, 25-g silica gel loading column, 10-60% EtOAc/Heptane with 10% DCM) to afford perfluorophenyl 1-(4-bromo-2-methoxy-5-methylphenyl)-2-oxo-1,2-dihydroquinoline-6-sulfonate (3.37 g, 5.71 mmol, 63% yield). m/z (ESI) 590.0 (M+H)$^+$.

Step 4: Perfluorophenyl (P)-1-(4-Bromo-2-Methoxy-5-Methylphenyl)-2-Oxo-1,2-Dihydroquinoline-6-Sulfonate Perfluorophenyl 1-(4-bromo-2-methoxy-5-methylphenyl)-2-oxo-1,2-dihydroquinoline-6-sulfonate (22.896 g, 38.79 mmol) was purified using a (S,S) Whelk-O, 5×25 cm column. The mobile phase was run under isocratic conditions; supercritical CO$_2$ with 50% dichloromethane; flow rate: 350 mL/min. The first eluting peak was assigned perfluorophenyl (P)-1-(4-bromo-2-methoxy-5-methylphenyl)-2-oxo-1,2-dihydroquinoline-6-sulfonate (10.425 g).

The second eluting peak was assigned perfluorophenyl (M)-1-(4-bromo-2-methoxy-5-methylphenyl)-2-oxo-1,2-dihydroquinoline-6-sulfonate (10.76 g). Data for peak 1: m/z (ESI) 590.0 (M+H)$^+$. Data for peak 2: m/z (ESI) 590.0 (M+H)$^+$.

Intermediate M: (P)-1-(4-Bromo-5-Fluoro-2-Methoxyphenyl)-N-(4-Methoxybenzyl)-2-Oxo-N-(Pyrimidin-2-Yl)-1,2-Dihydroquinoline-6-Sulfonamide

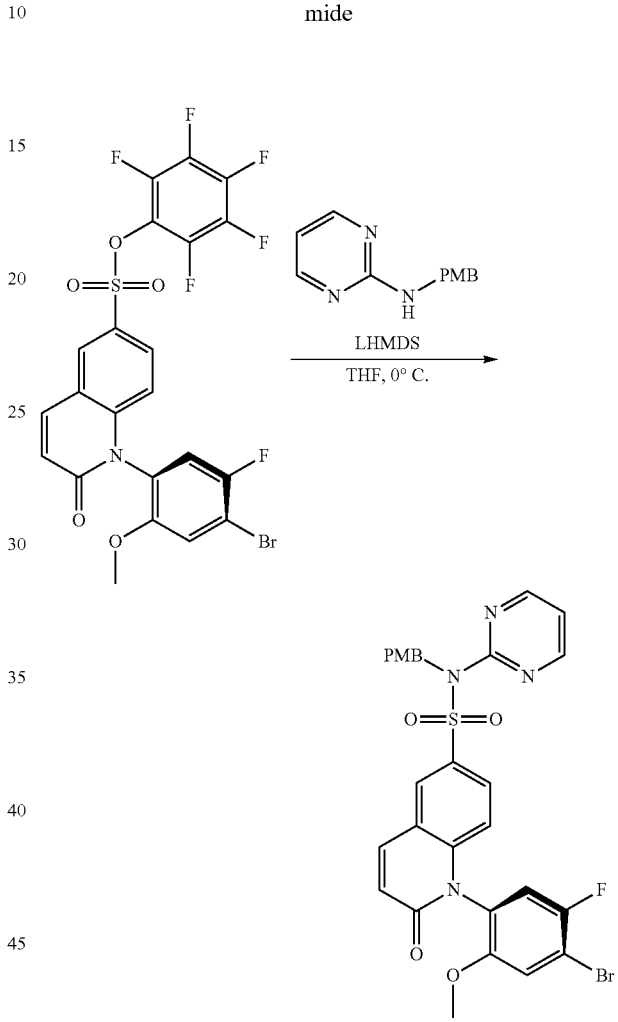

A 250-mL round-bottom flask was sequentially charged with perfluorophenyl (P)-1-(4-bromo-5-fluoro-2-methoxyphenyl)-2-oxo-1,2-dihydroquinoline-6-sulfonate (2.00 g, 3.37 mmol), tetrahydrofuran (17 mL), and N-(4-methoxybenzyl)pyrimidin-2-amine (0.724 g, 3.37 mmol), and the resulting solution was cooled to 0° C. Lithium bis(trimethylsilyl)amide (3.70 mL, 3.70 mmol, 1.0 M in THF) was then added dropwise to the stirred reaction mixture. After 15 min, aqueous HCl solution (1.0 M, 100 mL) and EtOAc (100 mL) were added to the reaction mixture, which was subsequently allowed to warm to ambient temperature. The layers were separated, and the aqueous layer was extracted with EtOAc (2×100 mL). The combined organic layers were then washed with brine (100 mL), dried over anhydrous sodium sulfate, filtered, and concentrated under reduced pressure. The residue was then purified by flash column chromatography (100 g BIOTAGE® column, gradient elution 0-100% EtOAc: heptane with 10% dichloromethane as co-eluent) to afford (P)-1-(4-bromo-5-fluoro-2-methoxyphenyl)-N-(4-methoxybenzyl)-2-oxo-N-(pyrimidin-2-yl)-1,2-dihydroquinoline-6-sulfonamide (1.10 g, 1.76 mmol, 52% yield) as a white solid. m/z (ESI, positive ion) 625.8 (M+H)$^+$.

Intermediate N: (P)-1-(4-Bromo-2-Methoxy-5-Methylphenyl)-N-(Isoxazol-3-Yl)-N-(4-Methoxybenzyl)-2-Oxo-1,2-Dihydroquinoline-6-Sulfonamide

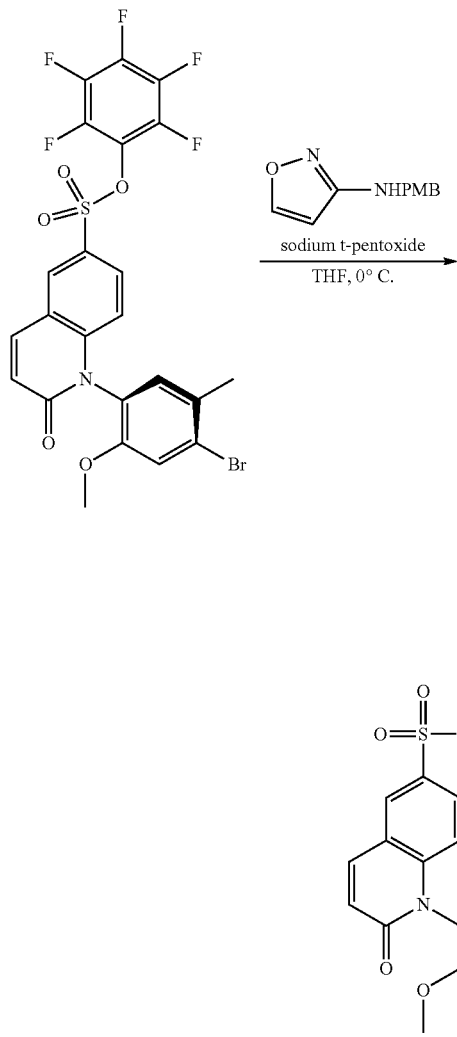

To a 0° C. solution of N-(4-methoxybenzyl)isoxazol-3-amine (83 mg, 0.407 mmol) and perfluorophenyl (P)-1-(4-bromo-2-methoxy-5-methylphenyl)-2-oxo-1,2-dihydroquinoline-6-sulfonate (200 mg, 0.339 mmol) in tetrahydrofuran (1.7 mL) was added sodium tert-pentoxide (30 wt % in THF, 176 µL, 0.440 mmol) slowly. The reaction was stirred for 30 minutes at 0° C. After 30 min, the reaction mixture was partitioned between ethyl acetate and saturated aqueous ammonium chloride. The organic layer was concentrated, and the residue was triturated with MTBE (2 mL) to provide (P)-1-(4-bromo-2-methoxy-5-methylphenyl)-N-(isoxazol-3-yl)-N-(4-methoxybenzyl)-2-oxo-1,2-dihydroquinoline-6-sulfonamide (191 mg, 0.313 mmol, 92% yield) as a white powder. m/z (ESI, positive ion) 609.8 (M+H)$^+$.

Intermediate O: N-(4-Methoxybenzyl)Oxazol-2-Amine

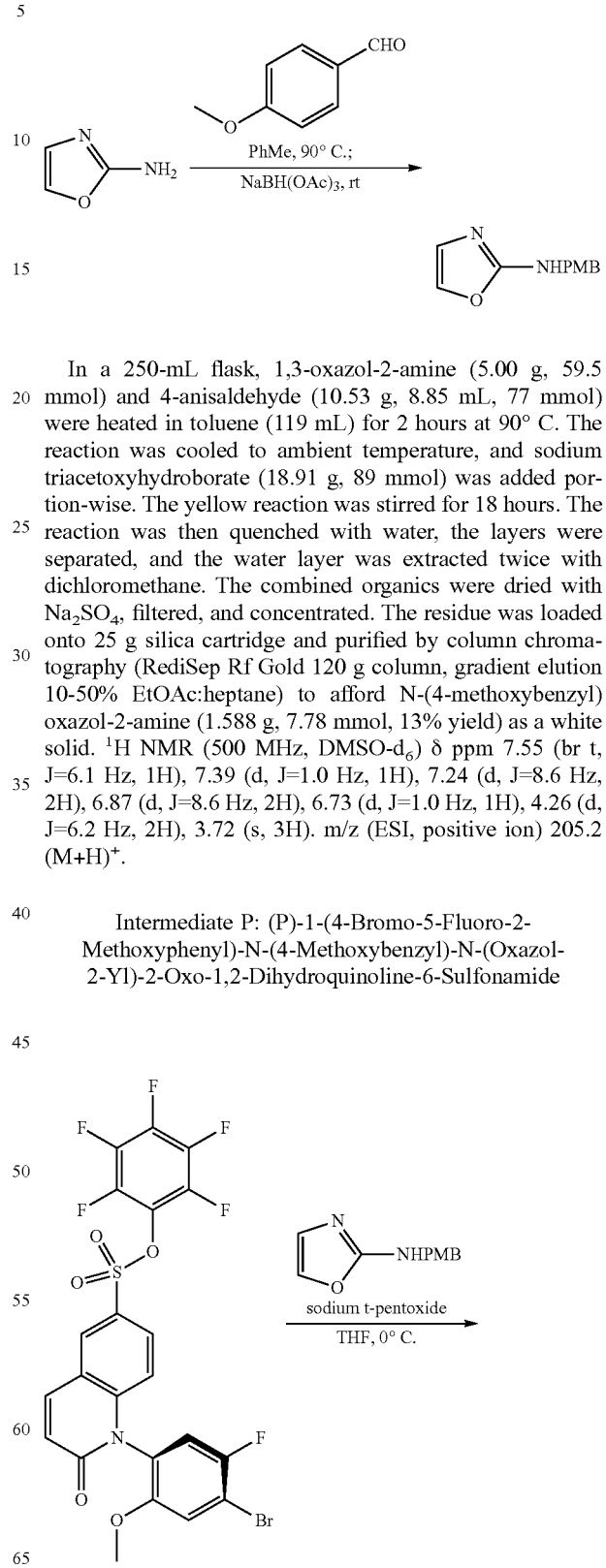

In a 250-mL flask, 1,3-oxazol-2-amine (5.00 g, 59.5 mmol) and 4-anisaldehyde (10.53 g, 8.85 mL, 77 mmol) were heated in toluene (119 mL) for 2 hours at 90° C. The reaction was cooled to ambient temperature, and sodium triacetoxyhydroborate (18.91 g, 89 mmol) was added portion-wise. The yellow reaction was stirred for 18 hours. The reaction was then quenched with water, the layers were separated, and the water layer was extracted twice with dichloromethane. The combined organics were dried with Na$_2$SO$_4$, filtered, and concentrated. The residue was loaded onto 25 g silica cartridge and purified by column chromatography (RediSep Rf Gold 120 g column, gradient elution 10-50% EtOAc:heptane) to afford N-(4-methoxybenzyl)oxazol-2-amine (1.588 g, 7.78 mmol, 13% yield) as a white solid. $^1$H NMR (500 MHz, DMSO-d$_6$) δ ppm 7.55 (br t, J=6.1 Hz, 1H), 7.39 (d, J=1.0 Hz, 1H), 7.24 (d, J=8.6 Hz, 2H), 6.87 (d, J=8.6 Hz, 2H), 6.73 (d, J=1.0 Hz, 1H), 4.26 (d, J=6.2 Hz, 2H), 3.72 (s, 3H). m/z (ESI, positive ion) 205.2 (M+H)$^+$.

Intermediate P: (P)-1-(4-Bromo-5-Fluoro-2-Methoxyphenyl)-N-(4-Methoxybenzyl)-N-(Oxazol-2-Yl)-2-Oxo-1,2-Dihydroquinoline-6-Sulfonamide

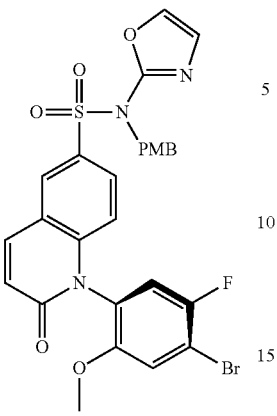

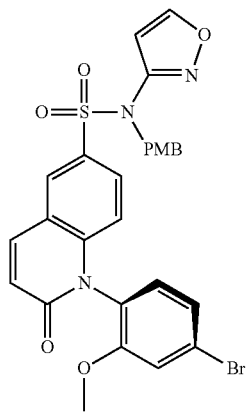

To a 0° C. solution of N-(4-methoxybenzyl)oxazol-2-amine (82 mg, 0.404 mmol) and perfluorophenyl (P)-1-(4-bromo-5-fluoro-2-methoxyphenyl)-2-oxo-1,2-dihydroquinoline-6-sulfonate (200 mg, 0.337 mmol) in tetrahydrofuran (1.6 mL) was slowly added sodium tert-pentoxide, (30 wt % in THF, 175 µL, 0.438 mmol). The reaction was stirred for 30 minutes at 0° C. The reaction mixture was then partitioned between ethyl acetate and saturated aqueous ammonium chloride. The organic layer was concentrated. The residue was purified by silica gel column chromatography (gradient elution 20-80% [3:1 ethyl acetate/ethanol]:heptane with 10% dichloromethane as a co-eluent) to provide (P)-1-(4-bromo-5-fluoro-2-methoxyphenyl)-N-(4-methoxybenzyl)-N-(oxazol-2-yl)-2-oxo-1,2-dihydroquinoline-6-sulfonamide (180 mg, 0.293 mmol, 87% yield) as a white powder. m/z (ESI, positive ion) 613.8 (M+H)+.

Intermediate Q: (P)-1-(4-Bromo-2-Methoxyphenyl)-N-(Isoxazol-3-Yl)-N-(4-Methoxybenzyl)-2-Oxo-1,2-Dihydroquinoline-6-Sulfonamide To a 0° C. solution of N-(4-methoxybenzyl)isoxazol-3-amine (128 mg, 0.625 mmol) and perfluorophenyl (P)-1-(4-bromo-2-methoxyphenyl)-2-oxo-1,2-dihydroquinoline-6-sulfonate (300 mg, 0.521 mmol) in tetrahydrofuran (2.6 mL) was slowly added sodium tert-pentoxide (30 wt % in THF, 271 µL, 0.677 mmol) slowly. The reaction was stirred for 30 minutes at 0° C. The reaction mixture was then partitioned between ethyl acetate and saturated aqueous ammonium chloride. The organic layer was concentrated. The residue was triturated with MTBE to provide 1-(4-bromo-2-methoxyphenyl)-N-(isoxazol-3-yl)-N-(4-methoxybenzyl)-2-oxo-1,2-dihydroquinoline-6-sulfonamide (350 mg, 0.587 mmol, >99% yield) as an off-white solid. m/z (ESI, positive ion) 595.8 (M+H)+.

Intermediate R: (P)-1-(4-Bromo-2-Methoxyphenyl)-N-(4-Methoxybenzyl)-2-Oxo-N-(Pyrimidin-2-Yl)-1,2-Dihydroquinoline-6-Sulfonamide

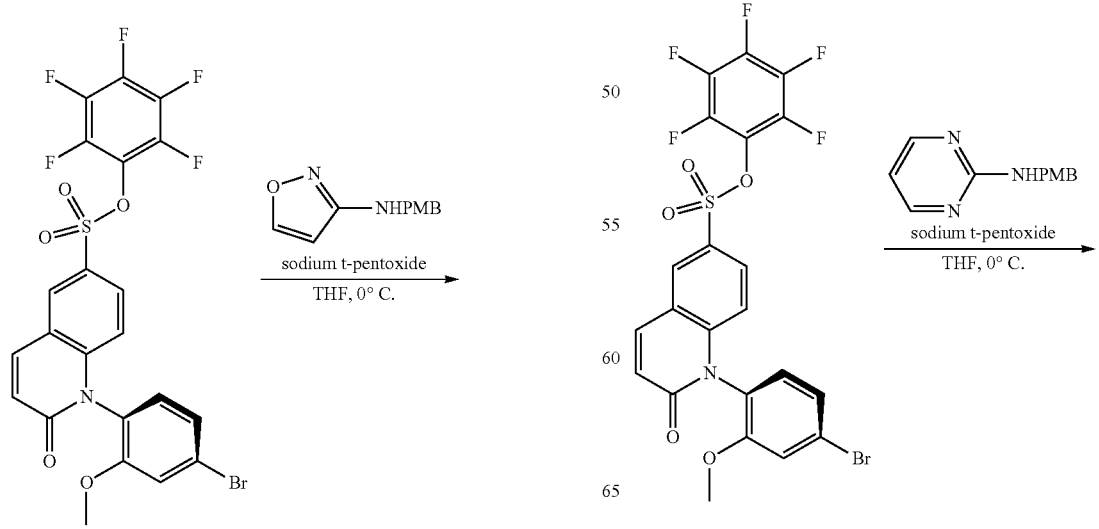

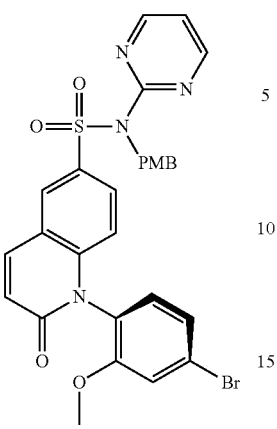

The title compound was prepared according to the method and purification protocol of Intermediate R using N-(4-methoxybenzyl)pyrimidin-2-amine (134 mg, 0.625 mmol). This afforded 1-(4-bromo-2-methoxyphenyl)-N-(4-methoxybenzyl)-2-oxo-N-(pyrimidin-2-yl)-1,2-dihydroquinoline-6-sulfonamide (140 mg, 0.230 mmol, 44% yield) as an off-white solid. m/z (ESI, positive ion) 606.8 (M+H)⁺.

Intermediate S: (P)-1-(4-Bromo-2-Methoxy-5-Methylphenyl)-N-(4-Methoxybenzyl)-2-Oxo-N-(Pyrimidin-2-Yl)-1,2-Dihydroquinoline-6-Sulfonamide

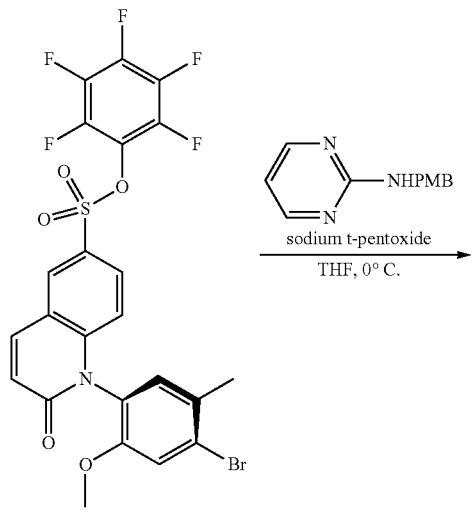

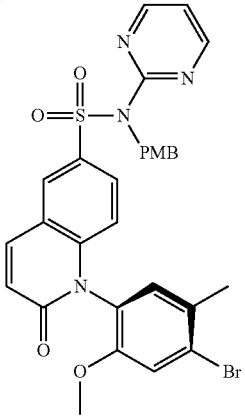

The title compound was prepared according to the method and purification protocol of Intermediate R using perfluorophenyl (P)-1-(4-bromo-2-methoxy-5-methylphenyl)-2-oxo-1,2-dihydroquinoline-6-sulfonate (200 mg, 0.339 mmol). This afforded (P)-1-(4-bromo-2-methoxy-5-methylphenyl)-N-(4-methoxybenzyl)-2-oxo-N-(pyrimidin-2-yl)-1,2-dihydroquinoline-6-sulfonamide (130 mg, 0.209 mmol, 62% yield) as a white solid. m/z (ESI, positive ion) 620.8 (M+H)⁺.

Intermediate T:
N-(2,4-Dimethoxybenzyl)Oxazol-2-Amine

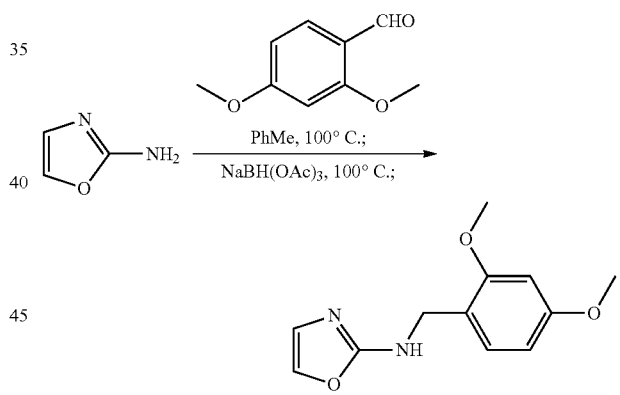

In a 250 mL flask, a mixture of 1,3-oxazol-2-amine (5.00 g, 59.5 mmol) and 2,4-dimethoxybenzaldehyde (10.87 g, 65.4 mmol) were heated in toluene (100 mL) at 90° C. for 1 h. The reaction was cooled to rt then treated with sodium triacetoxyborohydride (18.91 g, 89 mmol). The mixture was stirred at 100° C. for 1 h, then at rt for 60 h. Additional sodium triacetoxyborohydride (18.91 g, 89 mmol) was added and the reaction stirred at 100° C. for 2 h. The reaction was then cooled and diluted with ethyl acetate (500 mL) and water (100 mL). The organic layer was washed with saturated sodium bicarbonate solution (3×200 mL) and brine (2×100 mL) and dried over magnesium sulfate. The solvent was removed under reduced pressure to give a viscous brown oil, which was flushed through a plug of silica gel, washing with 50% [3:1 ethyl acetate:ethanol]:heptane. The filtrate was concentrated and then purified by flash chromatography (HP silica 220 g column, gradient elution 0-70% ethyl acetate:[9:1 heptane:DCM]) to afford N-(2,4-dimethoxybenzyl)oxazol-2-amine (1.18 g, 5.04 mmol, 8% yield) as a pale yellow solid. m/z (ESI, positive ion) 235.2 (M+H)+.

Intermediate U: (P)-1-(4-Bromo-2-Methoxyphenyl)-N-(2,4-Dimethoxybenzyl)-N-(Oxazol-2-Yl)-2-Oxo-1,2-Dihydroquinoline-6-Sulfonamide Intermediate V: (P)-1-(4-Bromo-2-Methoxy-5-Methylphenyl)-N-(4-Methoxybenzyl)-2-Oxo-N-(Pyridazin-3-Yl)-1,2-Dihydroquinoline-6-Sulfonamide

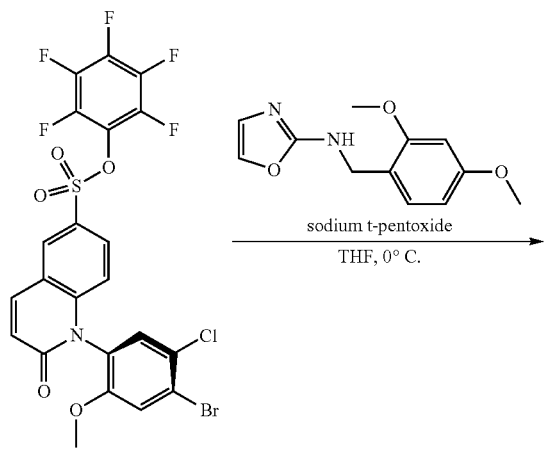

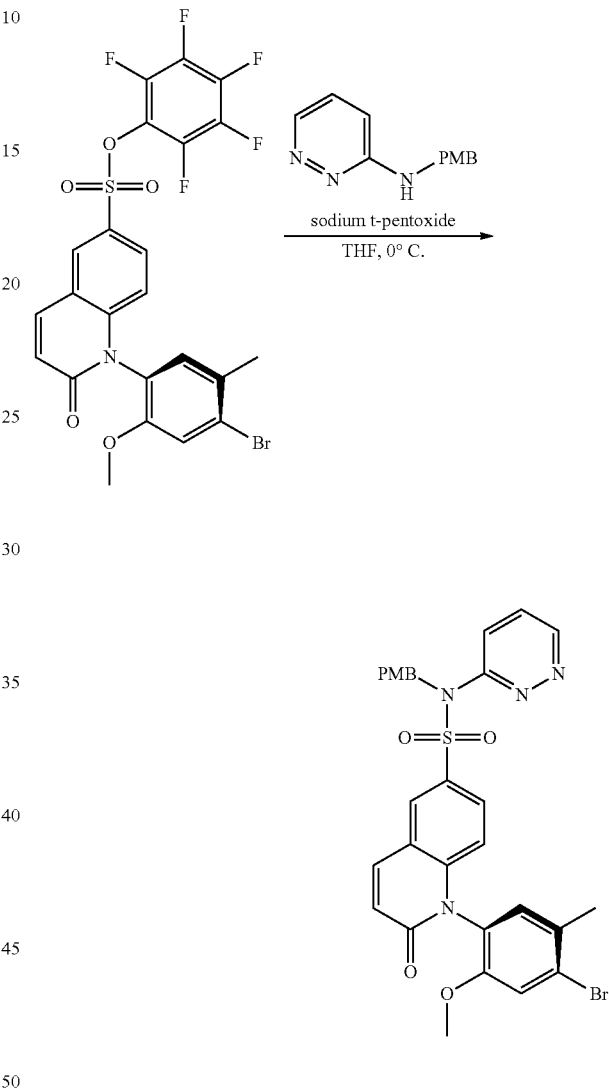

To a 0° C. solution of N-(2,4-dimethoxybenzyl)oxazol-2-amine (146 mg, 0.625 mmol) and perfluorophenyl (P)-1-(4-bromo-2-methoxyphenyl)-2-oxo-1,2-dihydroquinoline-6-sulfonate (300 mg, 0.521 mmol) in tetrahydrofuran (2.6 mL) was slowly added sodium tert-pentoxide (30 wt % in THF, 0.271 mL, 0.677 mmol). The reaction was stirred for 30 minutes at 0° C. The reaction mixture was then partitioned between ethyl acetate and saturated aqueous sodium bicarbonate. The organic layer was concentrated. The residue was purified by silica gel column chromatography (gradient elution 40-100% ethyl acetate:heptane with 10% dichloromethane as a co-eluent) to provide (P)-1-(4-bromo-2-methoxyphenyl)-N-(2,4-dimethoxybenzyl)-N-(oxazol-2-yl)-2-oxo-1,2-dihydroquinoline-6-sulfonamide (0.200 g, 0.319 mmol, 61.3% yield) as a colorless oil. m/z (ESI, positive ion) 625.8 (M+H)+.

To a 0° C. solution of N-(4-methoxybenzyl)pyridazin-3-amine (0.219 g, 1.02 mmol) and perfluorophenyl (P)-1-(4-bromo-2-methoxy-5-methylphenyl)-2-oxo-1,2-dihydroquinoline-6-sulfonate (0.5 g, 0.847 mmol) in tetrahydrofuran (4.2 mL) was slowly added sodium tert-pentoxide (30 wt % solution in THF, 0.41 mL, 1.0 mmol). The reaction was stirred for 30 minutes at 0° C. The reaction mixture was then partitioned between ethyl acetate and saturated aqueous ammonium chloride. The organic layer was concentrated. The residue was purified by silica gel column chromatography (gradient elution 40-100% ethyl acetate:heptane with 10% dichloromethane as a co-eluent) to provide (P)-1-(4-bromo-2-methoxy-5-methylphenyl)-N-(4-methoxybenzyl)-2-oxo-N-(pyridazin-3-yl)-1,2-dihydroquinoline-6-sulfonamide (367 mg, 0.591 mmol, 70% yield) as a white solid. m/z (ESI, positive ion) 620.8 (M+H)+.

Intermediate W: (P)-1-(4-Bromo-5-Chloro-2-Methoxyphenyl)-N-(2,4-Dimethoxybenzyl)-N-(Oxazol-2-Yl)-2-Oxo-1,2-Dihydroquinoline-6-Sulfonamide Intermediate X: (P)-1-(4-Bromo-2-Methoxyphenyl)-N-(4-Methoxybenzyl)-2-Oxo-N-(Pyridazin-3-Yl)-1,2-Dihydroquinoline-6-Sulfonamide

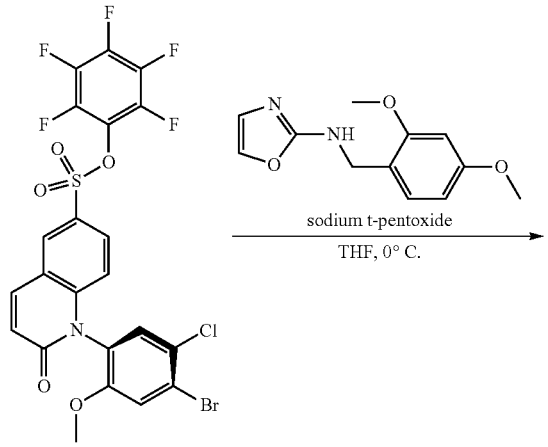

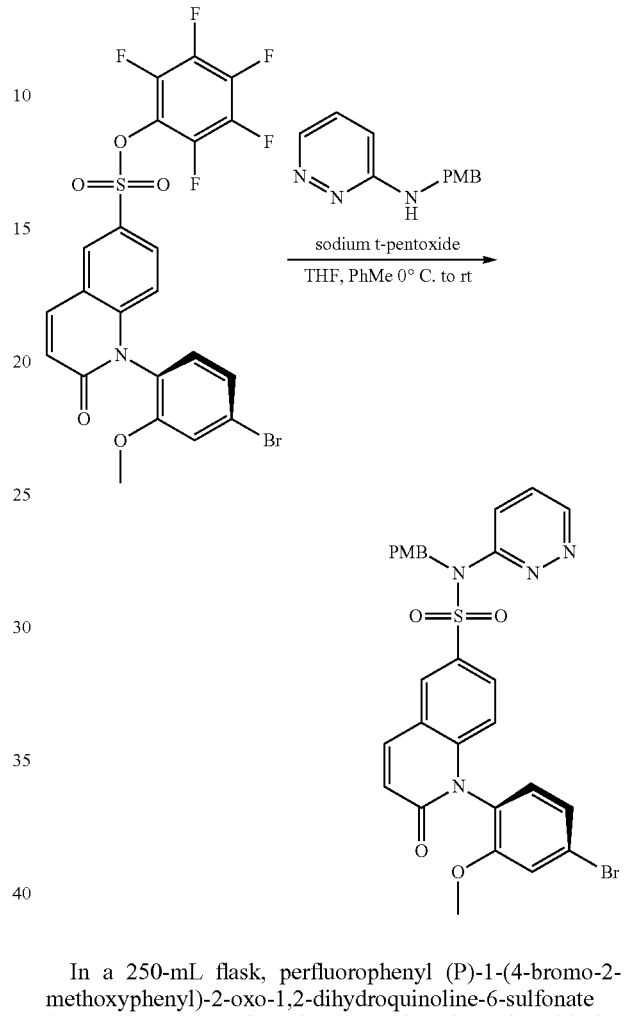

N-(2,4-dimethoxybenzyl)oxazol-2-amine (0.211 g, 0.901 mmol) and perfluorophenyl (P)-1-(4-bromo-5-chloro-2-methoxyphenyl)-2-oxo-1,2-dihydroquinoline-6-sulfonate (0.500 g, 0.819 mmol, Syngene) were added to a 40-mL vial. The vial was flushed with nitrogen, tetrahydrofuran (2.7 mL) was added, and then the reaction was cooled to 0° C. Sodium tert-pentoxide (3.2 M in PhMe, 0.33 mL, 1.1 mmol) was added slowly. After stirring for 30 min at ° C., sat. aq. ammonium chloride and EtOAc were added to the cold reaction. The phases were separated, and the water phase was extracted twice with EtOAc. The combined organic extracts were dried and evaporated. The residue was purified by column chromatography (two sequential RediSep Rf Gold 40 g columns, gradient elution 0-40% [3:1 EtOAc:EtOH]:[10:1 heptane:dichloromethane]) to provide (P)-1-(4-bromo-5-chloro-2-methoxyphenyl)-N-(2,4-dimethoxybenzyl)-N-(oxazol-2-yl)-2-oxo-1,2-dihydroquinoline-6-sulfonamide (0.347 g, 0.525 mmol, 64% yield) as a yellow solid. m/z (ESI, positive ion) 681.8 (M+Na)$^+$.

In a 250-mL flask, perfluorophenyl (P)-1-(4-bromo-2-methoxyphenyl)-2-oxo-1,2-dihydroquinoline-6-sulfonate (7.00 g, 12.15 mmol) and N-(4-methoxybenzyl)pyridazin-3-amine (3.14 g, 14.58 mmol) were suspended in tetrahydrofuran (100 mL). The pale brown suspension was cooled in an ice bath and treated dropwise with sodium tert-pentoxide (40 wt % in toluene, 7.77 mL, 19.43 mmol). The reaction was stirred at 0° C. for 30 min and allowed to warm to rt. After 2 h, additional base sodium tert-pentoxide (40 wt % in toluene, 1 mL) was added, and the reaction stirred at rt for an additional 15 h. Additional tert-pentoxide (40 wt % in toluene, 1 mL) was added, and the reaction stirred at rt for an additional 2 h. The reaction was cooled in an ice bath and quenched with saturated ammonium chloride solution (50 mL), and the reaction stirred vigorously for 15 min. The phases were separated, and the aqueous phase was extracted with ethyl acetate (3×50 mL). The residue was purified via silica gel column chromatography (gradient elution 0-100% [3:1 EtOAc:EtOH]:[9:1 heptane:dichloromethane]). The product was further purified by trituration with ethyl acetate:heptane (1:1) to give (P)-1-(4-bromo-2-methoxyphenyl)-N-(4-methoxybenzyl)-2-oxo-N-(pyridazin-3-yl)-1,2-dihydroquinoline-6-sulfonamide (1.56 g, 2.57 mmol, 21% yield) as an off-white solid. $^1$H NMR (500 MHz, DMSO-d$_6$) δ ppm 9.04 (dd, J=4.5, 1.7 Hz, 1H), 8.26 (d, J=2.3 Hz, 1H), 8.16 (d, J=9.3 Hz, 1H), 7.67-7.77 (m, 2H), 7.64 (dd, J=9.1, 2.3 Hz, 1H), 7.53 (d, J=1.8 Hz, 1H), 7.35-7.40 (m, 1H), 7.30-7.34 (m, 1H), 7.15 (d, J=8.8 Hz, 2H), 6.76-6.85 (m, 3H), 6.72 (d, J=9.1 Hz, 1H), 5.03 (s, 2H), 3.72 (s, 3H), 3.66 (s, 3H). m/z (ESI, positive ion) 607.0 (M+H)+.

Intermediate Y: (P)-1-(4-Bromo-5-Chloro-2-Methoxyphenyl)-N-(4-Methoxybenzyl)-2-Oxo-N-(Pyridazin-3-Yl)-1,2-Dihydroquinoline-6-Sulfonamide

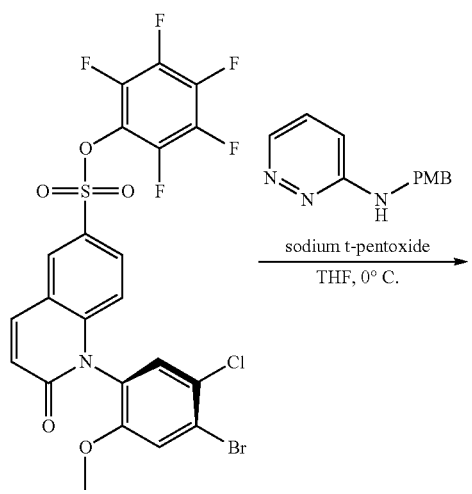

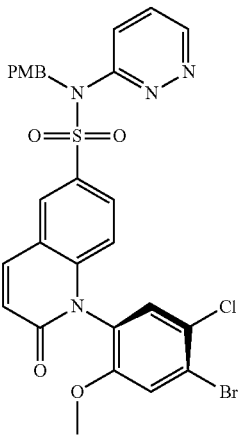

The title compound was prepared according to the method and purification protocol of Intermediate V using perfluorophenyl (P)-1-(4-bromo-5-chloro-2-methoxyphenyl)-2-oxo-1,2-dihydroquinoline-6-sulfonate (5.00 g, 8.19 mmol). This afforded (P)-1-(4-bromo-5-chloro-2-methoxyphenyl)-N-(4-methoxybenzyl)-2-oxo-N-(pyridazin-3-yl)-1,2-dihydroquinoline-6-sulfonamide (2.84 g, 4.42 mmol, 54% yield). m/z (ESI, positive ion) 641.0 (M+H)+.

Intermediate Z: (P)-1-(4-Bromo-2-Methoxy-5-Methylphenyl)-N-(2,4-Dimethoxybenzyl)-N-(Oxazol-2-Yl)-2-Oxo-1,2-Dihydroquinoline-6-Sulfonamide

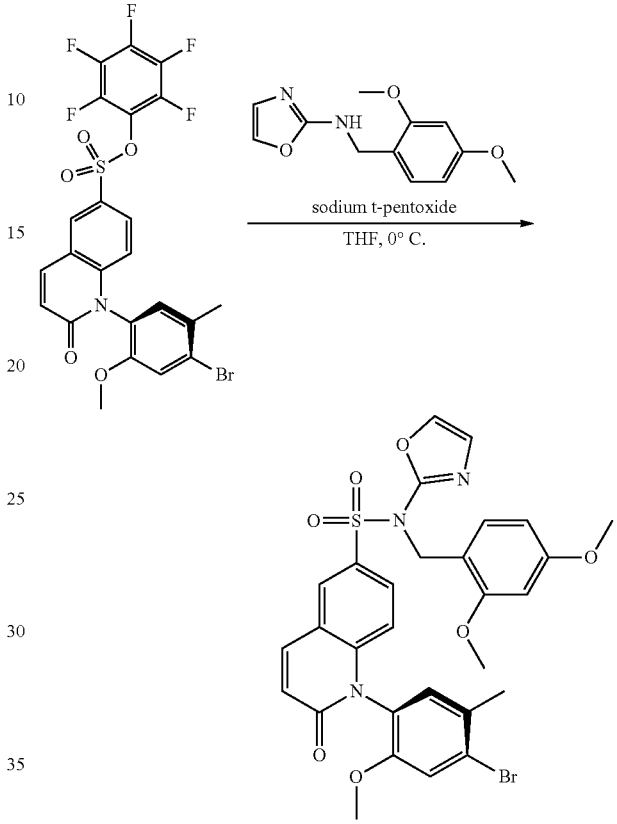

The title compound was prepared according to the method of Intermediate N using N-(2,4-dimethoxybenzyl)oxazol-2-amine (0.236 g, 1.01 mmol). The product was purified via column chromatography (two sequential RediSep Rf Gold 40 g columns, gradient elution 0-40% [3:1 EtOAc:EtOH]: [9:1 heptane:dichloromethane]) to afford (P)-1-(4-bromo-2-methoxy-5-methylphenyl)-N-(2,4-dimethoxybenzyl)-N-(oxazol-2-yl)-2-oxo-1,2-dihydroquinoline-6-sulfonamide (0.38 g, 0.59 mmol, 65% yield). 1H NMR (500 MHz, CHLOROFORM-d) δ ppm 7.92 (d, J=2.1 Hz, 1H), 7.86 (dd, J=9.0, 2.2 Hz, 1H), 7.69 (d, J=9.6 Hz, 1H), 7.46 (d, J=0.8 Hz, 1H), 7.33 (s, 1H), 7.16 (d, J=8.3 Hz, 1H), 7.08 (s, 1H), 7.01 (d, J=0.8 Hz, 1H), 6.82 (d, J=9.6 Hz, 1H), 6.68 (d, J=9.1 Hz, 1H), 6.37 (dd, J=8.3, 2.3 Hz, 1H), 6.17 (d, J=2.3 Hz, 1H), 4.94 (s, 2H), 3.74 (s, 3H), 3.73 (s, 3H), 3.44 (s, 3H), 2.40 (s, 3H).

Intermediate Ab: (3-(Trifluoromethyl)Bicyclo[1.1.1]Pentan-1-Yl)Zinc(II) Iodide

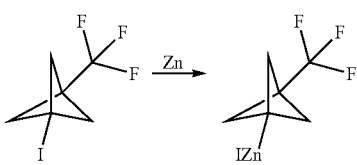

An oven-dried vial was charged with 1-iodo-3-(trifluoromethyl)bicyclo[1.1.1]pentane (100 mg, 0.382 mmol), purged with nitrogen, and was added Rieke zinc, 5% in tetrahydrofuran (27 mg, 0.549 mL, 0.420 mmol). The mixture was stirred at room temperature for 3 hours. The resulting suspension was allowed to settle down. The product was used without further purification.

Intermediate Ac: (P)-Perfluorophenyl 1-(4-Bromo-5-Fluoro-2-Methoxyphenyl)-7-Fluoro-2-Oxo-1,2-Dihydroquinoline-6-Sulfonate

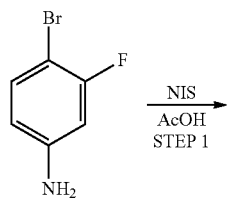

-continued

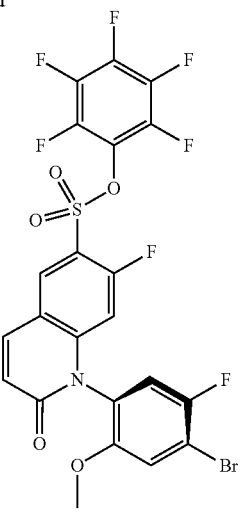

Step 1: 4-Bromo-5-Fluoro-2-Iodoaniline

N-iodosuccinimide (710 g, 3158 mmol) was added portion-wise to a solution of 4-bromo-3-fluoroaniline (500 g, 2631 mmol) in acetic acid (4000 mL) at 10-15° C. The reaction was stirred at rt for 1 hour. The reaction was then quenched with ice water (7 L) and the precipitated solid was filtered. The solid was washed with 5% sodium thiosulphate solution (6 L) and water (4 L), and dried to afford 4-bromo-5-fluoro-2-iodoaniline as brown solid (750 g, 2374 mmol, 90% yield). $^1$H NMR (400 MHz, DMSO-d6): δ ppm 7.76 (d, J=7.8 Hz, 1H), 6.68 (d, J=11.5 Hz, 1H), 5.68 (s, 2H).

Step 2: Ethyl (E)-3-(2-Amino-5-Bromo-4-Fluorophenyl)Acrylate

To a stirred solution of 4-bromo-5-fluoro-2-iodoaniline (500 g, 1583 mmol) in isopropanol (2550 mL) was added triethylamine (331 mL, 2374 mmol) at room temperature. The reaction mixture was degassed with nitrogen for 20 minutes. Tris(dibenzylideneacetone)dipalladium (0) (36.2 g, 39.6 mmol) was added, followed by slow addition of ethyl acrylate (162 g, 1614 mmol) under nitrogen atmosphere. Then the reaction mixture was heated to 70° C. and stirred for 6 hours. After completion, the reaction mixture was filtered through Celite and washed with dichloromethane (2 L). The filtrate was concentrated under reduced pressure to give the initial product. The initial product was stirred in 3% ethyl acetate in petroleum ether (6 L) and filtered. The solid obtained was washed with 3% EtOAc in petether (2 L) and dried to give ethyl (E)-3-(2-amino-5-bromo-4-fluorophenyl)acrylate (433 g, 1505 mmol, 95% yield) as a yellow solid. MS (ESI, positive ion) m/z: 288.0 (M+1). $^1$H NMR (400 MHz, DMSO-d6): δ ppm 7.69-7.98 (m, 2H), 6.61 (d, J=11.4 Hz, 1H), 6.45 (d, J=15.6 Hz, 1H), 6.12 (s, 2H), 4.17 (q, J=7.1 Hz, 2H), 1.26 (t, J=7.1 Hz, 3H).

Step 3: Ethyl (E)-3-(2-Amino-5-(Benzylthio)-4-Fluorophenyl)Acrylate

To a solution of ethyl (E)-3-(2-amino-5-bromo-4-fluorophenyl)acrylate (500.0 g, 1735 mmol) in 1,4-dioxane (2500 mL) was added N-ethyl-N-isopropylpropan-2-amine (449 g, 3471 mmol) and degassed with nitrogen for 20 minutes. (9,9-dimethyl-9H-xanthene-4,5-diyl)bis(diphenylphosphane) (50.2 g, 87 mmol) and tris(dibenzylideneacetone)dipalladium (0) (39.7 g, 43.4 mmol) were added to the reaction mixture. The mixture was purged with nitrogen and heated to 80° C. for 10 minutes. The reaction was cooled to room temperature and phenylmethanethiol (237 g, 1909 mmol) was added. The reaction was heated at 90° C. for 12 hours. The reaction was cooled to room temperature and diluted with ethyl acetate (1000 mL). The mixture was filtered through Celite and the Celite bed was washed with ethyl acetate (2500 mL). The filtrate was concentrated under reduced pressure to obtain the initial product. The initial product was purified by column chromatography (silica gel; mesh size 60-120, gradient elution 0-15% ethyl acetate and petroleum ether) to obtain ethyl (E)-3-(2-amino-5-(benzylthio)-4-fluorophenyl)acrylate (300.0 g, 905 mmol, 52% yield) as yellow solid. MS (ESI, positive ion) m/z: 332.1 (M+1). $^1$H NMR (400 MHz, DMSO-d6): δ ppm 7.72 (d, J=15.7 Hz, 1H), 7.41 (d, J=8.5 Hz, 1H), 7.01-7.32 (m, 5H), 6.38-6.55 (m, 1H), 6.24 (d, J=15.7 Hz, 1H), 6.11 (s, 2H), 4.17 (q, J=7.1 Hz, 2H), 3.89-4.07 (m, 2H), 1.26 (t, J=7.1 Hz, 3H).

Step 4: Ethyl (E)-3-(5-(Benzylthio)-2-((4-Bromo-5-Fluoro-2-Methoxyphenyl)Amino)-4-Fluorophenyl)Acrylate To a 250 mL 3-neck round-bottomed flask charged with ethyl (E)-3-(2-amino-5-(benzylthio)-4-fluorophenyl)acrylate (10 g, 30.2 mmol) and 1-bromo-2-fluoro-4-iodo-5-methoxybenzene (10.48 g, 31.7 mmol) in toluene (100 mL) was added cesium carbonate (39.3 g, 121 mmol). The mixture was degassed with nitrogen for 15 minutes. Tris(dibenzylideneacetone)dipalladium (0) (1.105 g, 1.207 mmol) and (9,9-dimethyl-9H-xanthene-4,5-diyl)bis(diphenylphosphane) (1.397 g, 2.414 mmol) were added to the reaction mixture and the mixture was heated at 110° C. for 16 hours. The reaction mixture was allowed to cool to room temperature, diluted with dichloromethane (200 mL) and filtered through Celite. The filtrate was concentrated under reduced pressure to obtain the initial product which was purified by stirring with methanol (250 mL) for 1 hour and filtered. The cake was washed with methanol (100 mL) and dried to obtain ethyl (E)-3-(5-(benzylthio)-2-((4-bromo-5-fluoro-2-methoxyphenyl)amino)-4-fluorophenyl)acrylate (13.5 g, 25.3 mmol, 84% yield) as yellow solid. MS (ESI, positive ion) m/z: 534.0 (M+1). $^1$H NMR (400 MHz, DMSO-d6): δ ppm 7.97 (s, 1H), 7.75 (d, J=8.4 Hz, 1H), 7.66 (d, J=15.9 Hz, 1H), 7.05-7.43 (m, 6H), 6.77 (d, J=11.1 Hz, 1H), 6.63 (d, J=10.2 Hz, 1H), 6.52 (d, J=15.9 Hz, 1H), 4.25 (s, 2H), 4.16 (q, J=7.1 Hz, 2H), 3.82 (s, 3H), 1.23 (t, J=7.1 Hz, 3H).

Step 5: 6-(Benzylthio)-1-(4-Bromo-5-Fluoro-2-Methoxyphenyl)-7-Fluoroquinolin-2(1H)-One To 500 mL 3-necked round-bottom flask was charged with ethyl (E)-3-(5-(benzylthio)-2-((4-bromo-5-fluoro-2-methoxyphenyl)amino)-4-fluorophenyl)acrylate (13.5 g, 25.3 mmol) in methanol (140 mL) was added tributylphosphane (50% solution in ethylacetate) (3.74 mL, 7.58 mmol). The reaction mixture was heated at 70° C. for 5 hours. The reaction mixture was allowed to cool 15° C., filtered and washed with cold methanol (100 mL) and dried to give 6-(benzylthio)-1-(4-bromo-5-fluoro-2-methoxyphenyl)-7-fluoroquinolin-2(1H)-one (9.5 g, 19.45 mmol, 77% yield) as yellow solid. MS (ESI, positive ion) m/z: 488.0 (M+1). $^1$H NMR (400 MHz, DMSO-d6): δ ppm 7.88-8.02 (m, 2H), 7.64 (d, J=6.3 Hz, 1H), 7.56 (d, J=8.6 Hz, 1H), 7.20-7.38 (m, 5H), 6.64 (d, J=9.6 Hz, 1H), 6.48 (d, J=11.3 Hz, 1H), 4.23 (s, 2H), 3.71 (s, 3H).

Step 6 & 7: Perfluorophenyl 1-(4-Bromo-5-Fluoro-2-Methoxyphenyl)-7-Fluoro-2-Oxo-1,2-Dihydroquinoline-6-Sulfonate To a 250 mL 3-necked round-bottom flask charged with 6-(benzylthio)-1-(4-bromo-5-fluoro-2-methoxyphenyl)-7-fluoroquinolin-2(1H)-one (9.5 g, 19.45 mmol) in acetonitrile (95 mL) were added acetic acid (6.4 mL) and water (4.13 mL). The resulting mixture was cooled to 0-5° C. and 1,3-dichloro-5,5-dimethylimidazolidine-2,4-dione (6.13 g, 31.1 mmol) was added portion-wise over 10-20 min keeping the internal temperature below 5-10° C. The resulting suspension was stirred at 5-10° C. under nitrogen for 45 minutes. Then a solution of 2,3,4,5,6-pentafluorophenol (7.16 g, 38.9 mmol) in acetonitrile (10 mL) was added over 10-15 min, followed by triethylamine (13.54 mL, 97 mmol) over 20 min keeping the internal temperature below 5-10° C. The mixture was continued to be stirred at 5-10° C. for 30 min. Ice water (200 mL) was added and the precipitated solid was filtered and washed with water (100 mL). The initial product was purified by stirring with methanol (50 mL), filtered, washed with MeOH (50 mL) and dried to obtain perfluorophenyl 1-(4-bromo-5-fluoro-2-methoxyphenyl)-7-fluoro-2-oxo-1,2-dihydroquinoline-6-sulfonate (9.5 g, 15.52 mmol, 80% yield) as an off white solid. MS (ESI, positive ion) m/z; 612.0 (M+1). $^1$H NMR (400 MHz, DMSO-d6): δ ppm 8.53 (d, J=7.4 Hz, 1H), 8.20 (d, J=9.8 Hz, 1H), 7.67 (dd, J=16.2, 7.4 Hz, 2H), 6.99 (d, J=12.1 Hz, 1H), 6.83 (d, J=9.8 Hz, 1H), 3.74 (s, 3H).

Step 8: (P)-Perfluorophenyl 1-(4-Bromo-5-Fluoro-2-Methoxyphenyl)-7-Fluoro-2-Oxo-1,2-Dihydroquinoline-6-Sulfonate Perfluorophenyl 1-(4-bromo-5-fluoro-2-methoxyphenyl)-7-fluoro-2-oxo-1,2-dihydroquinoline-6-sulfonate (135 g, 220 mmol) was purified by SFC via an Regis Whelk-O s,s 5×15 cm, 5 μm column; a mobile phase of 50% dichloromethane using a flowrate of 350 mL/min to generate (P)-perfluorophenyl 1-(4-bromo-5-fluoro-2-methoxyphenyl)-7-fluoro-2-oxo-1,2-dihydroquinoline-6-sulfonate (49.2 g, 80.4 mmol, 36% yield). MS (ESI, positive ion) m/z: 612.7 (M+1).

Chemical Examples

Examples 1 & 2: (M)-1-(4-(3-(Tert-Butyl)Cyclobutyl)-5-Fluoro-2-Methoxyphenyl)-N-(Isoxazol-3-Y1)-2-Oxo-1,2-Dihydroquinoline-6-Sulfonamide and 1-(4-(3-(Tert-Butyl)Cyclobutyl)-5-Fluoro-2-Methoxyphenyl)-N-(Isoxazol-3-Y1)-2-Oxo-1,2-Dihydroquinoline-6-Sulfonamide, Respectively

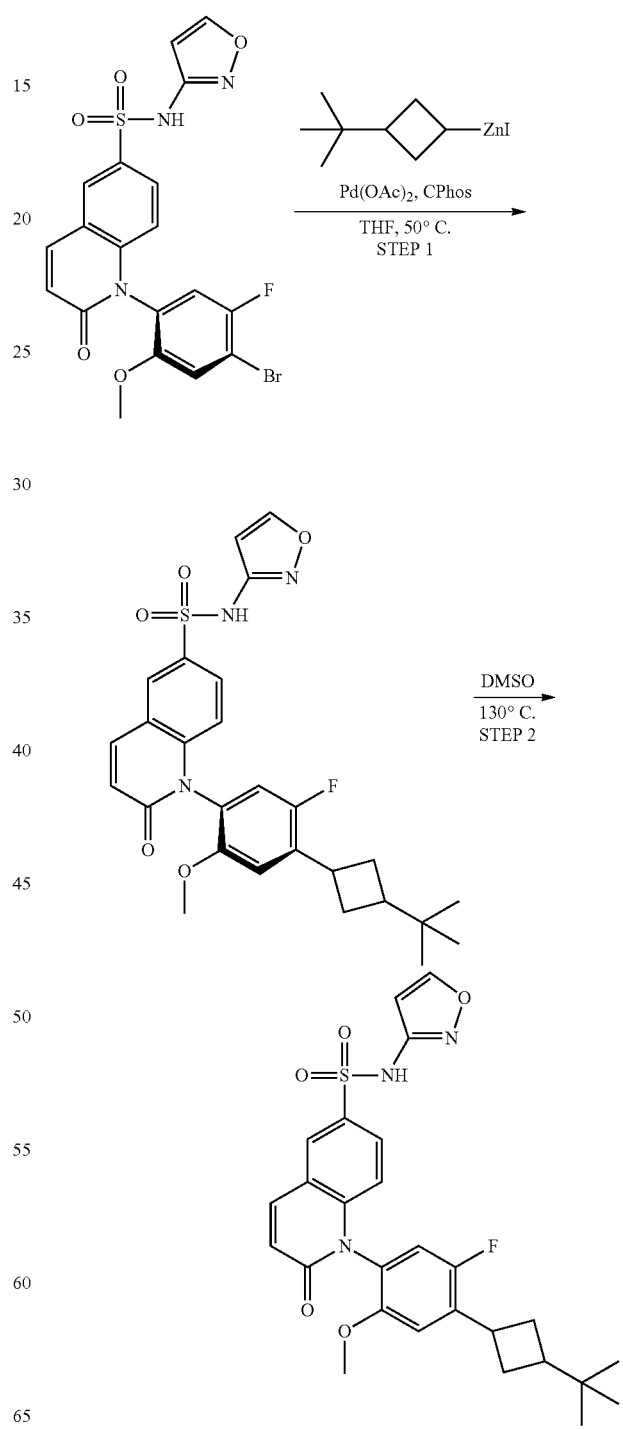

Step 1: (M)-1-(4-(3-(Tert-Butyl)Cyclobutyl)-5-Fluoro-2-Methoxyphenyl)-N-(Isoxazol-3-Yl)-2-Oxo-1,2-Dihydroquinoline-6-Sulfonamide A vial was charged with palladium(II) acetate (2.7 mg, 0.012 mmol), 2'-(dicyclohexylphosphino)-$N^2,N^2,N^6,N^6$-tetramethyl-[1,1'-biphenyl]-2,6-diamine (10.6 mg, 0.024 mmol), and (M)-1-(4-bromo-5-fluoro-2-methoxyphenyl)-N-(isoxazol-3-yl)-2-oxo-1,2-dihydroquinoline-6-sulfonamide (0.100 g, 0.202 mmol). (3-(tert-butyl)cyclobutyl)zinc(II) iodide (0.2 M in THF, 2.0 mL, 0.41 mmol) was added and the reaction was stirred for two hours at 50° C. The reaction was then diluted with ethyl acetate and washed twice with 1 N HCl. The organic layer was washed with brine, dried with sodium sulfate, filtered, and concentrated. The material was purified via column chromatography (RediSep Gold 40 g column, gradient elution 0-50% [3:1 EtOAc:EtOH]:heptane) to give (M)-1-(4-(3-(tert-butyl)cyclobutyl)-5-fluoro-2-methoxyphenyl)-N-(isoxazol-3-yl)-2-oxo-1,2-dihydroquinoline-6-sulfonamide (50 mg, 0.095 mmol, 47% yield) as a mixture of cis and trans isomers. $^1$H NMR (400 MHz, DMSO-$d_6$) δ ppm 11.65 (s, 1H), 8.73 (d, J=1.9 Hz, 1H), 8.30-8.41 (m, 1H), 8.20 (d, J=10.0 Hz, 1H), 7.72-8.00 (m, 1H), 7.04-7.29 (m, 2H), 6.73-6.85 (m, 2H), 6.44 (d, J=1.5 Hz, 1H), 3.64-3.75 (m, 3H), 3.45-3.63 (m, 1H), 2.18-2.38 (m, 4H), 1.89-2.04 (m, 1H), 0.83-0.97 (m, 9H). m/z (ESI, positive ion) 526.2 (M+H)$^+$.

Step 2: 1-(4-(3-(Tert-Butyl)Cyclobutyl)-5-Fluoro-2-Methoxyphenyl)-N-(Isoxazol-3-Yl)-2-Oxo-1,2-Dihydroquinoline-6-Sulfonamide (M)-1-(4-(3-(tert-Butyl)cyclobutyl)-5-fluoro-2-methoxyphenyl)-N-(isoxazol-3-yl)-2-oxo-1,2-dihydroquinoline-6-sulfonamide (44 mg) was epimerized by heating at 130° C. for 3 h in DMSO. This was then concentrated and dried to give 1-(4-(3-(tert-butyl)cyclobutyl)-5-fluoro-2-methoxyphenyl)-N-(isoxazol-3-yl)-2-oxo-1,2-dihydroquinoline-6-sulfonamide. $^1$H NMR (400 MHz, DMSO-$d_6$) δ ppm 11.66 (s, 1H), 8.74 (d, J=1.7 Hz, 1H), 8.31-8.41 (m, 1H), 8.14-8.30 (m, 1H), 7.75-7.93 (m, 1H), 7.03-7.32 (m, 2H), 6.74-6.84 (m, 2H), 6.45 (d, J=1.5 Hz, 1H), 3.70 (d, J=10.0 Hz, 3H), 3.57-3.64 (m, 1H), 2.19-2.41 (m, 4H), 1.91-2.06 (m, 1H), 0.86-0.96 (m, 9H). m/z (ESI, positive ion) 526.2 (M+H)$^+$.

Example 3: (P)-1-(4-(3-(Tert-Butyl)Cyclobutyl)-5-Fluoro-2-Methoxyphenyl)-N-(Isoxazol-3-Yl)-2-Oxo-1,2-Dihydroquinoline-6-Sulfonamide

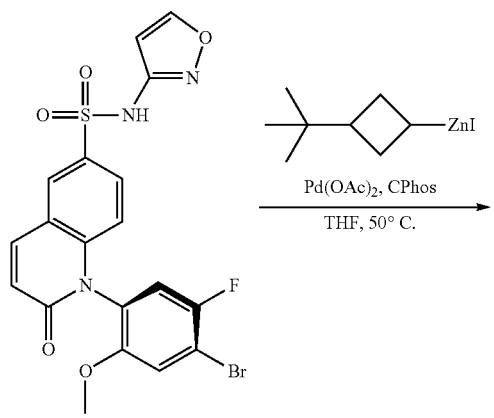

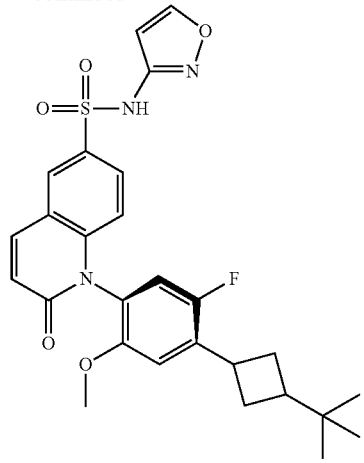

A vial was charged with palladium(II) acetate (7.3 mg, 0.032 mmol) 2'-(dicyclohexylphosphino)-$N^2,N^2,N^6,N^6$-tetramethyl-[1,1'-biphenyl]-2,6-diamine (28 mg, 0.065 mmol), and (P)-1-(4-bromo-5-fluoro-2-methoxyphenyl)-N-(isoxazol-3-yl)-2-oxo-1,2-dihydroquinoline-6-sulfonamide (160 mg, 0.324 mmol). (3-(tert-Butyl)cyclobutyl)zinc(II) iodide (0.2 M in THF, 3.2 mL, 0.65 mmol) was added, and the reaction was stirred for two hours at 50° C. The reaction was then diluted with ethyl acetate and washed twice with 1 N HCl. The organic layer was washed with brine, dried with sodium sulfate, filtered, and concentrated. The material was purified via column chromatography (RediSep Gold 40 g column, gradient elution 0-50% [3:1 EtOAc:EtOH]:heptane) to give (P)-1-(4-(3-(tert-butyl)cyclobutyl)-5-fluoro-2-methoxyphenyl)-N-(isoxazol-3-yl)-2-oxo-1,2-dihydroquinoline-6-sulfonamide (90 mg, 0.17 mmol, 53% yield). $^1$H NMR (400 MHz, DMSO-$d_6$) δ ppm 11.65 (s, 1H), 8.72 (d, J=1.9 Hz, 1H), 8.29-8.38 (m, 1H), 8.20 (d, J=10.0 Hz, 1H), 7.84 (dt, J=9.0, 1.9 Hz, 1H), 7.03-7.33 (m, 2H), 6.71-6.85 (m, 2H), 6.44 (d, J=1.7 Hz, 1H), 3.69 (d, J=10.2 Hz, 3H), 3.53-3.63 (m, 1H), 2.16-2.37 (m, 4H), 1.91-2.07 (m, 1H), 0.80-0.95 (m, 9H). m/z (ESI, positive ion) 526.2 (M+H)$^+$.

Example 4: (P)-1-(4-(3,3-Difluorocyclobutyl)-5-Fluoro-2-Methoxyphenyl)-N-(Isoxazol-3-Yl)-2-Oxo-1,2-Dihydroquinoline-6-Sulfonamide

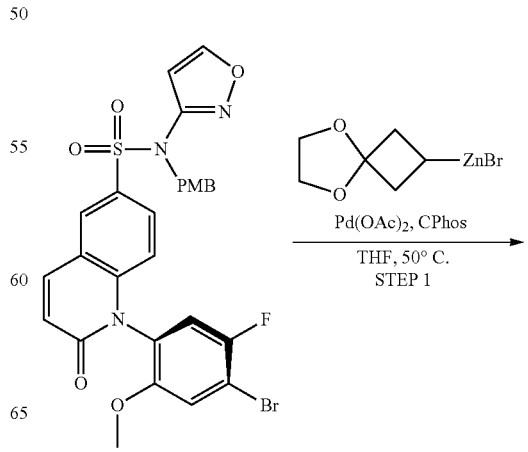

-continued

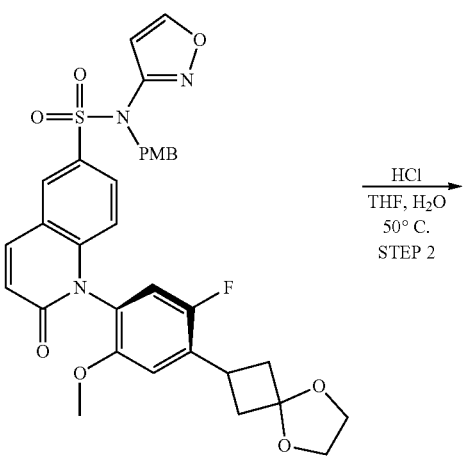

HCl
THF, H₂O
50° C.
STEP 2

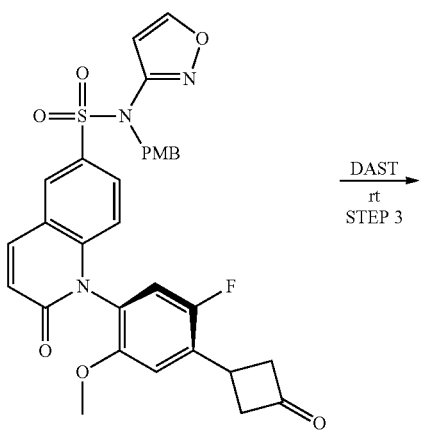

DAST
rt
STEP 3

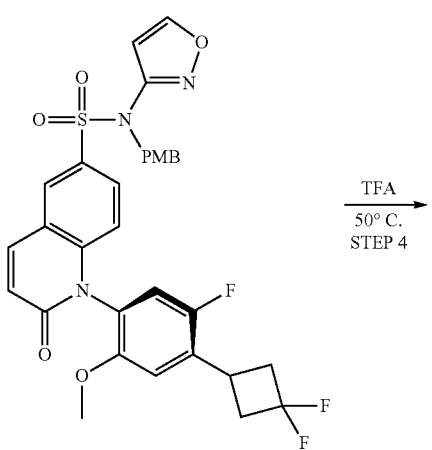

TFA
50° C.
STEP 4

-continued

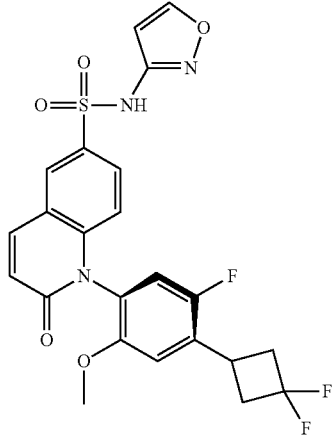

Step 1: (P)-1-(5-Fluoro-2-Methoxy-4-(5,8-Dioxaspiro[3.4]Octan-2-Yl)Phenyl)-N-(Isoxazol-3-Yl)-N-(4-Methoxybenzyl)-2-Oxo-1,2-Dihydroquinoline-6-Sulfonamide A vial was charged with (P)-1-(4-bromo-5-fluoro-2-methoxyphenyl)-N-(isoxazol-3-yl)-N-(4-methoxybenzyl)-2-oxo-1,2-dihydroquinoline-6-sulfonamide (Intermediate F) (0.500 g, 0.814 mmol), palladium(II) acetate (10.96 mg, 0.049 mmol), and 2'-(dicyclohexylphosphino)-$N^2,N^2,N^6,N^6$-tetramethyl-[1,1'-biphenyl]-2,6-diamine (0.043 g, 0.098 mmol). 5,8-Dioxaspiro[3.4]octan-2-ylzinc(II) bromide (0.1 M in THF, 14 mL, 0.70 mmol) was added and the reaction was stirred at 50° C. for 16 h. The reaction was then diluted with ethyl acetate and washed with water. The aqueous layer was extracted with ethyl acetate, and the combined organic layers were washed with brine, dried with sodium sulfate, filtered, and concentrated. The material was purified via column chromatography (RediSep Gold 40 g column, gradient elution 0-100% EtOAc:heptane) to afford (P)-1-(5-fluoro-2-methoxy-4-(5,8-dioxaspiro[3.4]octan-2-yl)phenyl)-N-(isoxazol-3-yl)-N-(4-methoxybenzyl)-2-oxo-1,2-dihydroquinoline-6-sulfonamide (0.258 g, 0.398 mmol, 49% yield) as a light yellow solid. m/z (ESI, positive ion) 648.2 (M+H)⁺.

Step 2: (P)-1-(5-Fluoro-2-Methoxy-4-(3-Oxocyclobutyl)Phenyl)-N-(Isoxazol-3-Yl)-N-(4-Methoxybenzyl)-2-Oxo-1,2-Dihydroquinoline-6-Sulfonamide (P)-1-(5-Fluoro-2-methoxy-4-(5,8-dioxaspiro[3.4]octan-2-yl)phenyl)-N-(isoxazol-3-yl)-N-(4-methoxybenzyl)-2-oxo-1,2-dihydroquinoline-6-sulfonamide (0.258 g, 0.398 mmol) was dissolved in tetrahydrofuran (4 mL). Hydrochloric acid (1 N in water, 2.0 mL, 2.0 mmol) was added and the reaction was stirred at 50° C. for three days. The reaction was then diluted with ethyl acetate and washed with water. The aqueous layer was extracted with ethyl acetate, and the combined organic layers were washed with brine, dried with sodium sulfate, filtered, and concentrated. The material was purified via column chromatography (RediSep Gold 40 g column, gradient elution 0-100% EtOAc:heptane) to afford (P)-1-(5-fluoro-2-methoxy-4-(3-oxocyclobutyl)phenyl)-N-(isoxazol-3-yl)-N-(4-methoxybenzyl)-2-oxo-1,2-dihydroquinoline-6-sulfonamide (0.179 g, 0.297 mmol, 74% yield) as a light yellow solid. m/z (ESI, positive ion) 604.2 (M+H)⁺.

Step 3: (P)-1-(4-(3,3-Difluorocyclobutyl)-5-Fluoro-2-Methoxyphenyl)-N-(Isoxazol-3-Yl)-N-(4-Methoxybenzyl)-2-Oxo-1,2-Dihydroquinoline-6-Sulfonamide A vial was charged with (P)-1-(5-fluoro-2-methoxy-4-(3-oxocyclobutyl)phenyl)-N-(isoxazol-3-yl)-N-(4-methoxybenzyl)-2-oxo-1,2-dihydroquinoline-6-sulfonamide (0.169 g, 0.280 mmol) and diethylaminosulfur trifluoride (1.85 mL, 14.0 mmol). The reaction was stirred for one hour at room temperature. The reaction was then poured into a 250-mL round-bottom flask, diluted with ethyl acetate, and saturated aqueous sodium bicarbonate solution was carefully added until bubbling ceased. The layers were separated, and the aqueous layer was extracted with ethyl acetate. The combined organic layers were washed with brine, dried with sodium sulfate, filtered, and concentrated. The material was purified via column chromatography (RediSep Gold 12 g column, gradient elution 0-100% EtOAc:heptane) to afford (P)-1-(4-(3,3-difluorocyclobutyl)-5-fluoro-2-methoxyphenyl)-N-(isoxazol-3-yl)-N-(4-methoxybenzyl)-2-oxo-1,2-dihydroquinoline-6-sulfonamide (0.142 g, 0.227 mmol, 81% yield) as a white solid. m/z (ESI, positive ion) 626.2 $(M+H)^+$.

Step 4: (P)-1-(4-(3,3-Difluorocyclobutyl)-5-Fluoro-2-Methoxyphenyl)-N-(Isoxazol-3-Yl)-2-Oxo-1,2-Dihydroquinoline-6-Sulfonamide (P)-1-(4-(3,3-Difluorocyclobutyl)-5-fluoro-2-methoxyphenyl)-N-(isoxazol-3-yl)-N-(4-methoxybenzyl)-2-oxo-1,2-dihydroquinoline-6-sulfonamide (0.142 g, 0.227 mmol) was dissolved in TFA (1 mL). The solution was heated to 50° C. and stirred for two hours. The reaction was concentrated and purified via column chromatography (RediSep Gold 40 g column, gradient elution 0-75% [3:1 EtOAc/EtOH]:heptane) to afford (P)-1-(4-(3,3-difluorocyclobutyl)-5-fluoro-2-methoxyphenyl)-N-(isoxazol-3-yl)-2-oxo-1,2-dihydroquinoline-6-sulfonamide (0.109 g, 0.216 mmol, 95% yield) as a white solid. $^1$H NMR (400 MHz, DMSO-$d_6$) δ ppm 11.66 (s, 1H), 8.74 (d, J=1.9 Hz, 1H), 8.37 (d, J=2.3 Hz, 1H), 8.22 (d, J=9.5 Hz, 1H), 7.84 (dd, J=8.9, 2.3 Hz, 1H), 7.36 (d, J=10.2 Hz, 1H), 7.27 (d, J=6.8 Hz, 1H), 6.76-6.84 (m, 2H), 6.45 (d, J=1.7 Hz, 1H), 3.71 (s, 3H), 3.57-3.68 (m, 1H), 2.91-3.13 (m, 4H). m/z (ESI, positive ion) 506.0 $(M+H)^+$.

Example 5: (P)-1-(5-Fluoro-4-(3-Fluoro-3-(Trifluoromethyl)Cyclobutyl)-2-Methoxyphenyl)-N-(Isoxazol-3-Yl)-2-Oxo-1,2-Dihydroquinoline-6-Sulfonamide

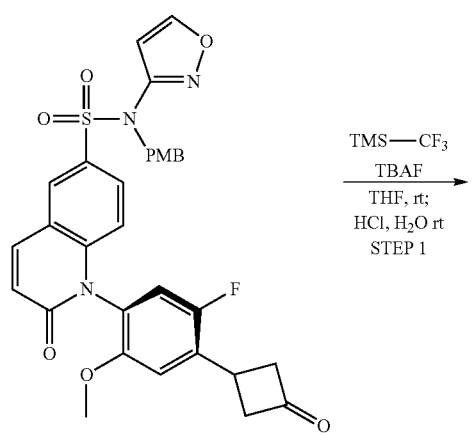

TMS—CF$_3$
TBAF
THF, rt;
HCl, H$_2$O rt
STEP 1

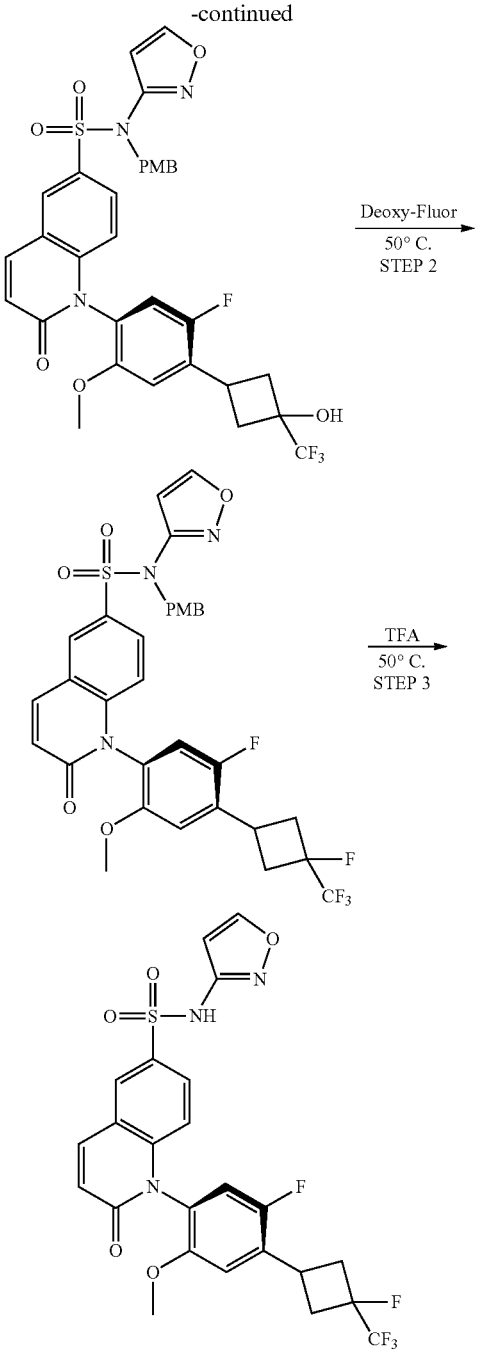

Step 1: (P)-1-(5-Fluoro-4-(3-Hydroxy-3-(Trifluoromethyl)Cyclobutyl)-2-Methoxyphenyl)-N-(Isoxazol-3-Yl)-N-(4-Methoxybenzyl)-2-Oxo-1,2-Dihydroquinoline-6-Sulfonamide A round-bottom flask was charged with (P)-1-(5-fluoro-2-methoxy-4-(3-oxocyclobutyl)phenyl)-N-(isoxazol-3-yl)-N-(4-methoxybenzyl)-2-oxo-1,2-dihydroquinoline-6-sulfonamide (0.500 g, 0.828 mmol) and THF (4.1 mL). Trifluoromethyltrimethylsilane (0.21 mL, 1.4 mmol) and tetra-n-butylammonium fluoride (1.0 M in THF, 0.083 mL, 0.083 mmol) were added in succession, and the reaction was stirred for one hour at room temperature. Additional (trifluoromethyl)trimethylsilane (0.208 ml, 1.408 mmol) and tetra-n-butylammonium fluoride (1.0 M in THF, 0.5 mL, 0.5 mmol) were added, and the reaction was stirred for 16 h. HCl (1 N in water, 5.8 mL, 5.8 mmol) was added, and the reaction was stirred for one hour. The reaction was then extracted twice with ethyl acetate. The combined organic layers were washed with brine, dried with sodium sulfate, filtered, and concentrated. The material was purified via column chromatography (BIOTAGE® SNAP 25 g column, gradient elution 0-100% EtOAc:heptane) to afford (P)-1-(5-fluoro-4-(3-hydroxy-3-(trifluoromethyl)cyclobutyl)-2-methoxyphenyl)-N-(isoxazol-3-yl)-N-(4-methoxybenzyl)-2-oxo-1,2-dihydroquinoline-6-sulfonamide (0.433 g, 0.643 mmol, 78% yield) as a tan solid. m/z (ESI, positive ion) 674.0 (M+H)$^+$.

Step 2: (P)-1-(5-Fluoro-4-(3-Fluoro-3-(Trifluoromethyl)Cyclobutyl)-2-Methoxyphenyl)-N-(Isoxazol-3-Yl)-N-(4-Methoxybenzyl)-2-Oxo-1,2-Dihydroquinoline-6-Sulfonamide To a vial charged with (P)-1-(5-fluoro-4-(3-hydroxy-3-(trifluoromethyl)cyclobutyl)-2-methoxyphenyl)-N-(isoxazol-3-yl)-N-(4-methoxybenzyl)-2-oxo-1,2-dihydroquinoline-6-sulfonamide (0.131 g, 0.194 mmol) was added bis(2-methoxyethyl)aminosulfur trifluoride (1.0 mL, 5.4 mmol). The reaction was heated to 50° C. and stirred for 16 h. The reaction was diluted with ethyl acetate and carefully quenched with saturated aqueous sodium bicarbonate solution. The aqueous layer was extracted with ethyl acetate, and the combined organic layers were washed with brine, dried with sodium sulfate, filtered, and concentrated. The material was purified via column chromatography (RediSep Gold 12 g column, gradient elution 0-100% EtOAc:heptane) and then via reverse phase HPLC using a XBridge Prep Shield RP18 19×100 mm column. The mobile was run under a gradient elution; 50-95% acetonitrile:water with 0.1% formic acid; flow rate: 40 mL/min. This afforded (P)-1-(5-fluoro-4-(3-fluoro-3-(trifluoromethyl)cyclobutyl)-2-methoxyphenyl)-N-(isoxazol-3-yl)-N-(4-methoxybenzyl)-2-oxo-1,2-dihydroquinoline-6-sulfonamide (0.027 g, 0.040 mmol, 21% yield) as a white solid. m/z (ESI, positive ion) 676.0 (M+H)$^+$.

Step 3: (P)-1-(5-Fluoro-4-(3-Fluoro-3-(Trifluoromethyl)Cyclobutyl)-2-Methoxyphenyl)-N-(Isoxazol-3-Yl)-2-Oxo-1,2-Dihydroquinoline-6-Sulfonamide A vial was charged with (P)-1-(5-fluoro-4-(3-fluoro-3-(trifluoromethyl)cyclobutyl)-2-methoxyphenyl)-N-(isoxazol-3-yl)-N-(4-methoxybenzyl)-2-oxo-1,2-dihydroquinoline-6-sulfonamide (0.027 g, 0.040 mmol) and TFA (0.2 mL) and stirred overnight at room temperature. The reaction was then concentrated and purified via column chromatography (BIOTAGE® SNAP 10 g column, gradient elution 0-75% [3:1 EtOAc/EtOH]:heptane) to afford (P)-1-(5-fluoro-4-(3-fluoro-3-(trifluoromethyl)cyclobutyl)-2-methoxyphenyl)-N-(isoxazol-3-yl)-2-oxo-1,2-dihydroquinoline-6-sulfonamide (0.018 g, 0.032 mmol, 81% yield) as an off-white solid. $^1$H NMR (400 MHz, DMSO-d$_6$) δ ppm 11.67 (s, 1H), 8.73 (d, J=1.7 Hz, 1H), 8.38 (d, J=2.1 Hz, 1H), 8.23 (d, J=9.5 Hz, 1H), 7.85 (dd, J=8.9, 2.3 Hz, 1H), 7.41-7.53 (m, 2H), 6.81 (d, J=9.7 Hz, 1H), 6.76 (d, J=9.1 Hz, 1H), 6.45 (d, J=1.9 Hz, 1H), 5.95-6.22 (m, 2H), 5.86 (s, 1H), 3.64-3.80 (m, 3H), 3.07-3.21 (m, 1H), 2.81-2.98 (m, 1H). m/z (ESI, positive ion) 556.0 (M+H)$^+$.

Examples 6 & 7: Cis-(P)-1-(5-Fluoro-2-Methoxy-4-(3-(Trifluoromethyl)Cyclobutyl)Phenyl)-N-(Isoxazol-3-Yl)-2-Oxo-1,2-Dihydroquinoline-6-Sulfonamide and Trans-(P)-1-(5-Fluoro-2-Methoxy-4-(3-(Trifluoromethyl)Cyclobutyl)Phenyl)-N-(Isoxazol-3-Yl)-2-Oxo-1,2-Dihydroquinoline-6-Sulfonamide, Respectively

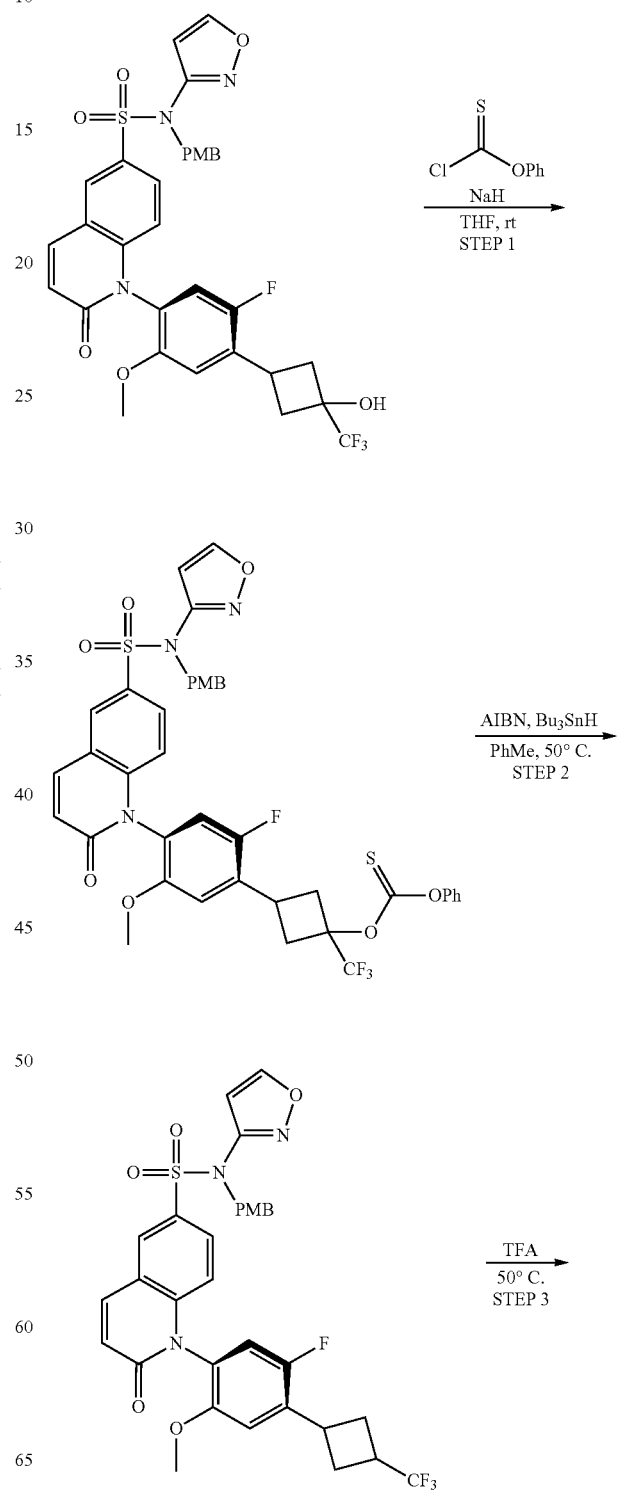

-continued

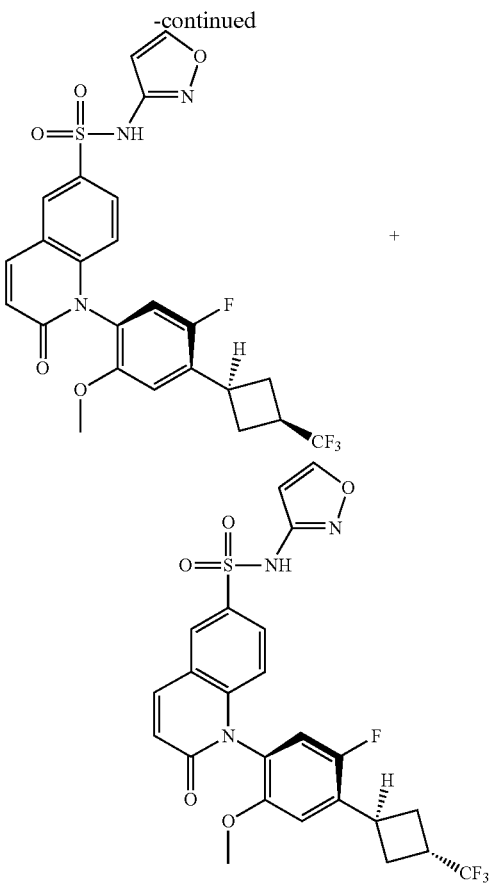

Step 1: (P)—O-(3-(2-Fluoro-4-(6-(N-(Isoxazol-3-Yl)-N-(4-Methoxybenzyl)Sulfamoyl)-2-Oxoquinolin-1(2H)-Yl)-5-Methoxyphenyl)-1-(Trifluoromethyl)Cyclobutyl) O-Phenyl Carbonothioate (P)-1-(5-Fluoro-4-(3-hydroxy-3-(trifluoromethyl)cyclobutyl)-2-methoxyphenyl)-N-(isoxazol-3-yl)-N-(4-methoxybenzyl)-2-oxo-1,2-dihydroquinoline-6-sulfonamide (0.200 g, 0.297 mmol), which was prepared according to procedures described in Steps 1-2 of Example 4 followed by Step 1 of Example 5, was dissolved in THF (1.5 mL) and cooled to 0° C. Sodium hydride (60% dispersion in mineral oil, 0.018 g, 0.45 mmol) was added and the reaction was allowed to warm to room temperature over 30 minutes. Phenyl chlorothionoformate (0.103 mL, 0.742 mmol) was added and the reaction was stirred for three hours. The reaction was then cooled to 0° C. and an additional portion of sodium hydride (60% dispersion in mineral oil, 0.018 g, 0.445 mmol) was added. The reaction was warmed to room temperature and stirred for 30 minutes, then additional phenyl chlorothionoformate (0.103 mL, 0.742 mmol) was added. The reaction was stirred at room temperature for 16 h. The reaction was then diluted with ethyl acetate and washed with saturated aqueous sodium bicarbonate solution. The aqueous layer was extracted with ethyl acetate, and the combined organic layers were washed with brine, dried with sodium sulfate, filtered, and concentrated. The material was purified via column chromatography (BIOTAGE® SNAP 25 g column, gradient elution 0-100% EtOAc:heptane) to afford (P)—O-(3-(2-fluoro-4-(6-(N-(isoxazol-3-yl)-N-(4-methoxybenzyl)sulfamoyl)-2-oxoquinolin-1(2H)-yl)-5-methoxyphenyl)-1-(trifluoromethyl)cyclobutyl) O-phenyl carbonothioate (0.215 g, 0.265 mmol, 89% yield) as a light yellow solid.

Step 2: (P)-1-(5-Fluoro-2-Methoxy-4-(3-(Trifluoromethyl)Cyclobutyl)Phenyl)-N-(Isoxazol-3-Yl)-N-(4-Methoxybenzyl)-2-Oxo-1,2-Dihydroquinoline-6-Sulfonamide (P)—O-(3-(2-Fluoro-4-(6-(N-(isoxazol-3-yl)-N-(4-methoxybenzyl)sulfamoyl)-2-oxoquinolin-1(2H)-yl)-5-methoxyphenyl)-1-(trifluoromethyl)cyclobutyl)-O-phenyl carbonothioate (0.119 g, 0.147 mmol) was dissolved in toluene (1.5 mL). Tri-n-butyl tin hydride (0.39 mL, 1.5 mmol) and azobisisobutyronitrile (0.024 g, 0.15 mmol) were added, and the reaction was degassed for 20 minutes with nitrogen, then heated to 50° C. and stirred for two hours. The reaction was also run twice under the same conditions and reagent stoichiometry using 0-(3-(2-fluoro-4-(6-(N-(isoxazol-3-yl)-N-(4-methoxybenzyl)sulfamoyl)-2-oxoquinolin-1(2H)-yl)-5-methoxyphenyl)-1-(trifluoromethyl)cyclobutyl) O-phenyl carbonothioate (0.025 g, 0.031 mmol). All three reactions were then combined, loaded onto a silica cartridge, and purified via column chromatography (BIOTAGE® SNAP 25 g column, gradient elution 0-100% EtOAc:heptane) to afford (P)-1-(5-fluoro-2-methoxy-4-(3-(trifluoromethyl)cyclobutyl)phenyl)-N-(isoxazol-3-yl)-N-(4-methoxybenzyl)-2-oxo-1,2-dihydroquinoline-6-sulfonamide (0.101 g, 0.154 mmol, 74% yield) as a light yellow solid. m/z (ESI, positive ion) 658.0 (M+H)$^+$.

Step 3: Cis-(P)-1-(5-Fluoro-2-Methoxy-4-(3-(Trifluoromethyl)Cyclobutyl)Phenyl)-N-(Isoxazol-3-Yl)-2-Oxo-1,2-Dihydroquinoline-6-Sulfonamide and Trans-(P)-1-(5-Fluoro-2-Methoxy-4-(3-(Trifluoromethyl)Cyclobutyl)Phenyl)-N-(Isoxazol-3-Yl)-2-Oxo-1,2-Dihydroquinoline-6-Sulfonamide A vial was charged with (P)-1-(5-fluoro-2-methoxy-4-(3-(trifluoromethyl)cyclobutyl)phenyl)-N-(isoxazol-3-yl)-N-(4-methoxybenzyl)-2-oxo-1,2-dihydroquinoline-6-sulfonamide (0.101 g, 0.154 mmol) and TFA (1.0 mL) and stirred overnight at room temperature. The reaction was then concentrated and purified via column chromatography (BIOTAGE® SNAP 10 g column, gradient elution 0-75% [3:1 EtOAc/EtOH]:heptane) to afford 81 mg of material as an off-white solid. This material was further purified using two sequential Chiralcel OJ-H, 2×25 cm columns. The mobile phase was run under isocratic conditions; supercritical CO$_2$ with 15% methanol; flow rate: 80 mL/min. The first eluting peak was assigned cis-(P)-1-(5-fluoro-2-methoxy-4-(3-(trifluoromethyl)cyclobutyl)phenyl)-N-(isoxazol-3-yl)-2-oxo-1,2-dihydroquinoline-6-sulfonamide (39 mg). The second eluting peak was assigned trans-(P)-1-(5-fluoro-2-methoxy-4-(3-(trifluoromethyl)cyclobutyl)phenyl)-N-(isoxazol-3-yl)-2-oxo-1,2-dihydroquinoline-6-sulfonamide (11 mg). Data for peak 1: $^1$H NMR (500 MHz, DMSO-d$_6$) δ ppm 11.65 (s, 1H), 8.60-8.83 (m, 1H), 8.35 (d, J=2.1 Hz, 1H), 8.20 (d, J=9.6 Hz, 1H), 7.83 (dd, J=9.0, 2.2 Hz, 1H), 7.31 (d, J=10.1 Hz, 1H), 7.14 (d, J=6.7 Hz, 1H), 6.71-6.89 (m, 2H), 6.44 (d, J=1.8 Hz, 1H), 3.71-3.83 (m, 1H), 3.69 (s, 3H), 3.24-3.31 (m, 1H), 2.56-2.65 (m, 2H), 2.31-2.44 (m, 2H). m/z (ESI, positive ion) 538.0 (M+H)$^+$. Data for peak 2: $^1$H NMR (500 MHz, DMSO-d$_6$) δ ppm 11.65 (s, 1H), 8.73 (d, J=1.8 Hz, 1H), 8.36 (d, J=2.3 Hz, 1H), 8.21 (d, J=9.6 Hz, 1H), 7.84 (dd, J=9.0, 2.2 Hz, 1H), 7.24-7.40 (m, 2H), 6.79 (d, J=9.6 Hz, 2H), 6.44 (d, J=1.6 Hz, 1H), 3.94 (quin, J=8.9

Hz, 1H), 3.71 (s, 3H), 3.25-3.31 (m, 1H), 2.56-2.75 (m, 4H). m/z (ESI, positive ion) 538.0 (M+H)+.

Example 7A: Trans-(P)-1-(5-Fluoro-2-Methoxy-4-(3-(Trifluoromethyl)Cyclobutyl)Phenyl)-N-(Isoxazol-3-Yl)-2-Oxo-1,2-Dihydroquinoline-6-Sulfonamide

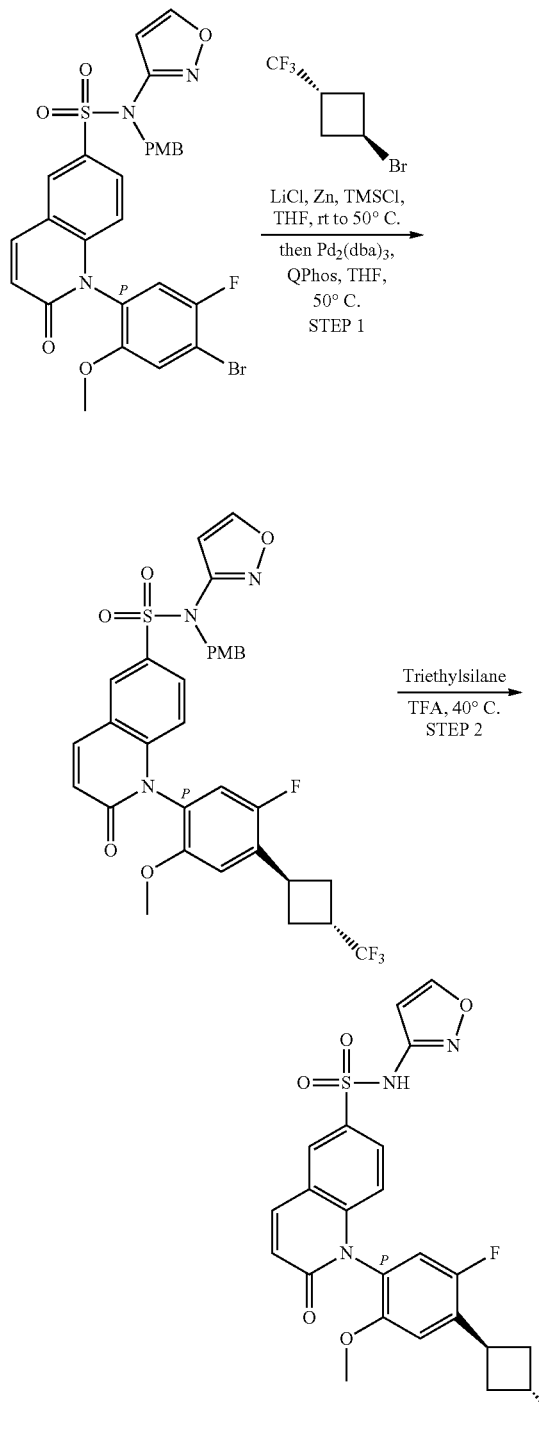

Step 1: (P)-1-(5-Fluoro-2-Methoxy-4-((1R,3R)-3-(Trifluoromethyl)Cyclobutyl)Phenyl)-N-(Isoxazol-3-Yl)-N-(4-Methoxybenzyl)-2-Oxo-1,2-Dihydroquinoline-6-Sulfonamide A 2 L three-neck round-bottom flask equipped with overhead stirrer, distillation head, thermocouple, addition funnel, and nitrogen inlet was charged with zinc dust (112 g, 1.72 mol), lithium chloride (16.0 g, 389 mmol), and anhydrous tetrahydrofuran (750 mL). Half of the tetrahydrofuran was removed via distillation at atmospheric pressure. The resultant mixture was cooled to 30° C. and chlorotrimethylsilane (3.0 mL, 23.5 mmol) was added. The mixture was warmed to 50° C. for 30 minutes, the temperature was raised, and the reaction volume was reduced by about 50 mL via distillation. The resultant mixture was cooled to 30° C. before trans-1-bromo-3-(trifluoromethyl)cyclobutane (75.0 g, 369 mmol, Enamine, LLC) was introduced. The mixture was then warmed to 40° C. A significant exotherm was observed and the heating mantle was replaced with an ambient temperature water bath. Once the exotherm had ceased, the water bath was removed and the reaction mixture stirred at 50° C. for 1 hour. The mixture was allowed to settle overnight and cool to ambient temperature. The supernatant was used without further manipulation. A separate 2 L three-neck round-bottom flask equipped with overhead stirrer, thermocouple, reflux condenser, and nitrogen inlet was charged with 1,2,3,4,5-pentaphenyl-1'-(di-t-butylphosphino)ferrocene (0.90 g, 1.27 mmol, Strem Chemicals, Inc.), tris(dibenzylideneacetone)dipalladium (0.60 g, 0.66 mmol, Strem Chemicals, Inc.), and anhydrous tetrahydrofuran (50 mL). The resultant mixture was warmed to 45° C. After 15 minutes, the reaction mixture was allowed to cool to room temperature before anhydrous tetrahydrofuran (250 mL) and (P)-1-(4-bromo-5-fluoro-2-methoxyphenyl)-N-(isoxazol-3-yl)-N-(4-methoxybenzyl)-2-oxo-1,2-dihydroquinoline-6-sulfonamide (Intermediate F) (187 g, 304 mmol) were introduced and the mixture was stirred until all solids dissolved. The resultant reaction mixture was warmed to 40° C. before the supernatant from the previous reaction containing trans-3-(trifluoromethyl)cyclobutyl)zinc(II) bromide in THF was added dropwise via cannula. The reaction was mildly exothermic and the rate of addition was adjusted to keep the internal temperature between 40-45° C. Once the addition was complete, the mixture was warmed to 50° C. After 3 hours, an aqueous solution of citric acid (1M, 400 mL) and water (500 mL) were introduced and the resultant mixture was extracted with ethyl acetate (1500 mL). The organic layer was washed with brine (500 mL) and concentrated under reduced pressure. The resultant solid was suspended in isopropanol (1 L) and stirred at 40° C. for 20 minutes. The mixture was cooled to ambient temperature and filtered through a sintered glass fritted filter. The solids were washed with isopropanol (40 mL) and transferred to a 2 L round-bottomed flask. Isopropyl acetate (1 L) was added and the mixture stirred at 40° C. for 20 minutes. The suspension was filtered through a sintered glass fritted filter and the solids were washed with additional isopropyl acetate (50 mL). The filtrate was transferred to a 2 L round-bottomed flask and SiliaMetS Thiol metal scavenger (20 g, Silicycle) and activated carbon (20 g) were added. The mixture stirred at ambient temperature for 20 minutes. The suspension was filtered through a pad of Celite and the solids washed with isopropyl acetate (500 mL). The filtrate was concentrated under reduced pressure. A mixture of dichloromethane and methyl tert-butyl ether (1:1 mixture, 1 L) was added to the solids and the resultant mixture stirred at 40° C.

for 20 minutes. The mixture was filtered through a sintered glass fritted filter and the trace solids were washed with methyl tert-butyl ether (30 mL). The combined filtrate was concentrated under reduced pressure to afford (P)-1-(5-fluoro-2-methoxy-4-((1R,3R)-3-(trifluoromethyl)cyclobutyl)phenyl)-N-(isoxazol-3-yl)-N-(4-methoxybenzyl)-2-oxo-1,2-dihydroquinoline-6-sulfonamide (150 g, 228 mmol, 75% yield) as a reddish solid that was used in the next step without further purification. m/z (ESI) 658.0 (M+H)$^+$.

Step 2: (P)-1-(5-Fluoro-2-Methoxy-4-((1R,3R)-3-(Trifluoromethyl)Cyclobutyl)Phenyl)-N-(Isoxazol-3-Yl)-2-Oxo-1,2-Dihydroquinoline-6-Sulfonamide A 2 L three-neck round-bottom flask equipped with an overhead stirrer, a Claisen adapter, addition funnel, a thermocouple, a reflux condenser, and a nitrogen inlet was charged with (P)-1-(5-fluoro-2-methoxy-4-(1R,3R)-3-(trifluoromethyl)cyclobutyl)phenyl)-N-(isoxazol-3-yl)-N-(4-methoxybenzyl)-2-oxo-1,2-dihydroquinoline-6-sulfonamide (150 g, 228 mmol) and triethylsilane (85 mL, 532 mmol). Trifluoroacetic acid (500 mL) was added dropwise over 60 min at a rate to prevent the internal temperature of the reaction exceeding 40° C.-50° C. The reaction mixture was warmed to 50° C. for 30 min before it was allowed to cool to room temperature. Heptane (800 mL) was introduced and the mixture was concentrated under reduced pressure. The resultant solid was azeotroped with heptane (2×800 mL) then suspended in heptane (800 mL). The mixture was stirred at ambient temperature for 10 minutes before the heptane was decanted away. The remaining material was dissolved in dichloromethane (1.5 L) and was washed with an aqueous solution of tribasic sodium phosphate (0.2 N, 2×300 mL). The organic layer was separated and concentrated under reduced pressure. The residue was suspended in methyl tert-butyl ether (2 L) and stirred at 40° C. for 20 minutes. The suspension was filtered through a sintered glass fritted filter and the solids washed with methyl tert-butyl ether (100 mL). The filtrate was evaporated to dryness under reduced pressure and the product was suspended in methanol (500 mL). The resultant suspension was concentrated under reduced pressure and the residue was purified via SFC in two steps (Step 1: Waters Torus 2-PIC, 5 µM, 3×15 cm column using 25% methanol as an eluent at 180 mL/min flow rate; Step 2: Chiralcel OJ-H, 5 µm, 5×40 cm column using 20% methanol as an eluent at 240 mL/min flow rate) to afford (P)-1-(5-fluoro-2-methoxy-4-((1R,3R)-3-(trifluoromethyl)cyclobutyl)phenyl)-N-(isoxazol-3-yl)-2-oxo-1,2-dihydroquinoline-6-sulfonamide (63.3 g, 118 mmol, 52% yield). $^1$H NMR (500 MHz, CDCl$_3$) δ: 8.58 (s, 1H), 8.26 (s, 1H), 8.16 (d, J=1.8 Hz, 1H), 7.78 (t, J=9.9 Hz, 2H), 6.92-6.98 (m, 2H), 6.86 (d, J=9.6 Hz, 1H), 6.77 (d, J=9.0 Hz, 1H), 6.59 (s, 1H), 3.98 (quin, J=9.0 Hz, 1H), 3.72-3.80 (m, 3H), 2.99-3.11 (m, 1H), 2.69-2.74 (m, 2H), 2.60-2.65 (m, 2H). $^{13}$C NMR (126 MHz, CDCl$_3$) δ: 161.57, 159.89, 156.85, 154.94 (d, J=241.6 Hz), 151.41 (d, J=2.7 Hz), 143.79, 139.41, 133.89 (d, J=15.4 Hz), 132.62, 128.19, 128.30 (q, J=276.1 Hz), 124.00, 123.34, 120.04, 117.16 (d, J=25.4 Hz), 116.42, 111.73 (d, J=5.5 Hz), 98.59, 56.39, 34.01 (q, J=30.0 Hz), 31.80, 27.76, 27.50, 27.31. m/z (ESI) 538.0 (M+H)$^+$.

Examples 8 and 9: Trans-(P)-1-(5-Fluoro-4-(3-Fluoro-3-(Trifluoromethyl)Cyclobutyl)-2-Methoxyphenyl)-N-(Isoxazol-3-Yl)-2-Oxo-1,2-Dihydroquinoline-6-Sulfonamide and Cis-(P)-1-(5-Fluoro-4-(3-Fluoro-3-(Trifluoromethyl)Cyclobutyl)-2-Methoxyphenyl)-N-(Isoxazol-3-Yl)-2-Oxo-1,2-Dihydroquinoline-6-Sulfonamide, Respectively

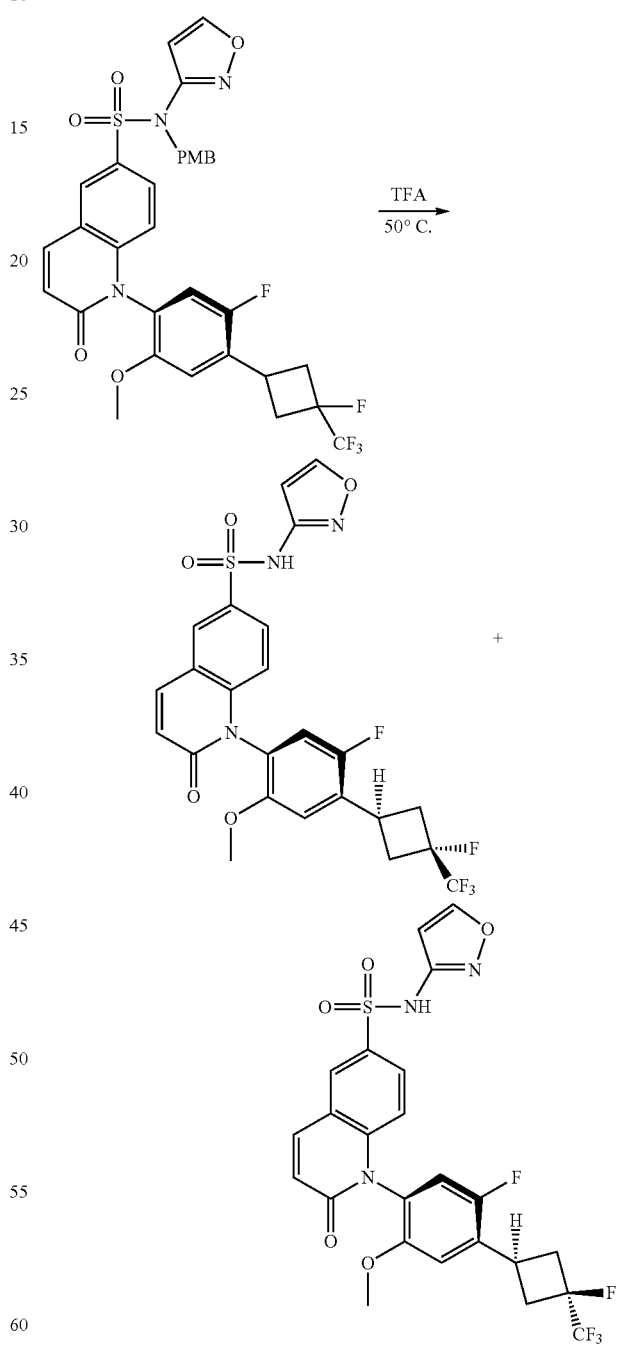

A vial was charged with (P)-1-(5-fluoro-4-(3-fluoro-3-(trifluoromethyl)cyclobutyl)-2-methoxyphenyl)-N-(isoxazol-3-yl)-N-(4-methoxybenzyl)-2-oxo-1,2-dihydroquinoline-6-sulfonamide (0.212 g, 0.314 mmol) and TFA (1 mL) and stirred at 50° C. for two hours. The reaction was then concentrated and purified using two sequential Chiralpak IC, 2×15 cm columns. The mobile phase was run under isocratic conditions; supercritical $CO_2$ with 25% methanol; flow rate: 80 mL/min. The first eluting peak was assigned trans-(P)-1-(5-fluoro-4-(3-fluoro-3-(trifluoromethyl)cyclobutyl)-2-methoxyphenyl)-N-(isoxazol-3-yl)-2-oxo-1,2-dihydroquinoline-6-sulfonamide (62 mg). The second eluting peak was assigned cis-(P)-1-(5-fluoro-4-(3-fluoro-3-(trifluoromethyl)cyclobutyl)-2-methoxyphenyl)-N-(isoxazol-3-yl)-2-oxo-1,2-dihydroquinoline-6-sulfonamide (42 mg). Data for peak 1: $^1$H NMR (400 MHz, DMSO-$d_6$) δ ppm 11.65 (s, 1H), 8.73 (d, J=1.7 Hz, 1H), 8.37 (d, J=2.3 Hz, 1H), 8.22 (d, J=9.5 Hz, 1H), 7.84 (dd, J=8.9, 2.3 Hz, 1H), 7.49 (d, J=10.2 Hz, 1H), 7.44 (d, J=6.2 Hz, 1H), 6.79 (dd, J=9.2, 5.7 Hz, 2H), 6.44 (d, J=1.9 Hz, 1H), 5.95-6.14 (m, 2H), 5.85 (s, 1H), 3.71 (s, 3H), 3.15 (td, J=15.3, 9.8 Hz, 1H), 2.79-2.99 (m, 1H). m/z (ESI, positive ion) 555.2 (M+H)$^+$. Data for peak 2: $^1$H NMR (400 MHz, DMSO-$d_6$) δ ppm 11.65 (s, 1H), 8.73 (d, J=1.7 Hz, 1H), 8.37 (d, J=2.3 Hz, 1H), 8.23 (d, J=9.7 Hz, 1H), 7.84 (dd, J=8.9, 2.3 Hz, 1H), 7.49 (d, J=10.0 Hz, 1H), 7.44 (d, J=6.2 Hz, 1H), 6.80 (d, J=9.7 Hz, 1H), 6.76 (d, J=9.1 Hz, 1H), 6.45 (d, J=1.7 Hz, 1H), 5.96-6.17 (m, 2H), 5.85 (s, 1H), 3.70 (s, 3H), 3.14 (td, J=15.5, 9.6 Hz, 1H), 2.79-2.99 (m, 1H). m/z (ESI, positive ion) 555.4 (M+H)$^+$.

Examples 10 and 11: Cis-(P)-1-(5-Chloro-4-(3-Fluoro-3-(Trifluoromethyl)Cyclobutyl)-2-Methoxyphenyl)-N-(Isoxazol-3-Yl)-2-Oxo-1,2-Dihydroquinoline-6-Sulfonamide and Trans-(P)-1-(5-Chloro-4-(3-Fluoro-3-(Trifluoromethyl)Cyclobutyl)-2-Methoxyphenyl)-N-(Isoxazol-3-Yl)-2-Oxo-1,2-Dihydroquinoline-6-Sulfonamide, Respectively

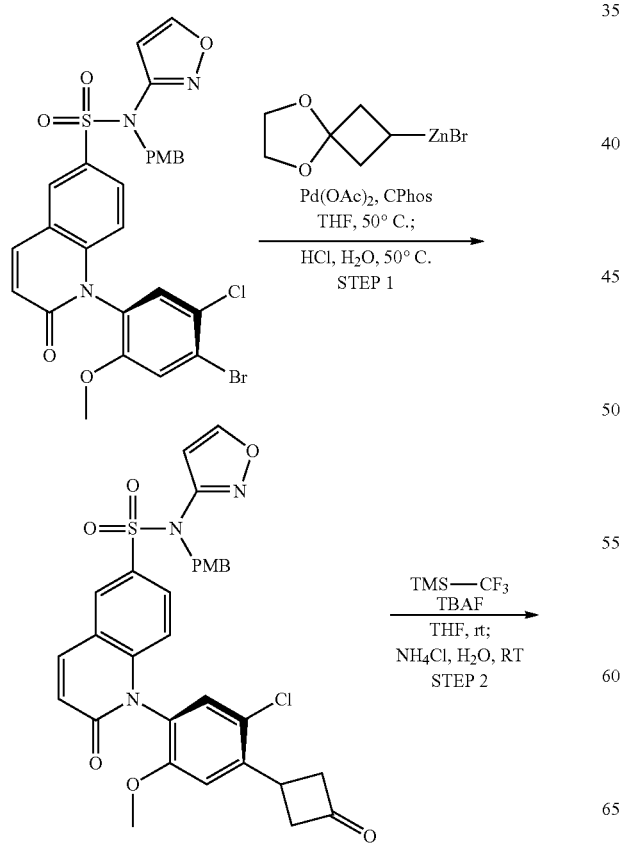

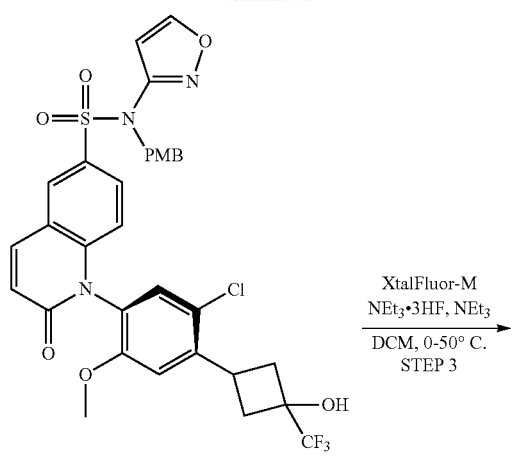

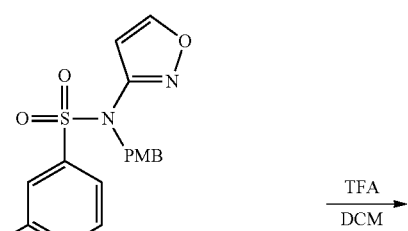

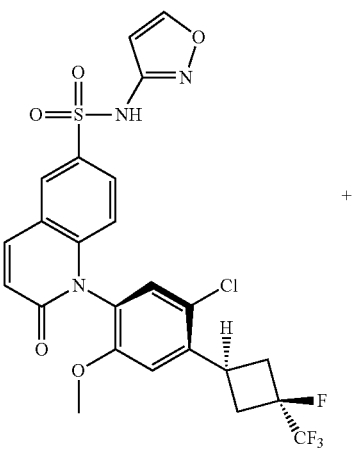

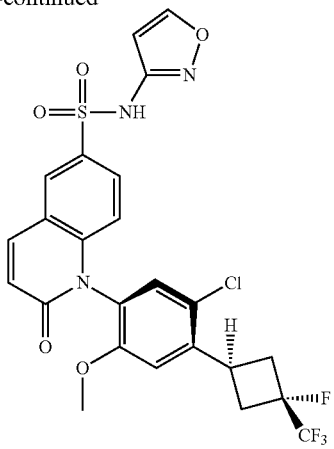

Step 1: (P)-1-(5-Chloro-2-Methoxy-4-(3-Oxocyclobutyl)Phenyl)-N-(Isoxazol-3-Yl)-N-(4-Methoxybenzyl)-2-Oxo-1,2-Dihydroquinoline-6-Sulfonamide A 3-neck 250-mL round-bottom flask equipped with reflux adapter and internal temp probe was charged with (P)-1-(4-bromo-5-chloro-2-methoxyphenyl)-N-(isoxazol-3-yl)-N-(4-methoxybenzyl)-2-oxo-1,2-dihydroquinoline-6-sulfonamide (5 g, 7.93 mmol), palladium(II) acetate (0.107 g, 0.476 mmol), and 2'-(dicyclohexylphosphino)-$N^2,N^2,N^6,N^6$-tetramethyl-[1,1'-biphenyl]-2,6-diamine (0.415 g, 0.951 mmol) then evacuated and backfilled with nitrogen. 5,8-Dioxaspiro[3.4]octan-2-ylzinc(II) bromide (0.4 M in THF, 30 mL, 12 mmol) was added, and the reaction was stirred at 50° C. for 20 h. The mixture was then quenched with 2 N aq. HCl (80 mL). The temperature was elevated to 50° C., and the mixture was stirred for 4 h. The mixture was then partitioned between water and EtOAc. The layers were separated. The aqueous extract was extracted with EtAOc (2×100 mL). The combined extracts were washed with brine and then concentrated to a black residue. The product was purified by column chromatography, (200 g silica column, gradient elution 0-100% EtOAc:heptane) to afford (P)-1-(5-chloro-2-methoxy-4-(3-oxocyclobutyl)phenyl)-N-(isoxazol-3-yl)-N-(4-methoxybenzyl)-2-oxo-1,2-dihydroquinoline-6-sulfonamide as a tan solid. $^1$H NMR (500 MHz, DMSO-$d_6$) δ ppm 8.80 (d, J=1.6 Hz, 1H), 8.36 (d, J=2.1 Hz, 1H), 8.15 (d, J=9.9 Hz, 1H), 7.78 (dd, J=9.1, 2.1 Hz, 1H), 7.56 (s, 1H), 7.47 (s, 1H), 7.25 (d, J=8.8 Hz, 2H), 6.86 (d, J=8.6 Hz, 2H), 6.82 (d, J=9.6 Hz, 1H), 6.69-6.76 (m, 2H), 4.91 (s, 2H), 3.97-4.07 (m, 2H), 3.75 (s, 3H), 3.71 (s, 3H), 3.47-3.52 (m, 3H). m/z (ESI, positive ion) 620.0 (M+H)$^+$.

Step 2: (P)-1-(5-Chloro-4-(3-Hydroxy-3-(Trifluoromethyl)Cyclobutyl)-2-Methoxyphenyl)-N-(Isoxazol-3-Yl)-N-(4-Methoxybenzyl)-2-Oxo-1,2-Dihydroquinoline-6-Sulfonamide A 25-mL round-bottom flask was charged with (P)-1-(5-chloro-2-methoxy-4-(3-oxocyclobutyl)phenyl)-N-(isoxazol-3-yl)-N-(4-methoxybenzyl)-2-oxo-1,2-dihydroquinoline-6-sulfonamide (0.806 g, 1.30 mmol) and THF (6.5 mL) and equipped with an internal temp probe. (Trifluoromethyl)trimethylsilane (0.38 mL, 2.6 mmol) was introduced and tetrabutylammonium fluoride, 1.0 m solution in tetrahydrofuran (1.300 ml, 1.300 mmol) was added dropwise to the reaction mixture ensuring the internal temperature did not exceed 35° C. An exotherm and bubbling was observed. The reaction was stirred for 3 h and then diluted with sat. aq. NH$_4$Cl and extracted twice with ethyl acetate. The combined organic layers were washed with brine, dried with sodium sulfate, filtered, and concentrated. The material was purified via column chromatography (BIOTAGE® SNAP 100 g column, gradient elution 0-100% EtOAc:heptane) to afford (P)-1-(5-chloro-4-(3-hydroxy-3-(trifluoromethyl)cyclobutyl)-2-methoxyphenyl)-N-(isoxazol-3-yl)-N-(4-methoxybenzyl)-2-oxo-1,2-dihydroquinoline-6-sulfonamide as an off-white solid. m/z (ESI, positive ion) 690.0 (M+H)$^+$.

Step 3: (P)-1-(5-Chloro-4-(3-Fluoro-3-(Trifluoromethyl)Cyclobutyl)-2-Methoxyphenyl)-N-(Isoxazol-3-Yl)-N-(4-Methoxybenzyl)-2-Oxo-1,2-Dihydroquinoline-6-Sulfonamide A 2-neck 50-mL round-bottom flask equipped with a reflux adapter was purged with nitrogen then charged with triethylamine trihydrofluoride (1.4 mL, 8.7 mmol), triethylamine (0.61 mL, 4.4 mmol), and dichloromethane (9.7 mL) and cooled to 0° C. Difluoro(morpholino)sulfonium tetrafluoroborate (1.58 g, 6.52 mmol) and a solution of (P)-1-(5-chloro-4-(3-hydroxy-3-(trifluoromethyl)cyclobutyl)-2-methoxyphenyl)-N-(isoxazol-3-yl)-N-(4-methoxybenzyl)-2-oxo-1,2-dihydroquinoline-6-sulfonamide (1.00 g, 1.45 mmol) in dichloromethane (4.8 mL) were added successively, and the reaction was warmed to 50° C. and stirred for 16 h. The reaction was then cooled to 0° C. and quenched carefully with saturated aqueous sodium bicarbonate solution and then extracted thrice with ethyl acetate. The combined organic layers were dried with magnesium sulfate, filtered, and concentrated. The material was purified via column chromatography (BIOTAGE® SNAP 50 g column, gradient elution 0-100% EtOAc:heptane) to afford (P)-1-(5-chloro-4-(3-fluoro-3-(trifluoromethyl)cyclobutyl)-2-methoxyphenyl)-N-(isoxazol-3-yl)-N-(4-methoxybenzyl)-2-oxo-1,2-dihydroquinoline-6-sulfonamide (599 mg, 0.866 mmol, 60% yield) as a tan solid. $^1$H NMR (500 MHz, DMSO-$d_6$) δ ppm 8.81 (d, J=1.0 Hz, 1H), 8.32-8.44 (m, 1H), 8.16 (d, J=9.6 Hz, 1H), 7.78 (dd, J=9.1, 2.1 Hz, 1H), 7.67 (d, J=4.2 Hz, 1H), 7.47 (d, J=6.2 Hz, 1H), 7.26 (d, J=8.6 Hz, 2H), 6.80-6.90 (m, 3H), 6.69-6.77 (m, 2H), 5.97-6.16 (m, 2H), 5.88 (s, 1H), 4.92 (s, 2H), 3.76 (d, J=4.7 Hz, 3H), 3.71 (s, 3H), 3.06 (tt, J=15.8, 10.8 Hz, 1H), 2.78-2.96 (m, 1H). m/z (ESI, positive ion) 692.2 (M+H)$^+$.

Step 4: Cis-(P)-1-(5-Chloro-4-(3-Fluoro-3-(Trifluoromethyl)Cyclobutyl)-2-Methoxyphenyl)-N-(Isoxazol-3-Yl)-2-Oxo-1,2-Dihydroquinoline-6-Sulfonamide and Trans-(P)-1-(5-Chloro-4-(3-Fluoro-3-(Trifluoromethyl)Cyclobutyl)-2-Methoxyphenyl)-N-(Isoxazol-3-Yl)-2-Oxo-1,2-Dihydroquinoline-6-Sulfonamide A 40-mL vial was charged with (P)-1-(5-chloro-4-(3-fluoro-3-(trifluoromethyl)cyclobutyl)-2-methoxyphenyl)-N-(isoxazol-3-yl)-N-(4-methoxybenzyl)-2-oxo-1,2-dihydroquinoline-6-sulfonamide (599 mg, 0.866 mmol) dichloromethane (1.3 mL), and TFA (1.3 mL). The vial was sealed and warmed to 50° C. and stirred for 16 h. The reaction was then concentrated under reduced pressure and purified by silica gel column chromatography (50 g column, gradient elution 0-75% [3:1 EtOAc/EtOH]:heptane). Further purification was accomplished using a Chiralpak IC, 2×25 cm column. The mobile phase was run under isocratic conditions; supercritical CO$_2$ with 30% methanol; flow rate: 80 mL/min. The first eluting peak was assigned cis-(P)-1-(5-chloro-4-(3-fluoro-3-(trifluoromethyl)cyclobutyl)-2-methoxyphenyl)-N-(isoxazol-3-yl)-2-oxo-1,2-dihydroquinoline-6-sulfonamide. The second eluting peak was assigned trans-(P)-1-(5-chloro-4-(3-fluoro-3-(trifluoromethyl)cyclobutyl)-2-methoxyphenyl)-N-(isoxazol-3-yl)-2-oxo-1,2-dihydroquinoline-6-sulfonamide. Data for peak 1: $^1$H NMR (500 MHz, DMSO-d$_6$) δ ppm 11.66 (s, 1H), 8.73 (d, J=1.8 Hz, 1H), 8.37 (d, J=1.8 Hz, 1H), 8.22 (d, J=9.9 Hz, 1H), 7.84 (dd, J=8.8, 2.1 Hz, 1H), 7.66 (s, 1H), 7.46 (s, 1H), 6.80 (dd, J=9.2, 4.3 Hz, 2H), 6.44 (d, J=1.6 Hz, 1H), 5.97-6.14 (m, 2H), 5.88 (s, 1H), 3.75 (s, 3H), 3.06 (td, J=15.8, 9.9 Hz, 1H), 2.78-2.94 (m, 1H). m/z (ESI, positive ion) 572.0 (M+H)$^+$. Data for peak 2: $^1$H NMR (500 MHz, DMSO-d$_6$) δ ppm 11.66 (s, 1H), 8.73 (d, J=1.6 Hz, 1H), 8.38 (d, J=2.1 Hz, 1H), 8.23 (d, J=9.6 Hz, 1H), 7.84 (dd, J=8.8, 2.1 Hz, 1H), 7.66 (s, 1H), 7.45 (s, 1H), 6.80 (d, J=9.9 Hz, 1H), 6.77 (d, J=8.8 Hz, 1H), 6.45 (d, J=1.6 Hz, 1H), 6.00-6.18 (m, 2H), 5.89 (s, 1H), 3.74 (s, 3H), 3.05 (td, J=16.2, 9.5 Hz, 1H), 2.79-2.94 (m, 1H). m/z (ESI, positive ion) 572.0 (M+H)$^+$.

Examples 12 & 13: Cis-(P)-1-(5-Chloro-2-Methoxy-4-(3-(Trifluoromethyl)Cyclobutyl)Phenyl)-N-(Isoxazol-3-Yl)-2-Oxo-1,2-Dihydroquinoline-6-Sulfonamide and Trans-(P)-1-(5-Chloro-2-Methoxy-4-(3-(Trifluoromethyl)Cyclobutyl)Phenyl)-N-(Isoxazol-3-Yl)-2-Oxo-1,2-Dihydroquinoline-6-Sulfonamide, Respectively

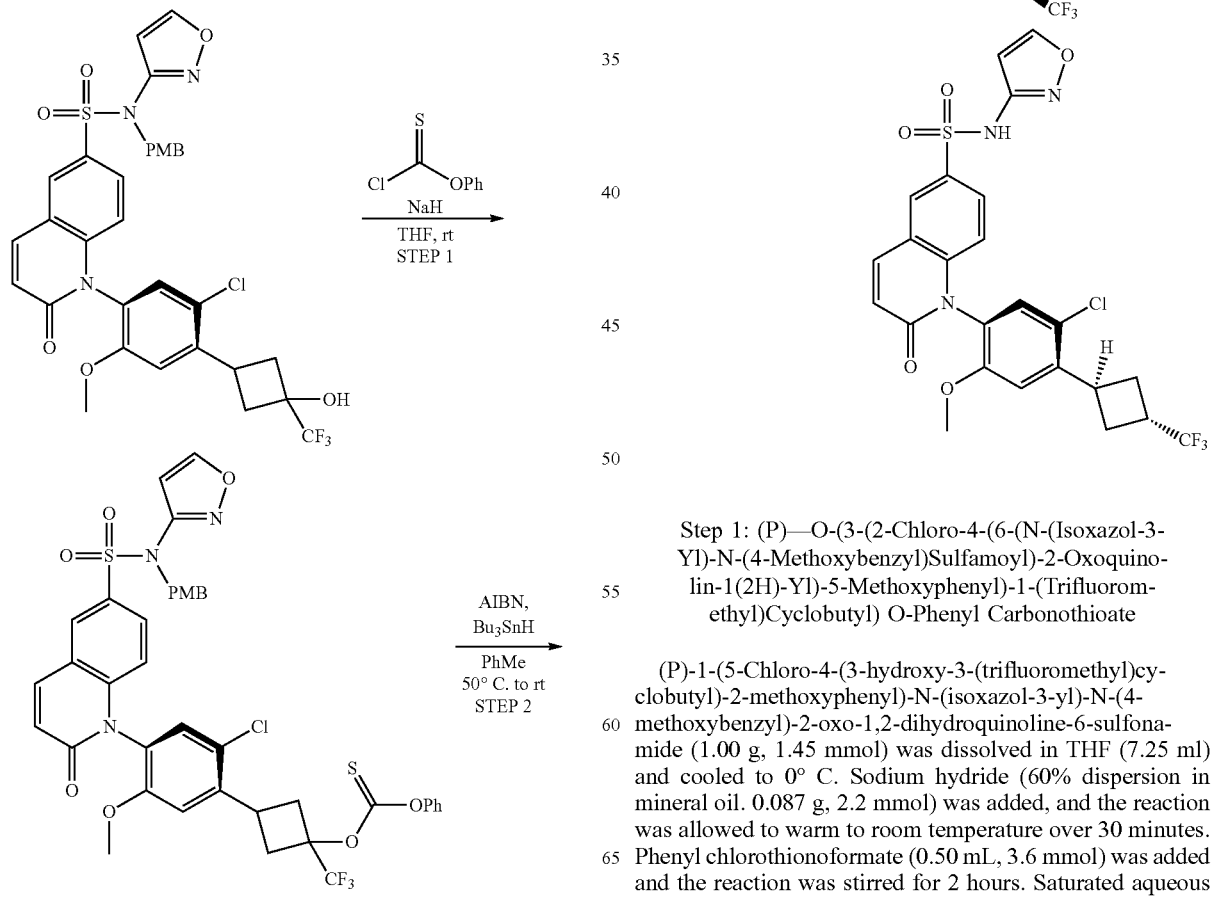

Step 1: (P)—O-(3-(2-Chloro-4-(6-(N-(Isoxazol-3-Yl)-N-(4-Methoxybenzyl)Sulfamoyl)-2-Oxoquinolin-1(2H)-Yl)-5-Methoxyphenyl)-1-(Trifluoromethyl)Cyclobutyl) O-Phenyl Carbonothioate (P)-1-(5-Chloro-4-(3-hydroxy-3-(trifluoromethyl)cyclobutyl)-2-methoxyphenyl)-N-(isoxazol-3-yl)-N-(4-methoxybenzyl)-2-oxo-1,2-dihydroquinoline-6-sulfonamide (1.00 g, 1.45 mmol) was dissolved in THF (7.25 ml) and cooled to 0° C. Sodium hydride (60% dispersion in mineral oil. 0.087 g, 2.2 mmol) was added, and the reaction was allowed to warm to room temperature over 30 minutes. Phenyl chlorothionoformate (0.50 mL, 3.6 mmol) was added and the reaction was stirred for 2 hours. Saturated aqueous sodium bicarbonate solution was then introduced. The mixture was extracted thrice with ethyl acetate and the combined organic layers were dried with magnesium sulfate, filtered, and concentrated. The material was purified via column chromatography (BIOTAGE® SNAP 50 g column, gradient elution 0-100% EtOAc:heptane) to afford (P)—O-(3-(2-chloro-4-(6-(N-(isoxazol-3-yl)-N-(4-methoxybenzyl)sulfamoyl)-2-oxoquinolin-1(2H)-yl)-5-methoxyphenyl)-1-(trifluoromethyl)cyclobutyl) O-phenyl carbonothioate (896 mg, 1.08 mmol, 75% yield) as a light yellow solid. $^{1}$H NMR (500 MHz, DMSO-$d_6$) δ ppm 8.71-8.87 (m, 1H), 8.37 (d, J=1.8 Hz, 1H), 8.15 (d, J=9.6 Hz, 1H), 7.73-7.82 (m, 1H), 7.56 (s, 1H), 7.44-7.55 (m, 2H), 7.29-7.42 (m, 3H), 7.25 (d, J=8.3 Hz, 3H), 6.86 (d, J=8.8 Hz, 2H), 6.82 (d, J=9.9 Hz, 1H), 6.65-6.77 (m, 2H), 4.91 (s, 2H), 3.75-3.80 (m, 3H), 3.71 (s, 3H), 3.67 (br d, J=9.1 Hz, 1H), 3.53-3.62 (m, 1H), 3.33-3.42 (m, 2H), 3.04-3.18 (m, 1H). m/z (ESI, positive ion) 826.1 (M+H)$^+$.

Step 2: (P)-1-(5-Chloro-2-Methoxy-4-(3-(Trifluoromethyl)Cyclobutyl)Phenyl)-N-(Isoxazol-3-Yl)-N-(4-Methoxybenzyl)-2-Oxo-1,2-Dihydroquinoline-6-Sulfonamide A 40-mL vial was charged with (P)—O-(3-(2-chloro-4-(6-(N-(isoxazol-3-yl)-N-(4-methoxybenzyl)sulfamoyl)-2-oxoquinolin-1(2H)-yl)-5-methoxyphenyl)-1-(trifluoromethyl)cyclobutyl) O-phenyl carbonothioate (896 mg, 1.08 mmol), toluene (11 mL), tri-n-butyltin hydride (2.87 mL, 10.8 mmol) and azobisisobutyronitrile (178 mg, 1.08 mmol). The reaction mixture was degassed with nitrogen for 20 minutes, then sealed and heated to 50° C. for 1 hour. The reaction was then stirred at rt for 16 h. During this time, a white solid had formed, which was isolated and washed with heptane to afford (P)-1-(5-chloro-2-methoxy-4-(3-(trifluoromethyl)cyclobutyl)phenyl)-N-(isoxazol-3-yl)-N-(4-methoxybenzyl)-2-oxo-1,2-dihydroquinoline-6-sulfonamide (596 mg, 0.884 mmol, 82% yield) as an off-white solid. m/z (ESI, positive ion) 674.2 (M+H)$^+$.

Step 3: Cis-(P)-1-(5-Chloro-2-Methoxy-4-(3-(Trifluoromethyl)Cyclobutyl)Phenyl)-N-(Isoxazol-3-Yl)-2-Oxo-1,2-Dihydroquinoline-6-Sulfonamide and Trans-(P)-1-(5-Chloro-2-Methoxy-4-(3-(Trifluoromethyl)Cyclobutyl)Phenyl)-N-(Isoxazol-3-Yl)-2-Oxo-1,2-Dihydroquinoline-6-Sulfonamide A 20 mL vial was charged with (P)-1-(5-chloro-2-methoxy-4-(3-(trifluoromethyl)cyclobutyl)phenyl)-N-(isoxazol-3-yl)-N-(4-methoxybenzyl)-2-oxo-1,2-dihydroquinoline-6-sulfonamide (596 mg, 0.884 mmol), dichloromethane (1.4 mL) and TFA (1.4 mL). The vial was sealed and warmed to 50° C. for 16 h. The reaction was then cooled to RT and concentrated under reduced pressure. The residue was purified by column chromatography (50 g silica gel column, gradient elution 0-75% [3:1 EtOAc/EtOH]: heptane). Further purification was accomplished using two sequential Chiralcel OJ-H, 2×25 cm columns. The mobile phase was run under isocratic conditions; supercritical $CO_2$ with 15% methanol; flow rate: 80 mL/min. The first eluting peak was assigned cis-(P)-1-(5-chloro-2-methoxy-4-((1S,3S)-3-(trifluoromethyl)cyclobutyl)phenyl)-N-(isoxazol-3-yl)-2-oxo-1,2-dihydroquinoline-6-sulfonamide (305 mg). The second eluting peak was assigned trans-(P)-1-(5-chloro-2-methoxy-4-((1S,3S)-3-(trifluoromethyl)cyclobutyl)phenyl)-N-(isoxazol-3-yl)-2-oxo-1,2-dihydroquinoline-6-sulfonamide (72 mg). Data for peak 1: $^{1}$H NMR (500 MHz, DMSO-$d_6$) δ ppm 11.65 (s, 1H), 8.73 (d, J=1.8 Hz, 1H), 8.36 (d, J=2.1 Hz, 1H), 8.21 (d, J=9.6 Hz, 1H), 7.83 (dd, J=9.0, 2.2 Hz, 1H), 7.50 (s, 1H), 7.18 (s, 1H), 6.79 (d, J=9.6 Hz, 2H), 6.44 (d, J=1.8 Hz, 1H), 3.79 (br t, J=9.2 Hz, 1H), 3.73 (s, 3H), 3.27-3.34 (m, 1H), 2.61-2.71 (m, 2H), 2.26-2.43 (m, 2H). m/z (ESI, positive ion) 554.0 (M+H)$^+$. Data for peak 2: $^{1}$H NMR (500 MHz, DMSO-$d_6$) δ ppm 11.65 (br s, 1H), 8.72 (d, J=1.6 Hz, 1H), 8.35 (d, J=1.8 Hz, 1H), 8.21 (d, J=9.6 Hz, 1H), 7.84 (dd, J=9.1, 2.1 Hz, 1H), 7.51 (s, 1H), 7.37 (s, 1H), 6.78 (dd, J=9.3, 6.0 Hz, 2H), 6.44 (d, J=1.6 Hz, 1H), 4.00 (quin, J=8.9 Hz, 1H), 3.76 (s, 3H), 3.22-3.28 (m, 1H), 2.93 (br d, J=3.6 Hz, 1H), 2.66-2.75 (m, 1H), 2.59-2.63 (m, 2H). m/z (ESI, positive ion) 554.0 (M+H)$^+$.

Example 14: (P)-1-(4-Cyclobutyl-5-Fluoro-2-Methoxyphenyl)-N-(Isoxazol-3-Yl)-2-Oxo-1,2-Dihydroquinoline-6-Sulfonamide

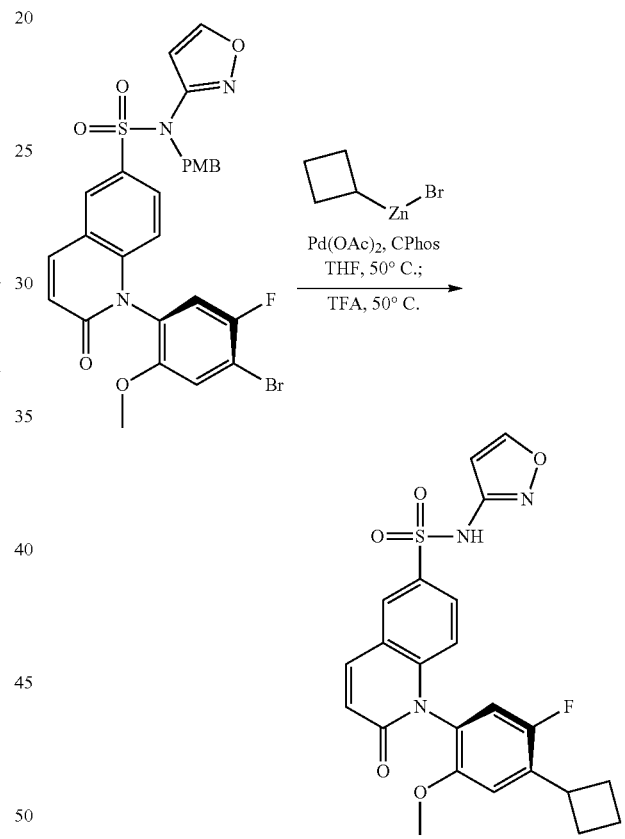

To a vial was added (P)-1-(4-bromo-5-fluoro-2-methoxyphenyl)-N-(isoxazol-3-yl)-N-(4-methoxybenzyl)-2-oxo-1,2-dihydroquinoline-6-sulfonamide (146 mg, 0.238 mmol), palladium(II) acetate (2.7 mg, 0.012 mmol), 2'-(dicyclohexylphosphino)-$N^2,N^2,N^6,N^6$-tetramethyl-[1,1'-biphenyl]-2,6-diamine (8.3 mg, 0.019 mmol), and cyclobutylzinc bromide (0.5 M in THF, 0.95 mL, 0.47 mmol). The reaction mixture was flushed with nitrogen and stirred at 50° C. for 1 h. The mixture was then purified directly via column chromatography (gradient elution 0-30% [3:1 EtOAc/EtOH]:heptane). The isolated product was then taken up in TFA (0.5 mL) and heated to 50° C. for 16 h. The reaction was then concentrated in vacuo and purified using a Torus 2-PIC, 30×150 cm column. The mobile phase was run under gradient elution conditions; supercritical $CO_2$ with 20-50% methanol; flow rate: 100 mL/min. This afforded (P)-1-(4-cyclobutyl-5-fluoro-2-methoxyphenyl)-N-(isoxazol-3-yl)-2-oxo-1,2-dihydroquinoline-6-sulfonamide (101 mg, 0.215 mmol, 90% yield). $^1$H NMR (600 MHz, DMSO-$d_6$) δ ppm 11.23-12.01 (m, 1H), 8.70 (d, J=1.5 Hz, 1H), 8.34 (d, J=2.2 Hz, 1H), 8.19 (d, J=9.4 Hz, 1H), 7.83 (dd, J=9.1, 2.2 Hz, 1H), 7.24 (d, J=9.8 Hz, 1H), 7.19 (d, J=6.9 Hz, 1H), 6.77 (d, J=9.4 Hz, 2H), 6.43 (d, J=1.8 Hz, 1H), 3.74-3.83 (m, 1H), 3.69 (s, 3H), 2.32-2.40 (m, 3H), 2.22-2.31 (m, 1H), 2.01-2.13 (m, 1H), 1.84-1.94 (m, 1H). m/z (ESI, positive ion) 470.0 (M+H)$^+$.

Example 15: Trans-(P)-1-(5-Fluoro-2-Methoxy-4-(3-(Trifluoromethyl)Cyclobutyl)Phenyl)-2-Oxo-N-(Pyrimidin-2-Yl)-1,2-Dihydroquinoline-6-Sulfonamide

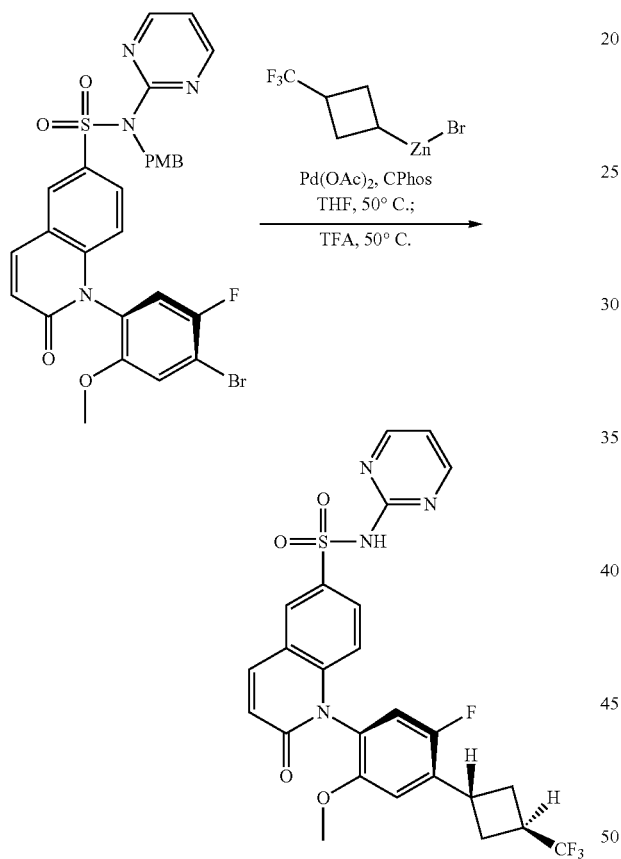

To a vial was added (P)-1-(4-bromo-5-fluoro-2-methoxyphenyl)-N-(4-methoxybenzyl)-2-oxo-N-(pyrimidin-2-yl)-1,2-dihydroquinoline-6-sulfonamide (359 mg, 0.573 mmol), palladium(II) acetate (6.4 mg, 0.029 mmol), 2'-(dicyclohexylphosphino)-$N^2,N^2,N^6,N^6$-tetramethyl-[1,1'-biphenyl]-2,6-diamine (25 mg, 0.057 mmol), (3-(trifluoromethyl)cyclobutyl)zinc(II) bromide (0.15 M in THF, 5.7 mL, 0.86 mmol) was added. The reaction mixture was flushed with nitrogen and stirred at 50° C. for 1 h. The mixture was then purified directly via column chromatography (gradient elution 0-30% [3:1 EtOAc/EtOH]:heptane). The isolated product was then taken up in TFA (0.5 mL) and heated to 50° C. for 16 h. The reaction was then concentrated in vacuo and purified using sequential Chiralcel OJ-H, 2×15 and 2×25 cm columns. The mobile phase was run under isocratic conditions; supercritical $CO_2$ with 20% methanol; flow rate: 80 mL/min. This afforded trans-(P)-1-(5-fluoro-2-methoxy-4-(3-(trifluoromethyl)cyclobutyl)phenyl)-2-oxo-N-(pyrimidin-2-yl)-1,2-dihydroquinoline-6-sulfonamide (63 mg). $^1$H NMR (500 MHz, CHLOROFORM-d) δ ppm 9.60-9.88 (m, 1H), 8.51-8.63 (m, 2H), 8.44 (d, J=2.1 Hz, 1H), 8.06 (dd, J=9.0, 2.2 Hz, 1H), 7.85 (d, J=9.9 Hz, 1H), 6.99 (t, J=4.9 Hz, 1H), 6.91-6.96 (m, 2H), 6.85 (d, J=9.6 Hz, 1H), 6.77 (d, J=8.8 Hz, 1H), 3.98 (quin, J=8.8 Hz, 1H), 3.73 (s, 3H), 3.04 (dtd, J=14.9, 9.8, 9.8, 4.9 Hz, 1H), 2.67-2.79 (m, 2H), 2.54-2.66 (m, 2H). m/z (ESI, positive ion) 549.2 (M+H)$^+$.

Examples 16 & 17: Cis-(P)-1-(5-Chloro-2-Methoxy-4-(3-(Trifluoromethyl)Cyclobutyl)Phenyl)-2-Oxo-N-(Pyrimidin-2-Yl)-1,2-Dihydroquinoline-6-Sulfonamide and Trans-(P)-1-(5-Chloro-2-Methoxy-4-(3-(Trifluoromethyl)Cyclobutyl)Phenyl)-2-Oxo-N-(Pyrimidin-2-Yl)-1,2-Dihydroquinoline-6-Sulfonamide, Respectively

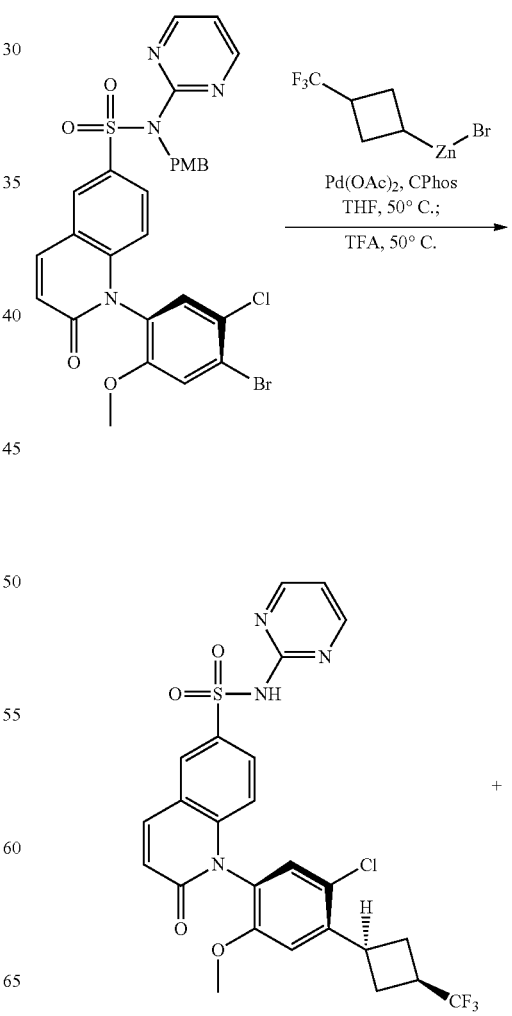

Example 18: (P)-1-(5-Chloro-4-Cyclobutyl-2-Methoxyphenyl)-2-Oxo-N-(Pyrimidin-2-Yl)-1,2-Dihydroquinoline-6-Sulfonamide

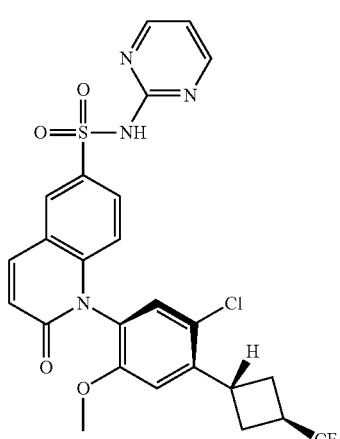

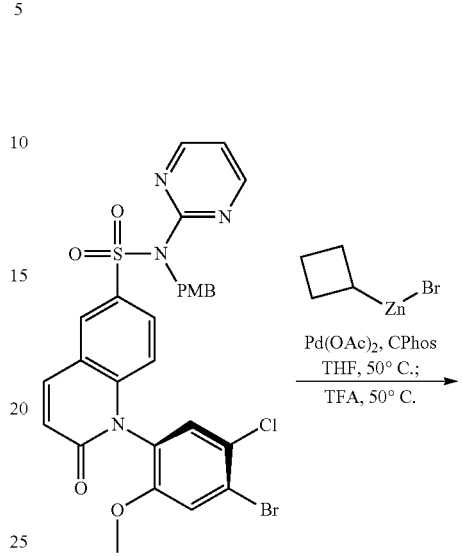

The title compounds were prepared according to the method of Example 15 using (P)-1-(4-bromo-5-chloro-2-methoxyphenyl)-N-(4-methoxybenzyl)-2-oxo-N-(pyrimidin-2-yl)-1,2-dihydroquinoline-6-sulfonamide (368 mg, 0.573 mmol). The sample was purified using a Chiralcel OJ-H, 2×15 cm column. The mobile phase was run under isocratic conditions; supercritical $CO_2$ with 30% methanol; flow rate: 80 mL/min. The sample was further purified using a Chiralcel OJ-H, 3×25 cm column. The mobile phase was run under isocratic conditions; supercritical $CO_2$ with 20% methanol; flow rate: 100 mL/min. The first eluting peak was assigned cis-(P)-1-(5-chloro-2-methoxy-4-(3-(trifluoromethyl)cyclobutyl)phenyl)-2-oxo-N-(pyrimidin-2-yl)-1,2-dihydroquinoline-6-sulfonamide (21.8 mg). The second eluting peak was assigned trans-(P)-1-(5-chloro-2-methoxy-4-(3-(trifluoromethyl)cyclobutyl)phenyl)-2-oxo-N-(pyrimidin-2-yl)-1,2-dihydroquinoline-6-sulfonamide (142.8 mg). Data for peak 1: $^1$H NMR (500 MHz, CHLOROFORM-d) δ ppm 9.99-10.35 (m, 1H), 8.59 (d, J=4.7 Hz, 2H), 8.43 (d, J=2.1 Hz, 1H), 8.07 (dd, J=9.0, 2.2 Hz, 1H), 7.85 (d, J=9.6 Hz, 1H), 7.19 (s, 1H), 7.02 (s, 1H), 6.99 (t, J=4.9 Hz, 1H), 6.85 (d, J=9.6 Hz, 1H), 6.76 (d, J=9.1 Hz, 1H), 3.82 (quin, J=9.3 Hz, 1H), 3.76 (s, 3H), 2.99-3.11 (m, 1H), 2.66-2.77 (m, 2H), 2.37 (quin, J=10.8 Hz, 2H). m/z (ESI, positive ion) 564.8 (M+H)$^+$. Data for peak 2: $^1$H NMR (500 MHz, CHLOROFORM-d) δ ppm 9.09-9.31 (m, 1H), 8.54 (d, J=4.9 Hz, 2H), 8.44 (d, J=2.1 Hz, 1H), 8.07 (dd, J=9.0, 2.2 Hz, 1H), 7.85 (d, J=9.6 Hz, 1H), 7.21 (s, 1H), 7.05 (s, 1H), 6.98 (t, J=4.9 Hz, 1H), 6.85 (d, J=9.6 Hz, 1H), 6.76 (d, J=8.8 Hz, 1H), 4.04-4.13 (m, 1H), 3.77 (s, 3H), 2.92-3.05 (m, 1H), 2.71-2.84 (m, 2H), 2.47-2.66 (m, 2H). m/z (ESI, positive ion) 564.8 (M+H)$^+$.

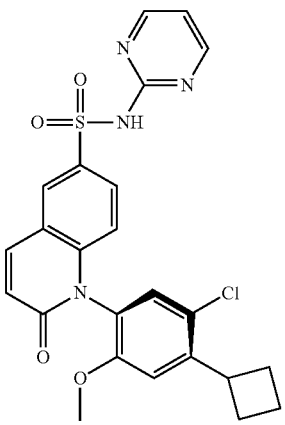

The title compound was prepared according to the method of Example 14 using (P)-1-(4-bromo-5-chloro-2-methoxyphenyl)-N-(4-methoxybenzyl)-2-oxo-N-(pyrimidin-2-yl)-1,2-dihydroquinoline-6-sulfonamide (153 mg, 0.238 mmol). The sample was purified via reverse phase HPLC using a XBridge Prep Shield RP18 19×100 mm column. The mobile was run under a gradient elution; 25-70% acetonitrile:water with 0.1% formic acid; flow rate: 40 mL/min. This afforded (P)-1-(5-chloro-4-cyclobutyl-2-methoxyphenyl)-2-oxo-N-(pyrimidin-2-yl)-1,2-dihydroquinoline-6-sulfonamide (18 mg, 0.036 mmol, 15% yield). $^1$H NMR (500 MHz, CHLOROFORM-d) δ ppm 11.20-11.51 (m, 1H), 8.65 (d, J=4.9 Hz, 2H), 8.41 (d, J=2.1 Hz, 1H), 8.04 (dd, J=9.1, 2.1 Hz, 1H), 7.84 (d, J=9.6 Hz, 1H), 7.15 (s, 1H), 7.06 (s, 1H), 7.01 (t, J=5.1 Hz, 1H), 6.85 (d, J=9.9 Hz, 1H), 6.77 (d, J=8.8 Hz, 1H), 3.87 (quin, J=8.8 Hz, 1H), 3.75 (s, 3H), 2.44-2.53 (m, 2H), 2.15-2.30 (m, 2H), 2.03-2.15 (m, 1H), 1.85-1.97 (m, 1H). m/z (ESI, positive ion) 497.0 (M+H)$^+$.

Example 19: Trans-(P)-1-(5-Chloro-2-Methoxy-4-(3-(Trifluoromethyl)Cyclobutyl)Phenyl)-2-Oxo-N-(Pyridazin-3-Yl)-1,2-Dihydroquinoline-6-Sulfonamide

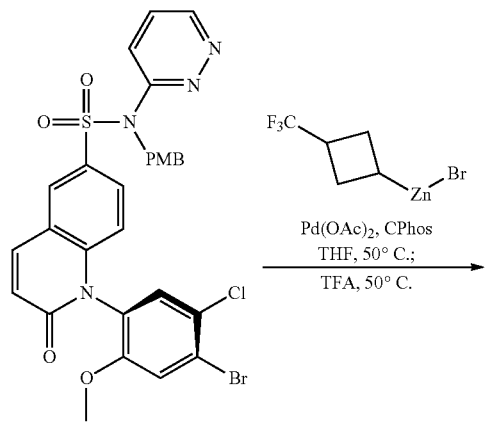

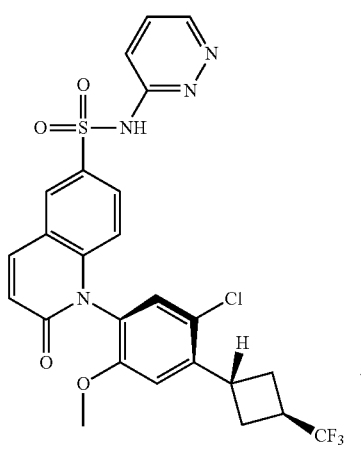

The title compound was prepared according to the method of Example 15 using (P)-1-(4-bromo-5-chloro-2-methoxyphenyl)-N-(4-methoxybenzyl)-2-oxo-N-(pyridazin-3-yl)-1,2-dihydroquinoline-6-sulfonamide (368 mg, 0.573 mmol). The sample was purified using a Zorbax Eclipse Plus C18, 2.1×10 cm column. The mobile phase was run under gradient elution conditions; 41.3-61.3% water:acetonitrile with 0.1% formic acid as co-eluent; flow rate: 40 mL/min. The material was further purified using a Chiralcel OJ-H, 2×15 cm column. The mobile phase was run under isocratic conditions; supercritical $CO_2$ with 25% methanol; flow rate: 80 mL/min. This afforded trans-(P)-1-(5-chloro-2-methoxy-4-(3-(trifluoromethyl)cyclobutyl)phenyl)-2-oxo-N-(pyridazin-3-yl)-1,2-dihydroquinoline-6-sulfonamide (38.4 mg). $^1$H NMR (500 MHz, CHLOROFORM-d) δ ppm 12.38-12.76 (m, 1H), 8.24 (d, J=2.1 Hz, 1H), 8.10 (dd, J=3.9, 1.6 Hz, 1H), 7.91 (dd, J=9.1, 2.1 Hz, 1H), 7.83 (d, J=9.6 Hz, 1H), 7.33-7.37 (m, 1H), 7.29 (d, J=1.6 Hz, 1H), 7.21 (s, 1H), 7.05 (s, 1H), 6.84 (d, J=9.6 Hz, 1H), 6.75 (d, J=8.8 Hz, 1H), 4.08 (quin, J=8.9 Hz, 1H), 3.77 (s, 3H), 2.91-3.06 (m, 1H), 2.69-2.83 (m, 2H), 2.48-2.62 (m, 2H). m/z (ESI, positive ion) 565.2 (M+H)$^+$.

Example 20: Trans-(P)—N-(Isoxazol-3-Yl)-1-(2-Methoxy-5-Methyl-4-(3-(Trifluoromethyl)Cyclobutyl)Phenyl)-2-Oxo-1,2-Dihydroquinoline-6-Sulfonamide

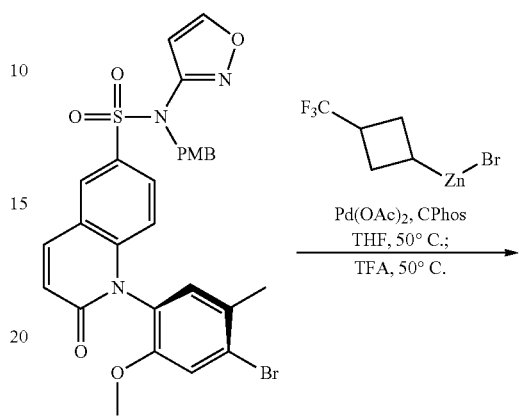

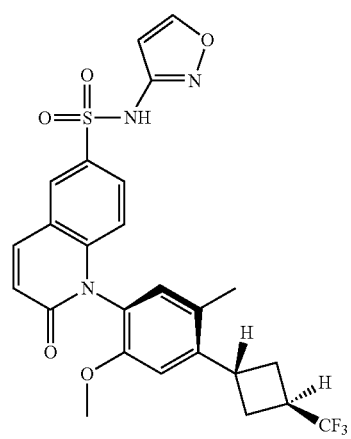

The title compound was prepared according to the method of Example 15 using (P)-1-(4-bromo-2-methoxy-5-methylphenyl)-N-(isoxazol-3-yl)-N-(4-methoxybenzyl)-2-oxo-1,2-dihydroquinoline-6-sulfonamide (350 mg, 0.573 mmol). The sample was purified using a Zorbax Eclipse Plus C18, 2.1×10 cm column. The mobile phase was run under gradient elution conditions; 46.4-66.4% acetonitrile:water with 0.1% formic acid as co-eluent; flow rate: 40 mL/min. The material was further purified using a Chiralcel OJ-H, 2×15 cm column. The mobile phase was run under isocratic conditions; supercritical $CO_2$ with 20% methanol; flow rate: 80 mL/min. This afforded trans-(P)—N-(isoxazol-3-yl)-1-(2-methoxy-5-methyl-4-(3-(trifluoromethyl)cyclobutyl)phenyl)-2-oxo-1,2-dihydroquinoline-6-sulfonamide (65.8 mg). $^1$H NMR (500 MHz, CHLOROFORM-d) δ ppm 8.25 (d, J=1.8 Hz, 1H), 8.11 (d, J=2.1 Hz, 1H), 7.83-8.04 (m, 1H), 7.76 (d, J=9.6 Hz, 1H), 7.72 (dd, J=9.0, 2.2 Hz, 1H), 7.01 (s, 1H), 6.95 (s, 1H), 6.86 (d, J=9.6 Hz, 1H), 6.76 (d, J=9.1 Hz, 1H), 6.60 (d, J=1.8 Hz, 1H), 3.94 (quin, J=8.8 Hz, 1H), 3.75 (s, 3H), 2.89-3.07 (m, 1H), 2.70 (ddd, J=12.8, 8.8, 4.0 Hz, 2H), 2.46-2.60 (m, 2H), 2.19 (s, 3H). m/z (ESI, positive ion) 534.2 (M+H)$^+$.

Example 21: (P)-1-(5-Chloro-4-Cyclobutyl-2-Methoxyphenyl)-N-(Isoxazol-3-Yl)-2-Oxo-1,2-Dihydroquinoline-6-Sulfonamide

Example 22: (P)-1-(4-Cyclobutyl-2-Methoxy-5-Methylphenyl)-N-(Isoxazol-3-Yl)-2-Oxo-1,2-Dihydroquinoline-6-Sulfonamide

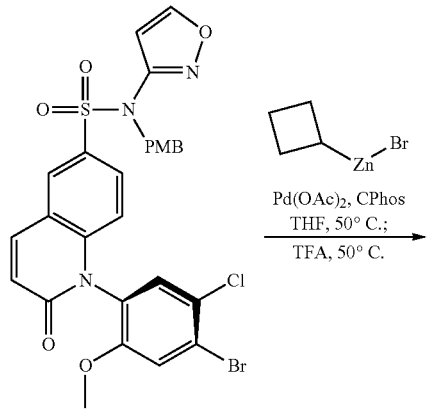

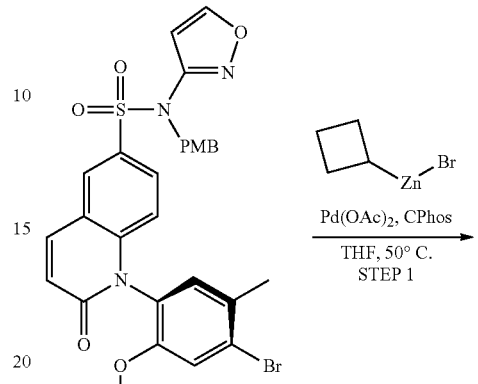

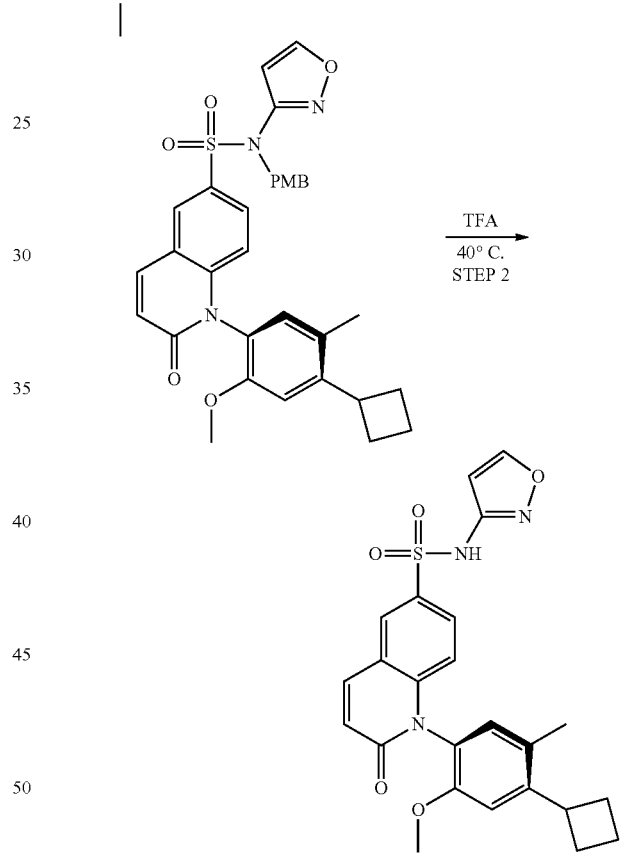

The title compound was prepared according to the method of Example 14 using (P)-1-(4-bromo-5-chloro-2-methoxyphenyl)-N-(isoxazol-3-yl)-N-(4-methoxybenzyl)-2-oxo-1,2-dihydroquinoline-6-sulfonamide (150 mg, 0.238 mmol). The sample was purified via reverse phase HPLC using a XBridge Prep Shield RP18 19×100 mm column. The mobile was run under a gradient elution; 25-70% acetonitrile:water with 0.1% formic acid; flow rate: 40 mL/min. This afforded (P)-1-(5-chloro-4-cyclobutyl-2-methoxyphenyl)-N-(isoxazol-3-yl)-2-oxo-1,2-dihydroquinoline-6-sulfonamide (92 mg, 80% yield). $^1$H NMR (500 MHz, CHLOROFORM-d) δ ppm 8.40 (br s, 1H), 8.25 (d, J=1.6 Hz, 1H), 8.13 (d, J=2.1 Hz, 1H), 7.78 (d, J=9.6 Hz, 1H), 7.75 (dd, J=9.0, 2.2 Hz, 1H), 7.15 (s, 1H), 7.05 (s, 1H), 6.87 (d, J=9.6 Hz, 1H), 6.77 (d, J=9.1 Hz, 1H), 6.59 (d, J=1.8 Hz, 1H), 3.80-3.91 (m, 1H), 3.75 (s, 3H), 2.42-2.56 (m, 2H), 2.16-2.27 (m, 2H), 2.04-2.16 (m, 1H), 1.84-1.96 (m, 1H). m/z (ESI, positive ion) 486.0 (M+H)$^+$.

Step 1: (P)-1-(4-Cyclobutyl-2-Methoxy-5-Methylphenyl)-N-(Isoxazol-3-Yl)-N-(4-Methoxybenzyl)-2-Oxo-1,2-Dihydroquinoline-6-Sulfonamide To a THF (1 mL) solution of (P)-1-(4-bromo-2-methoxy-5-methylphenyl)-N-(isoxazol-3-yl)-N-(4-methoxybenzyl)-2-oxo-1,2-dihydroquinoline-6-sulfonamide (191 mg, 0.313 mmol) was added 2-dicyclohexylphosphino-2',6'-dimethylamino-1,1'-biphenyl (27.3 mg, 0.063 mmol), and palladium (II) acetate (14.05 mg, 0.063 mmol). The reaction mixture was sparged with argon, and then cyclobutylzinc bromide (0.5 M in THF, 1.9 mL, 0.94 mmol) was added. The reaction was stirred at 50° C. After 2 h, additional portions of 2-dicyclohexylphosphino-2',6'-dimethylamino-1,1'-biphenyl (27.3 mg, 0.063 mmol), palladium(II) acetate (14.1 mg, 0.063 mmol), and cyclobutylzinc bromide (0.5 M in THF, 1.9 mL, 0.94 mmol) were added. After stirring for 1 h at 50° C., the reaction was cooled to room temperature, quenched with saturated aqueous sodium bicarbonate, and partitioned between water and ethyl acetate. The organic extract was concentrated and purified by silica gel column chromatography (gradient elution, 40-100% EtOAc:heptane with 10% dichloromethane co-eluent) to afford (P)-1-(4-cyclobutyl-2-methoxy-5-methylphenyl)-N-(isoxazol-3-yl)-N-(4-methoxybenzyl)-2-oxo-1,2-dihydroquinoline-6-sulfonamide (123 mg, 0.210 mmol, 67% yield) as a brown solid. m/z (ESI, positive ion) 586.0 (M+H)+.

Step 2: (P)-1-(4-Cyclobutyl-2-Methoxy-5-Methylphenyl)-N-(Isoxazol-3-Yl)-2-Oxo-1,2-Dihydroquinoline-6-Sulfonamide (P)-1-(4-Cyclobutyl-2-methoxy-5-methylphenyl)-N-(isoxazol-3-yl)-N-(4-methoxybenzyl)-2-oxo-1,2-dihydroquinoline-6-sulfonamide (123 mg, 0.210 mmol) was dissolved in TFA (2 mL) and stirred at 40° C. After 2 h, the reaction was concentrated, and the residue was purified via silica gel column chromatography (gradient elution 20-80% [3:1 EtOAc/EtOH]:heptane with 10% dichloromethane co-eluent) to afford (P)-1-(4-cyclobutyl-2-methoxy-5-methylphenyl)-N-(isoxazol-3-yl)-2-oxo-1,2-dihydroquinoline-6-sulfonamide (73 mg, 0.157 mmol, 75% yield) as a light purple solid. $^1$H NMR (500 MHz, DMSO-$d_6$) δ ppm 11.60 (br s, 1H), 8.71 (d, J=1.8 Hz, 1H), 8.33 (d, J=2.1 Hz, 1H), 8.18 (d, J=9.6 Hz, 1H), 7.82 (dd, J=9.0, 2.2 Hz, 1H), 7.09 (s, 1H), 7.00 (s, 1H), 6.77 (d, J=9.6 Hz, 1H), 6.72 (d, J=8.8 Hz, 1H), 6.43 (d, J=1.8 Hz, 1H), 3.69-3.74 (m, 1H), 3.68 (s, 3H), 2.33-2.43 (m, 2H), 2.26 (quin, J=9.6 Hz, 1H), 2.11-2.19 (m, 4H), 1.98-2.09 (m, 1H), 1.79-1.90 (m, 1H). m/z (ESI, positive ion) 465.8 (M+H)+.

Example 23: (P)-1-(4-Cyclobutyl-5-Fluoro-2-Methoxyphenyl)-2-Oxo-N-(Pyridazin-3-Yl)-1,2-Dihydroquinoline-6-Sulfonamide

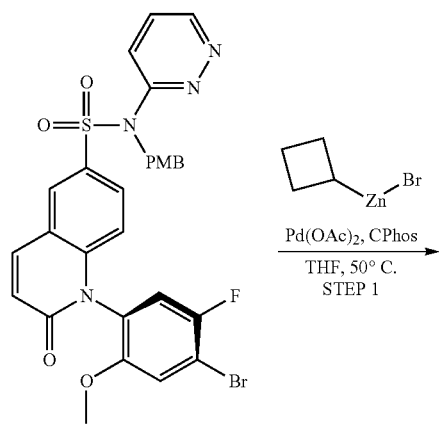

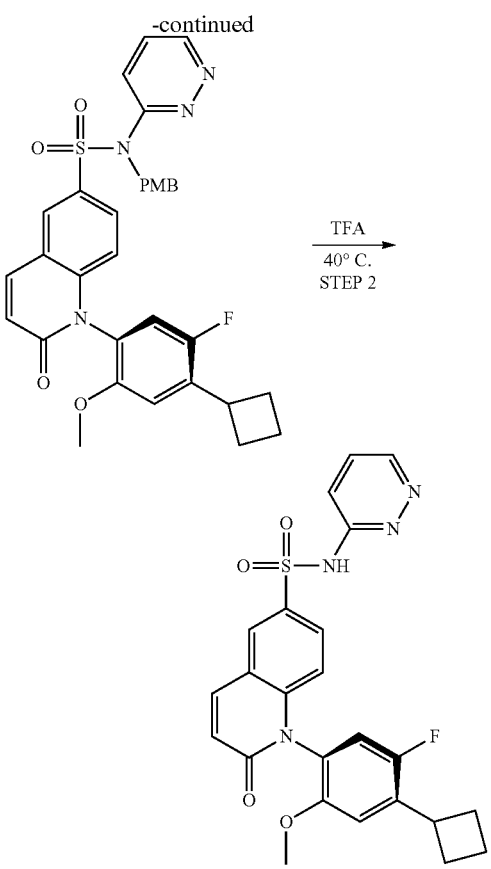

Step 1: (P)-1-(4-Cyclobutyl-5-Fluoro-2-Methoxyphenyl)-N-(4-Methoxybenzyl)-2-Oxo-N-(Pyridazin-3-Yl)-1,2-Dihydroquinoline-6-Sulfonamide To a THF (0.8 mL) solution of a (P)-1-(4-bromo-5-fluoro-2-methoxyphenyl)-N-(4-methoxybenzyl)-2-oxo-N-(pyridazin-3-yl)-1,2-dihydroquinoline-6-sulfonamide (150 mg, 0.240 mmol) was added 2-dicyclohexylphosphino-2',6'-dimethylamino-1,1'-biphenyl (20.9 mg, 0.048 mmol), and palladium(II) acetate (10.8 mg, 0.048 mmol). The reaction mixture was sparged with argon, and then cyclobutylzinc bromide (0.5 m in THF, 1.4 mL, 0.72 mmol) was added. The reaction was stirred at 50° C. After 90 min, the reaction mixture was quenched with saturated aqueous sodium bicarbonate and partitioned between water and ethyl acetate. The organic layers were concentrated. The residue was purified by silica gel column chromatography (gradient elution 40-100% EtOAc:heptane with 10% dichloromethane co-eluent) to afford (P)-1-(4-cyclobutyl-5-fluoro-2-methoxyphenyl)-N-(4-methoxybenzyl)-2-oxo-N-(pyridazin-3-yl)-1,2-dihydroquinoline-6-sulfonamide (156 mg, 0.260 mmol, >99% yield) as a brown solid. m/z (ESI, positive ion) 601.0 (M+H)+.

Step 2: (P)-1-(4-Cyclobutyl-5-Fluoro-2-Methoxyphenyl)-2-Oxo-N-(Pyridazin-3-Yl)-1,2-Dihydroquinoline-6-Sulfonamide (P)-1-(4-cyclobutyl-5-fluoro-2-methoxyphenyl)-N-(4-methoxybenzyl)-2-oxo-N-(pyridazin-3-yl)-1,2-dihydroquinoline-6-sulfonamide (156 mg, 0.260 mmol) was dissolved in TFA (3.0 mL) and stirred at 40° C. After 2 h, the reaction was concentrated, and the residue was purified by silica gel chromatography 20-80% [3:1 EtOAc/EtOH]:heptane with 10% dichloromethane co-eluent) to afford 1-(4-cyclobutyl-5-fluoro-2-methoxyphenyl)-2-oxo-N-(pyridazin-3-yl)-1,2-dihydroquinoline-6-sulfonamide (86 mg, 0.179 mmol, 69% yield) as an off-white solid. $^1$H NMR (500 MHz, DMSO-$d_6$) δ ppm 14.28-14.68 (m, 1H), 8.23-8.39 (m, 2H), 8.17 (d, J=9.6 Hz, 1H), 7.89-8.00 (m, 1H), 7.79-7.86 (m, 1H), 7.68 (dd, J=9.5, 4.0 Hz, 1H), 7.22 (d, J=9.9 Hz, 1H), 7.19 (d, J=6.7 Hz, 1H), 6.75 (d, J=9.6 Hz, 1H), 6.70 (d, J=8.8 Hz, 1H), 3.78 (quin, J=8.9 Hz, 1H), 3.69 (s, 3H), 2.32-2.38 (m, 3H), 2.23-2.32 (m, 1H), 2.02-2.14 (m, 1H), 1.84-1.95 (m, 1H). m/z (ESI, positive ion) 480.8 (M+H)$^+$.

Example 24: (P)-1-(4-Cyclobutyl-5-Fluoro-2-Methoxyphenyl)-N-(Oxazol-2-Yl)-2-Oxo-1,2-Dihydroquinoline-6-Sulfonamide The title compound was prepared according to the method and purification protocol of Example 23 using (P)-1-(4-bromo-5-fluoro-2-methoxyphenyl)-N-(4-methoxybenzyl)-N-(oxazol-2-yl)-2-oxo-1,2-dihydroquinoline-6-sulfonamide (180 mg, 0.293 mmol). This afforded (P)-1-(4-cyclobutyl-5-fluoro-2-methoxyphenyl)-N-(oxazol-2-yl)-2-oxo-1,2-dihydroquinoline-6-sulfonamide (54 mg, 0.115 mmol, 39% yield over 2 steps) as a light purple solid. $^1$H NMR (500 MHz, CHLOROFORM-d) δ ppm 9.65-10.09 (m, 1H), 8.19 (d, J=2.1 Hz, 1H), 7.87 (dd, J=9.0, 2.2 Hz, 1H), 7.81 (d, J=9.6 Hz, 1H), 7.08 (d, J=1.8 Hz, 1H), 6.98 (d, J=6.2 Hz, 1H), 6.88 (d, J=9.3 Hz, 1H), 6.86 (d, J=1.8 Hz, 1H), 6.84 (d, J=9.6 Hz, 1H), 6.76 (d, J=9.1 Hz, 1H), 3.82 (quin, J=8.8 Hz, 1H), 3.72 (s, 3H), 2.39-2.49 (m, 2H), 2.21-2.34 (m, 2H), 2.08-2.18 (m, 1H), 1.88-1.99 (m, 1H). m/z (ESI, positive ion) 469.8 (M+H)$^+$.

Example 25: (P)-1-(4-Cyclobutyl-2-Methoxyphenyl)-N-(Isoxazol-3-Yl)-2-Oxo-1,2-Dihydroquinoline-6-Sulfonamide

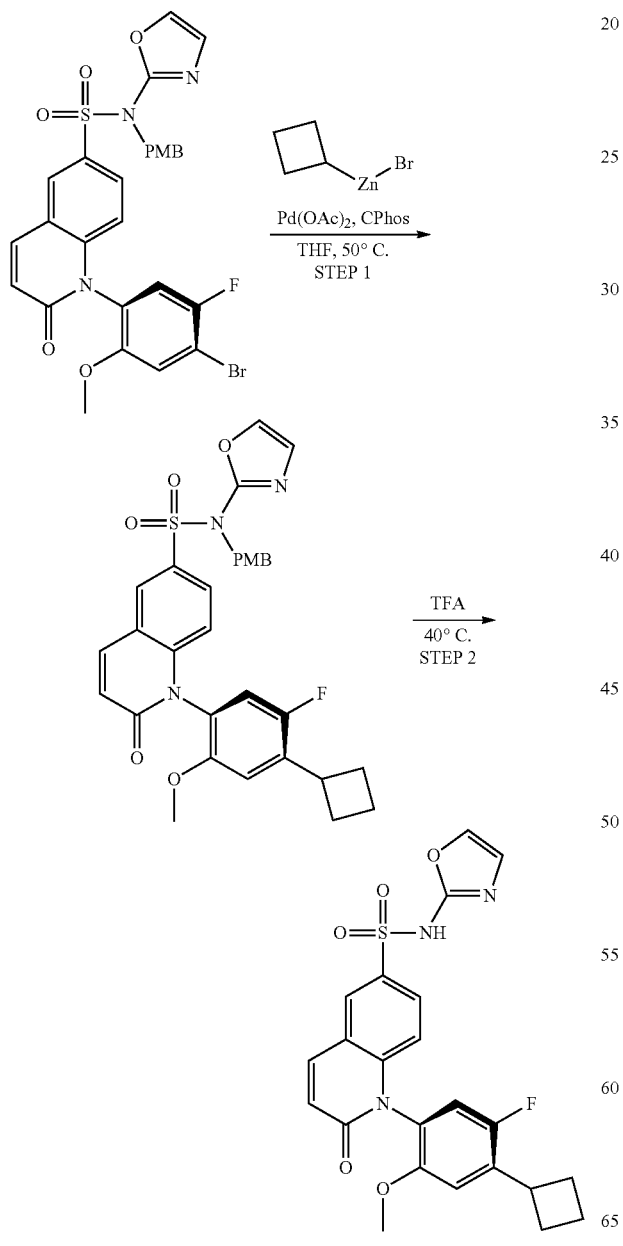

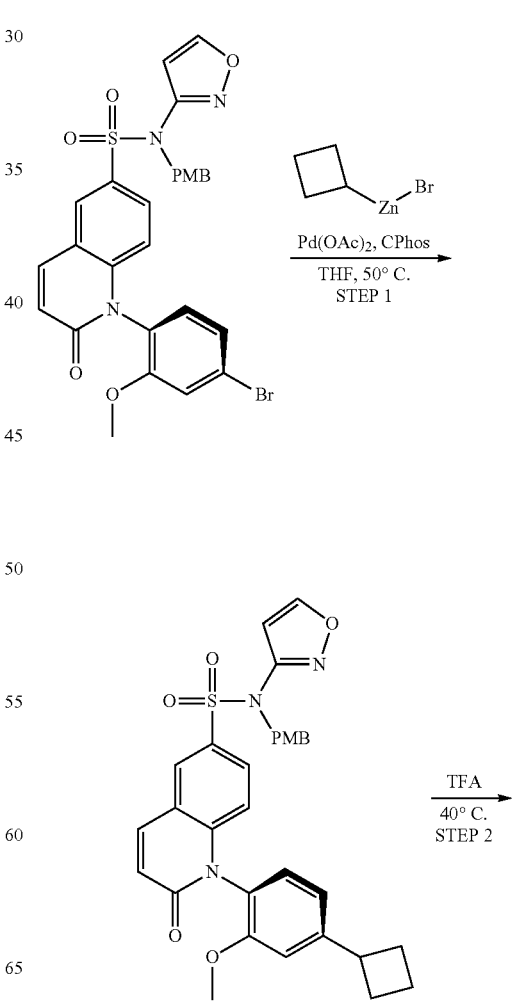

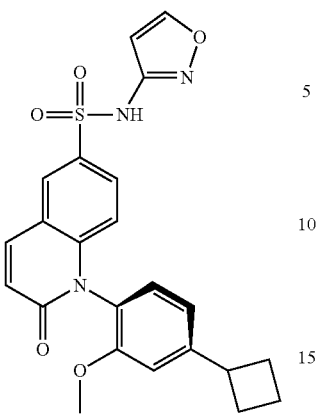

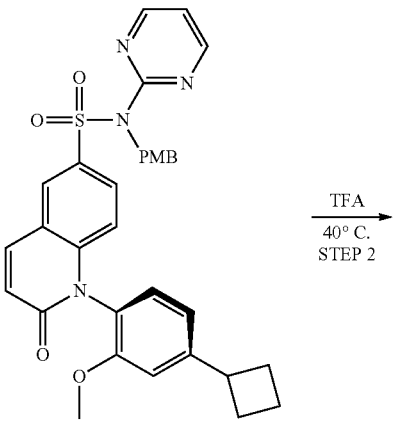

The title compound was prepared according to the method and purification protocol of Example 23 using (P)-1-(4-bromo-2-methoxyphenyl)-N-(isoxazol-3-yl)-N-(4-methoxybenzyl)-2-oxo-1,2-dihydroquinoline-6-sulfonamide (140 mg, 0.235 mmol). This afforded (P)-1-(4-cyclobutyl-2-methoxyphenyl)-N-(isoxazol-3-yl)-2-oxo-1,2-dihydroquinoline-6-sulfonamide (89 mg, 0.197 mmol, 84% yield over 2 steps) as an off-white solid. $^1$H NMR (500 MHz, DMSO-$d_6$) δ ppm 11.60 (s, 1H), 8.72 (d, J=1.8 Hz, 1H), 8.34 (d, J=2.3 Hz, 1H), 8.19 (d, J=9.9 Hz, 1H), 7.83 (dd, J=9.0, 2.2 Hz, 1H), 7.18 (d, J=8.0 Hz, 1H), 7.12 (d, J=1.6 Hz, 1H), 7.02 (dd, J=7.9, 1.7 Hz, 1H), 6.77 (d, J=9.6 Hz, 1H), 6.72 (d, J=8.8 Hz, 1H), 6.44 (d, J=1.8 Hz, 1H), 3.67 (s, 3H), 3.58-3.67 (m, 1H), 2.32-2.42 (m, 2H), 2.16-2.27 (m, 2H), 1.99-2.08 (m, 1H), 1.82-1.92 (m, 1H). m/z (ESI, positive ion) 452.0 (M+H)$^+$.

Example 26: (P)-1-(4-Cyclobutyl-2-Methoxyphenyl)-2-Oxo-N-(Pyrimidin-2-Yl)-1,2-Dihydroquinoline-6-Sulfonamide

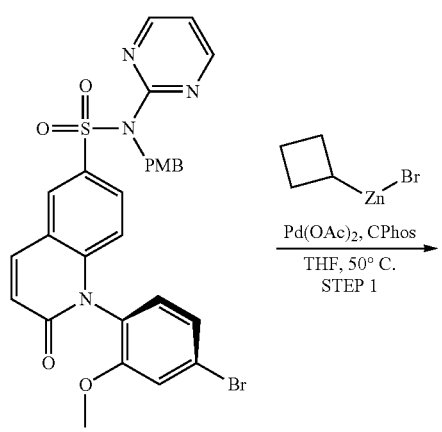

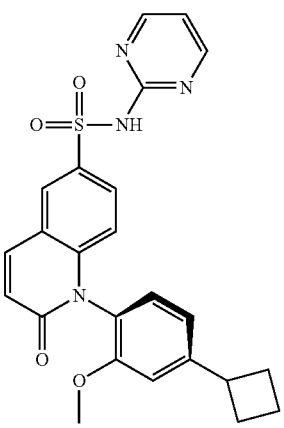

The title compound was prepared according to the method and purification protocol of Example 23 using (P)-1-(4-bromo-2-methoxyphenyl)-N-(4-methoxybenzyl)-2-oxo-N-(pyrimidin-2-yl)-1,2-dihydroquinoline-6-sulfonamide (140 mg, 0.230 mmol). This afforded (P)-1-(4-cyclobutyl-2-methoxyphenyl)-2-oxo-N-(pyrimidin-2-yl)-1,2-dihydroquinoline-6-sulfonamide (50 mg, 0.108 mmol, 47% yield over 2 steps) as a white solid. $^1$H NMR (500 MHz, CHLOROFORM-d) δ ppm 8.57 (d, J=4.9 Hz, 2H), 8.42 (d, J=2.1 Hz, 1H), 8.02 (dd, J=9.1, 2.1 Hz, 1H), 7.84 (d, J=9.6 Hz, 1H), 7.07-7.10 (m, 1H), 6.93-7.03 (m, 3H), 6.87 (d, J=9.6 Hz, 1H), 6.78 (d, J=9.1 Hz, 1H), 3.72 (s, 3H), 3.65 (quin, J=9.0 Hz, 1H), 2.34-2.46 (m, 2H), 2.18-2.31 (m, 2H), 2.06-2.14 (m, 1H), 1.85-1.96 (m, 1H). m/z (ESI, positive ion) 463.0 (M+H)$^+$.

Example 27: (P)-1-(4-Cyclobutyl-2-Methoxy-5-Methylphenyl)-2-Oxo-N-(Pyrimidin-2-Yl)-1,2-Dihydroquinoline-6-Sulfonamide

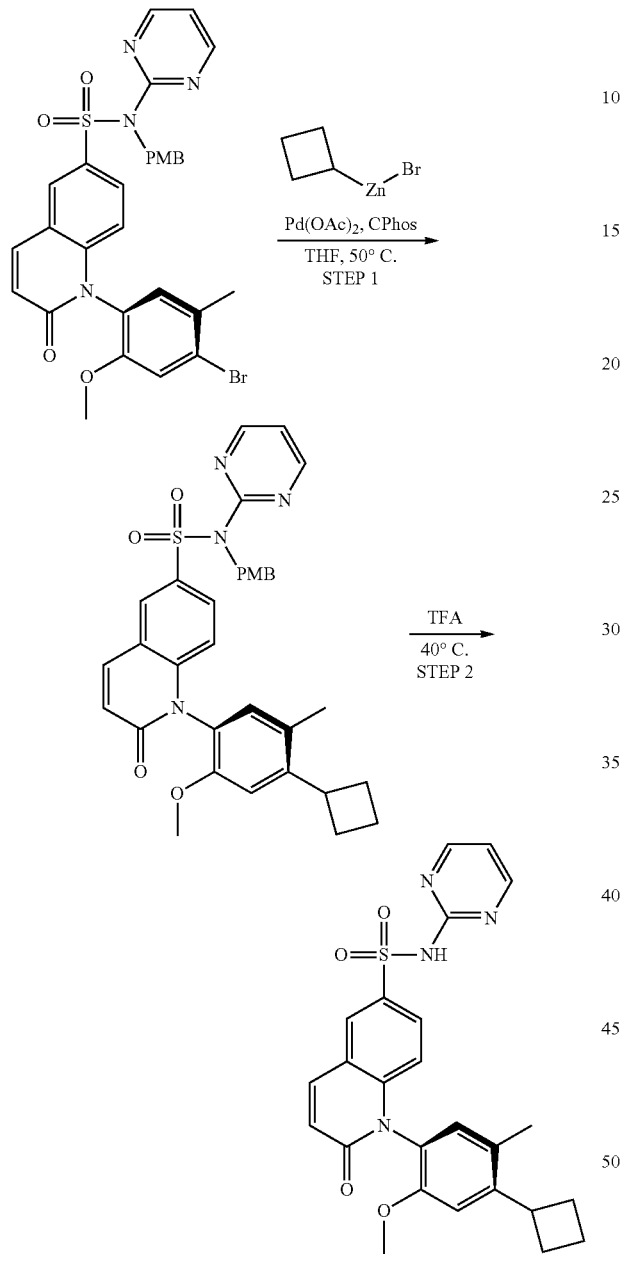

The title compound was prepared according to the method and purification protocol of Example 22 using (P)-1-(4-bromo-2-methoxy-5-methylphenyl)-N-(4-methoxybenzyl)-2-oxo-N-(pyrimidin-2-yl)-1,2-dihydroquinoline-6-sulfonamide (130 mg, 0.209 mmol). This afforded (P)-1-(4-cyclobutyl-2-methoxy-5-methylphenyl)-N-(4-methoxybenzyl)-2-oxo-N-(pyrimidin-2-yl)-1,2-dihydroquinoline-6-sulfonamide (60 mg, 0.126 mmol, 60% yield over 2 steps) as a white solid. $^1$H NMR (500 MHz, DMSO-d$_6$) δ ppm 11.43-12.18 (m, 1H), 8.50 (d, J=4.9 Hz, 2H), 8.44 (d, J=2.1 Hz, 1H), 8.21 (d, J=9.6 Hz, 1H), 7.95 (dd, J=9.0, 2.2 Hz, 1H), 7.09 (s, 1H), 7.05 (br t, J=4.8 Hz, 1H), 6.99 (s, 1H), 6.75 (d, J=9.9 Hz, 1H), 6.69 (d, J=9.1 Hz, 1H), 3.68-3.75 (m, 1H), 3.67 (s, 3H), 2.32-2.44 (m, 2H), 2.26 (quin, J=9.7 Hz, 1H), 2.11-2.20 (m, 4H), 1.99-2.07 (m, 1H), 1.80-1.90 (m, 1H). m/z (ESI, positive ion) 477.0 (M+H)$^+$.

Example 28: (P)-1-(4-Cyclobutyl-5-Fluoro-2-Methoxyphenyl)-2-Oxo-N-(Pyrimidin-2-Yl)-1,2-Dihydroquinoline-6-Sulfonamide

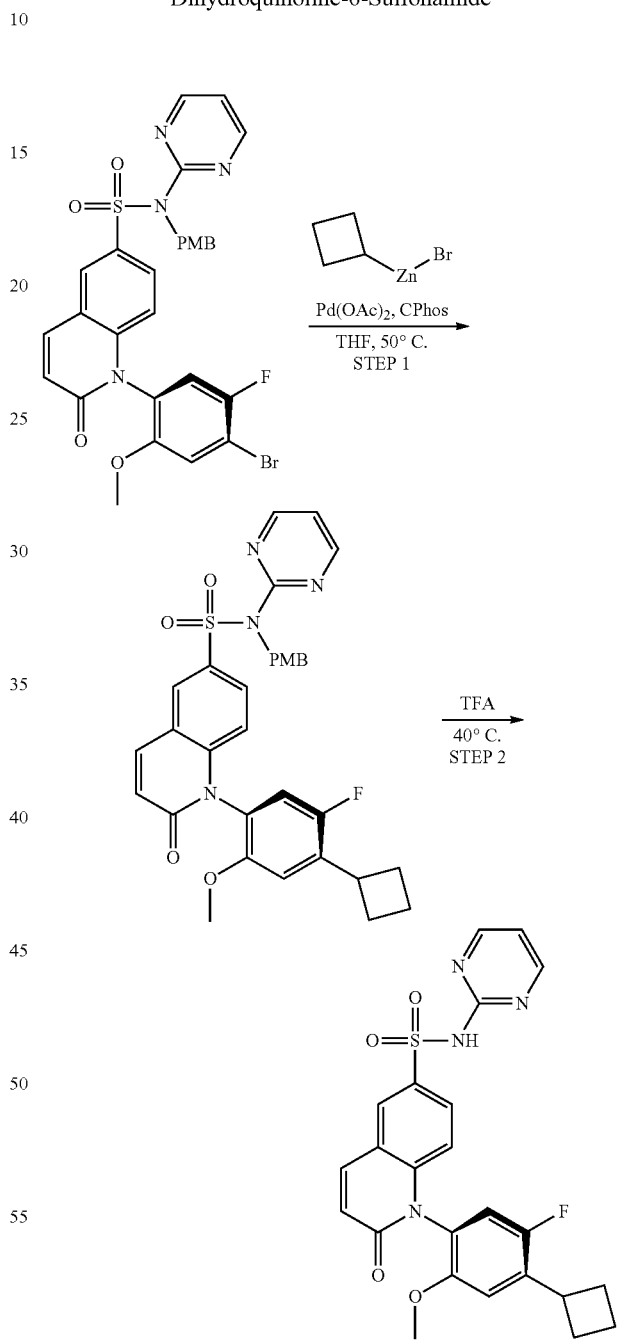

The title compound was prepared according to the method and purification protocol of Example 23 using (P)-1-(4-bromo-5-fluoro-2-methoxyphenyl)-N-(4-methoxybenzyl)-2-oxo-N-(pyrimidin-2-yl)-1,2-dihydroquinoline-6-sulfonamide (120 mg, 0.192 mmol). This afforded (P)-1-(4-cyclobutyl-5-fluoro-2-methoxyphenyl)-2-oxo-N-

(pyrimidin-2-yl)-1,2-dihydroquinoline-6-sulfonamide (20 mg, 0.042 mmol, 22% yield). $^1$H NMR (500 MHz, CHLOROFORM-d) δ ppm 8.59 (d, J=4.9 Hz, 2H), 8.43 (d, J=2.1 Hz, 1H), 8.06 (dd, J=9.0, 2.2 Hz, 1H), 7.84 (d, J=9.6 Hz, 1H), 6.96-7.02 (m, 2H), 6.87 (d, J=3.6 Hz, 1H), 6.85 (d, J=4.4 Hz, 1H), 6.78 (d, J=9.1 Hz, 1H), 3.82 (quin, J=9.1 Hz, 1H), 3.72 (s, 3H), 2.37-2.48 (m, 2H), 2.23-2.35 (m, 2H), 2.07-2.18 (m, 1H), 1.88-2.00 (m, 1H). m/z (ESI, positive ion) 481.0 (M+H)$^+$.

Example 29: (P)-1-(4-Cyclobutyl-2-Methoxyphenyl)-N-(Oxazol-2-Yl)-2-Oxo-1,2-Dihydroquinoline-6-Sulfonamide

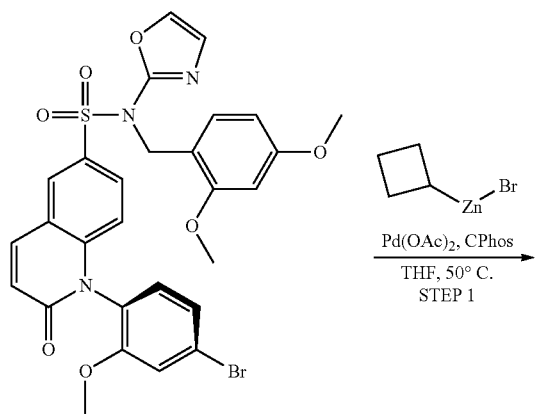

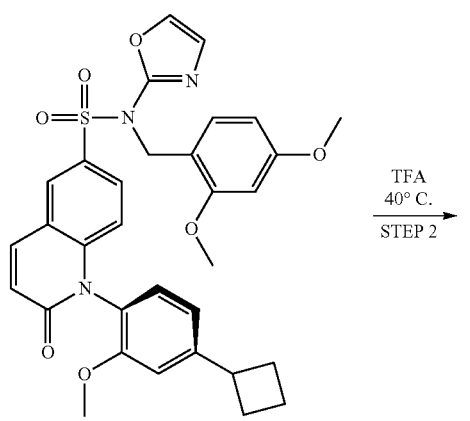

Step 1: (P)-1-(4-Cyclobutyl-2-Methoxyphenyl)-N-(2,4-Dimethoxybenzyl)-N-(Oxazol-2-Yl)-2-Oxo-1,2-Dihydroquinoline-6-Sulfonamide To a THF (1.2 mL) solution of (P)-1-(4-bromo-2-methoxyphenyl)-N-(2,4-dimethoxybenzyl)-N-(oxazol-2-yl)-2-oxo-1,2-dihydroquinoline-6-sulfonamide (200 mg, 0.319 mmol) was added 2-dicyclohexylphosphino-2',6'-dimethylamino-1,1'-biphenyl (41.8 mg, 0.096 mmol) and palladium(II) acetate (21.50 mg, 0.096 mmol). The reaction mixture was sparged with argon, and then cyclobutylzinc bromide (0.5 M in THF, 2.55 mL, 1.28 mmol) was added. The reaction was stirred at 50° C. After 3 h, the reaction was quenched with saturated aqueous sodium bicarbonate and partitioned between water and ethyl acetate. The organic layer was concentrated. The residue were purified by silica gel column chromatography (gradient elution 40-100% ethyl acetate:heptane with 10% dichloromethane as a co-eluent) to provide (P)-1-(4-cyclobutyl-2-methoxyphenyl)-N-(2,4-dimethoxybenzyl)-N-(oxazol-2-yl)-2-oxo-1,2-dihydroquinoline-6-sulfonamide (73 mg, 0.12 mmol, 38% yield) as a yellow oil. m/z (ESI, positive ion) 602.0 (M+H)$^+$.

Step 2: (P)-1-(4-Cyclobutyl-2-Methoxyphenyl)-N-(Oxazol-2-Yl)-2-Oxo-1,2-Dihydroquinoline-6-Sulfonamide (P)-1-(4-Cyclobutyl-2-methoxyphenyl)-N-(2,4-dimethoxybenzyl)-N-(oxazol-2-yl)-2-oxo-1,2-dihydroquinoline-6-sulfonamide (73 mg, 0.12 mmol) was dissolved in TFA (3.0 mL). The reaction mixture was stirred at 40° C. After 1 h, the reaction was concentrated, and the residue was purified by silica gel column chromatography (gradient elution 20-80% [3:1 EtOAc/EtOH]:heptane with 10% dichloromethane co-eluent) to afford (P)-1-(4-cyclobutyl-2-methoxyphenyl)-N-(oxazol-2-yl)-2-oxo-1,2-dihydroquinoline-6-sulfonamide (46 mg, 0.10 mmol, 85% yield) as a white solid. $^1$H NMR (500 MHz, DMSO-d$_6$) δ ppm 12.12 (br s, 1H), 8.29 (d, J=2.1 Hz, 1H), 8.15 (d, J=9.6 Hz, 1H), 7.83 (dd, J=9.0, 2.2 Hz, 1H), 7.59 (d, J=1.8 Hz, 1H), 7.26 (d, J=1.6 Hz, 1H), 7.17 (d, J=7.8 Hz, 1H), 7.12 (d, J=1.6 Hz, 1H), 7.02 (dd, J=8.0, 1.6 Hz, 1H), 6.74 (d, J=9.6 Hz, 1H), 6.64 (d, J=8.8 Hz, 1H), 3.68 (s, 3H), 3.58-3.67 (m, 1H), 2.31-2.39 (m, 2H), 2.17-2.28 (m, 2H), 1.96-2.10 (m, 1H), 1.82-1.92 (m, 1H). m/z (ESI, positive ion) 451.8 (M+H)$^+$.

Example 30: (P)-1-(4-Cyclobutyl-2-Methoxy-5-Methylphenyl)-2-Oxo-N-(Pyridazin-3-Yl)-1,2-Dihydroquinoline-6-Sulfonamide

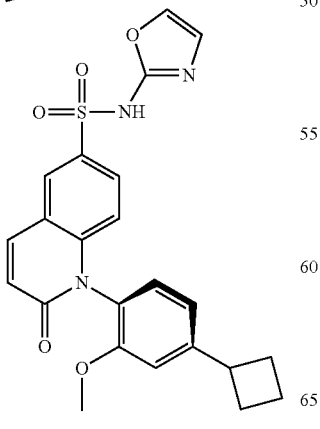

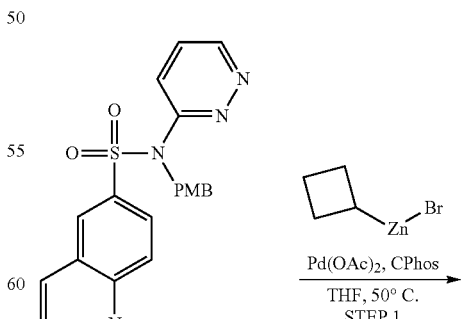

125
-continued

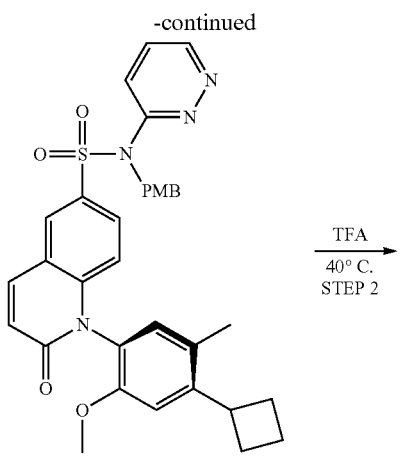

Example 31: (P)-1-(4-Cyclobutyl-2-Methoxyphenyl)-2-Oxo-N-(Pyridazin-3-Yl)-1,2-Dihydroquinoline-6-Sulfonamide

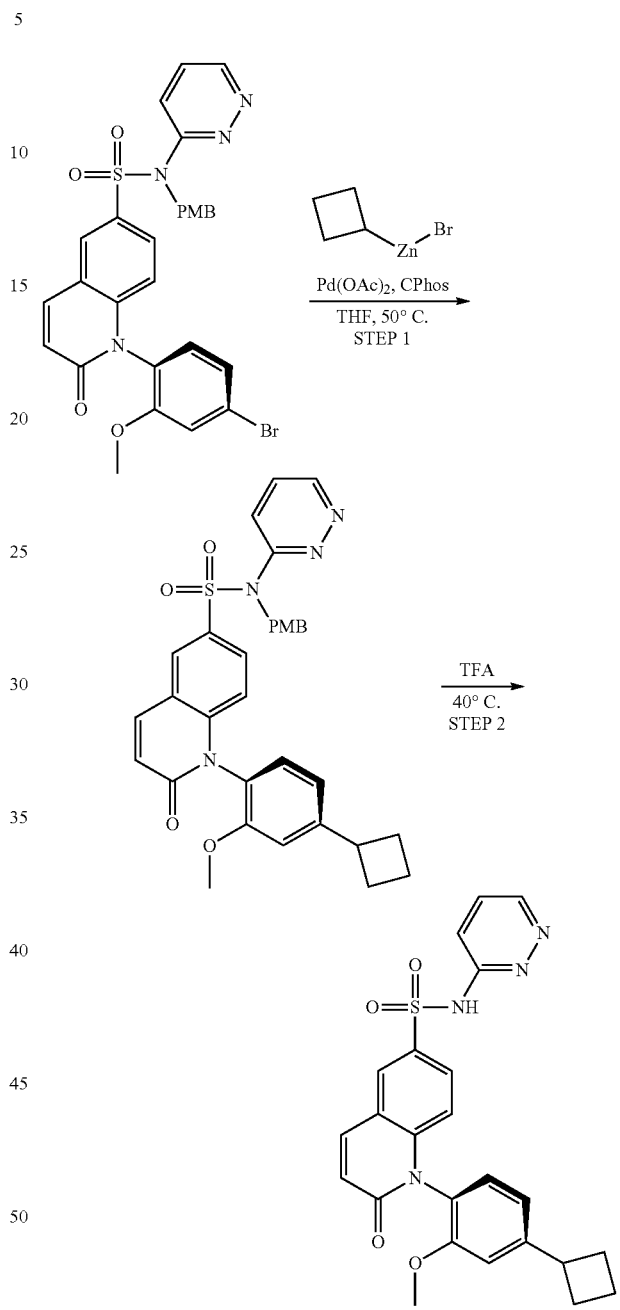

The title compound was prepared according to the method and purification protocol of Example 23 using (P)-1-(4-bromo-2-methoxy-5-methylphenyl)-N-(4-methoxybenzyl)-2-oxo-N-(pyridazin-3-yl)-1,2-dihydroquinoline-6-sulfonamide (367 mg, 0.591 mmol). This afforded (P)-1-(4-cyclobutyl-2-methoxy-5-methylphenyl)-2-oxo-N-(pyridazin-3-yl)-1,2-dihydroquinoline-6-sulfonamide (144 mg, 0.302 mmol, 51% yield over 2 steps) as a white solid. $^1$H NMR (400 MHz, DMSO-$d_6$) δ ppm 14.35-14.59 (m, 1H), 8.23-8.34 (m, 2H), 8.16 (d, J=9.5 Hz, 1H), 7.88-7.98 (m, 1H), 7.82 (br d, J=8.3 Hz, 1H), 7.59-7.73 (m, 1H), 7.08 (s, 1H), 6.99 (s, 1H), 6.74 (d, J=9.5 Hz, 1H), 6.65 (d, J=8.9 Hz, 1H), 3.63-3.76 (m, 4H), 2.31-2.44 (m, 2H), 2.21-2.30 (m, 1H), 2.13-2.20 (m, 4H), 2.00-2.09 (m, 1H), 1.81-1.92 (m, 1H). m/z (ESI, positive ion) 477.0 (M+H)$^+$.

The title compound was prepared according to the method of Example 23 using (P)-1-(4-bromo-2-methoxyphenyl)-N-(4-methoxybenzyl)-2-oxo-N-(pyridazin-3-yl)-1,2-dihydroquinoline-6-sulfonamide (300 mg, 0.494 mmol). The sample was purified via reverse phase HPLC using a XBridge Prep Shield RP18 19×100 mm column. The mobile was run under a gradient elution; 15-70% acetonitrile:water with 0.1% formic acid; flow rate: 40 mL/min. This afforded (P)-1-(4-cyclobutyl-2-methoxyphenyl)-2-oxo-N-(pyridazin-3-yl)-1,2-dihydroquinoline-6-sulfonamide (130 mg, 0.281 mmol, 57% yield over 2 steps) as a white solid. $^1$H NMR (500 MHz, DMSO-$d_6$) δ ppm 14.39 (br s, 1H), 8.31 (d, J=2.1 Hz, 2H), 8.16 (d, J=9.6 Hz, 1H), 7.85-7.93 (m, 1H), 7.82 (dd, J=9.0, 2.2 Hz, 1H), 7.66 (dd, J=9.6, 4.2 Hz, 1H), 7.16 (d, J=8.0 Hz, 1H), 7.11 (d, J=1.6 Hz, 1H), 7.02 (dd, J=8.0, 1.3 Hz, 1H), 6.74 (d, J=9.6 Hz, 1H), 6.64 (d, J=8.8 Hz, 1H), 3.67 (s, 3H), 3.59-3.66 (m, 1H), 2.30-2.41 (m, 2H), 2.16-2.29 (m, 2H), 1.96-2.10 (m, 1H), 1.81-1.93 (m, 1H). m/z (ESI, positive ion) 463.0 (M+H)+.

Example 32: (P)-1-(5-Chloro-4-Cyclobutyl-2-Methoxyphenyl)-N-(Oxazol-2-Yl)-2-Oxo-1,2-Dihydroquinoline-6-Sulfonamide

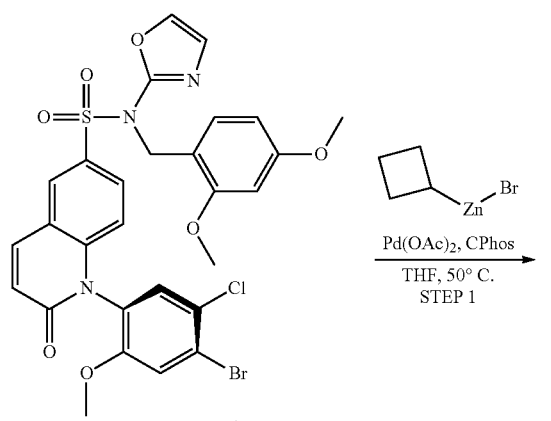

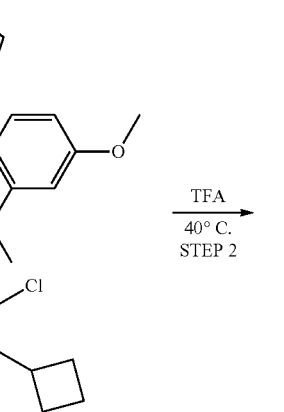

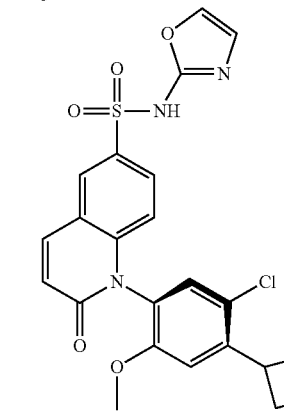

The title compound was prepared according to the method of Example 23 using (P)-1-(4-bromo-5-chloro-2-methoxyphenyl)-N-(2,4-dimethoxybenzyl)-N-(oxazol-2-yl)-2-oxo-1,2-dihydroquinoline-6-sulfonamide (347 mg, 0.525 mmol). The sample was purified via reverse phase HPLC using a XBridge Prep Shield RP18 19×100 mm column. The mobile was run under a gradient elution; 15-60% acetonitrile:water with 0.1% formic acid; flow rate: 40 mL/min. The material was further purified using a Whelk-O, 2×15 cm column. The mobile phase was run under isocratic conditions; supercritical $CO_2$ with 60% isopropanol; flow rate: 70 mL/min. This afforded (P)-1-(5-chloro-4-cyclobutyl-2-methoxyphenyl)-N-(oxazol-2-yl)-2-oxo-1,2-dihydroquinoline-6-sulfonamide (74 mg, 0.15 mmol, 29% yield over 2 steps) as a white solid. $^1$H NMR (500 MHz, DMSO-$d_6$) δ ppm 12.15 (br s, 1H), 8.30 (d, J=2.1 Hz, 1H), 8.16 (d, J=9.6 Hz, 1H), 7.84 (dd, J=9.0, 2.2 Hz, 1H), 7.59 (d, J=1.6 Hz, 1H), 7.43 (s, 1H), 7.23-7.30 (m, 2H), 6.75 (d, J=9.6 Hz, 1H), 6.69 (d, J=8.8 Hz, 1H), 3.82 (quin, J=8.8 Hz, 1H), 3.74 (s, 3H), 2.39-2.44 (m, 2H), 2.29-2.35 (m, 1H), 2.23 (quin, J=9.5 Hz, 1H), 2.00-2.12 (m, 1H), 1.81-1.92 (m, 1H). m/z (ESI, positive ion) 486.0 (M+H)+.

Example 33: (P)-1-(5-Chloro-4-Cyclobutyl-2-Methoxyphenyl)-2-Oxo-N-(Pyridazin-3-Yl)-1,2-Dihydroquinoline-6-Sulfonamide

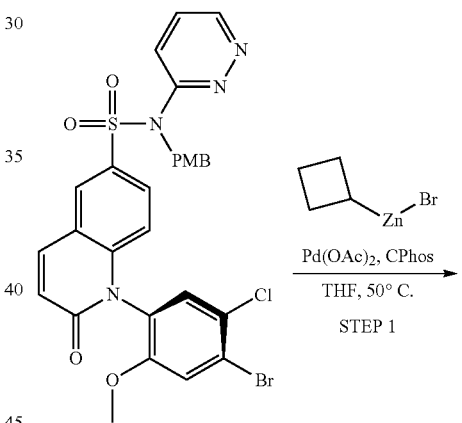

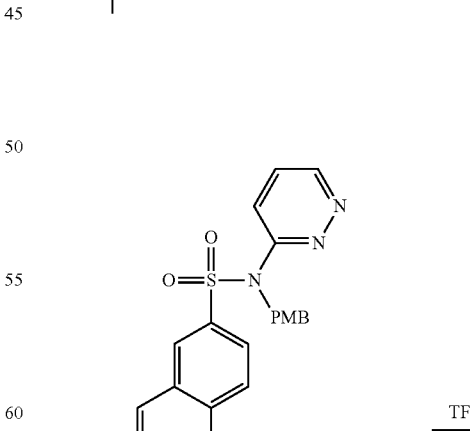

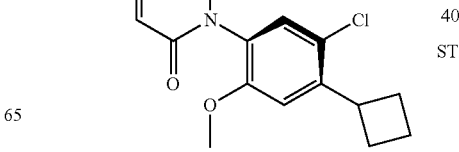

Step 1: (P)-1-(5-Chloro-4-Cyclobutyl-2-Methoxyphenyl)-N-(4-Methoxybenzyl)-2-Oxo-N-(Pyridazin-3-Yl)-1,2-Dihydroquinoline-6-Sulfonamide

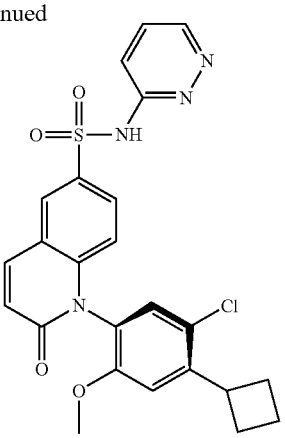

To a 20-mL scintillation vial was added 2-dicyclohexylphosphino-2',6'-dimethylamino-1,1'-biphenyl (20.4 mg, 0.047 mmol), palladium(II) acetate (5.3 mg, 0.023 mmol), and (P)-1-(4-bromo-5-chloro-2-methoxyphenyl)-N-(4-methoxybenzyl)-2-oxo-N-(pyridazin-3-yl)-1,2-dihydroquinoline-6-sulfonamide (300 mg, 0.467 mmol). The reaction mixture was sparged with nitrogen, and then cyclobutylzinc bromide (0.5 M in THF, 1.87 mL, 0.935 mmol) was added. After stirring at 50° C. for 1 h, an additional portion of cyclobutylzinc bromide (0.5 M in THF, 1.87 mL, 0.935 mmol) was added. After stirring an additional 2 h at 50° C., the reaction mixture was quenched with saturated aqueous sodium bicarbonate and partitioned between water and ethyl acetate. The organic layer was concentrated. The initial products were purified by silica gel column chromatography (gradient elution 0-60% [3:1 EtOAc/EtOH]:heptane with 10% dichloromethane co-eluent) to provide (P)-1-(5-chloro-4-cyclobutyl-2-methoxyphenyl)-N-(4-methoxybenzyl)-2-oxo-N-(pyridazin-3-yl)-1,2-dihydroquinoline-6-sulfonamide (216 mg, 0.350 mmol, 75% yield) as a yellow solid. m/z (ESI, positive ion) 616.8 (M+H)+.

Step 2: (P)-1-(5-Chloro-4-Cyclobutyl-2-Methoxyphenyl)-2-Oxo-N-(Pyridazin-3-Yl)-1,2-Dihydroquinoline-6-Sulfonamide (P)-1-(5-Chloro-4-cyclobutyl-2-methoxyphenyl)-N-(4-methoxybenzyl)-2-oxo-N-(pyridazin-3-yl)-1,2-dihydroquinoline-6-sulfonamide (216 mg, 0.350 mmol) was taken up in trifluoroacetic acid (2.6 mL) and the reaction was heated to 40° C. After 2 h, the reaction was then concentrated and purified via reverse phase HPLC using a XBridge Prep Shield RP18 19×100 mm column. The mobile was run under a gradient elution; 15-70% acetonitrile:water with 0.1% formic acid; flow rate: 40 mL/min. This afforded (P)-1-(5-chloro-4-cyclobutyl-2-methoxyphenyl)-2-oxo-N-(pyridazin-3-yl)-1,2-dihydroquinoline-6-sulfonamide (83 mg, 0.167 mmol, 48% yield) as a yellow solid. $^1$H NMR (500 MHz, DMSO-$d_6$) δ ppm 14.46 (br s, 1H), 8.33 (d, J=2.1 Hz, 2H), 8.17 (d, J=9.6 Hz, 1H), 7.88 (br d, J=3.9 Hz, 1H), 7.83 (dd, J=9.0, 2.2 Hz, 1H), 7.67 (dd, J=9.6, 4.2 Hz, 1H), 7.42 (s, 1H), 7.24 (s, 1H), 6.75 (d, J=9.6 Hz, 1H), 6.69 (d, J=8.8 Hz, 1H), 3.82 (quin, J=8.8 Hz, 1H), 3.73 (s, 3H), 2.35-2.47 (m, 2H), 2.28-2.34 (m, 1H), 2.22 (quin, J=9.9 Hz, 1H), 1.97-2.11 (m, 1H), 1.80-1.91 (m, 1H). m/z (ESI, positive ion) 497.0 (M+H)+.

Example 34: (P)-1-(4-Cyclobutyl-2-Methoxy-5-Methylphenyl)-N-(2,4-Dimethoxybenzyl)-N-(Oxazol-2-Yl)-2-Oxo-1,2-Dihydroquinoline-6-Sulfonamide

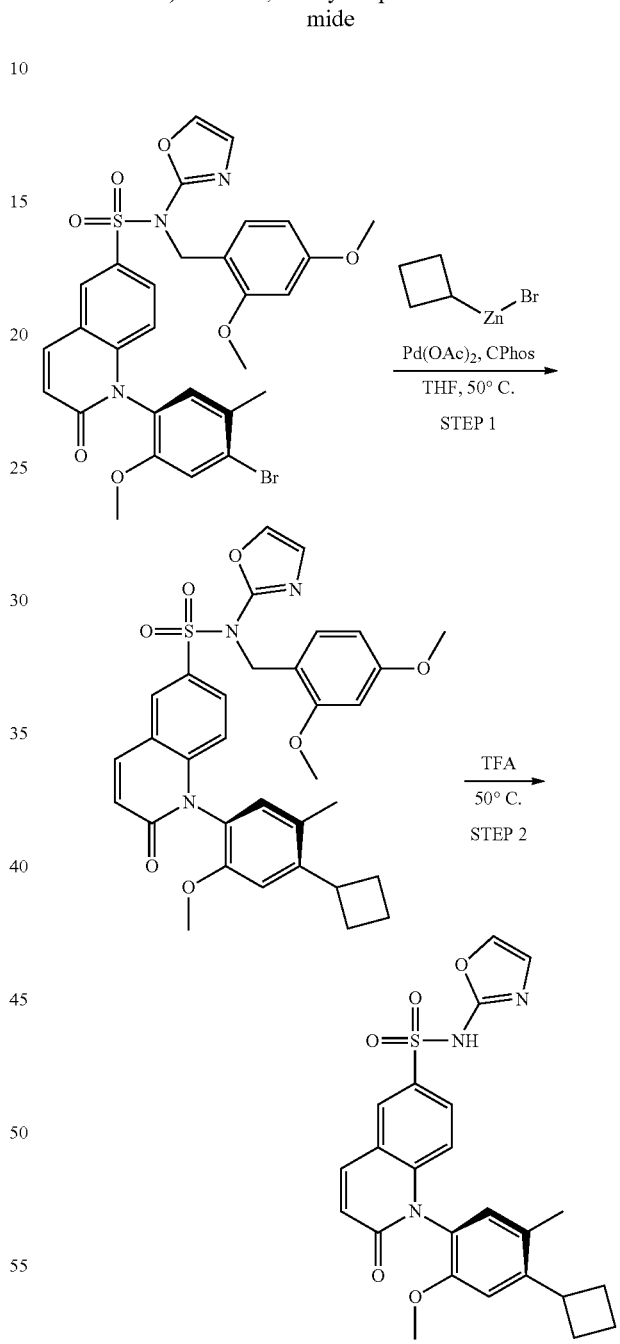

Step 1: (P)-1-(4-Cyclobutyl-2-Methoxy-5-Methylphenyl)-N-(2,4-Dimethoxybenzyl)-N-(Oxazol-2-Yl)-2-Oxo-1,2-Dihydroquinoline-6-Sulfonamide To a 20-mL scintillation vial was added 2-dicyclohexylphosphino-2',6'-dimethylamino-1,1'-biphenyl (26 mg, 0.060 mmol), palladium(II) acetate (6.7 mg, 0.030 mmol), and (P)-1-(4-bromo-2-methoxy-5-methylphenyl)-N-(2,4-dimethoxybenzyl)-N-(oxazol-2-yl)-2-oxo-1,2-dihydroquinoline-6-sulfonamide (384 mg, 0.600 mmol). The reaction mixture was sparged with nitrogen, and then cyclobutylzinc bromide (0.5 M in tetrahydrofuran, 3.60 mL, 1.80 mmol) was added. The reactions were stirred at 50° C. After 1 h, the reaction mixture was quenched with saturated aqueous sodium bicarbonate and partitioned between water and ethyl acetate. The organic layer was dried over sodium sulfate and concentrated. The residue was purified by silica gel column chromatography (gradient elution 0-30% [3:1 EtOAc/EtOH]:heptane with 10% dichloromethane co-eluent) to provide (P)-1-(4-cyclobutyl-2-methoxy-5-methylphenyl)-N-(2,4-dimethoxybenzyl)-N-(oxazol-2-yl)-2-oxo-1,2-dihydroquinoline-6-sulfonamide (255 mg, 0.414 mmol, 69% yield) as a white solid. m/z (ESI, positive ion) 616.2 (M+H)$^+$.

Step 2: (P)-1-(4-Cyclobutyl-2-Methoxy-5-Methylphenyl)-N-(2,4-Dimethoxybenzyl)-N-(Oxazol-2-Yl)-2-Oxo-1,2-Dihydroquinoline-6-Sulfonamide (P)-1-(4-Cyclobutyl-2-methoxy-5-methylphenyl)-N-(2,4-dimethoxybenzyl)-N-(oxazol-2-yl)-2-oxo-1,2-dihydroquinoline-6-sulfonamide (255 mg, 0.414 mmol) was taken up in TFA (3 mL) and heated to 50° C. After stirring for 1 h, the reaction was concentrated and purified using a Torus 2-PIC, 3×15 cm column. The mobile phase was run under gradient elution conditions; supercritical $CO_2$ with 10-40% methanol; flow rate: 100 mL/min. This afforded (P)-1-(4-cyclobutyl-2-methoxy-5-methylphenyl)-N-(oxazol-2-yl)-2-oxo-1,2-dihydroquinoline-6-sulfonamide (71 mg, 0.15 mmol, 25% yield over 2 steps). $^1$H NMR (600 MHz, DMSO-$d_6$) δ ppm 12.12 (br s, 1H), 8.29 (d, J=1.8 Hz, 1H), 8.15 (d, J=9.4 Hz, 1H), 7.83 (dd, J=8.9, 2.0 Hz, 1H), 7.59 (d, J=1.5 Hz, 1H), 7.26 (d, J=1.5 Hz, 1H), 7.09 (s, 1H), 6.99 (s, 1H), 6.74 (d, J=9.4 Hz, 1H), 6.65 (d, J=8.7 Hz, 1H), 3.63-3.75 (m, 4H), 2.33-2.44 (m, 2H), 2.27 (quin, J=9.7 Hz, 1H), 2.12-2.21 (m, 4H), 1.97-2.10 (m, 1H), 1.80-1.92 (m, 1H). m/z (ESI, positive ion) 466.0 (M+H)$^+$.

Example 35: Trans-(P)—N-(Isoxazol-3-Yl)-1-(2-Methoxy-4-((Trifluoromethyl)Cyclobutyl)Phenyl)-2-Oxo-1,2-Dihydroquinoline-6-Sulfonamide

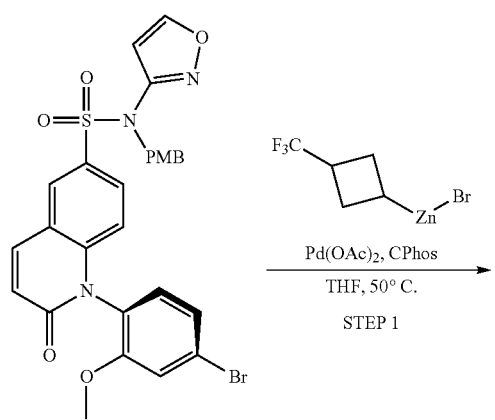

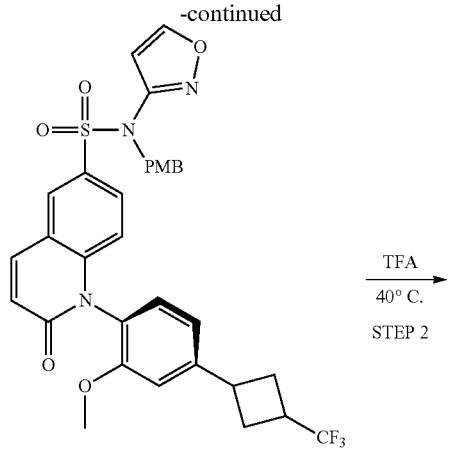

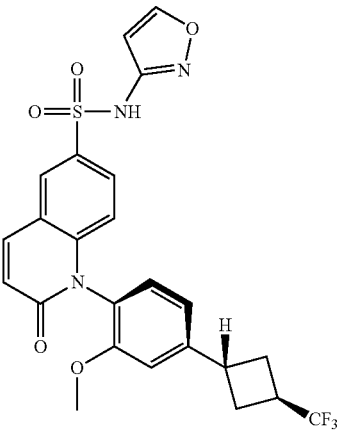

Step 1: (P)—N-(Isoxazol-3-Yl)-1-(2-Methoxy-4-(3-(Trifluoromethyl)Cyclobutyl)Phenyl)-N-(4-Methoxybenzyl)-2-Oxo-1,2-Dihydroquinoline-6-Sulfonamide (P)-1-(4-Bromo-2-methoxyphenyl)-N-(isoxazol-3-yl)-N-(4-methoxybenzyl)-2-oxo-1,2-dihydroquinoline-6-sulfonamide (0.47 g, 0.788 mmol), palladium(II) acetate (0.023 g, 0.10 mmol), and 2-dicyclohexylphosphino-2',6'-dimethylamino-1,1'-biphenyl (0.076 g, 0.173 mmol) were placed in a vial, and the resulting mixture was sparged with nitrogen prior to the addition of tetrahydrofuran (3.1 mL). (3-(Trifluoromethyl)cyclobutyl)zinc(II) bromide (0.125 M in THF, 9.46 mL, 1.182 mmol) was then added dropwise. The reaction mixture was then warmed to 50° C. and stirred at this temperature for 1.25 h. After cooling to ambient temperature, the reaction mixture was quenched with 5 M aqueous ammonium chloride solution, and the aqueous phase was extracted twice with ethyl acetate. The combined organic extracts were dried over magnesium sulfate, filtered, and concentrated under vacuum. The resulting residue was purified by flash column chromatography (gradient elution 0-50% [3:1 EtOAc/EtOH]:heptane with 10% dichloromethane co-eluent) to afford (P)—N-(isoxazol-3-yl)-1-(2-methoxy-4-(3-(trifluoromethyl)cyclobutyl)phenyl)-N-(4-methoxybenzyl)-2-oxo-1,2-dihydroquinoline-6-sulfonamide (0.489 g, 0.764 mmol, 97% yield). m/z (ESI, positive ion) 640.2 (M+H)$^+$.

Step 2: Trans-(P)—N-(Isoxazol-3-Yl)-1-(2-Methoxy-4-((Trifluoromethyl)Cyclobutyl)Phenyl)-2-Oxo-1,2-Dihydroquinoline-6-Sulfonamide (P)—N-(Isoxazol-3-yl)-1-(2-methoxy-4-(3-(trifluoromethyl)cyclobutyl)phenyl)-N-(4-methoxybenzyl)-2-oxo-1,2-dihydroquinoline-6-sulfonamide (0.489 g, 0.764 mmol) was dissolved in TFA (1.3 mL) and stirred at 40° C. for 2.5 h. After cooling to ambient temperature, volatiles were removed under vacuum, and the residue was purified using a ChromegaChiral CC4, 2×25 cm column. The mobile phase was run under isocratic conditions; supercritical $CO_2$ with 40% methanol; flow rate: 80 mL/min. This afforded trans-(P)—N-(isoxazol-3-yl)-1-(2-methoxy-4-(3-(trifluoromethyl)cyclobutyl)phenyl)-2-oxo-1,2-dihydroquinoline-6-sulfonamide (296 mg, 0.570 mmol, 72% yield over 2 steps). $^1$H NMR (500 MHz, DMSO-$d_6$) δ ppm 11.60 (s, 1H), 8.71 (d, J=1.6 Hz, 1H), 8.34 (d, J=2.1 Hz, 1H), 8.19 (d, J=9.6 Hz, 1H), 7.83 (dd, J=9.1, 2.3 Hz, 1H), 7.20-7.28 (m, 2H), 7.11 (dd, J=7.9, 1.4 Hz, 1H), 6.78 (d, J=9.6 Hz, 1H), 6.71 (d, J=9.1 Hz, 1H), 6.43 (d, J=1.8 Hz, 1H), 3.80 (quin, J=8.6 Hz, 1H), 3.69 (s, 3H), 3.22-3.28 (m, 1H), 2.54-2.61 (m, 4H). m/z (ESI, positive ion) 520.0 (M+H)$^+$.

Example 36: Trans-(P)-1-(2-Methoxy-4-(3-(Trifluoromethyl)Cyclobutyl)Phenyl)-2-Oxo-N-(Pyrimidin-2-Yl)-1,2-Dihydroquinoline-6-Sulfonamide

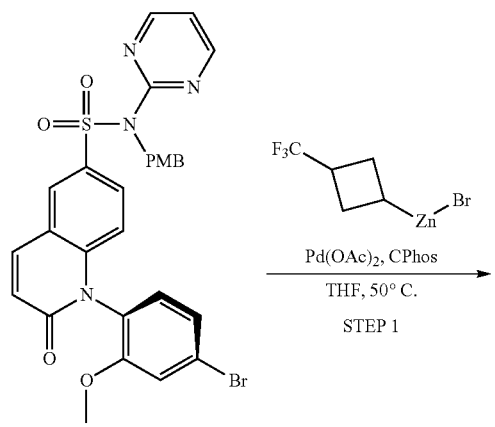

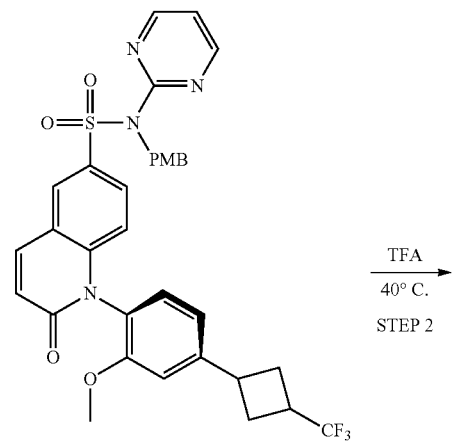

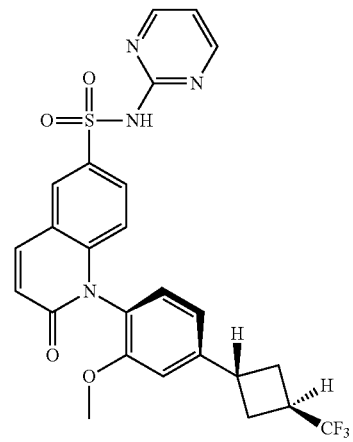

The title compound was prepared according to the method of Example 23 by using (P)-1-(4-bromo-2-methoxyphenyl)-N-(4-methoxybenzyl)-2-oxo-N-(pyrimidin-2-yl)-1,2-dihydroquinoline-6-sulfonamide (479 mg, 0.788 mmol) in place of (P)-1-(4-bromo-5-fluoro-2-methoxyphenyl)-N-(4-methoxybenzyl)-2-oxo-N-(pyridazin-3-yl)-1,2-dihydroquinoline-6-sulfonamide. The sample was purified using a Chiralpak IC, 2×15 cm column. The mobile phase was run under isocratic conditions; supercritical $CO_2$ with 60% [1:1 methanol:dichloromethane]; flow rate: 80 mL/min. This afforded trans-(P)-1-(2-methoxy-4-((1R,3R)-3-(trifluoromethyl)cyclobutyl)phenyl)-2-oxo-N-(pyrimidin-2-yl)-1,2-dihydroquinoline-6-sulfonamide (204 mg, 0.384 mmol, 49% yield over 2 steps). $^1$H NMR (500 MHz, DMSO-$d_6$) δ ppm 11.57-12.03 (m, 1H), 8.50 (br d, J=4.9 Hz, 2H), 8.45 (d, J=1.8 Hz, 1H), 8.22 (d, J=9.6 Hz, 1H), 7.82-8.03 (m, 1H), 7.18-7.25 (m, 2H), 7.11 (dd, J=8.0, 1.6 Hz, 1H), 7.05 (br s, 1H), 6.76 (d, J=9.6 Hz, 1H), 6.69 (d, J=8.8 Hz, 1H), 3.80 (quin, J=9.0 Hz, 1H), 3.68 (s, 3H), 3.21-3.28 (m, 1H), 2.53-2.63 (m, 4H). m/z (ESI, positive ion) 531.0 (M+H)$^+$.

Example 37: Trans-(P)-1-(2-Methoxy-5-Methyl-4-(3-(Trifluoromethyl)Cyclobutyl)Phenyl)-2-Oxo-N-(Pyrimidin-2-Yl)-1,2-Dihydroquinoline-6-Sulfonamide

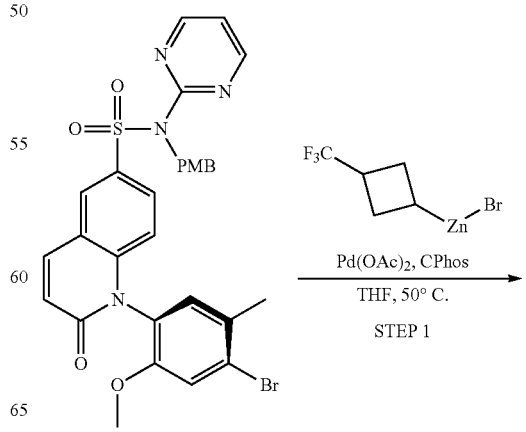

-continued

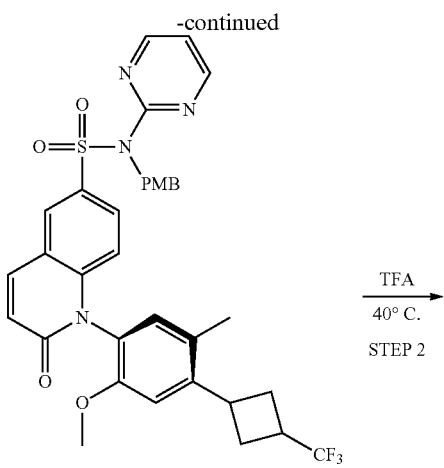

The title compound was prepared according to the method of Example 35 by using (P)-1-(4-bromo-2-methoxy-5-methylphenyl)-N-(4-methoxybenzyl)-2-oxo-N-(pyrimidin-2-yl)-1,2-dihydroquinoline-6-sulfonamide (470 mg, 0.756 mmol) in place of (P)-1-(4-Bromo-2-methoxyphenyl)-N-(isoxazol-3-yl)-N-(4-methoxybenzyl)-2-oxo-1,2-dihydroquinoline-6-sulfonamide. The sample was purified using two sequential Chiralpak OJ-H, 3×15 cm columns. The mobile phase was run under isocratic conditions; supercritical $CO_2$ with 20% methanol; flow rate: 80 mL/min. The sample was further purified via silica gel column chromatography (gradient elution 0-100% EtOAc:heptane with 10% dichloromethane co-eluent) to afford trans-(P)-1-(2-methoxy-5-methyl-4-(3-(trifluoromethyl)cyclobutyl)phenyl)-2-oxo-N-(pyrimidin-2-yl)-1,2-dihydroquinoline-6-sulfonamide (103 mg, 0.189 mmol, 25% yield over 2 steps) as a light pink solid. $^1$H NMR (500 MHz, DMSO-$d_6$) δ ppm 14.17-14.75 (m, 1H), 8.25-8.35 (m, 2H), 8.16 (d, J=9.9 Hz, 1H), 7.86-7.99 (m, 1H), 7.83 (dd, J=8.7, 1.7 Hz, 1H), 7.67 (br dd, J=8.6, 3.9 Hz, 1H), 7.22 (s, 1H), 7.04 (s, 1H), 6.74 (d, J=9.6 Hz, 1H), 6.65 (d, J=9.1 Hz, 1H), 3.88 (quin, J=8.9 Hz, 1H), 3.71 (s, 3H), 3.18-3.28 (m, 1H), 2.54-2.66 (m, 4H), 2.16 (s, 3H). m/z (ESI, positive ion) 545.0 (M+H)$^+$.

Example 38: Trans-(P)-1-(2-Methoxy-4-(3-(Trifluoromethyl)Cyclobutyl)Phenyl)-2-Oxo-N-(Pyridazin-3-Yl)-1,2-Dihydroquinoline-6-Sulfonamide

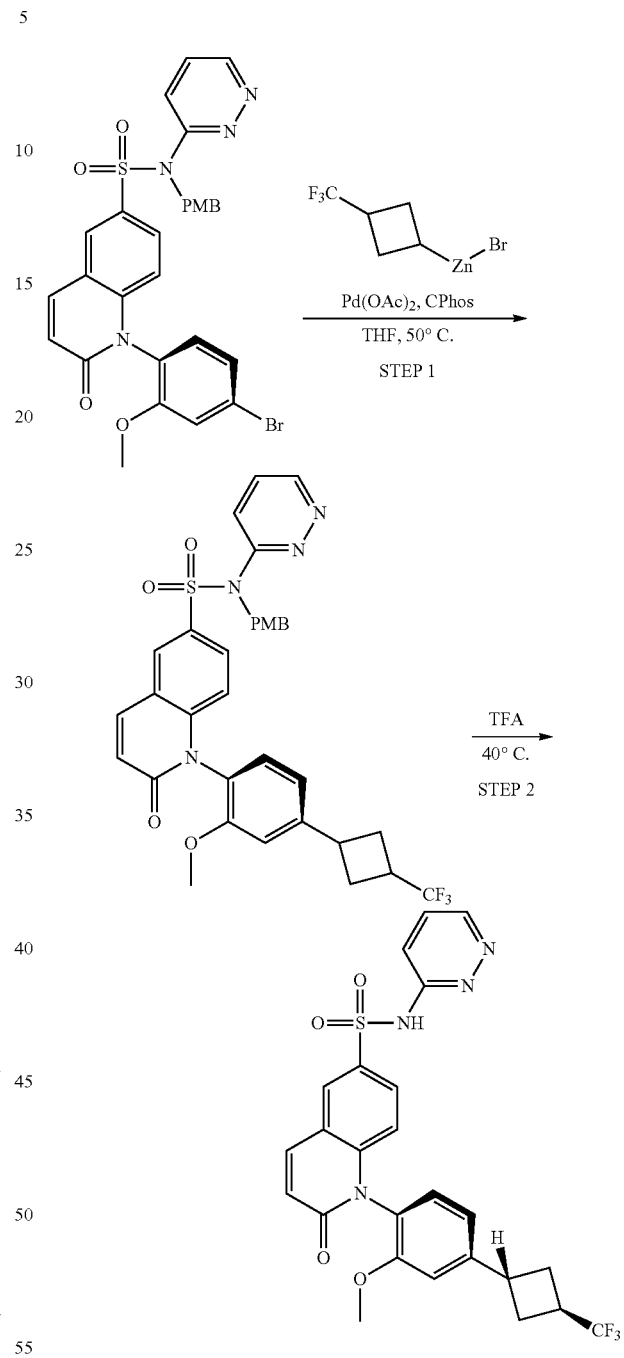

The title compound was prepared according to the method of Example 35 by using (P)-1-(4-bromo-2-methoxyphenyl)-N-(4-methoxybenzyl)-2-oxo-N-(pyridazin-3-yl)-1,2-dihydroquinoline-6-sulfonamide (459 mg, 0.756 mmol) in place of (P)-1-(4-Bromo-2-methoxyphenyl)-N-(isoxazol-3-yl)-N-(4-methoxybenzyl)-2-oxo-1,2-dihydroquinoline-6-sulfonamide. The sample was purified using a Chiralpak AS-H, 2×25 cm column. The mobile phase was run under isocratic conditions; supercritical $CO_2$ with 35% methanol; flow rate: 50 mL/min. The sample was further purified via silica gel column chromatography (gradient elution 0-100% EtOAc:

heptane with 10% dichloromethane co-eluent) to afford trans-(P)-1-(2-methoxy-4-(3-(trifluoromethyl)cyclobutyl)phenyl)-2-oxo-N-(pyridazin-3-yl)-1,2-dihydroquinoline-6-sulfonamide (247 mg, 466 mmol, 62% yield over 2 steps) as alight pink solid. $^1$H NMR (500 MHz, DMSO-$d_6$) δ ppm 14.26-14.69 (m, 1H), 8.23-8.35 (m, 2H), 8.16 (d, J=9.6 Hz, 1H), 7.89-7.98 (m, 1H), 7.82 (br d, J=8.0 Hz, 1H), 7.68 (br dd, J=9.7, 4.0 Hz, 1H), 7.18-7.25 (m, 2H), 7.11 (dd, J=8.0, 1.6 Hz, 1H), 6.75 (d, J=9.6 Hz, 1H), 6.65 (d, J=9.1 Hz, 1H), 3.80 (quin, J=8.8 Hz, 1H), 3.69 (s, 3H), 3.24-3.28 (m, 1H), 2.54-2.62 (m, 4H). m/z (ESI, positive ion) 531.0 (M+H)$^+$.

Example 39: Trans-(P)-1-(5-Fluoro-2-Methoxy-4-((1R,3R)-3-(Trifluoromethyl)Cyclobutyl)Phenyl)-2-Oxo-N-(Pyridazin-3-Yl)-1,2-Dihydroquinoline-6-Sulfonamide

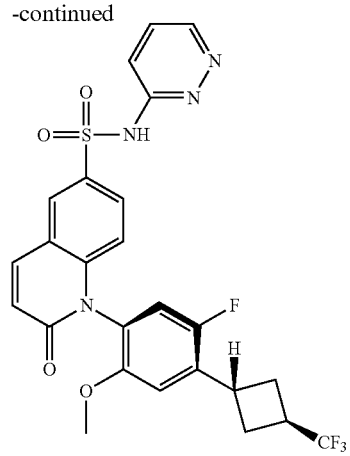

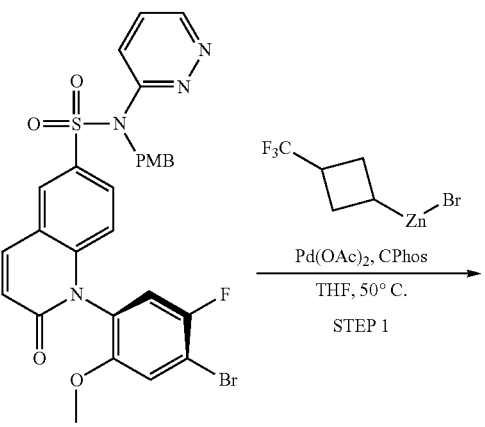

The title compound was prepared according to the method of Example 35, by using (P)-1-(4-bromo-5-fluoro-2-methoxyphenyl)-N-(4-methoxybenzyl)-2-oxo-N-(pyridazin-3-yl)-1,2-dihydroquinoline-6-sulfonamide (382 mg, 0.756 mmol) in place of (P)-1-(4-Bromo-2-methoxyphenyl)-N-(isoxazol-3-yl)-N-(4-methoxybenzyl)-2-oxo-1,2-dihydroquinoline-6-sulfonamide. The sample was purified using two sequential Chiralcel, 3×15 cm columns. The mobile phase was run under isocratic conditions; supercritical $CO_2$ with 20% methanol; flow rate: 80 mL/min. The sample was further purified via silica gel column chromatography (gradient elution 0-100% EtOAc:heptane with 10% dichloromethane co-eluent) to afford trans-(P)-1-(5-fluoro-2-methoxy-4-(3-(trifluoromethyl)cyclobutyl)phenyl)-2-oxo-N-(pyridazin-3-yl)-1,2-dihydroquinoline-6-sulfonamide (59.5 mg, 0.108 mmol, 14% yield over 2 steps) as a white solid. $^1$H NMR (500 MHz, DMSO-$d_6$) δ ppm 14.23-14.74 (m, 1H), 8.24-8.37 (m, 2H), 8.18 (d, J=9.6 Hz, 1H), 7.88-7.98 (m, 1H), 7.80-7.86 (m, 1H), 7.68 (br dd, J=9.5, 3.8 Hz, 1H), 7.32 (d, J=7.0 Hz, 1H), 7.29 (d, J=9.9 Hz, 1H), 6.75 (d, J=9.6 Hz, 1H), 6.70 (d, J=9.1 Hz, 1H), 3.95 (quin, J=9.0 Hz, 1H), 3.71 (s, 3H), 3.24-3.28 (m, 1H), 2.56-2.70 (m, 4H). m/z (ESI, positive ion) 549.0 (M+H)$^+$.

Example 40: (P)-7-Fluoro-1-(5-Fluoro-2-Methoxy-4-((1R,3R)-3-(Trifluoromethyl)Cyclobutyl)Phenyl)-N-(Isoxazol-3-Yl)-2-Oxo-1,2-Dihydroquinoline-6-Sulfonamide

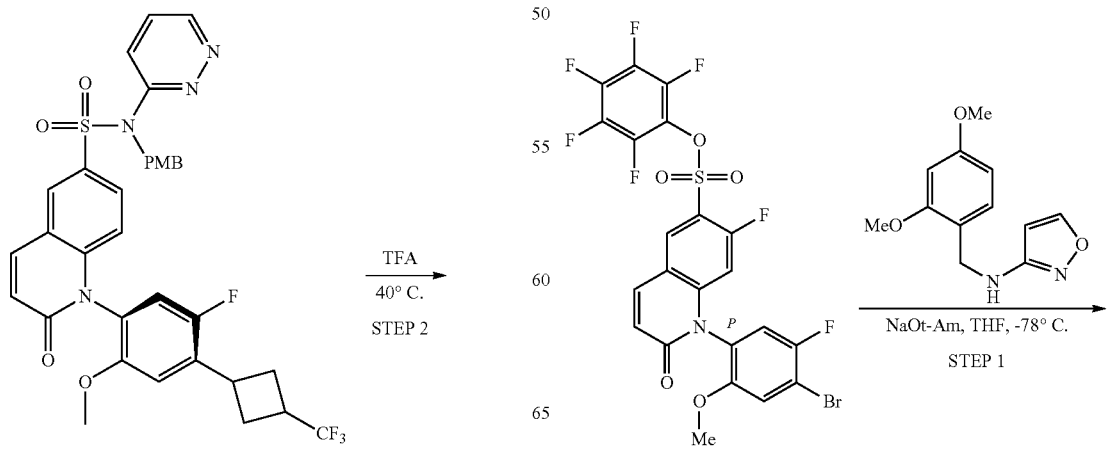

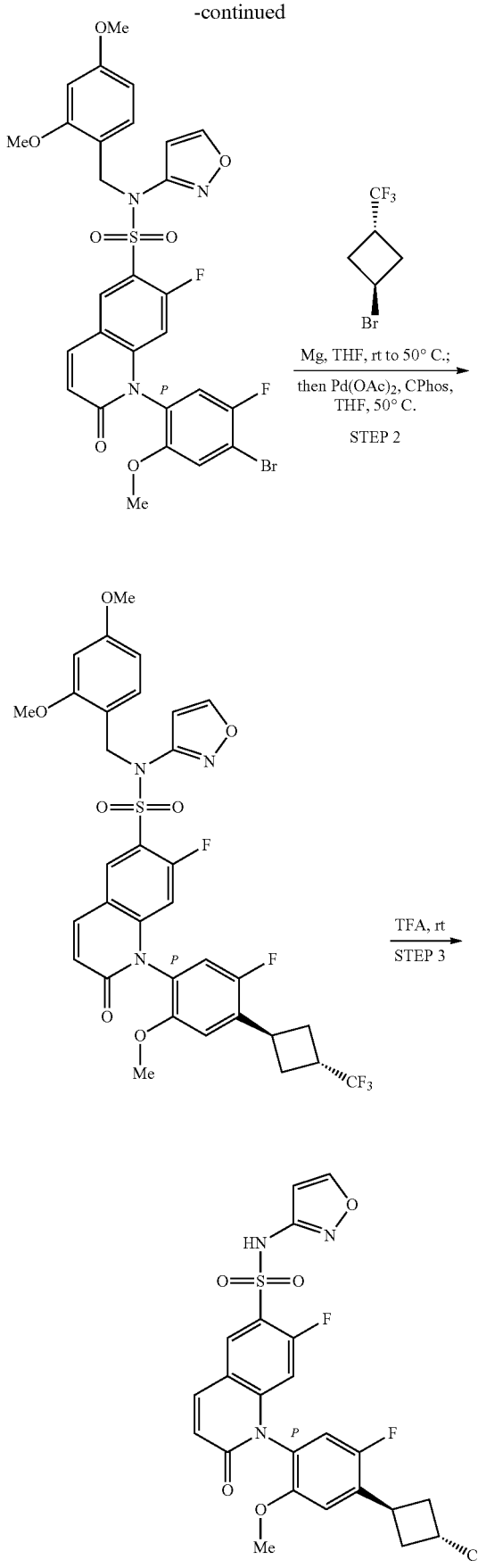

-continued

Step 1: (P)-1-(4-Bromo-5-Fluoro-2-Methoxyphenyl)-N-(2,4-Dimethoxybenzyl)-7-Fluoro-N-(Isoxazol-3-Yl)-2-Oxo-1,2-Dihydroquinoline-6-Sulfonamide A 250 mL round-bottom flask was charged with (P)-perfluorophenyl 1-(4-bromo-5-fluoro-2-methoxyphenyl)-7-fluoro-2-oxo-1,2-dihydroquinoline-6-sulfonate (5.0 g, 8.17 mmol) and N-(2,4-dimethoxybenzyl)isoxazol-3-amine (2.37 g, 10.1 mmol). The flask was purged with nitrogen for 5 minutes before tetrahydrofuran (20 mL) was introduced. The resultant mixture was cooled to −78° C. in dry ice-acetone bath and sodium tert-pentoxide (30% solution in THF, 5.0 mL, 12.5 mmol) was added dropwise. The reaction mixture then stirred for 15 min. An aqueous solution of ammonium chloride (5 M) was introduced, the resultant mixture was allowed to warm to ambient temperature, and was then extracted with EtOAc. The organic layer was dried over anhydrous sodium sulfate, filtered, and concentrated under reduced pressure. The residue was purified by flash column chromatography (BIOTAGE®, 100 g Silica Cartridge, eluent: 0-80% ethyl acetate in heptane with 10% dichloromethane additive) to afford (P)-1-(4-bromo-5-fluoro-2-methoxyphenyl)-N-(2,4-dimethoxybenzyl)-7-fluoro-N-(isoxazol-3-yl)-2-oxo-1,2-dihydroquinoline-6-sulfonamide (1.92 g, 2.90 mmol, 35.5% yield) as a white solid. m/z (ESI) 662.0 and 664.0 (M+H)$^+$.

Step 2: (P)—N-(2,4-Dimethoxybenzyl)-7-Fluoro-1-(5-Fluoro-2-Methoxy-4-((1R,3R)-3-(Trifluoromethyl)Cyclobutyl)Phenyl)-N-(Isoxazol-3-Yl)-2-Oxo-1,2-Dihydroquinoline-6-Sulfonamide A 100 mL round-bottom flask equipped with a reflux condenser was charged with magnesium turnings (796 mg, 32.8 mmol) and purged with nitrogen for 15 minutes. Iodine (151 mg, 0.596 mmol) was introduced and the flask was warmed with a heat gun until the iodine visibly sublimated. After cooling to ambient temperature, a slight vacuum was applied to remove excess of iodine. Tetrahydrofuran (12.5 mL) was introduced. Trans-1-bromo-3-(trifluoromethyl)cyclobutane (5.00 g, 24.6 mmol, Enamine, LLC) was then slowly added to the stirred reaction mixture via syringe, resulting in a slight exotherm and loss of iodine color. The reaction vessel was submerged in an ice/water bath as needed to prevent excessive exotherm. After stirring for 1 h, tetrahydrofuran (12.5 mL) was added. After an additional 1 h, zinc chloride solution (1.9 M in 2-methyltetrahydrofuran, 14.0 mL, 26.6 mmol, Sigma-Aldrich Corporation) was added, resulting in the formation of a white precipitate. The resulting mixture was stirred at ambient temperature overnight and used without further manipulation. The organozinc solution was titration with iodine to provide an estimated concentration of 0.33 M. A separate 100 mL round-bottom flask was charged with 2-dicyclohexylphosphino-2',6'-dimethylamino-1,1'-biphenyl (0.501 g, 1.15 mmol), (P)-1-(4-bromo-5-fluoro-2-methoxyphenyl)-N-(2,4-dimethoxybenzyl)-7-fluoro-N-(isoxazol-3-yl)-2-oxo-1,2-dihydroquinoline-6-sulfonamide (1.90 g, 2.87 mmol), palladium(II) acetate (129 mg, 0.57 mmol), and tetrahydrofuran (14.0 mL). The reaction mixture was sparged with nitrogen for 10 minutes. A portion of the (3-(trifluoromethyl)cyclobutyl)zinc(II) bromide solution prepared above (10 mL, 3.30 mmol) was added dropwise via syringe to the reaction mixture. Following addition, the resultant mixture was warmed to 50° C. After 1.5 h, water was introduced and the mixture was extracted with ethyl acetate. The organic layer was dried over anhydrous sodium sulfate, filtered, and concentrated under reduced pressure. The residue was purified by flash column chromatography (BIOTAGE®, 100 g Silica Cartridge, eluent: 0-50% ethyl acetate in heptane with 10% DCM additive) to afford (P)—N-(2,4-dimethoxybenzyl)-7-fluoro-1-(5-fluoro-2-methoxy-4-((1R,3R)-3-(trifluoromethyl)cyclobutyl)phenyl)-N-(isoxazol-3-yl)-2-oxo-1,2-dihydroquinoline-6-sulfonamide (2.0 g, 2.83 mmol, 99% yield). m/z (ESI) 705.8 (M+H)$^+$.

Step 3: (P)-7-Fluoro-1-(5-Fluoro-2-Methoxy-4-((1R,3R)-3-(Trifluoromethyl)Cyclobutyl)Phenyl)-N-(Isoxazol-3-Yl)-2-Oxo-1,2-Dihydroquinoline-6-Sulfonamide A 50 mL round-bottomed flask was charged with (P)—N-(2,4-dimethoxybenzyl)-7-fluoro-1-(5-fluoro-2-methoxy-4-((1R,3R)-3-(trifluoromethyl)cyclobutyl)phenyl)-N-(isoxazol-3-yl)-2-oxo-1,2-dihydroquinoline-6-sulfonamide (2.0 g, 2.83 mmol), dichloromethane (12 mL), and trifluoroacetic acid (2.8 mL). The reaction mixture stirred at room temperature for 2 hours before the solvent was removed under a stream of nitrogen. The residue was purified by flash column chromatography (BIOTAGE®, 25 g Silica Cartridge, eluent: 0-70% ethyl acetate in heptane with 10% DCM additive). Fractions containing desired product were combined, the solvent was removed under reduced pressure, and the residue (1.5 g) was further purified by SFC using a Chiralpak AD-H column (3×25 cm, 5 micron), with a mobile phase of 20% ethanol using a flowrate of 160 mL/min to afford (P)-7-fluoro-1-(5-fluoro-2-methoxy-4-((1R,3R)-3-(trifluoromethyl)cyclobutyl)phenyl)-N-(isoxazol-3-yl)-2-oxo-1,2-dihydroquinoline-6-sulfonamide (844 mg, 1.52 mmol, 54% yield). $^1$H NMR (500 MHz, DMSO-d$_6$) δ: 11.97 (br s, 1H), 8.72 (d, J=1.8 Hz, 1H), 8.46 (d, J=7.8 Hz, 1H), 8.22 (d, J=9.7 Hz, 1H), 7.23-7.40 (m, 2H), 6.75 (d, J=9.7 Hz, 1H), 6.53 (d, J=11.9 Hz, 1H), 6.39 (d, J=1.8 Hz, 1H), 3.86-4.02 (m, 1H), 3.73 (s, 3H), 3.17-3.30 (m, 1H), 2.53-2.75 (m, 4H). m/z (ESI) 556.0 (M+H)$^+$.

Example 41: (P)-1-(4-(3,3-Difluorocyclobutyl)-5-Fluoro-2-Methoxyphenyl)-7-Fluoro-N-(Isoxazol-3-Yl)-2-Oxo-1,2-Dihydroquinoline-6-Sulfonamide

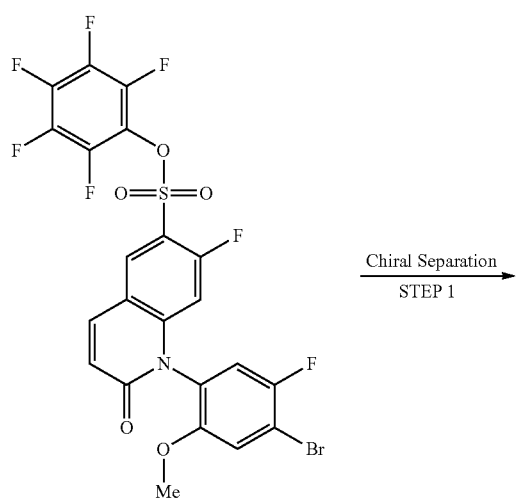

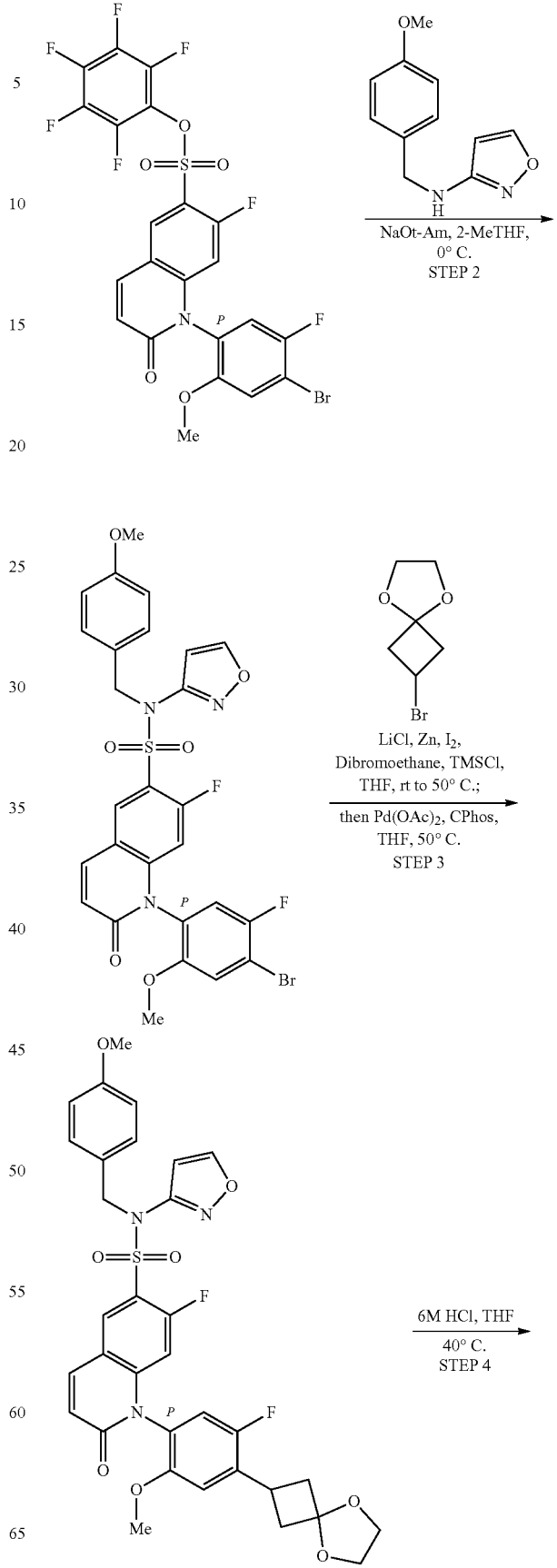

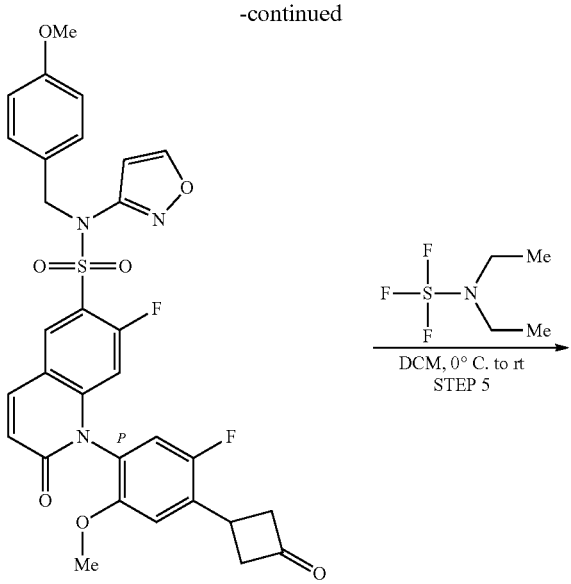

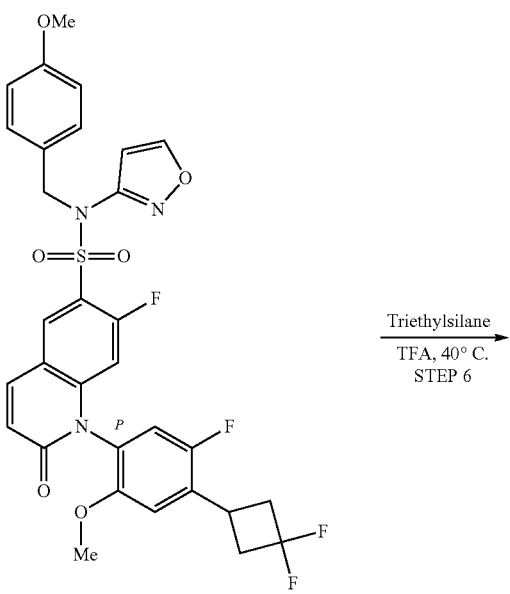

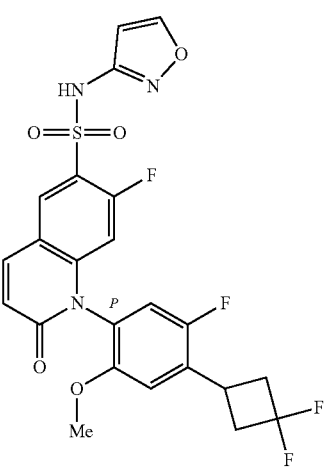

Step 1: (P)-Perfluorophenyl 1-(4-Bromo-5-Fluoro-2-Methoxyphenyl)-7-Fluoro-2-Oxo-1,2-Dihydroquinoline-6-Sulfonate and (M)-Perfluorophenyl 1-(4-Bromo-5-Fluoro-2-Methoxyphenyl)-7-Fluoro-2-Oxo-1,2-Dihydroquinoline-6-Sulfonate rac-Perfluorophenyl 1-(4-bromo-5-fluoro-2-methoxyphenyl)-7-fluoro-2-oxo-1,2-dihydroquinoline-6-sulfonate (see Intermediate AB) (257 g, 420 mmol) was purified by SFC via an Regis Whelk-O s,s, 5×15 cm, 5 μm column; a mobile phase of 40% isopropanol/dichloromethane (1:1 mix) using a flowrate of 350 mL/min; to generate (P)-perfluorophenyl 1-(4-bromo-5-fluoro-2-methoxyphenyl)-7-fluoro-2-oxo-1, 2-dihydroquinoline-6-sulfonate as the first eluting peak (123 g, 201 mmol) and (M)-perfluorophenyl 1-(4-bromo-5-fluoro-2-methoxyphenyl)-7-fluoro-2-oxo-1,2-dihydroquinoline-6-sulfonate as the second eluting peak (137 g, 224 mmol).

Step 2: (P)-1-(4-Bromo-5-Fluoro-2-Methoxyphenyl)-7-Fluoro-N-(Isoxazol-3-Yl)-N-(4-Methoxybenzyl)-2-Oxo-1,2-Dihydroquinoline-6-Sulfonamide A 3 L three-neck round-bottom flask equipped with thermocouple, overhead stirrer, addition funnel, and nitrogen inlet was charged with (P)-perfluorophenyl 1-(4-bromo-5-fluoro-2-methoxyphenyl)-7-fluoro-2-oxo-1,2-dihydroquinoline-6-sulfonate (175 g, 286 mmol), N-(4-methoxybenzyl)isoxazol-3-amine (64.2 g, 314 mmol), and 2-methyltetrahydrofuran (953 mL). The reaction vessel was then purged with nitrogen. The reaction mixture was cooled to 0° C. The addition funnel was charged with a 30% solution of sodium tert-pentoxide in THF (149 mL, 372 mmol) and added dropwise to the stirred reaction mixture over 15 mins. After 10 min, an aqueous solution of HCl (2 N, 200 mL) was added to the reaction mixture at 0° C. The resultant mixture was allowed to warm to room temperature and the layers were separated. The aqueous layer was extracted with and EtOAc (2×100 mL). The combined organic layers were washed with brine, dried over anhydrous sodium sulfate, filtered, and concentrated under reduced pressure. The residue was purified by SFC via a Regis Whelk-O s,s 5×15 cm, 5 μm column; a mobile phase of 40% methanol/dichloromethane (1:1 mix) using a flowrate of 350 mL/min to afford (P)-1-(4-bromo-5-fluoro-2-methoxyphenyl)-7-fluoro-N-(isoxazol-3-yl)-N-(4-methoxybenzyl)-2-oxo-1,2-dihydroquinoline-6-sulfonamide (148 g, 234 mmol, 82% yield). m/z (ESI) 632.0/634.0 (M+H)+.

Step 3: (P)-7-Fluoro-1-(5-Fluoro-2-Methoxy-4-(5,8-Dioxaspiro[3.4]Octan-2-Yl)Phenyl)-N-(Isoxazol-3-Yl)-N-(4-Methoxybenzyl)-2-Oxo-1,2-Dihydroquinoline-6-Sulfonamide An oven-dried 100 mL three-neck round-bottom flask was charged with zinc dust (10.3 g, 158 mmol) and lithium chloride solution in THF (0.5 M, 45.0 mL, Sigma Aldrich). The mixture was stirred at 50° C. under a stream of nitrogen until the reaction volume was reduced by half 1,2-Dibromoethane (0.74 g, 0.34 mL, 3.95 mmol) was introduced and the reaction mixture was warmed to 50° C. Once the internal temperature reached 50° C., the reaction mixture was held at that temperature for 20 min, then cooled to room temperature. Chlorotrimethylsilane (0.43 g, 0.50 mL, 3.95 mmol) was added and the reaction mixture was warmed to 50° C. and held for 20 min, then cooled to room temperature. A solution of iodine (0.40 g, 1.58 mmol) in THF (1.0 mL) was then added and the reaction mixture was warmed to 50° C. and held for 20 min. 2-Bromo-5,8-dioxaspiro[3.4]octane (15.3 g, 15.3 mL, 79.0 mmol, Enamine, LLC) was added and the reaction mixture stirred at 50° C. for 48 hours. The reaction mixture was then cooled to room temperature and the residual zinc dust was allowed to settle before the supernatant solution was removed via syringe and used without further purification. A separate oven-dried 100 mL round-bottom flask was charged with palladium (II) acetate (0.36 g, 1.58 mmol), CPhos (1.38 g, 3.16 mmol), and THF (10 mL). A solution of (P)-1-(4-bromo-5-fluoro-2-methoxyphenyl)-7-fluoro-N-(isoxazol-3-yl)-N-(4-methoxybenzyl)-2-oxo-1,2-dihydroquinoline-6-sulfonamide (10.0 g, 15.8 mmol) in THF (10 mL) was then introduced and the resultant mixture was sparged with nitrogen for 10 min. The previously prepared solution of organozinc complex was then added to the reaction mixture via syringe and the resultant mixture stirred at 50° C. After 2 h, methanol (5 mL) and silica gel (about 25 g) were added to the reaction mixture and the volatiles were removed under reduced pressure. The silica-adsorbed material was purified by flash column chromatography (ISCO CombiFlash, 330 g Silica Cartridge, eluent: 0-70% ethyl acetate/ethanol (3:1 mix) gradient in heptane/DCM (9:1 mix)) to afford (P)-7-fluoro-1-(5-fluoro-2-methoxy-4-(5,8-dioxaspiro[3.4]octan-2-yl)phenyl)-N-(isoxazol-3-yl)-N-(4-methoxybenzyl)-2-oxo-1,2-dihydroquinoline-6-sulfonamide (9.56 g, 14.4 mmol, 91% yield). m/z (ESI) 666.2 (M+H)+.

Step 4: (P)-7-Fluoro-1-(5-Fluoro-2-Methoxy-4-(3-Oxocyclobutyl)Phenyl)-N-(Isoxazol-3-Yl)-N-(4-Methoxybenzyl)-2-Oxo-1,2-Dihydroquinoline-6-Sulfonamide A 100 mL round-bottom flask was charged with (P)-7-fluoro-1-(5-fluoro-2-methoxy-4-(5,8-dioxaspiro[3.4]octan-2-yl)phenyl)-N-(isoxazol-3-yl)-N-(4-methoxybenzyl)-2-oxo-1,2-dihydroquinoline-6-sulfonamide (9.56 g, 14.4 mmol) and THF (20 mL). An aqueous solution of HCl (6 M, 10 mL) was introduced, and the resultant reaction mixture was warmed to 40° C. After 2 h, the reaction mixture was cooled to room temperature before a saturated sodium bicarbonate solution (100 mL) and DCM (100 mL) were introduced. The layers were separated and the aqueous layer was extracted with DCM (2×50 mL). The combined organic layers were dried over anhydrous magnesium sulfate, filtered, concentrated under reduced pressure, and purified by flash column chromatography (ISCO CombiFlash, 330 g Silica Cartridge, eluent: 0-70% ethyl acetate/ethanol (3:1 mix) gradient in heptane/DCM (9:1 mix)) to afford (P)-7-fluoro-1-(5-fluoro-2-methoxy-4-(3-oxocyclobutyl)phenyl)-N-(isoxazol-3-yl)-N-(4-methoxybenzyl)-2-oxo-1,2-dihydroquinoline-6-sulfonamide (8.56 g, 13.8 mmol, 87% yield). m/z (ESI) 622.0 (M+H)+.

Step 5: (P)-1-(4-(3,3-Difluorocyclobutyl)-5-Fluoro-2-Methoxyphenyl)-7-Fluoro-N-(Isoxazol-3-Yl)-N-(4-Methoxybenzyl)-2-Oxo-1,2-Dihydroquinoline-6-Sulfonamide A 250 mL round-bottom flask was charged with (P)-7-fluoro-1-(5-fluoro-2-methoxy-4-(3-oxocyclobutyl)phenyl)-N-(isoxazol-3-yl)-N-(4-methoxybenzyl)-2-oxo-1,2-dihydroquinoline-6-sulfonamide (5.00 g, 8.04 mmol) and DCM (40.2 mL). The reaction mixture was cooled to 0° C. in an ice-water bath before DAST (25.9 g, 21.3 mL, 161 mmol) was added slowly via syringe. The ice-water bath was removed and the reaction mixture was allowed to warm to room temperature. After 2 h, the reaction mixture was carefully transferred into a mixture of a saturated aqueous solution of sodium bicarbonate and ice (about 300 mL, 1:1). The layers were separated and the aqueous layer was extracted with DCM. The combined organic layers were washed with brine, dried over anhydrous magnesium sulfate, filtered, concentrated under reduced pressure, and purified by flash column chromatography (ISCO CombiFlash, 100 g Silica Cartridge, eluent: 0-70% ethyl acetate/ethanol (3:1 mix) gradient in heptane/DCM (9:1 mix) to afford (P)-1-(4-(3,3-difluorocyclobutyl)-5-fluoro-2-methoxyphenyl)-7-fluoro-N-(isoxazol-3-yl)-N-(4-methoxybenzyl)-2-oxo-1,2-dihydroquinoline-6-sulfonamide (4.32 g, 6.71 mmol, 83% yield). m/z (ESI) 644.0 (M+H)+.

Step 6: (P)-1-(4-(3,3-Difluorocyclobutyl)-5-Fluoro-2-Methoxyphenyl)-7-Fluoro-N-(Isoxazol-3-Yl)-2-Oxo-1,2-Dihydroquinoline-6-Sulfonamide A 250 mL round-bottom flask was charged with (P)-1-(4-(3,3-difluorocyclobutyl)-5-fluoro-2-methoxyphenyl)-7-fluoro-N-(isoxazol-3-yl)-N-(4-methoxybenzyl)-2-oxo-1,2-dihydroquinoline-6-sulfonamide (9.90 g, 15.4 mmol), triethylsilane (8.94 g, 8.94 mL, 77.0 mmol), and 1,1,1-trifluoroacetic acid (52.3 g, 35.1 mL, 459 mmol). The reaction mixture was warmed to 40° C. After 6 hours, the reaction mixture was concentrated under reduced pressure and carefully poured into a saturated aqueous solution of sodium bicarbonate. The mixture was extracted with EtOAc (3×) and the combined organic layers were washed with brine, dried over anhydrous magnesium sulfate, filtered, and concentrated under reduced pressure. The product was azeotroped with heptane (3×70 mL) and purified by flash column chromatography (BIOTAGE®, 100 g Silica Cartridge, eluant: 0-50% EtOAc/heptane) to afford (P)-1-(4-(3,3-difluorocyclobutyl)-5-fluoro-2-methoxyphenyl)-7-fluoro-N-(isoxazol-3-yl)-2-oxo-1,2-dihydroquinoline-6-sulfonamide (6.85 g, 13.1 mmol, 85% yield). $^1$H NMR (DMSO-d$_6$, 500 MHz) δ: 11.8-12.1 (m, 1H), 8.70 (d, 1H, J=1.7 Hz), 8.44 (d, 1H, J=7.7 Hz), 8.22 (d, 1H, J=9.6 Hz), 7.33 (d, 1H, J=10.0 Hz), 7.24 (d, 1H, J=6.9 Hz), 6.74 (d, 1H, J=9.7 Hz), 6.51 (s, 1H), 6.54 (s, 1H), 6.37 (d, 1H, J=1.7 Hz), 3.72 (s, 3H), 3.62 (br t, 1H, J=8.8 Hz), 2.9-3.1 (m, 4H). m/z (ESI) 524.0 (M+H)+.

Example 42: (P)-1-(5-Fluoro-2-Methoxy-4-(3-(Trifluoromethyl)Bicyclo[1.1.1]Pentan-1-Yl)Phenyl)-N-(Isoxazol-3-Yl)-2-Oxo-1,2-Dihydroquinoline-6-Sulfonamide

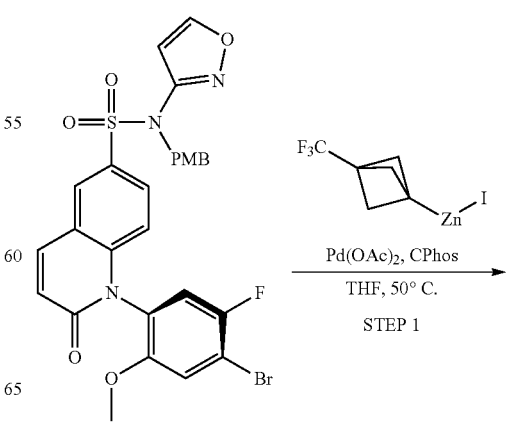

-continued

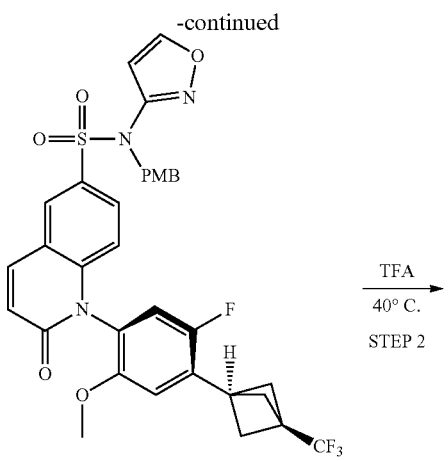

Step 1: (P)-1-(5-Fluoro-2-Methoxy-4-(3-(Trifluoromethyl)Bicyclo[1.1.1]Pentan-1-Yl)Phenyl)-N-(Isoxazol-3-Yl)-N-(4-Methoxybenzyl)-2-Oxo-1,2-Dihydroquinoline-6-Sulfonamide An oven-dried 40-mL vial was charged with 2'-(dicyclohexylphosphino)-N$^2$,N$^2$,N$^6$,N$^6$-tetramethyl-[1,1'-biphenyl]-2,6-diamine (32.9 mg, 0.075 mmol) and palladium(II) acetate (8.47 mg, 0.038 mmol) and 1-(4-bromo-5-fluoro-2-methoxyphenyl)-N-(isoxazol-3-yl)-N-(4-methoxybenzyl)-2-oxo-1,2-dihydroquinoline-6-sulfonamide (464 mg, 0.755 mmol). The reaction mixture was sparged with nitrogen for 15 min, and then (3-(trifluoromethyl)bicyclo[1.1.1]pentan-1-yl)zinc(II) iodide solution (272 mg, 0.83 mmol) was added after filtering through a 0.45 micron PTFE filter. The reactions were stirred at 50° C. After 2 hours, the reaction mixture was quenched with saturated aqueous sodium bicarbonate and partitioned between water and ethyl acetate; the organic layer was dried over sodium sulfate and concentrated. The initial product was purified via column chromatography (elution with 0-40% ethyl acetate in heptane with 10% dichloromethane) to provide (P)-1-(5-fluoro-2-methoxy-4-(3-(trifluoromethyl)bicyclo[1.1.1]pentan-1-yl)phenyl)-N-(isoxazol-3-yl)-N-(4-methoxybenzyl)-2-oxo-1,2-dihydroquinoline-6-sulfonamide (128 mg, 0.191 mmol, 25% yield) as a brown foam. m/z (ESI, positive ion) 670.0 (M+H)$^+$.

Step 2: (P)-1-(5-Fluoro-2-Methoxy-4-(3-(Trifluoromethyl)Bicyclo[1.1.1]Pentan-1-Yl)Phenyl)-N-(Isoxazol-3-Yl)-2-Oxo-1,2-Dihydroquinoline-6-Sulfonamide (P)-1-(5-fluoro-2-methoxy-4-(3-(trifluoromethyl)bicyclo[1.1.1]pentan-1-yl)phenyl)-N-(isoxazol-3-yl)-N-(4-methoxybenzyl)-2-oxo-1,2-dihydroquinoline-6-sulfonamide (190 mg, 0.284 mmol) was dissolved in TFA (1.2 mL) and stirred at 40° C. After completion, the reaction was concentrated, and subjected to reverse phase purification, eluted with 35 to 80% acetonitrile in water (with 0.1% formic acid) to provide (P)-1-(5-fluoro-2-methoxy-4-(3-(trifluoromethyl)bicyclo[1.1.1]pentan-1-yl)phenyl)-N-(isoxazol-3-yl)-2-oxo-1,2-dihydroquinoline-6-sulfonamide (112 mg, 0.204 mmol, 72% yield) as a white solid after lyophilization. $^1$H NMR (500 MHz, CHLOROFORM-d) δ ppm 8.28 (d, J=1.7 Hz, 1H), 8.13 (d, J=2.1 Hz, 1H), 7.80 (d, J=9.6 Hz, 1H), 7.76 (dd, J=2.2, 9.0 Hz, 1H), 7.72 (s, 1H), 6.94 (d, J=9.1 Hz, 1H), 6.87 (d, J=9.7 Hz, 1H), 6.8-6.8 (m, 1H), 6.77 (d, J=9.0 Hz, 1H), 6.62 (d, J=1.8 Hz, 1H), 3.73 (s, 3H), 2.43 (s, 6H). m/z (ESI, positive ion) 550.0 (M+H)$^+$.

Example 43: Trans-(P)-1-(5-Fluoro-2-Methoxy-4-(3-(Trifluoromethyl)Cyclobutyl)Phenyl)-N-(Oxazol-2-Yl)-2-Oxo-1,2-Dihydroquinoline-6-Sulfonamide

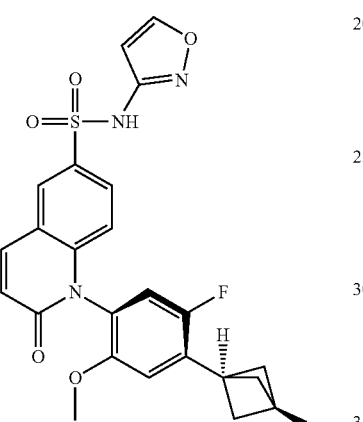

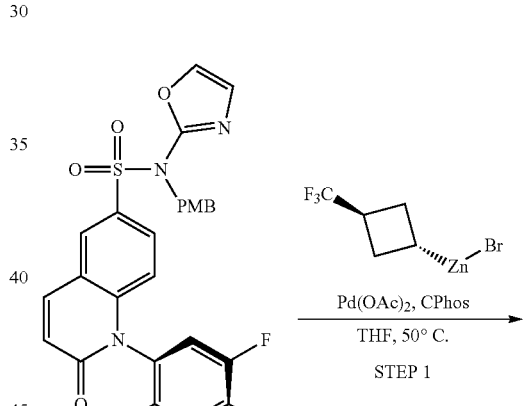

-continued

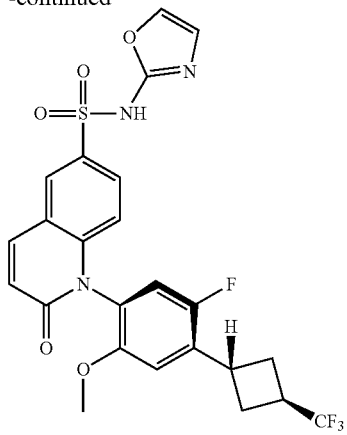

Step 1: Trans-(P)-1-(5-Fluoro-2-Methoxy-4-(3-(Trifluoromethyl)Cyclobutyl)Phenyl)-N-(4-Methoxybenzyl)-N-(Oxazol-2-Yl)-2-Oxo-1,2-Dihydroquinoline-6-Sulfonamide A vial was charged with (P)-1-(4-bromo-5-fluoro-2-methoxyphenyl)-N-(4-methoxybenzyl)-N-(oxazol-2-yl)-2-oxo-1,2-dihydroquinoline-6-sulfonamide (0.494 g, 0.804 mmol), palladium(ii) acetate (0.023 g, 0.102 mmol), and 2-dicyclohexylphosphino-2',6'-dimethylamino-1,1'-biphenyl (0.076 g, 0.173 mmol). The resulting mixture was sealed via septum cap and sparged with nitrogen for 10 minutes prior to the addition of tetrahydrofuran (3.09 mL). trans-(3-(trifluoromethyl)cyclobutyl)zinc(II) bromide (9.46 mL, 1.182 mmol) solution was then dropwise via syringe. After complete addition, the reaction was warmed to 50° C. and stirred at this temperature for 1.25 hours. After cooling to ambient temperature, the reaction was quenched with 5 M aqueous ammonium chloride solution. The mixture was extracted with ethyl acetate (2×). After removal of solvent, the residue was purified by flash column chromatography (elution 0-50% 3:1 ethyl acetate:ethanol in heptane with 10% dichloromethane additive) to afford trans-(P)-1-(5-fluoro-2-methoxy-4-(3-(trifluoromethyl)cyclobutyl)phenyl)-N-(4-methoxybenzyl)-N-(oxazol-2-yl)-2-oxo-1,2-dihydroquinoline-6-sulfonamide (0.384 g, 0.584 mmol, 73% yield). m/z (ESI, positive ion) 658.0 (M+H)+.

Step 2: Trans-(P)-1-(5-Fluoro-2-Methoxy-4-(3-(Trifluoromethyl)Cyclobutyl)Phenyl)-N-(Oxazol-2-Yl)-2-Oxo-1,2-Dihydroquinoline-6-Sulfonamide (P)-1-(5-fluoro-2-methoxy-4-(3-(trifluoromethyl)cyclobutyl)phenyl)-N-(4-methoxybenzyl)-N-(oxazol-2-yl)-2-oxo-1,2-dihydroquinoline-6-sulfonamide (0.384 g, 0.584 mmol) was dissolved in 1,1,1-trifluoroacetic acid (1.348 g, 1.348 mL, 11.82 mmol) and stirred under a nitrogen atmosphere at 40° C. for 2.5 hours. After cooling to ambient temperature, excess TFA was removed under vacuum and the resulting solid was triturated with diethyl ether and filtered. The initial product was purified by column chromatography (gradient elution of 0-100% EtOAc in heptane with 10% dichloromethane as additive) to afford (P)-1-(5-fluoro-2-methoxy-4-(3-(trifluoromethyl)cyclobutyl)phenyl)-N-(oxazol-2-yl)-2-oxo-1,2-dihydroquinoline-6-sulfonamide (70.8 mg, 0.132 mmol, 23% yield). $^1$H NMR (500 MHz, DMSO-d6) δ ppm 12.13 (br s, 1H), 8.31 (d, J=2.21 Hz, 1H), 8.17 (d, J=9.60 Hz, 1H), 7.84 (dd, J=8.89 Hz, 2.14 Hz, 1H), 7.59 (d, J=1.56 Hz, 1H), 7.34-7.25 (m, 3H), 6.75 (d, J=9.32 Hz, 1H), 6.70 (d, J=8.76 Hz, 1H), 3.95 (quin, J=8.99 Hz, 1H), 3.72 (s, 3H), 3.29-3.21 (m, 1H), 2.75-2.56 (m, 4H). m/z (ESI, positive ion) 538.0 (M+H)+.

Examples 44 & 45: 1-(5-Fluoro-2-Methoxy-4-((1R,3R)-3-(Trifluoromethoxy)Cyclobutyl)Phenyl)-N-(Isoxazol-3-Yl)-2-Oxo-1,2-Dihydroquinoline-6-Sulfonamide and 1-(5-Fluoro-2-Methoxy-4-((1R,3R)-3-(Trifluoromethoxy)Cyclobutyl)Phenyl)-N-(Isoxazol-3-Yl)-2-Oxo-1,2-Dihydroquinoline-6-Sulfonamide

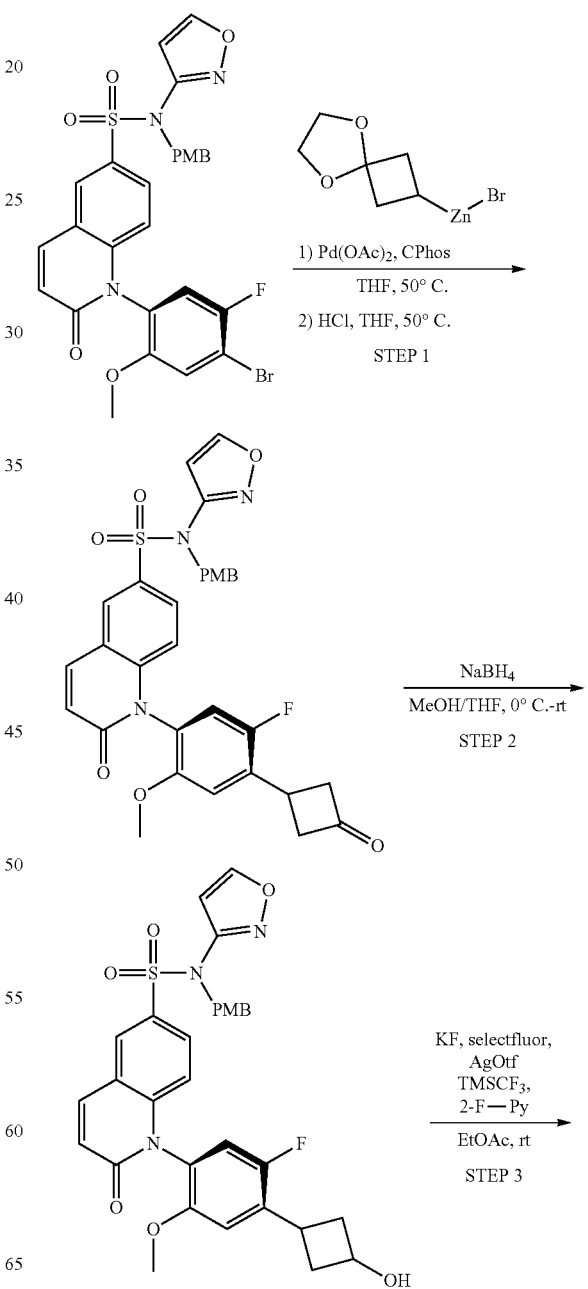

151
-continued

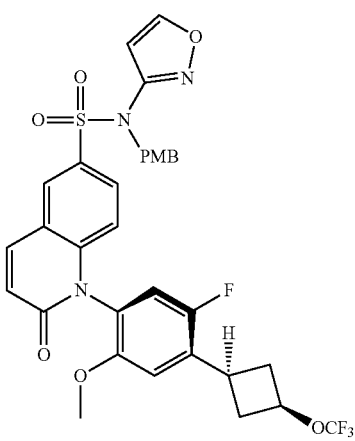

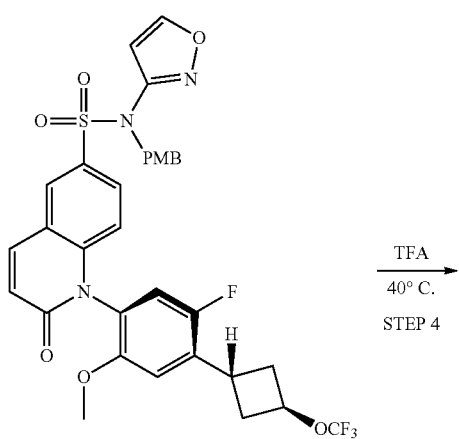
TFA
40° C.
STEP 4

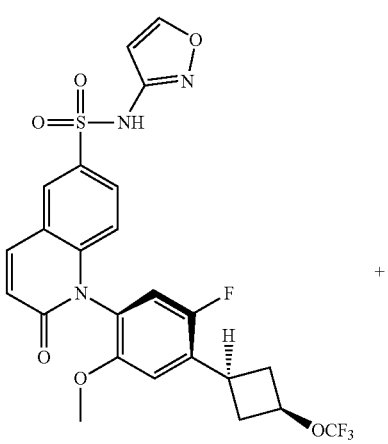

+

152
-continued

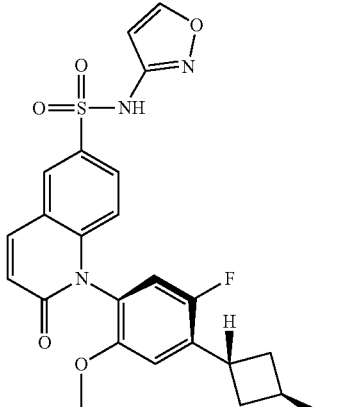

+

Step 1: (P)-1-(5-Fluoro-2-Methoxy-4-(3-Oxocyclobutyl)Phenyl)-N-(Isoxazol-3-Yl)-N-(4-Methoxybenzyl)-2-Oxo-1,2-Dihydroquinoline-6-Sulfonamide A vial was charged with (P)-1-(4-bromo-5-fluoro-2-methoxyphenyl)-N-(isoxazol-3-yl)-N-(4-methoxybenzyl)-2-oxo-1,2-dihydroquinoline-6-sulfonamide (0.850 g, 1.383 mmol), diacetoxypalladium (0.040 g, 0.180 mmol), and 2'-(dicyclohexylphosphaneyl)-N2,N2,N6,N6-tetramethyl-[1,1'-biphenyl]-2,6-diamine (0.133 g, 0.304 mmol). The resulting mixture was sealed via septum cap and sparged with nitrogen for 10 minutes prior to the addition of tetrahydrofuran (6.92 mL). (5,8-dioxaspiro[3.4]octan-2-yl)zinc (II) bromide solution (1.660 mmol) was then added dropwise via syringe. After complete addition, the reaction was warmed to 50° C. and stirred for 1.25 hours. After cooling to ambient temperature, the reaction was quenched with 5 M aqueous ammonium chloride solution and the product extracted with ethyl acetate (2×). The combined organic phases were dried over MgSO$_4$, filtered and concentrated. The residue was purified by flash column chromatography (elution 0-50% 3:1 ethyl acetate:ethanol in heptane with 10% dichloromethane as additive) to afford (P)-1-(5-fluoro-2-methoxy-4-(5,8-dioxaspiro[3.4]octan-2-yl)phenyl)-N-(isoxazol-3-yl)-N-(4-methoxybenzyl)-2-oxo-1,2-dihydroquinoline-6-sulfonamide (0.896 g, 1.383 mmol, 100% yield). m/z (ESI, positive ion) 648.0 (M+H)+.

(P)-1-(5-fluoro-2-methoxy-4-(5,8-dioxaspiro[3.4]octan-2-yl)phenyl)-N-(isoxazol-3-yl)-N-(4-methoxybenzyl)-2-oxo-1,2-dihydroquinoline-6-sulfonamide (0.896 g, 1.383 mmol) was dissolved in THF (13.8 ml). Hydrogen chloride (1 N in water) (6.92 mL, 6.92 mmol) was added and the reaction was stirred at 50° C. overnight. The reaction was diluted with ethyl acetate and washed with water. The aqueous layer was extracted with ethyl acetate, and the combined organic layers were washed with brine, dried with MgSO$_4$, filtered, and concentrated. The (P)-1-(5-fluoro-2-methoxy-4-(3-oxocyclobutyl)phenyl)-N-(isoxazol-3-yl)-N-(4-methoxybenzyl)-2-oxo-1,2-dihydroquinoline-6-sulfonamide (0.835 g, 1.383 mmol, 100% yield) thus obtained was used as such in the next step. m/z (ESI, positive ion) 604.0 (M+H)$^+$.

Step 2: (P)-1-(5-Fluoro-4-(3-Hydroxycyclobutyl)-2-Methoxyphenyl)-N-(Isoxazol-3-Yl)-N-(4-Methoxybenzyl)-2-Oxo-1,2-Dihydroquinoline-6-Sulfonamide A vial was charged with (P)-1-(5-fluoro-2-methoxy-4-(3-oxocyclobutyl)phenyl)-N-(isoxazol-3-yl)-N-(4-methoxybenzyl)-2-oxo-1,2-dihydroquinoline-6-sulfonamide (0.835 g, 1.383 mmol) in methanol (6.92 mL) and THF (6.92 mL) at 0° C. was added portionwise sodium tetra hydroborate (0.052 g, 1.383 mmol). The reaction mixture was stirred 15 minutes a 0° C. and then 30 minutes at RT. The reaction mixture was quenched with water and extracted with DCM (3×). The combined organic phases were concentrated in vacuo. The initial product was purified by column chromatography (gradient elution 0-40% EtOAc/EtOH (3/1) in heptanes with 10% dichloromethane as additive) to afford (P)-1-(5-fluoro-4-(3-hydroxycyclobutyl)-2-methoxyphenyl)-N-(isoxazol-3-yl)-N-(4-methoxybenzyl)-2-oxo-1,2-dihydroquinoline-6-sulfonamide (0.454 g, 0.749 mmol, 54% yield). m/z (ESI, positive ion) 606.0 (M+H)+.

Step 3: Cis-(P)-1-(5-Fluoro-2-Methoxy-4-(3-(Trifluoromethoxy)Cyclobutyl)Phenyl)-N-(Isoxazol-3-Yl)-N-(4-Methoxybenzyl)-2-Oxo-1,2-Dihydroquinoline-6-Sulfonamide and Trans-(P)-1-(5-Fluoro-2-Methoxy-4-(3-(Trifluoromethoxy)Cyclobutyl) Phenyl)-N-(Isoxazol-3-Yl)-N-(4-Methoxybenzyl)-2-Oxo-1,2-Dihydroquinoline-6-Sulfonamide A vial was charged with silver trifluoromethanesulfonate (0.513 g, 1.996 mmol), selectfluor (0.354 g, 0.998 mmol), potassium fluoride (0.155 g, 2.66 mmol) and (P)-1-(5-fluoro-4-(3-hydroxycyclobutyl)-2-methoxyphenyl)-N-(isoxazol-3-yl)-N-(4-methoxybenzyl)-2-oxo-1,2-dihydroquinoline-6-sulfonamide (0.4029 g, 0.665 mmol) in a nitrogen-filled glovebox. Then anhydrous ethyl acetate (3.33 mL), 2-fluoropyridine (0.194 g, 0.172 mL, 1.996 mmol) and trimethyl(trifluoromethyl)silane (0.284 g, 0.295 mL, 1.996 mmol) were added successively under nitrogen atmosphere. The reaction mixture was stirred at room temperature for 18 hours. The reaction mixture was filtered through a plug of silica (eluted with ethyl acetate). The filtrate was concentrated, and the product was purified by column chromatography (gradient elution 0-40% EtOAc-EtOH (3/1) in heptanes with 10% dichloromethane as additive) to give (P)-1-(5-fluoro-2-methoxy-4-(3-(trifluoromethoxy)cyclobutyl)phenyl)-N-(isoxazol-3-yl)-N-(4-methoxybenzyl)-2-oxo-1,2-dihydroquinoline-6-sulfonamide (358 mg, 0.531 mmol, 80% yield). m/z (ESI, positive ion) 674.0 (M+H)+.

The two isomers were separated by SFC via two Chiralpak AD-H, 5 µm columns (3×25 cm+3×15 cm) with a mobile phase of 25% ethanol using a flowrate of 80 mL/min. Peak 1 was assigned as cis-(P)-1-(5-fluoro-2-methoxy-4-(3-(trifluoromethoxy)cyclobutyl)phenyl)-N-(isoxazol-3-yl)-N-(4-methoxybenzyl)-2-oxo-1,2-dihydroquinoline-6-sulfonamide (28.8 mg) and peak 2 was assigned as trans-(P)-1-(5-fluoro-2-methoxy-4-(3-(trifluoromethoxy)cyclobutyl)phenyl)-N-(isoxazol-3-yl)-N-(4-methoxybenzyl)-2-oxo-1,2-dihydroquinoline-6-sulfonamide (228.4 mg).

Step 4: 1-(5-Fluoro-2-Methoxy-4-((1R,3R)-3-(Trifluoromethoxy)Cyclobutyl)Phenyl)-N-(Isoxazol-3-Yl)-2-Oxo-1,2-Dihydroquinoline-6-Sulfonamide and 1-(5-Fluoro-2-Methoxy-4-((1R,3R)-3-(Trifluoromethoxy)Cyclobutyl)Phenyl)-N-(Isoxazol-3-Yl)-2-Oxo-1,2-Dihydroquinoline-6-Sulfonamide cis-(P)-1-(5-fluoro-2-methoxy-4-(3-(trifluoromethoxy)cyclobutyl)phenyl)-N-(isoxazol-3-yl)-N-(4-methoxybenzyl)-2-oxo-1,2-dihydroquinoline-6-sulfonamide (0.0288 g, 0.043 mmol), triethylsilane (0.044 g, 0.061 mL, 0.375 mmol), and trifluoracetic acid (0.370 g, 0.242 mL, 3.25 mmol) were combined under nitrogen. The reaction mixture was stirred at 50° C. for 5 hours. The mixture was cooled, diluted with heptane and evaporated to dryness under reduced pressure. The product was then purified by flash chromatography (gradient elution 0-40% ethyl acetate/EtOH (3:1) in heptane with 10% dichloromethane as additive) to afford cis-(P)-1-(5-fluoro-2-methoxy-4-(3-(trifluoromethoxy)cyclobutyl)phenyl)-N-(isoxazol-3-yl)-2-oxo-1,2-dihydroquinoline-6-sulfonamide (13.3 mg, 0.024 mmol, 56% yield). 1H NMR (500 MHz, DMSO-d6) δ ppm 11.62 (s, 1H), 8.71 (s, 1H), 8.34 (d, J=2.08 Hz, 1H), 8.20 (d, J=9.60 Hz, 1H), 7.83 (dd, J=8.95, 2.21 Hz, 1H), 7.32-7.27 (m, 2H), 6.78 (d, J=9.38 Hz, 2H), 6.43 (d, J=1.43 Hz, 1H), 5.11 (t, J=5.77 Hz, 1H), 4.00-3.92 (m, 1H), 3.71 (s, 3H), 2.83-2.71 (m, 4H), 2.55-2.52 (m, 1H). m/z (ESI, positive ion) 554.0 (M+H)+.

trans-(P)-1-(5-fluoro-2-methoxy-4-(3-(trifluoromethoxy)cyclobutyl)phenyl)-N-(isoxazol-3-yl)-N-(4-methoxybenzyl)-2-oxo-1,2-dihydroquinoline-6-sulfonamide (0.2284 g, 0.339 mmol), triethylsilane (0.346 g, 0.481 mL, 2.98 mmol), and trifluoracetic acid (2.94 g, 1.920 mL, 25.8 mmol) were combined under nitrogen. The reaction mixture was stirred at 50° C. for 5 hours. The mixture was cooled, diluted with heptane and evaporated to dryness under reduced pressure. The product was then purified by flash chromatography (gradient elution 0-40% ethyl acetate/EtOH (3:1) in heptane with 10% dichloromethane as additive) to afford trans-(P)-1-(5-fluoro-2-methoxy-4-(3-(trifluoromethoxy)cyclobutyl)phenyl)-N-(isoxazol-3-yl)-2-oxo-1,2-dihydroquinoline-6-sulfonamide (0.1623 g, 0.293 mmol, 86% yield). 1H NMR (500 MHz, DMSO-d6) δ ppm 11.62 (s, 1H), 8.72 (d, J=1.82 Hz, 1H), 8.35 (d, J=2.21 Hz, 1H), 8.20 (d, J=9.60 Hz, 1H), 7.83 (dd, J=9.02, 2.27 Hz, 1H), 7.30 (d, J=9.99 Hz, 1H), 7.23 (d, J=6.62 Hz, 1H), 6.78 (d, J=9.47 Hz, 2H), 6.44 (d, J=1.82 Hz, 1H), 4.92 (quin, J=7.40 Hz, 1H), 3.38 (tt, J=10.46, 7.51 Hz, 1H), 3.32-3.25 (m, 3H), 2.84 (dquin, J=12.05, 6.07, 6.07, 6.07, 6.07 Hz, 2H), 2.55-2.52 (m, 1H), 2.47-2.41 (m, 1H). m/z (ESI, positive ion) 554.0 (M+H)+.

Example 46: Trans-(P)-5-Fluoro-1-(5-Fluoro-2-Methoxy-4-(3-(Trifluoromethyl)Cyclobutyl)Phenyl)-N-(Isoxazol-3-Yl)-2-Oxo-1,2-Dihydroquinoline-6-Sulfonamide

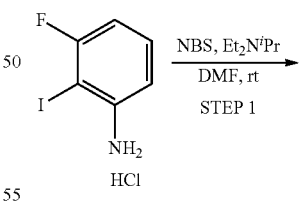

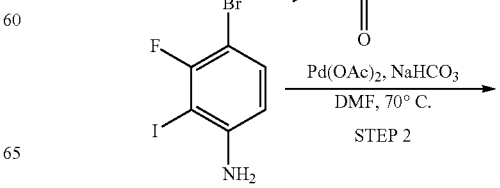

155
-continued
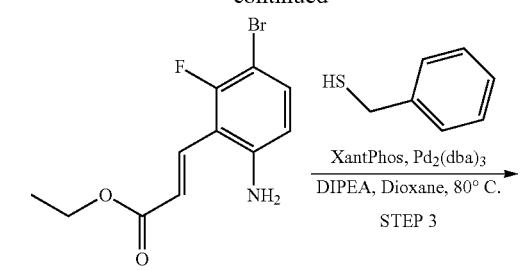
STEP 3
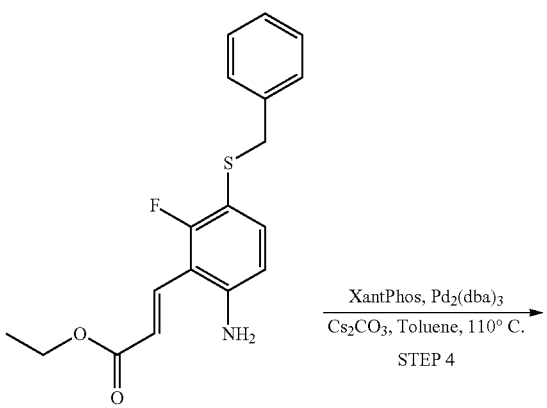
STEP 4
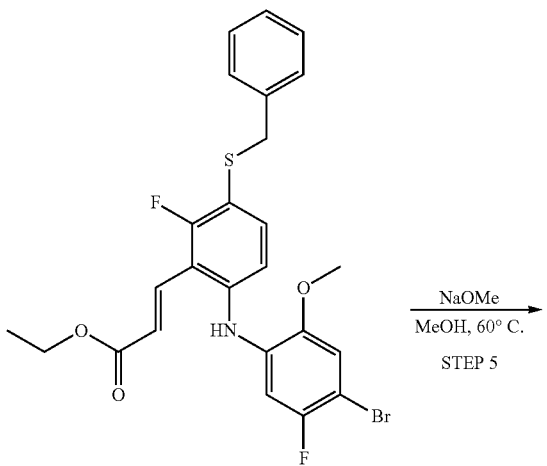
STEP 5
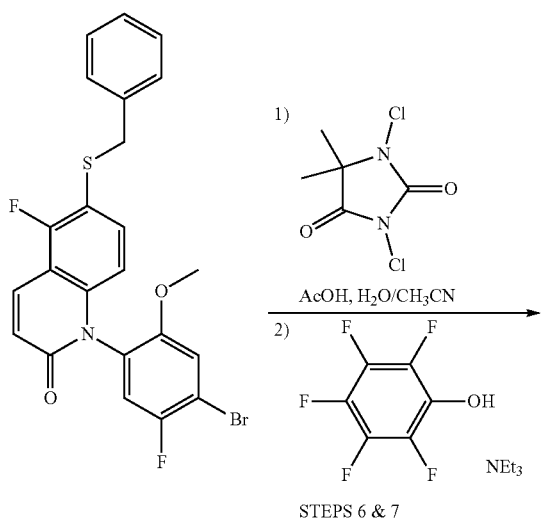
STEPS 6 & 7
156
-continued
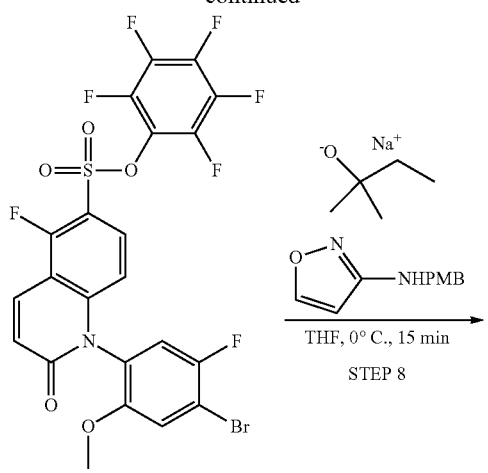
STEP 8
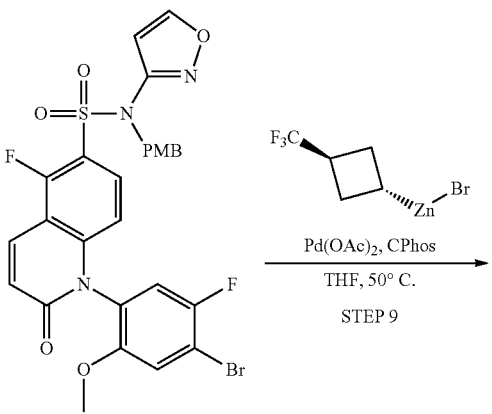
STEP 9
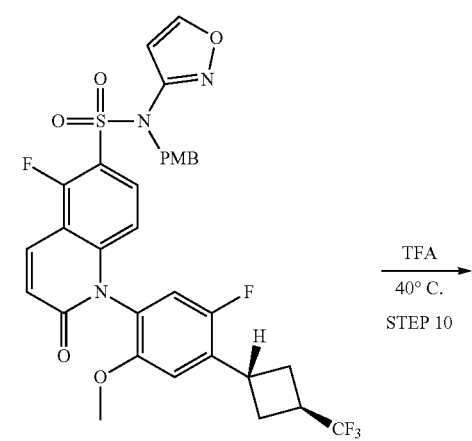
STEP 10

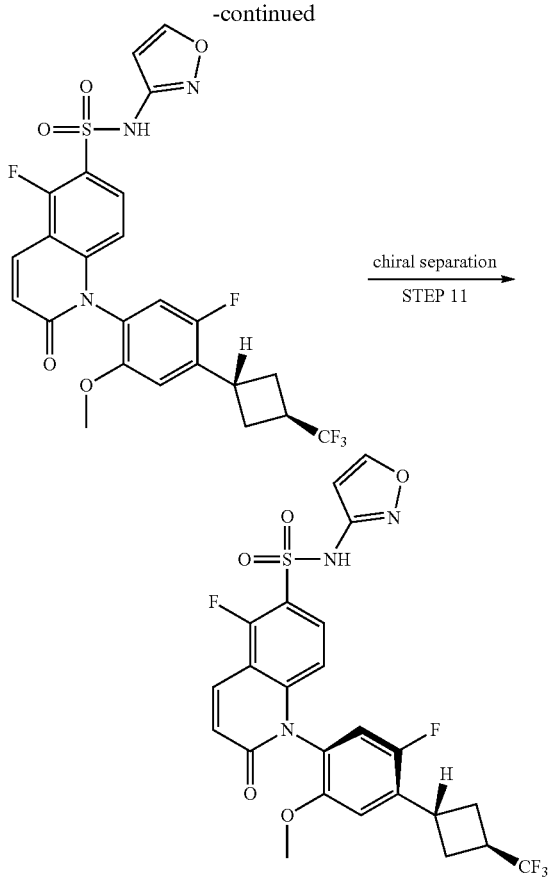

chiral separation
STEP 11

Step 1: 4-Bromo-3-Fluoro-2-Iodoaniline

To a solution of 2-iodo-3-fluoroaniline hydrogen chloride (6.45 g, 23.59 mmol) and N,N'-diisopropylethylamine (3.05 g, 4.11 mL, 23.59 mmol) in N, N-dimethylformamide (59.0 mL) was added N-bromosuccinimide (4.20 g, 23.59 mmol). After 20 minutes, the reaction was quenched with water. The mixture was extracted with ethyl acetate. The organic layer was separated, dried over magnesium sulfate, filtered and concentrated under reduced pressure to obtain the initial product which was purified by column chromatography (BIOTAGE® ISOLERA ONE, BIOTAGE SFÄR SILICA50 g, 0-30% ethyl acetate in heptane) to afford 4-bromo-3-fluoro-2-iodoaniline (6.8 g, 21.52 mmol, 91% yield) as a tan, almost copper-colored solid. m/z (ESI, positive ion) 315.8 (M+H)+.

Step 2: Ethyl (E)-3-(6-Amino-3-Bromo-2-Fluorophenyl)Acrylate

A 100 mL flask was charged with sodium hydrogen carbonate (4.19 g, 49.9 mmol), ethyl acrylate (2.096 g, 2.355 mL, 20.94 mmol), and palladium(ii) acetate (0.090 g, 0.399 mmol). A solution of 4-bromo-3-fluoro-2-iodoaniline (6.3 g, 19.94 mmol) in N, N-dimethylformamide (13.29 mL) was added to the reaction mixture. The reaction was stirred at 100° C. under nitrogen for 3 hours. The reaction was diluted with ethyl acetate and filtered through CELITE. The filtrate was concentrated under reduced pressure to obtain the initial product which was purified by column chromatography to give ethyl (E)-3-(6-amino-3-bromo-2-fluorophenyl)acrylate (5.92 g, 20.55 mmol, 103% yield). $^1$H NMR (400 MHz, DMSO-d6) δ ppm 7.50-7.68 (m, 1H), 7.29 (t, J=8.3 Hz, 1H), 6.34-6.60 (m, 2H), 6.07 (s, 1H), 3.98-4.24 (m, 2H), 3.35 (br s, 1H), 1.08-1.36 (m, 3H).

Step 3: Ethyl (E)-3-(6-Amino-3-(Benzylthio)-2-Fluorophenyl)Acrylate

A 250 mL round-bottom flask was charged with ethyl (E)-3-(6-amino-3-bromo-2-fluorophenyl)acrylate (4.0 g, 13.88 mmol), 1,4-dioxane (34.7 mL) and 1,1'-dimethyltriethylamine (3.59 g, 4.85 mL, 27.8 mmol). The flask was sealed and sparged with nitrogen for 20 minutes. In a separate 20 mL vial, bis[tris(dibenzylideneacetone)palladium(0)] (0.890 g, 0.972 mmol) and (5-diphenylphosphanyl-9,9-dimethylxanthen-4-yl)-diphenylphosphane (1.125 g, 1.944 mmol) were added. The vial was sparged with nitrogen for 5 minutes prior to the addition of 1,4-dioxane (5 mL). This catalyst solution was transferred via syringe to the acrylate-containing flask. Then 1-toluenethiol (1.379 g, 1.379 mL, 11.11 mmol) was added in one portion. The mixture was stirred at 80° C. for 16 hours. The reaction was cooled and filtered over CELITE. The CELITE was washed with ethyl acetate. The solvent was removed under reduced pressure. The residue was purified by column chromatography (BIOTAGE® Isolera One, BIOTAGE® SNAP Ultra 100 g, 0-30% ethyl acetate in heptane) to afforded ethyl (E)-3-(6-amino-3-(benzylthio)-2-fluorophenyl)acrylate (2.78 g, 8.39 mmol, 60% yield) as a yellow orange solid. m/z (ESI, positive ion) 332.2 (M+H)+.

Step 4: Ethyl (E)-3-(3-(Benzylthio)-6-((4-Bromo-5-Fluoro-2-Methoxyphenyl)Amino)-2-Fluorophenyl) Acrylate A 40 mL vial was charged with ethyl (E)-3-(6-amino-3-(benzylthio)-2-fluorophenyl)acrylate (0.876 g, 2.64 mmol), 1-bromo-2-fluoro-4-iodo-5-methoxybenzene (1.07 g, 3.23 mmol), and cesium carbonate (2.58 g, 7.93 mmol). Toluene (8.81 mL) was added to the vial. The mixture was sparged with nitrogen for 20 minutes before tris (dibenzylideneacetone)-dipalladium(0) (0.194 g, 0.194 mL, 0.211 mmol) and 4,5-bis(diphenylphosphino)-9,9-dimethylxanthene (0.245 g, 0.423 mmol) were quickly added. After sparging with nitrogen for an additional 5 minutes, the reaction was warmed to 110° C. After stirring for 16 hours, the reaction was cooled to ambient temperature, diluted with dichloromethane, and filtered over CELITE. Solvent was removed under reduced pressure. The residue was purified by column chromatography (BIOTAGE® ISOLERA ONE, BIOTAGE SFÄR SILICAHC D 25 g, 0-40% ethyl acetate in heptane) to afforded ethyl (E)-3-(3-(benzylthio)-6-((4-bromo-5-fluoro-2-methoxyphenyl)amino)-2-fluorophenyl)acrylate (0.600 g, 1.123 mmol, 43% yield) as a yellow solid. m/z (ESI, positive ion) 535.8 (M+H)$^+$.

Step 5: 6-(Benzylthio)-1-(4-Bromo-5-Fluoro-2-Methoxyphenyl)-5-Fluoroquinolin-2(1H)-One Ethyl (E)-3-(3-(benzylthio)-6-((4-bromo-5-fluoro-2-methoxyphenyl)amino)-2-fluorophenyl)acrylate (1.44 g, 2.69 mmol) was dissolved in methanol (33 mL). Sodium methoxide, 25 wt % solution in methanol (0.582 g, 0.616 mL, 2.69 mmol) was added at ambient temperature. The reaction was warmed to 60° C. and stirred at this temperature for 2 hours. The reaction was cooled to ambient temperature and quenched by the addition of water. The product was extracted with ethyl acetate (2×). The organic layer was separated and solvent was removed in vacuo. The residue was purified by column chromatography (BIOTAGE® Isolera One, BIOTAGE® Sfar Silica HC D 50 g, 0-40% Ethyl acetate in heptane with 10% dichloromethane as additive) to provided 6-(benzylthio)-1-(4-bromo-5-fluoro-2-methoxyphenyl)-5-fluoroquinolin-2(1H)-one (0.717 g, 1.468 mmol, 55% yield) as an off white solid. m/z (ESI, positive ion) 490.0 (M+H)+.

Step 6 & 7: Perfluorophenyl 1-(4-Bromo-5-Fluoro-2-Methoxyphenyl)-5-Fluoro-2-Oxo-1,2-Dihydroquinoline-6-Sulfonate A 40 mL vial was charged with 6-(benzylthio)-1-(4-bromo-5-fluoro-2-methoxyphenyl)-5-fluoroquinolin-2(1H)-one (0.710 g, 1.454 mmol), acetonitrile (7.04 mL), acetic acid (0.134 mL), and water (0.095 mL). The reaction was cooled to 0° C. by means of an ice bath before 1,3-dichloro-5,5-dimethyl-2,4-imidazolidinedione (0.430 g, 2.181 mmol) was added in one portion. After 10 minutes, pentafluorophenol (0.321 g, 1.745 mmol) and then triethylamine, anhydrous (0.588 g, 0.817 mL, 5.82 mmol) were added. After 1 hour the reaction was quenched with 2 M aqueous HCl and was extracted with ethyl acetate. The organic layer was separated and solvent was removed in vacuo. The residue was purified by column chromatography (BIOTAGE® Isolera One, BIOTAGE® Sfar 25 g silica HC D, 0-40% ethyl acetate in heptane with 10% dichloromethane as additive) to provide perfluorophenyl 1-(4-bromo-5-fluoro-2-methoxyphenyl)-5-fluoro-2-oxo-1,2-dihydroquinoline-6-sulfonate (0.676 g, 1.104 mmol, 76% yield) as a white solid. m/z (ESI, positive ion) 614.0 (M+H)+.

Steps 8: 1-(4-Bromo-5-Fluoro-2-Methoxyphenyl)-5-Fluoro-N-(Isoxazol-3-Yl)-N-(4-Methoxybenzyl)-2-Oxo-1,2-Dihydroquinoline-6-Sulfonamide A 40 mL vial was charged with perfluorophenyl 1-(4-bromo-5-fluoro-2-methoxyphenyl)-5-fluoro-2-oxo-1,2-dihydroquinoline-6-sulfonate (0.676 g, 1.104 mmol) and N-(4-methoxybenzyl)isoxazol-3-amine (0.271 g, 1.325 mmol). The vial was purged with nitrogen for 5 minutes prior to the addition of tetrahydrofuran (2.208 mL). The reaction was then cooled to −78° C. and sodium tert-pentoxide, 30% solution in thf (0.574 mL, 1.435 mmol) was slowly added. After 10 minutes the reaction was warmed to 0° C. prior to quenching the reaction with 5 M aqueous ammonium chloride solution. The mixture was extracted with ethyl acetate. The organic layer was separated and solvent was removed under reduce pressure. The residue was purified by column chromatography (BIOTAGE® ISOLERA ONE, BIOTAGE SFÄR SILICA25 g, 0-50% ethyl acetate in heptane with 10% dichloromethane as additive) to provides 1-(4-bromo-5-fluoro-2-methoxyphenyl)-5-fluoro-N-(isoxazol-3-yl)-N-(4-methoxybenzyl)-2-oxo-1,2-dihydroquinoline-6-sulfonamide (0.302 g, 0.478 mmol, 43% yield) as a white solid. m/z (ESI, positive ion) 634.0 (M+H)+.

Step 9: 5-Fluoro-1-(5-Fluoro-2-Methoxy-4-(3-(Trifluoromethyl)Cyclobutyl)Phenyl)-N-(Isoxazol-3-Yl)-N-(4-Methoxybenzyl)-2-Oxo-1,2-Dihydroquinoline-6-Sulfonamide A 40 mL vial was charged with 1-(4-bromo-5-fluoro-2-methoxyphenyl)-5-fluoro-N-(isoxazol-3-yl)-N-(4-methoxybenzyl)-2-oxo-1,2-dihydroquinoline-6-sulfonamide (0.320 g, 0.506 mmol), palladium(ii) acetate (0.011 g, 0.051 mmol), and 2'-(dicyclohexylphosphino)-$N^2,N^2,N^6,N^6$-tetramethyl-[1,1'-biphenyl]-2,6-diamine (0.044 g, 0.101 mmol). The vial was sealed and sparged with nitrogen for 5 minutes. Tetrahydrofuran (2.53 mL) was then added, followed by the addition of (3-(trifluoromethyl)cyclobutyl)zinc(II) bromide (1.381 mmol). The reaction was then stirred at 50° C. for 1.5 hours. The reaction was cooled to ambient temperature, quenched with 5M aqueous ammonium chloride solution, and extracted with ethyl acetate. The organic layer was separated and solvent was removed under reduced pressure. The residue was purified by column chromatography (BIOTAGE® ISOLERA ONE, BIOTAGE SFÄR SILICAHC D 10 g, 0-40% ethyl acetate in heptane with 10% dichloromethane as additive) to affords 5-fluoro-1-(5-fluoro-2-methoxy-4-(3-(trifluoromethyl)cyclobutyl)phenyl)-N-(isoxazol-3-yl)-N-(4-methoxybenzyl)-2-oxo-1,2-dihydroquinoline-6-sulfonamide (0.208 g, 0.308 mmol, 61% yield) as a light pink solid. m/z (ESI, positive ion) 676.2 (M+H)+.

Step 10: 5-Fluoro-1-(5-Fluoro-2-Methoxy-4-(3-(Trifluoromethyl)Cyclobutyl)Phenyl)-N-(Isoxazol-3-Yl)-2-Oxo-1,2-Dihydroquinoline-6-Sulfonamide A 40 mL vial was charged with 5-fluoro-1-(5-fluoro-2-methoxy-4-(3-(trifluoromethyl)cyclobutyl)phenyl)-N-(isoxazol-3-yl)-N-(4-methoxybenzyl)-2-oxo-1,2-dihydroquinoline-6-sulfonamide (0.208 g, 0.308 mmol), triethylsilane (0.179 g, 0.249 mL, 1.539 mmol) and 1,1,1-trifluoroacetic acid (2.282 g, 2.282 mL, 20.01 mmol). The mixture was stirred at 40° C. for 2 hours. Solvent was removed in vacuo. The mixture was purified by column chromatography (BIOTAGE® ISOLERA ONE, BIOTAGE SFÄR SILICA HC D 10 g, 0-100% ethyl acetate in heptane with 10% dichloromethane as additive) to afforded 5-fluoro-1-(5-fluoro-2-methoxy-4-(3-(trifluoromethyl)cyclobutyl)phenyl)-N-(isoxazol-3-yl)-2-oxo-1,2-dihydroquinoline-6-sulfonamide (0.153 g, 0.275 mmol, 89% yield) as an off white solid. m/z (ESI, positive ion) 556.2 (M+H)+.

Step 11: Trans-(P)-5-Fluoro-1-(5-Fluoro-2-Methoxy-4-(3-(Trifluoromethyl)Cyclobutyl)Phenyl)-N-(Isoxazol-3-Yl)-2-Oxo-1,2-Dihydroquinoline-6-Sulfonamide 5-fluoro-1-(5-fluoro-2-methoxy-4-(3-(trifluoromethyl)cyclobutyl)phenyl)-N-(isoxazol-3-yl)-2-oxo-1,2-dihydroquinoline-6-sulfonamide (0.153 g, 0.275 mmol) was purified by SFC via 2 steps. Step 1: a Regis Whelk-O s,s 2×15 cm, 5 μm column; a mobile phase of 35% methanol using a flowrate of 60 mL/min; Step 2: (separation of Peak1 & Peak2): two Chiralpak AD-H, 5 μm columns (3×15 cm+3× 25 cm); a mobile phase of 30% ethanol using a flowrate of 80 mL/min. Peak 1 was lyophilized to yield trans-(P)-5-fluoro-1-(5-fluoro-2-methoxy-4-(3-(trifluoromethyl)cyclobutyl)phenyl)-N-(isoxazol-3-yl)-2-oxo-1,2-dihydroquinoline-6-sulfonamide (0.0305 g, 0.055 mmol, 18% yield) as a white solid. $^1$H NMR (500 MHz, DMSO-d6) δ ppm 12.01 (br s, 1H), 8.72 (d, J=1.8 Hz, 1H), 8.18 (d, J=9.9 Hz, 1H), 7.87 (t, J=8.1 Hz, 1H), 7.34 (s, 1H), 7.33 (d, J=3.4 Hz, 1H), 6.83 (d, J=9.9 Hz, 1H), 6.59 (d, J=9.2 Hz, 1H), 6.37 (d, J=1.8 Hz, 1H), 3.95 (t, J=9.0 Hz, 1H), 3.73 (s, 3H), 3.22-3.28 (m, 1H), 2.55-2.72 (m, 4H). m/z (ESI, positive ion) 556.2 (M+H)+.

Example 47: (P)-1-(5-Fluoro-2-Methoxy-4-(3-(Trifluoromethyl)Bicyclo[1.1.1]Pentan-1-Yl)Phenyl)-N-(Isoxazol-3-Yl)-2-Oxo-1,2-Dihydroquinoline-6-Sulfonamide

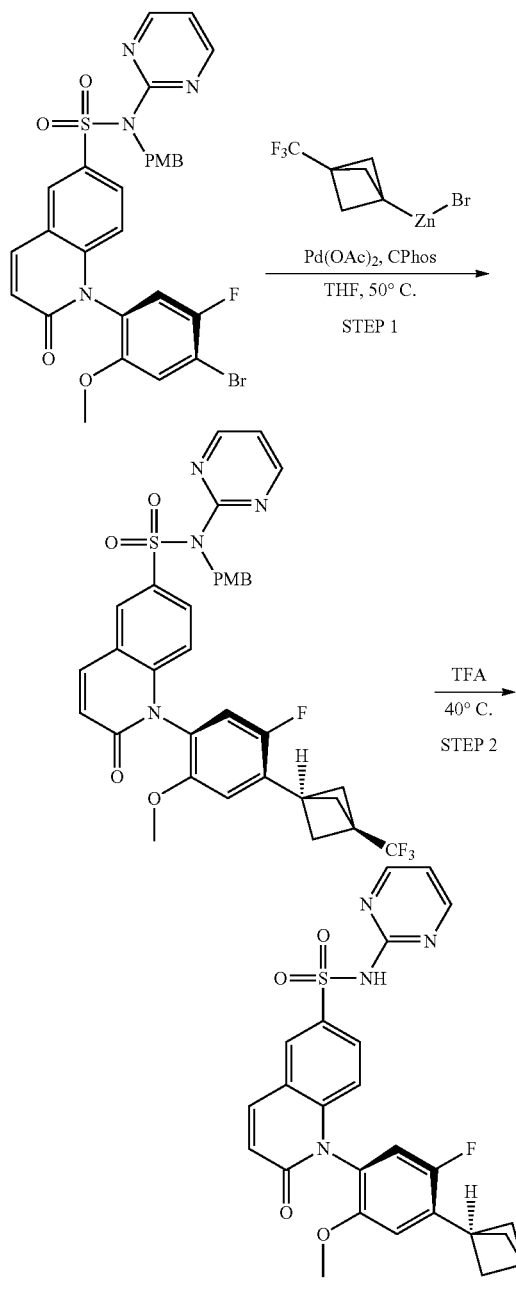

Step 1: (P)-1-(5-Fluoro-2-Methoxy-4-(3-(Trifluoromethyl)Bicyclo[1.1.1]Pentan-1-Yl)Phenyl)-N-(4-Methoxybenzyl)-2-Oxo-N-(Pyrimidin-2-Yl)-1,2-Dihydroquinoline-6-Sulfonamide An oven-dried 40 mL vial was charged with 2'-(dicyclohexylphosphaneyl)-$N^2,N^2,N^6,N^6$-tetramethyl-[1,1'-biphenyl]-2,6-diamine (0.046 g, 0.106 mmol), palladium(II) acetate (0.012 g, 0.053 mmol) and (P)-1-(4-bromo-5-fluoro-2-methoxyphenyl)-N-(4-methoxybenzyl)-2-oxo-N-(pyrimidin-2-yl)-1,2-dihydroquinoline-6-sulfonamide (0.663 g, 1.060 mmol). The reaction mixture was sparged with nitrogen for 15 minutes, and then (3-(trifluoromethyl)bicyclo[1.1.1]pentan-1-yl)zinc(II) iodide solution (1.59 mmol) was added after filtering through a 0.45 micron PTFE filter. The reactions were stirred at 50° C. for 3 hours. The reaction mixture was quenched with saturated aqueous sodium bicarbonate and partitioned between water and ethyl acetate. The organic layer was dried over sodium sulfate and concentrated. The initial product was purified by column chromatography (gradient elution 0-60% ethyl acetate in heptane with 10% dichloromethane as additive) to afford (P)-1-(5-fluoro-2-methoxy-4-(3-(trifluoromethyl)bicyclo[1.1.1]pentan-1-yl)phenyl)-N-(4-methoxybenzyl)-2-oxo-N-(pyrimidin-2-yl)-1,2-dihydroquinoline-6-sulfonamide (0.241 g, 0.354 mmol, 33% yield) as a light grey foam. m/z (ESI, positive ion) 681.1 (M+H)$^+$.

Step 2: (P)-1-(5-Fluoro-2-Methoxy-4-(3-(Trifluoromethyl)Bicyclo[1.1.1]Pentan-1-Yl)Phenyl)-2-Oxo-N-(Pyrimidin-2-Yl)-1,2-Dihydroquinoline-6-Sulfonamide (P)-1-(5-fluoro-2-methoxy-4-(3-(trifluoromethyl)bicyclo[1.1.1]pentan-1-yl)phenyl)-N-(4-methoxybenzyl)-2-oxo-N-(pyrimidin-2-yl)-1,2-dihydroquinoline-6-sulfonamide (241 mg, 0.354 mmol) was dissolved in trifluoroacetic acid (3.63 g, 2.44 mL, 31.9 mmol) in a 20 mL vial and the reaction was heated to 40° C. and stirred for 2 hours. The reaction was cooled to RT. The reaction was made basic using saturated NaHCO$_3$ solution, extracted with dichloromethane. The combined organic layer was dried over sodium sulfate and concentrated. The initial product was subjected to reverse phase purification (gradient elution 25 to 70% acetonitrile in water with 0.1% formic acid to afford (P)-1-(5-fluoro-2-methoxy-4-(3-(trifluoromethyl)bicyclo[1.1.1]pentan-1-yl)phenyl)-2-oxo-N-(pyrimidin-2-yl)-1,2-dihydroquinoline-6-sulfonamide (103 mg, 0.184 mmol, 52% yield) as a white solid after lyophilization. $^1$H NMR (CHLOROFORM-d, 500 MHz) δ ppm 10.27 (br s, 1H), 8.60 (d, J=4.9 Hz, 2H), 8.43 (d, J=2.1 Hz, 1H), 8.07 (dd, J=2.1, 9.0 Hz, 1H), 7.85 (d, J=9.6 Hz, 1H), 7.00 (t, J=4.9 Hz, 1H), 6.93 (d, J=9.2 Hz, 1H), 6.85 (d, J=9.6 Hz, 1H), 6.83 (d, J=6.4 Hz, 1H), 6.77 (d, J=9.0 Hz, 1H), 3.72 (s, 3H), 2.42 (s, 6H). m/z (ESI, positive ion) 561.0 (M+H)$^+$.

Example 48: (P)-1-(5-Chloro-4-(3,3-Difluorocyclobutyl)-2-Methoxyphenyl)-N-(Isoxazol-3-Yl)-2-Oxo-1,2-Dihydroquinoline-6-Sulfonamide

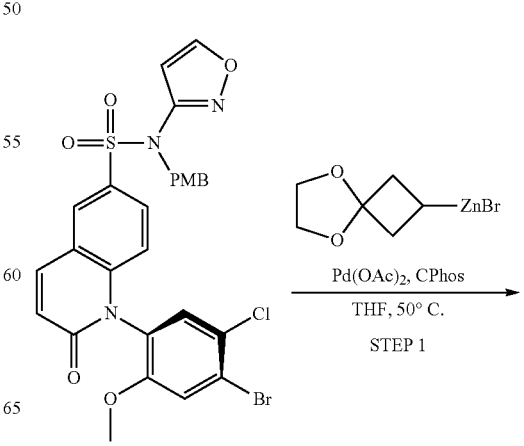

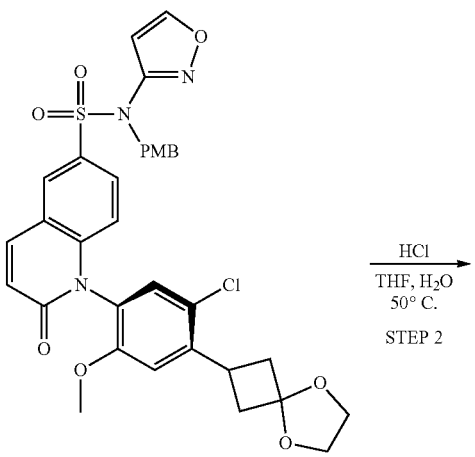

HCl
THF, H₂O
50° C.
STEP 2

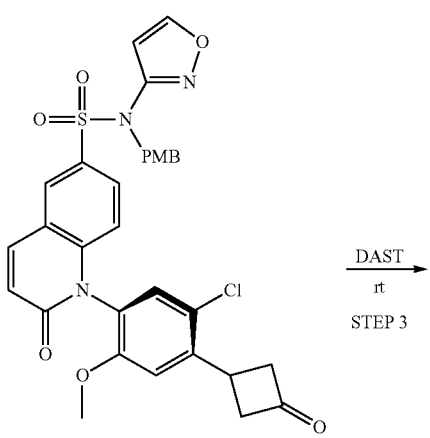

DAST
rt
STEP 3

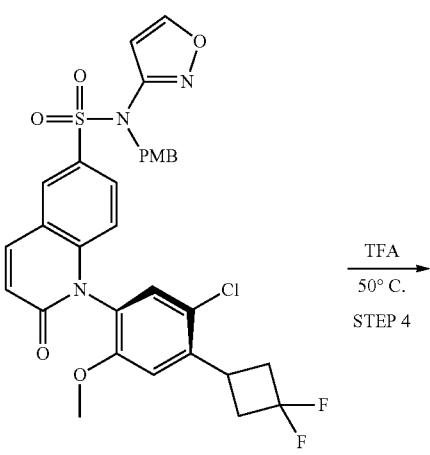

TFA
50° C.
STEP 4

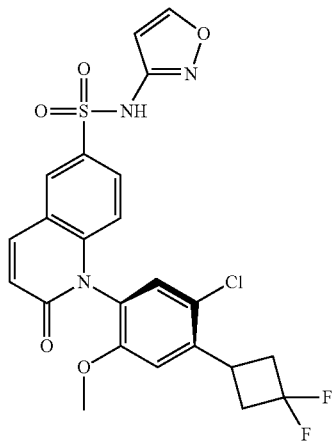

Step 1: (P)-1-(5-Chloro-2-Methoxy-4-(5,8-Dioxaspiro[3.4]Octan-2-Yl)Phenyl)-N-(Isoxazol-3-Yl)-N-(4-Methoxybenzyl)-2-Oxo-1,2-Dihydroquinoline-6-Sulfonamide A vial was charged with (P)-1-(4-bromo-5-chloro-2-methoxyphenyl)-N-(isoxazol-3-yl)-N-(4-methoxybenzyl)-2-oxo-1,2-dihydroquinoline-6-sulfonamide (0.500 g, 0.793 mmol), tetrahydrofuran (1.585 mL), palladium(II) acetate (0.018 g, 0.079 mmol), and 2-dicyclohexylphosphino-2',6'-dimethylamino-1,1'-biphenyl (0.069 g, 0.159 mmol). 5,8—The vial was purged with nitrogen before dioxaspiro[3.4]octan-2-ylzinc(II) bromide (0.1 M in THF, 1.110 mmol) was added and the reaction was stirred at 50° C. for 1 hour. The reaction was then diluted with ethyl acetate and acidified with 1 N hydrochloric acid. The organic layer was separated and the aqueous layer was extracted with ethyl acetate. The combined organic layers were washed with brine, dried with sodium sulfate, filtered, and concentrated. The material was purified via column chromatography (gradient elution 0-100% EtOAc:heptane) to afford (P)-1-(5-chloro-2-methoxy-4-(5,8-dioxaspiro[3.4]octan-2-yl)phenyl)-N-(isoxazol-3-yl)-N-(4-methoxybenzyl)-2-oxo-1,2-dihydroquinoline-6-sulfonamide (0.420 g, 0.632 mmol, 80% yield). m/z (ESI, positive ion) 664.0 (M+H)⁺.

Step 2: (P)-1-(5-Chloro-2-Methoxy-4-(3-Oxocyclobutyl)Phenyl)-N-(Isoxazol-3-Yl)-N-(4-Methoxybenzyl)-2-Oxo-1,2-Dihydroquinoline-6-Sulfonamide (P)-1-(5-chloro-2-methoxy-4-(5,8-dioxaspiro[3.4]octan-2-yl)phenyl)-N-(isoxazol-3-yl)-N-(4-methoxybenzyl)-2-oxo-1,2-dihydroquinoline-6-sulfonamide (0.420 g, 0.632 mmol) was dissolved in dichloromethane (2 mL). Hydro chloric acid (2 N in water, 2.0 mL, 4.0 mmol) was added and the reaction was stirred at 50° C. for three days. The reaction was then diluted with dichloromethane and washed with water. The aqueous layer was extracted with dichloromethane. The combined organic layers were washed with brine, dried with sodium sulfate, filtered, and concentrated. The resulting (P)-1-(5-chloro-2-methoxy-4-(3-oxocyclobutyl)phenyl)-N-(isoxazol-3-yl)-N-(4-methoxybenzyl)-2-oxo-1,2-dihydroquinoline-6-sulfonamide (0.330 g, 0.532 mmol, 67% yield) was used in the next step without further purification. m/z (ESI, positive ion) 620.0 (M+H)+.

Step 3: (P)-1-(5-Chloro-4-(3,3-Difluorocyclobutyl)-2-Methoxyphenyl)-N-(Isoxazol-3-Yl)-N-(4-Methoxybenzyl)-2-Oxo-1,2-Dihydroquinoline-6-Sulfonamide A vial was charged with (P)-1-(5-chloro-2-methoxy-4-(3-oxocyclobutyl)phenyl)-N-(isoxazol-3-yl)-N-(4-methoxybenzyl)-2-oxo-1,2-dihydroquinoline-6-sulfonamide (0.330 g, 0.532 mmol), dichloromethane (1.064 mL), and diethylaminosulfurtrifluoride (2.145 g, 1.758 mL, 13.30 mmol). The reaction was stirred for 3 hours at room temperature. The reaction was then poured into a round-bottom flask, diluted with dichloromethane, and saturated aqueous sodium bicarbonate solution was carefully added until bubbling ceased. The layers were separated, and the aqueous layer was extracted with dichloromethane. The combined organic layers were washed with brine, dried with sodium sulfate, filtered, and concentrated. The material was purified via column chromatography (gradient elution 0-50% EtOAc: heptane) to afford (P)-1-(5-chloro-4-(3,3-difluorocyclobutyl)-2-methoxyphenyl)-N-(isoxazol-3-yl)-N-(4-methoxybenzyl)-2-oxo-1,2-dihydroquinoline-6-sulfonamide (0.350 g, 0.545 mmol, 102% yield).

Step 4: (P)-1-(5-Chloro-4-(3,3-Difluorocyclobutyl)-2-Methoxyphenyl)-N-(Isoxazol-3-Yl)-2-Oxo-1,2-Dihydroquinoline-6-Sulfonamide (P)-1-(5-chloro-4-(3,3-difluorocyclobutyl)-2-methoxyphenyl)-N-(isoxazol-3-yl)-N-(4-methoxybenzyl)-2-oxo-1,2-dihydroquinoline-6-sulfonamide (0.350 g, 0.545 mmol) was dissolved in TFA (1 mL) and dichloromethane (1 mL). The solution was heated to 40° C. and stirred overnight. Solvents were removed in vacuo and the residue was washed with aqueous solution of NaHCO$_3$. The mixture was extracted with dichloromethane, dried over MgSO$_4$ and filtered. The initial product was purified via flash column chromatography (gradient elution 0-50% EtOAc in heptane). The sample was re-purified by SFC via a Regis Whelk-O s,s 2×15 cm, 5 μm column with a mobile phase of 40% methanol using a flowrate of 70 mL/min to afford (P)-1-(5-chloro-4-(3,3-difluorocyclobutyl)-2-methoxyphenyl)-N-(isoxazol-3-yl)-2-oxo-1,2-dihydroquinoline-6-sulfonamide (0.173 g, 0.331 mmol, 62% yield). $^1$H NMR (600 MHz, DMSO-d6) δ ppm 11.63 (br s, 1H), 8.71 (d, J=1.63 Hz, 1H), 8.35 (d, J=2.18 Hz, 1H), 8.20 (d, J=9.63 Hz, 1H), 7.83 (dd, J=8.99, 2.27 Hz, 1H), 7.54 (s, 1H), 7.30 (s, 1H), 6.78 (dd, J=9.35, 5.36 Hz, 2H), 6.44 (d, J=1.82 Hz, 1H), 3.74 (s, 3H), 3.67 (quin, J=8.67 Hz, 1H), 3.09 (dtt, J=18.20, 9.04, 9.04, 4.38, 4.38 Hz, 2H), 3.02-2.89 (m, 2H). m/z (ESI, positive ion) 521.8 (M+H)+.

Example 49: Trans-(P)-1-(5-Chloro-2-Methoxy-4-(3-(Trifluoromethyl)Cyclobutyl)Phenyl)-N-(Oxazol-2-Yl)-2-Oxo-1,2-Dihydroquinoline-6-Sulfonamide

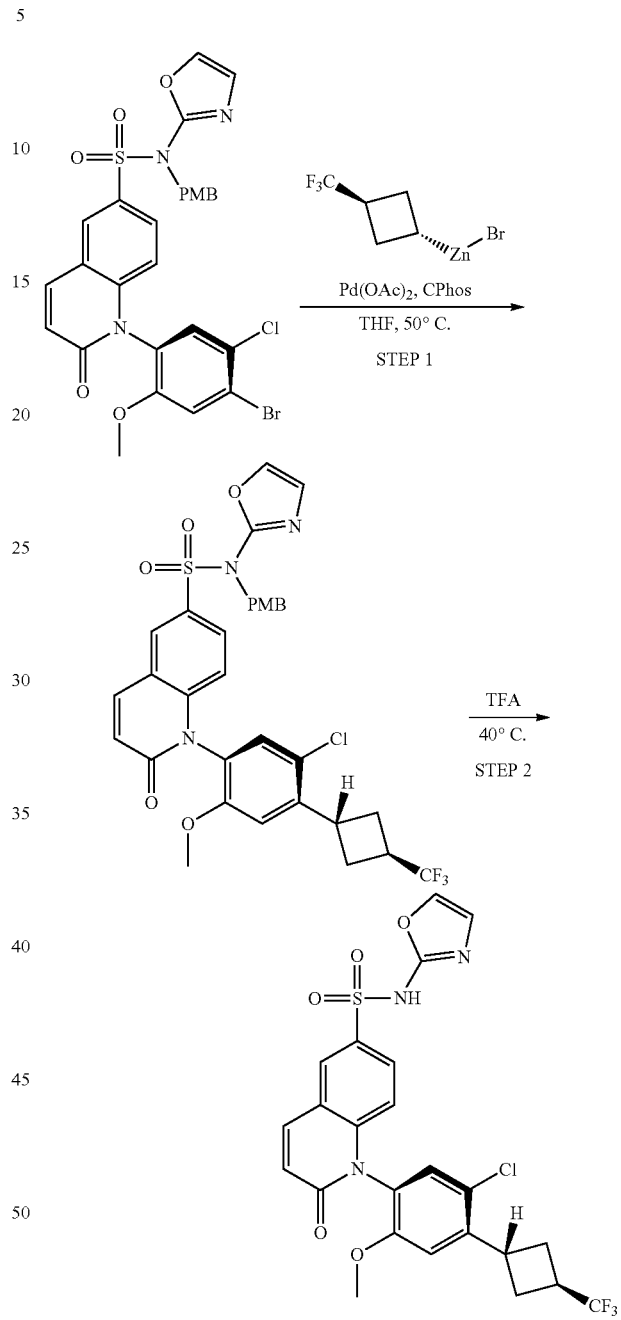

Step 1: Trans-(P)-1-(5-Chloro-2-Methoxy-4-(3-(Trifluoromethyl)Cyclobutyl)Phenyl)-N-(4-Methoxybenzyl)-N-(Oxazol-2-Yl)-2-Oxo-1,2-Dihydroquinoline-6-Sulfonamide A vial was charged with (P)-1-(4-bromo-5-chloro-2-methoxyphenyl)-N-(4-methoxybenzyl)-N-(oxazol-2-yl)-2-oxo-1,2-dihydroquinoline-6-sulfonamide (0.508 g, 0.804 mmol), palladium(ii) acetate (0.023 g, 0.102 mmol), and 2-dicyclohexylphosphino-2',6'-dimethylamino-1,1'-biphenyl (0.076 g, 0.173 mmol). The resulting mixture was sealed via septum cap and sparged with nitrogen for 10 minutes prior to the addition of tetrahydrofuran (3.09 mL). (3-(trifluoromethyl)cyclobutyl)zinc(II) bromide (1.182 mmol) solution. After complete addition, the reaction was warmed to 50° C. and stirred at this temperature for 1.25 hours. After cooling to ambient temperature, the reaction was quenched with 5 M aqueous ammonium chloride solution. The mixture was extracted with ethyl acetate (2×). The organic layer was separated. After removal of solvent, the residue was purified by flash column chromatography (gradient elution 0-50% 3:1 ethyl acetate:ethanol in heptane with 10% dichloromethane as additive) to afford trans-(P)-1-(5-chloro-2-methoxy-4-(3-(trifluoromethyl)cyclobutyl)phenyl)-N-(4-methoxybenzyl)-N-(oxazol-2-yl)-2-oxo-1,2-dihydroquinoline-6-sulfonamide (0.368 g, 0.546 mmol, 68% yield). m/z (ESI, positive ion) 673.6 (M+H)+.

Step 2: Trans-(P)-1-(5-Chloro-2-Methoxy-4-(3-(Trifluoromethyl)Cyclobutyl)Phenyl)-N-(Oxazol-2-Yl)-2-Oxo-1,2-Dihydroquinoline-6-Sulfonamide (P)-1-(5-chloro-2-methoxy-4-(3-(trifluoromethyl)cyclobutyl)phenyl)-N-(4-methoxybenzyl)-N-(oxazol-2-yl)-2-oxo-1,2-dihydroquinoline-6-sulfonamide (0.368 g, 0.546 mmol) was dissolved in 1,1,1-trifluoroacetic acid (1.348 g, 1.348 mL, 11.82 mmol). The reaction was stirred under a nitrogen atmosphere at 40° C. for 2.5 hours. After cooling to ambient temperature, excess TFA was removed in vacuo and the resulting solid was triturated with diethyl ether and filtered. The initial product was purified by column chromatography (gradient elution 0-100% in heptanes with 10% dichloromethane as additive to afford trans (P)-1-(5-chloro-2-methoxy-4-((1R,3R)-3-(trifluoromethyl)cyclobutyl)phenyl)-N-(oxazol-2-yl)-2-oxo-1,2-dihydroquinoline-6-sulfonamide (49.6 mg, 0.092 mmol, 17% yield). $^1$H NMR (500 MHz, DMSO-d6) δ ppm 12.13 (br s, 1H), 8.31 (d, J=2.08 Hz, 1H), 8.17 (d, J=9.60 Hz, 1H), 7.84 (dd, J=8.95, 2.21 Hz, 1H), 7.59 (d, J=1.56 Hz, 1H), 7.49 (s, 1H), 7.38 (s, 1H), 7.25 (d, J=1.43 Hz, 1H), 6.75 (d, J=9.60 Hz, 1H), 6.69 (d, J=8.95 Hz, 1H), 4.00 (quin, J=8.99 Hz, 1H), 3.77 (s, 3H), 3.27-3.20 (m, 1H), 2.75-2.60 (m, 4H). m/z (ESI, positive ion) 554.0 (M+H)+.

Biological Examples

The following assays were used in testing the exemplary compounds of the invention. Data for those examples tested in accordance with the procedures described below are presented in Table 1 below.

IonWorks Barracuda (IWB) Automated Patch Clamp Assay (Same Protocol for Both Human and Mouse)

Human Nav1.7 currents were recorded in population patch-clamp mode with the IWB automated electrophysiology system (Molecular Devices, LLC, Sunnyvale, CA). Spiking HEK cells (without Kir2.1 transfection) were cultured and prepared for recordings as previously described for IonWorks Quattro testing[1]. The external solution consisted of the following (in mM): NaCl 140, KCl 5, CaCl$_2$ 2, MgCl$_2$ 1, HEPES 10, and glucose 11, pH 7.4, with N-methyl-D-glucamine at 320 mOsmol. The internal solution consisted of the following (in mM): KCl 70, KF 70, MgCl$_2$ 0.25, HEDTA 5, and HEPES 10, pH 7.25, with Nmethyl-D-glucamine, 300 mOsmol. From a holding potential of −110 mV, currents were elicited by a train of 26 depolarizations of 150 ms duration to −20 mV at a frequency of 5 Hz. Cells were then clamped to −20 mV for a period of 4 minutes in the presence of a single concentration of test compound. Following this compound incubation period, cells were clamped to −110 mV for three seconds to recover unbound channels and put through the same 26 pulse voltage protocol as above. Peak inward current during the 26th pulse to −20 mV in the presence of compound was divided by the peak inward current evoked by the 26th pulse to −20 mV in the absence of compound to determine percent inhibition. Concentration-response curves of percent inhibition as a function of concentration were generated to calculate IC$_{50}$ values as described in Kornecook, T. J.; Yin, R.; Altmann, S.; et al. Pharmacologic Characterization of AMG8379, a Potent and Selective Small Molecule Sulfonamide Antagonist of the Voltage-Gated Sodium Channel NaV1. 7. *J Pharmacol. Exp. Ther.* 2017, 362, 146-160.

Microsomal Intrinsic Clearance Assay

The purpose of this assay is to determine the intrinsic clearance of test compound in microsomes from preclinical species and human by monitoring the disappearance of test article over time in hepatic microsomes. 20 mg/mL stock, stored at −80° C. microsome was used. List of chemical used: (1) Test article, 10 mM stock (DMSO) or powder from sample bank; (2) Verapamil, 10 mM stock; (3) NADPH, powder (Sigma); (4) Potassium phosphate buffer, 100 mM, pH 7.4; and (5) Tolbutamide (or equivalent). Final incubation concentrations were 0.25 mg/mL microsomal protein and 0.5 µM test article, and incubations are performed in triplicate. The typical time points for the assay were 1, 5, 10, 20, 30, and 40. The assay was carried out in 96-well format, and serially sampled from 400 µL incubation. At the appropriate timepoints, the incubations were quenched with acetonitrile containing internal standard (tolbutamide). Tolbutamide was the default internal standard because it has a signal by positive or negative ion mass spectrometry. The positive control for microsomal intrinsic clearance assay was verapamil. Samples were subjected to LC-MS/MS analysis, and relative amount of compound was calculated by peak area of compound normalized to peak area of internal standard (A/IS). Calculations of intrinsic clearance were performed with Galileo.

Procedure:

Microsomes were removed from −80° C. freezer and thawed at room temperature or in 37° C. water bath. Once thawed, they were stored on ice. Microsomes were added (0.53 mg) to 0.1 M phosphate buffer and 250 µL aliquot was taken per reaction. 10 mM stock of test article was prepared in DMSO. A 1/100 portion was diluted into acetonitrile: water 50:50 to make 100 µM stock. About 2.5 µL of the 100 µM test article stock was added to each reaction to a final concentration of 1.05 µM substrate. (NB: At this stage, concentrations were about 2× higher than the final incubation conditions, to account for about 1:1 dilution with NADPH).

1.9 mM NADPH solution was prepared in 0.1 mM phosphate buffer. 4×250 µL replicate wells of substrate and the microsomes containing 1.05 µM substrate and 0.53 mg/mL protein were the prepared. 3 replicate wells containing 210 µL 1.90 mM NADPH+1 well of buffer (-NADPH) were also prepared. The microsomes, 0.1 M phosphate buffer, and the test article were preincubated for 5 minutes at 37° C. To initiate the reaction, 190 µL of the substrate was added to the wells containing NADPH, to yield a final concentration of 0.25 mg/mL microsomes, 0.5 µM test article, and 1 mM NADPH. 35 µL aliquots were removed at 1, 5, 10, 20, 30, and 40 minutes. The reaction was then quenched at a 1:1 ratio with acetonitrile containing internal standard, placed in a Vortex mixer and centrifuged. The solution was then transferred for bioanalysis by LC-MS/MS.

Open-Field Locomotor Activity in Mice.

On the day of testing, C57Bl/6 male mice were orally administered either Nav1.7 compound or a vehicle control formulation at a dose volume of 10 ml/kg. The vehicle used was 2% HPMC/1% Tween 80 pH 10 with NaOH; DI water at pH 10 w/NaOH; or 2% HPMC/1% Tween 80 pH 2.2.

Two to three hours following test article treatment, depending on the cmax of the each Nav1.7 test compound of the invention, animals were placed into open-field chamber and the animal behavior was monitored over a 30-minute period. For the Thousand Oaks Site Experiments, 16"×16" open-field chamber, KINDER SCIENTIFIC®, San Diego, CA, was used. For the Cambridge Massachusetts Site Experiments, 16"×16" open-field chamber, SAN DIEGO INSTRUMENTS®, San Diego, CA, was used. Locomotor activity (horizontal movement and rearing activity) parameters were measured in an automated manner via infrared photo-beam breaks.

Human CYP3A4 Induction Assay

Cryopreserved human hepatocytes were seeded in 96-well collagen coated plates at 70,000 cells per well in hepatocyte plating media (HPM, final concentrations: 1× Dulbecco's Modified Eagle's Medium, 0.1 µM dexamethasone, 10% fetal bovine serum, 1×ITS, 1×PSG) followed by incubation at 37° C. under 5% CO2 and 90% relative humidity for 2 days to allow hepatocytes to form a confluent layer. On Day 3, hepatocytes were treated with either test compound or rifampin (20 µM, positive control for CYP3A induction) prepared in hepatocyte incubation media ((HIM, final concentrations: 1× William's Medium E, 0.1 µM dexamethasone, 1×ITS, 1×PSG). Treatment was performed for 72 hours with either 2 concentrations (2 µM or 10 µM) or a range of concentrations (0.001 µM to 100 µM) of the test compound to obtain full dose-response curve. Fresh media containing the relevant concentrations of the test compound was replaced every day until the samples were processed. After 72 hours of incubation, samples were processed for mRNA analysis using bDNA technology using manufacturer's instructions (Affymetrix, Fremont, CA). Cell viability was tested at the end of the experiment using MTT assay kit (Roche Diagnostics, Basel, Switzerland). Data was analyzed and presented as percent of control (POC) and $E_{max}$ and $EC_{50}$ obtained when appropriate according to guidance from Center for Drug Evaluation and Research (CDER), 2006, Guidance for Industry, Drug Interaction Studies—Study Design, Data Analysis, and Implications for Dosing and Labeling.

Cryopreserved human hepatocytes were seeded in 96-well collagen coated plates at 70,000 cells per well in hepatocyte plating media (HPM, final concentrations: 1× Dulbecco's Modified Eagle's Medium, 0.1 µM dexamethasone, 10% fetal bovine serum, 1×ITS, 1×PSG) followed by incubation at 37° C. under 5% CO2 and 90% relative humidity for 2 days to allow hepatocytes to form a confluent layer. On Day 3, hepatocytes were treated with either test compound or rifampin (20 µM, positive control for CYP3A induction) prepared in hepatocyte incubation media ((HIM, final concentrations: 1× William's Medium E, 0.1 µM dexamethasone, 1×ITS, 1×PSG). Treatment was performed for 72 hours with either 2 concentrations (2 µM or 10 µM) or a range of concentrations (0.001 µM to 100 µM) of the test compound to obtain full dose-response curve. Fresh media containing the relevant concentrations of the test compound was replaced every day until the samples were processed. After 72 hours of incubation, samples were processed for mRNA analysis using bDNA technology using manufacturer's instructions (Affymetrix, Fremont, CA). Cell viability was tested at the end of the experiment using MTT assay kit (Roche Diagnostics, Basel, Switzerland). Data was analyzed and presented as percent of control (POC) and $E_{max}$ and $EC_{50}$ obtained when appropriate, as described in Halladay, J. et al, 2012, An "all-inclusive" 96-well cytochrome P450 induction method: Measuring enzyme activity, mRNA levels, protein levels, and cytotoxicity from one well using cryopreserved human hepatocytes, *Pharmacological and Toxicological Methods*, 66:270-275.

The compounds of the present invention may also be tested in the following in vivo assays.

Rat Formalin Model of Persistent Pain

On the test day, animals (Naïve, male Sprague Dawley rats) weighing between 260-300 g at the start of testing can be obtained from Harlan (Indianapolis, IN). All animals may be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. Animals are pretreated with the appropriate test compound either by oral gavage or intraperitoneal injection at the desired pretreatment time (typically two hours before test onset) and then returned to their home cages. After dosing and at least 30 minutes prior to test onset, animals can be acclimated to the individual testing chambers. At test time, each animal can be gently wrapped in a towel with the left hind paw exposed. A dilute solution of formalin (2.5%) in phosphate buffered saline can be injected subcutaneously into the dorsal surface of the left hind paw in a volume to 50 µL with a 30 g needle. Immediately following injection, a small metal band can be affixed to the plantar side of the left hind paw with a drop of LOCTITE (adhesive). Animals may be then placed into the testing chambers and the number of flinches can be recorded between 10 to 40 minutes after formalin injection. A flinch is defined as a quick and spontaneous movement of the injected hind paw not associated with ambulation. Flinches can be quantified with the aid of the Automated Nociception Analyzer built by the University of California, San Diego Department of Anesthesiology. Individual data can be expressed as a % maximal potential effect (% MPE) calculated with the following formula: (−(Individual score−Vehicle average score)/Vehicle average score))*100=% MPE Statistical analysis can be performed by analysis of variance (ANOVA), with post-hoc analysis using Bonferroni compared to the vehicle group for a significant main effect. Data can be represented as mean % MPE+/−standard error for each group.

Rat Open Field Assay

On the test day, animals (Naïve, male Sprague Dawley rats) weighing between 260-300 g at the start of testing may be obtained from Harlan (Indianapolis, IN). All animals can be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. In a room separate from the testing room, animals can be pretreated with the appropriate test compound either by oral gavage or intraperitoneal injection at the desired pretreatment time (typically two hours before test onset) and then can be returned to their home cages until the pretreatment has elapsed. At test time, animal can be transferred to the open field testing room in their home cages. Each animal may be placed in a separate testing chamber and the motion tracking system is started. The house lights in the testing room should be turned off and the animals can be allowed to explore the novel open field for 30 minutes. An automated motion tracker, made by San Diego Instruments, San Diego, CA, can be used to capture animal exploration with the aid of infrared photo beams to detect animal movement. These behaviors include basic movement and vertical rearing, which can be used as the primary endpoints for this assay. At the end of the test, house lights can be turned on and the animals should be removed from the testing apparatus. Data can be expressed as a percent change from the vehicle control using the following equation.

(1−(Test mean/Vehicle mean))*100=% Change.

Statistical analysis can be performed by analysis of variance (ANOVA), with post-hoc analysis using Dunnett to follow up significant main effects.

Mouse Formalin Model of Persistent Pain

Mice (Naïve, male C57Bl/6) weighing between 22-30 g at the start of testing were obtained from Harlan (Indianapolis, IN). All animals were housed under a 12/12 h light/dark cycle with lights on at 0630. Rodents were singly housed on solid bottom cages with corn cob bedding and had access to food and water ad libitum. Animals were allowed to habituate to the vivarium for at least five days before testing was begun and were brought into the testing room at least 30 minutes prior to dosing. Animals were pretreated with the appropriate test compound either by oral gavage or intraperitoneal injection at the desired pretreatment time (typically two hours before test onset) and then returned to their home cages. After dosing and at least 5 minutes prior to test onset, animals were acclimated to the individual testing chambers. At test time, each animal was gently wrapped in a cloth glove with the left hind paw exposed. A dilute solution of formalin (2%) in phosphate buffered saline was injected subcutaneously into the dorsal surface of the left hind paw in a volume to 20 µL with a 30 g needle. Animals were then placed into the observation chambers and the behaviors were recorded for 60 minutes following the formalin injection. A pain-like behavior was defined as licking and/or non-weight bearing of the injected hind paw not associated with ambulation.

Statistical analysis was performed by analysis of variance (ANOVA), with post-hoc analysis using the Dunnett post-hoc test compared to the vehicle group for any significant main effect. Data were represented as mean+/−standard error for each group.

Table 1 provides data for compounds exemplified in the present application and priority document thereof, as representative compounds of the present invention, as follows: compound name (as named using ChemDraw Ultra version 15.1; specific stereochemical designations such as P, M, cis, and trans were added); and biological data including in-vitro human Nav 1.7 IWQ data ($IC_{50}$ in uM) and Human CYP3A4 mRNA Induction at 10 uM percent of control (POC) (%), where available. Ex. # refers to Example No. ND means no data was available.

The potency of the compounds of the present invention were evaluated on human $Na_v1.7$ channels using the above described IonWorks Barracuda automated electrophysiology platform that evaluates the ability of compounds to block sodium conductance through $Na_v1.7$ channels. A voltage-protocol that prosecutes both state-dependent as well as use-dependent inhibition was used as these modes of action are thought to be more relevant for the native state of $Na_v1.7$ channels in pain sensing neurons in vivo.

The cytochrome P450 (CYP) is a well-known superfamily of enzymes that are responsible for the oxidative and reductive metabolic transformation of medications used in clinical practice. In addition, the CYP enzymes are commonly associated with causing many clinically relevant drug-drug interactions. Of the CYP enzymes, CYP3A4 is not only the most prevalent CYP enzyme in the liver and intestine, but is responsible for metabolism and elimination of approximately 50% of marketed drugs. In addition, CYP3A4 activity can be induced (or increased) or inhibited (decreased) in response to administration of certain drugs, thereby affecting concentrations of their own or certain concomitant drugs present in the body. Typically, the induction of CYP3A4 is an undesired property of the drug molecule as it can result in the reduction of parent drug concentrations that may put patients at increased risk for lack of efficacy or increased metabolite formation that can lead to safety risk. The CYP3A4 induction property was evaluated in an in vitro induction assay where human hepatocytes were exposed to the test compounds at physiologically relevant concentrations. Changes in the levels of CYP3A4 were evaluated at the end of the experiment and compared against the increased levels upon treatment with rifampin, a well-established CYP3A4 inducer.

Representative compounds of the present invention show either favorable activities against hNav1.7 IWQ or favorable human CYP3A4 induction data as compared to Compound X, which is named 1-(4-cyclopropyl-5-fluoro-2-methoxyphenyl)-N-(isoxazol-3-yl)-2-oxo-1,2-dihydroquinoline-6-sulfonamide, having the structure below:

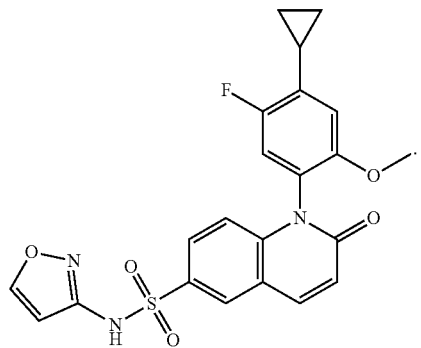 [SMILES: COc1cc(C2CC2)c(F)cc1-n1c(=O)ccc2cc(S(=O)(=O)Nc3ccon3)ccc21]

Compound X was exemplified in International Patent Publication No. WO2014201206A1, Example No. 1145. Preferred compounds of the present invention have both favorable activities against human Nav1.7 IWQ and favorable human CYP3A4 induction data as compared to Compound X.

TABLE 1

| BIOLOGICAL DATA | | |
|---|---|---|
| Ex. # | hNaV1.7 IWB-U IC50 | Hu CYP3A4 mRNA Induction (10 uM POC) |
| Compound X | 0.048 | 84.31 |
| 1 | ND | ND |
| 2 | 0.025 | ND |
| 3 | 0.033 | ND |
| 4 | 0.015 | 14.71 |
| 5 | 0.002 | ND |
| 6 | 0.011 | 83.89 |
| 7 | 0.007 | 16.35 |

TABLE 1-continued

BIOLOGICAL DATA

| Ex. # | hNaV1.7 IWB-U IC50 | Hu CYP3A4 mRNA Induction (10 uM POC) |
|---|---|---|
| 8 | 0.005 | 10.51 |
| 9 | 0.002 | ND |
| 10 | 0.008 | 5.66 |
| 11 | 0.002 | 7.29 |
| 12 | 0.007 | 68.98 |
| 13 | 0.006 | 46.85 |
| 14 | 0.016 | 18.3 |
| 15 | 0.017 | 36 |
| 16 | 0.018 | 130.1 |
| 17 | 0.015 | 61.91 |
| 18 | 0.022 | 20.78 |
| 19 | 0.015 | 60.73 |
| 20 | 0.012 | 42.22 |
| 21 | 0.012 | 17.07 |
| 22 | 0.05 | 24.14 |
| 23 | 0.102 | 14.37 |
| 24 | 0.013 | 89.26 |
| 25 | 0.037 | 18.57 |
| 26 | 0.08 | 14.58 |
| 27 | 0.104 | 48.14 |
| 28 | 0.054 | 60.29 |
| 29 | 0.037 | 34.63 |
| 30 | 0.137 | ND |
| 31 | ND | ND |
| 32 | 0.01 | 88 |
| 33 | ND | ND |
| 34 | 0.028 | 69.54 |
| 35 | 0.02 | 13.33 |
| 36 | 0.014 | 19.16 |
| 37 | 0.062 | 49.51 |
| 38 | 0.021 | 4.43 |
| 39 | 0.011 | 21.68 |
| 40 | 0.005 | 74.43 |
| 41 | 0.011 | 52.8 |
| 42 | 0.006 | 19.25 |
| 43 | 0.007 | 68.28 |
| 44 | 0.007 | ND |
| 45 | 0.008 | 36.685 |
| 46 | 0.008 | 6.6 |
| 47 | 0.008 | 19.64 |
| 48 | 0.01 | 110.2 |
| 49 | 0.01 | 64.94 |

The foregoing invention has been described in some detail by way of illustration and example, for purposes of clarity and understanding. Those skilled in the art understand that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited herein are hereby incorporated by reference in their entirety for all purposes to the same extent as if each individual patent, patent application or publication were so individually denoted.

What is claimed is:

1. A compound of Formula (Ia), or an enantiomer, diastereoisomer, atropisomer, or a mixture thereof, or a pharmaceutically acceptable salt thereof:

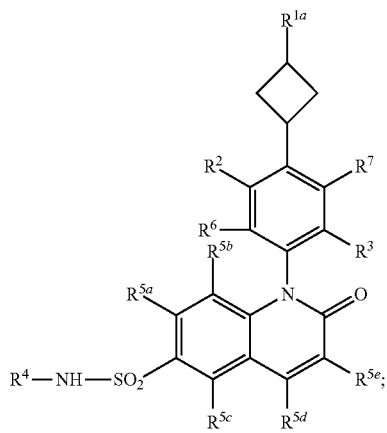

(Ia)

wherein: $R^{1a}$ is fluoro, chloro, methyl, —O—$CF_3$, or $CF_3$;
$R^2$ is H, halo, $C_{1-6}$alk, or $C_{1-6}$haloalk;
$R^3$ is $C_{1-6}$alk, $C_{1-6}$haloalk, —O—$C_{1-6}$alk, or —CN;
$R^4$ is a 5- to 6-membered heteroaryl;
each of $R^6$ and $R^7$ is hydrogen; and
each of $R^{5a}$; $R^{5b}$; $R^{5c}$; $R^{5d}$; and $R^{5e}$ is independently hydrogen or halo.

2. The compound according to claim 1, or an enantiomer, atropisomer, or a mixture thereof, or a pharmaceutically acceptable salt thereof, wherein said $R^{1a}$ is $CF_3$; the cyclobutyl ring is a trans isomer; and $R^4$ is isoxazolyl, pyridazinyl, thiazolyl, thiadiazolyl, or oxazolyl.

3. The compound according to claim 1, or an enantiomer, atropisomer, or a mixture thereof, or a pharmaceutically acceptable salt thereof, wherein said $R^{1a}$ is $CF_3$; the cyclobutyl ring is a cis isomer; $R^2$ is F; and $R^4$ is isoxazolyl, pyridazinyl, thiazolyl, thiadiazolyl, or oxazolyl.

4. The compound according to claim 1, or an enantiomer, diastereoisomer, atropisomer, or a mixture thereof, or a pharmaceutically acceptable salt thereof, wherein said atropisomer, when present, is a P atropisomer.

5. The compound according to claim 1, or an enantiomer, diastereoisomer, atropisomer, or a mixture thereof, or a pharmaceutically acceptable salt thereof, wherein said $R^{1a}$ is F.

6. The compound according to claim 1, or an enantiomer, diastereoisomer, atropisomer, or a mixture thereof, or a pharmaceutically acceptable salt thereof, wherein said $R^{1a}$ is $CF_3$ or —O—$CF_3$; $R^2$ is H, F, or methyl; and $R^4$ is isoxazolyl or pyridazinyl.

7. The compound according to claim 1, or an enantiomer, diastereoisomer, atropisomer, or a mixture thereof, or a pharmaceutically acceptable salt thereof, wherein said $R^{1a}$ is $CF_3$; $R^2$ is F; and $R^4$ is isoxazolyl.

8. The compound according to claim 1, or a pharmaceutically acceptable salt thereof, wherein the compound is trans-(P)-1-(5-fluoro-2-methoxy-4-(3-(trifluoromethyl)cyclobutyl)phenyl)-N-(isoxazol-3-yl)-2-oxo-1,2-dihydroquinoline-6-sulfonamide.

9. The compound according to claim 1, or a pharmaceutically acceptable salt thereof, wherein the compound is trans-(P)—N-(isoxazol-3-yl)-1-(2-methoxy-5-methyl-4-(3-(trifluoromethyl)cyclobutyl)phenyl)-2-oxo-1,2-dihydroquinoline-6-sulfonamide.

10. The compound according to claim 1, or a pharmaceutically acceptable salt thereof, wherein the compound is trans-(P)-1-(2-methoxy-4-(3-(trifluoromethyl)cyclobutyl)phenyl)-2-oxo-N-(pyrimidin-2-yl)-1,2-dihydroquinoline-6-sulfonamide.

11. The compound according to claim 1, or a pharmaceutically acceptable salt thereof, wherein the compound is trans-(P)-1-(5-fluoro-2-methoxy-4-(3-(trifluoromethyl)cyclobutyl)phenyl)-2-oxo-N-(pyridazin-3-yl)-1,2-dihydroquinoline-6-sulfonamide.

12. The compound according to claim 1, or a pharmaceutically acceptable salt thereof, wherein the compound is trans-(P)-1-(5-fluoro-2-methoxy-4-(3-(trifluoromethoxy)cyclobutyl)phenyl)-N-(isoxazol-3-yl)-N-(4-methoxybenzyl)-2-oxo-1,2-dihydroquinoline-6-sulfonamide.

13. The compound according to claim 1, or a pharmaceutically acceptable salt thereof, wherein the compound is trans-(P)-5-fluoro-1-(5-fluoro-2-methoxy-4-(3-(trifluoromethyl)cyclobutyl)phenyl)-N-(isoxazol-3-yl)-2-oxo-1,2-dihydroquinoline-6-sulfonamide.

14. A pharmaceutical composition comprising the compound according to claim 1, or an enantiomer, diastereoisomer, atropisomer, or a mixture thereof, or a pharmaceutically acceptable salt thereof, and a pharmaceutically acceptable excipient.

* * * * *